United States Patent [19]

Farge et al.

[11] 4,307,233
[45] Dec. 22, 1981

[54] 3-VINYL-CEPHALOSPORIN DERIVATIVES

[75] Inventors: Daniel Farge, Thiais; Claude Moutonnier, Le Plessis Robinson; Pierre Le Roy, Thiais; Jean-Francois Peyronel, Palaisseau, all of France

[73] Assignee: Rhone-Poulenc Industries, Paris, France

[21] Appl. No.: 152,085

[22] Filed: May 21, 1980

[30] Foreign Application Priority Data

May 23, 1979 [FR] France .................. 79 13096

[51] Int. Cl.³ .......................................... C07D 501/24
[52] U.S. Cl. .................................. 544/16; 542/413; 542/420; 542/437; 542/443; 544/22; 544/29
[58] Field of Search ................ 544/16, 22, 30; 542/413, 420, 437, 443

[56] References Cited
U.S. PATENT DOCUMENTS 4,065,620 12/1977 Webber ............................ 544/16
4,098,888 7/1978 Ochiai et al. ...................... 544/22
4,103,084 7/1978 Bradshaw et al. ................. 544/22

Primary Examiner—Paul M. Coughlan, Jr.
Attorney, Agent, or Firm—Stevens, Davis, Miller & Mosher

[57] ABSTRACT

Novel 3-vinyl-cephalosporin derivates of the general formula

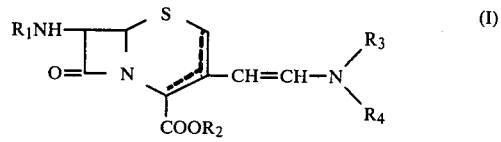

in the bicyclooct-2-ene or bicyclooct-3-ene form, in which $R_1$ is a protective radical or is a radical of the general formula

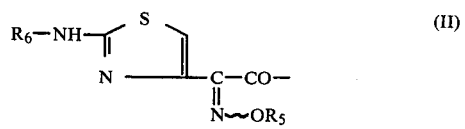

in which $R_5$ is hydrogen, alkyl, vinyl or cyanomethyl, or a protective radical, and $R_6$ is hydrogen or a protective radical, and $R_2$ is a protective radical or an enzymatically removable radical, or $R_1$ is an acyl radical, which may carry various substituents, and $R_2$ represents a protective radical, and $R_3$ and $R_4$, which are identical or different, represent alkyl (optionally substituted by hydroxyl, alkoxy, amino, alkylamino or dialkylamino) or phenyl, or form, together with the nitrogen atom, a saturated 5-membered or 6-membered heterocyclic ring optionally containing another hetero-atom, their E- and Z-forms and their mixtures, are useful as intermediates for the preparation of 3-thiovinyl cephalosporins useful as antibacterial agents.

7 Claims, No Drawings

3-VINYL-CEPHALOSPORIN DERIVATIVES

The present invention relates to novel 3-vinylcephalosporin derivatives of the general formula

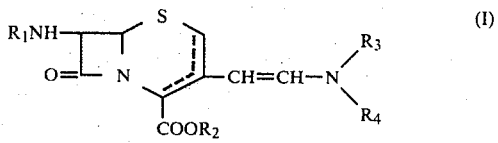

and their preparation,

The product of the general formula (I) is in the bicyclooct-2-ene or bicyclooct-3-ene form (according to the Chemical Abstracts nomenclature), the substituent on the carbon atom in the 3-position of the bicyclooctene exhibits the cis- or trans-stereoisomeric configuration and (a) the symbol $R_1$ represents a radical of the general formula

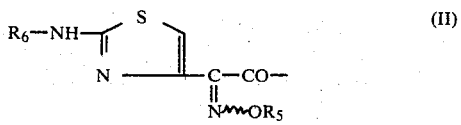

(in which $R_5$ is a hydrogen atom, an alkyl, vinyl or cyanomethyl radical or a protective group such as trityl, tetrahydropyranyl or 2-methoxy-prop-2-yl and $R_6$ is a protective radical chosen from amongst tert.-butoxycarbonyl, 2,2,2-trichloro-ethoxycarbonyl, chloroacetyl, trichloroacetyl, trityl, benzyl, dibenzyl, benzyloxycarbonyl, p-nitrobenzyloxycarbonyl and p-methoxybenzyloxycarbonyl, formyl or trifluoroacetyl), a benzhydryl or trityl radical, an acyl radical of the general formula

(in which $R_7$ is a hydrogen atom or an alkyl radical [which is optionally substituted by one or more halogen atoms or by a phenyl or phenoxy radical] or phenyl) a radical of the general formula

(in which $R_8$ is a branched unsubstituted alkyl radical or a branched or straight alkyl radical carrying 1 or more substituents [chosen from amongst halogen atoms and cyano, trialkylsilyl, phenyl, and phenyl substituted by 1 or more alkoxy, nitro or phenyl radicals], vinyl, allyl or quinolyl),
or a nitrophenylthio radical,
or $R_1$NH is replaced by a methyleneimino radical in which the methylene radical is substituted by a dialkylamino or aryl group (itself optionally substituted by one or more methoxy or nitro radicals) and
the symbol $R_2$ represents an enzymatically easily removable radical of the general formula

(in which $R_9$ represents a hydrogen atom or an alkyl radical and $R_{10}$ represents an alkyl or the cyclohexyl radical) or a methoxymethyl, tert.-butyl, benzhydryl, p-nitrobenzyl or p-methoxybenzyl radical, or (b) the symbol $R_1$ represents an alkanoyl radical containing 1 to 8 carbon atoms, an alkanoyl radical containing 2 to 8 carbon atoms substituted by chlorine or bromine atoms, an acyl radical of the general formula

(in which each Q is H or methyl and Ar represents a thien-2-yl, thien-3-yl, fur-2-yl, fur-3-yl, pyrrol-2-yl or pyrrol-3-yl radical or a phenyl radical [optionally substituted by halogen atoms or by hydroxyl radicals, by alkyl radicals (containing 1 to 3 carbon atoms) or by alkoxy radicals (containing 1 to 3 carbon atoms) of which at least one is situated in the meta- or para-position of the phenyl radical]),
an acyl radical of the general formula

(in which X is oxygen or sulphur and Ar is defined as above or X represents sulphur and Ar represents pyrid-4-yl),
an acyl radical corresponding to the general formula

(in which Ar is defined as above and B represents an amino radical which is protected [by a benzyloxycarbonyl, alkoxycarbonyl, cyclopentyloxycarbonyl, cyclohexyloxycarbonyl, benzhydryloxycarbonyl, trityl or 2,2,2-trichloro-ethoxycarbonyl group], a sulpho radical, a hydroxyl or carboxyl radical [optionally protected by esterification, respectively with an alkanoic acid or an alcohol (containing 1 to 6 carbon atoms)]) or a 5-aminoadipyl radical [in which the amino group is optionally protected by an alkanoyl radical (containing 1 to 3 carbon atoms and optionally substituted by a chlorine atom) and in which the carboxyl group is protected by a benzhydryl, 2,2,2-trichloroethyl, tert.-alkyl (containing 4 to 6 carbon atoms) or nitrobenzyl group] or $R_1$NH- is replaced by a cyclic imide group of a dicarboxylic acid and $R_2$ represents a tert.-alkyl radical containing 4 to 6 carbon atoms, a tert.-alkenyl radical containing 6 or 7 carbon atoms, tert.-alkynyl radical containing 6 or 7 carbon atoms, benzyl, methoxybenzyl, nitrobenzyl, 2,2,2-trichloroethyl, benzhydryl, succinimidomethyl or phthalimidomethyl and the symbols $R_3$ and $R_4$, which are identical or different, represent alkyl radicals (optionally substituted by a hydroxyl, alkoxy, amino, alkylamino or dialkylamino radical) or phenyl radicals or form, together with the nitrogen atom to which they are attached, a saturated heterocyclic ring of 5 or 6 members, optionally containing another hetero-atom chosen from amongst nitrogen, oxygen or sulphur, and optionally substituted by an alkyl radical, it being understood that the alkyl or acyl portions or radicals mentioned above (or which will be mentioned later) are (unless stated to the contrary) straight or branched and contain 1 to 4 carbon atoms.

It is also to be understood that the mixtures of the bicyclooct-2-ene and bicyclooct-3-ene isomers and/or cis- and trans-isomers fall within the scope of the present invention.

In the text which follows, the trans-stereoisomeric configuration will be designated E and the cis-stereoisomeric configuration will be designated Z.

Furthermore, it is to be understood that the -OR$_5$ group of the radical of the general formula (II) can be in the syn- or anti-position and that these isomers and their mixtures also fall within the scope of the present invention.

The syn-form can be represented by the formula

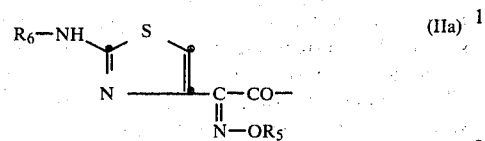
(IIa)

The anti-form can be represented by the formula

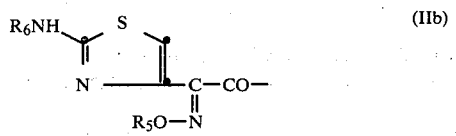
(IIb)

Amongst the meanings of R$_1$ defined above, the following may be mentioned especially: 2-methoxyimino-2-(2-tritylamino-thiazol-4-yl)-acetyl, 2-methoxyimino-2-(2-tert.-butoxycarbonylamino-thiazol-4-yl)acetyl, 2-trityloxyimino-2-(2-tritylamino-thiazol-4-)-acetyl, 2-tetrahydropyranyloxyimino-2-(2-tritylamino-thiazol-4-yl)-acetyl, trityl, formyl, acetyl, chloroacetyl, trichloroacetyl, phenylacetyl, phenoxyacetyl, benzoyl, tert.-butoxycarbonyl, 2-chloro-1,1-dimethyl-ethoxycarbonyl, 2,2,2-trichloro-ethoxycarbonyl, 2,2,2-trichloro-1,1-dimethyl-ethoxycarbonyl, 2-cyano-1,1-dimethyl-ethoxycarbonyl, 2-trimethylsilyl-ethoxycarbonyl, benzyloxycarbonyl, p-methoxybenzyloxycarbonyl, 3,5-dimethyoxybenzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio and p-nitrophenylthio.

As examples of methyleneimino radicals there may be mentioned: dimethylaminomethyleneimino, 3,4-dimethoxybenzylideneimino and 4-nitrobenzylideneimino.

1. According to the invention, the products of the general formula (I) for which R$_3$ and R$_4$ have the definitions given above, except for representing alkyl substituted by hydroxyl, amino or alkylamino, can be obtained by the action of a product, optionally prepared in situ, of the general formula

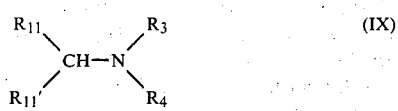
(IX)

[in which R$_3$ and R$_4$ are defined as above and R$_{11}$ and R'$_{11}$, which are identical or different, represent either groups of the general formula $-X_2R_{12}$ (X)

in which X$_2$ is an oxygen atom and R$_{12}$ represents an alkyl or phenyl radical, or one of R$_{11}$ and R'$_{11}$ represents a radical of the general formula (X), in which X$_2$ is oxygen or sulphur, and the other represents an amino radical of the general formula

(XI)

in which R$_{13}$ and R$_{14}$ are defined like R$_3$ and R$_4$ in the general formula (IX), or R$_{11}$ and R'$_{11}$ each represent a radical of the general formula (XI)] with a cephalosporin derivative of the general formula

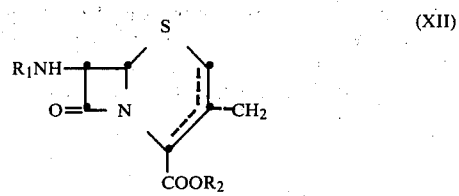
(XII)

in which R$_1$ and R$_2$ are defined as above, and the derivative is in the 3-methyl-bicyclooct-2-ene or 3-methyl-bicyclooct-3-ene or 3-methylene-bicyclooctane form.

The reaction is in general carried out in an organic solvent, such as dimethylformamide, hexamethyl-phosphorotriamide, acetonitrile, dimethylacetamide or a mixture of solvents (e.g. dimethylformamide/tetrahydrofurane, dimethylformamide/dimethylacetamide, dimethylformamide/ether or dimethylformamide/dioxane) at a temperature between 20° C. and the reflux temperature of the reaction mixture.

If a product of the general formula (IX), in which the radical (XI) is different from -NR$_3$R$_4$, is chosen, it is preferable to choose a product of this type in such a way that the amine HNR$_{13}$R$_{14}$ is more volatile than HNR$_3$R$_4$.

2. According to the invention, the products of the general formula (I) in which R$_1$ and R$_2$ are defined as above and R$_3$ and R$_4$, which are identical or different, represent alkyl radicals susbstituted by hydroxyl, amino or alkylamino, can be obtained by transenamination from a product of the general formula (I), in which R$_3$ and R$_4$ represent alkyl radicals, preferably methyl.

The reaction is carried out by the action of an amine of the general formula

(XIII)

(in which R$_3$ and R$_4$ have the corresponding definitions) on a product of the general formula (I), and the conditions used are similar to those described previously for the action of a product of the general formula (IX) on a derivative of the general formula (XII).

The products of the general formula (IX) can be prepared in accordance with the methods described by H. BREDERECK et al., Chem. Ber. 101, 41 (1968), Chem. Ber. 101, 3058 (1968) and Chem. Ber. 106, 3725 (1973).

The cephalosporin derivatives of the general formula (XII), in which R$_1$ represents a radical of the general formula (II), can be prepared from products of the general formula

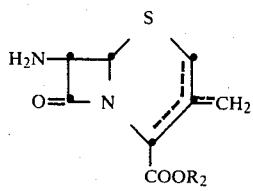
(XIV)

[in which R₂ is defined as above and the position of the double bond is defined as for the product of the general formula (XII)] by the action of an acid of the general formula

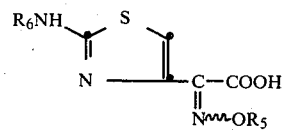
(XV)

[in which R₅ and R₆ are defined as above, except for R₅ representing hydrogen] or of a reactive derivative of this acid, followed, where appropriate, by removal of the protective radical of the oxime. It is to be understood that the acid of the general formula (XV) in the syn- or anti-form, or as a mixture of these forms, respectively gives the products of the general formula (XII) in the syn- or anti-form or as a mixture of these forms.

In general, the condensation of the products of the general formula (XV), in which the acid group is free, with the 7-amino-cephalosporin of the general formula (XIV) is carried out in an organic solvent such as dimethylformamide, acetonitrile, tetrahydrofurane, methylene chloride or chloroform, in the presence of a condensation agent such as a carbodiimide (for example dicyclohexylcarbodiimide), N,N'-carbonyldiimidazole or 2-ethoxy-1-ethoxycarbonyl-1,2-dihydro-quinoline, at a temperature of between −20° and 40° C.

If a reactive derivative of the acid of the general formula (XV) is used, it is possible to employ the anhydride, a mixed anhydride or a reactive ester of the general formula

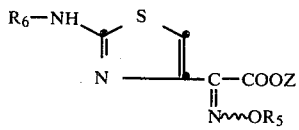
(XVI)

(in which R₅ and R₆ are defined as above, and Z represents a succinimido, benzotriazol-1-yl, 4-nitrophenyl, 2,4-dinitrophenyl, pentachlorophenyl or phthalimido radical or an acid halide for example the acid chloride.

If the anhydride, a mixed anhydride or an acid halide (any of which may be prepared in situ) is employed, the condensation is carried out in an inert organic solvent such as an ether (for example tetrahydrofurane or dioxane), a chlorinated solvent (for example chloroform or methylene chloride), an amide (for example dimethylformamide or dimethylacetamide) or a ketone (for example acetone), or in mixtures of the above solvents [in the presence of an acid acceptor such as an epoxide (for example propylene oxide) or such as a nitrogen-containing organic base, e.g. pyridine, dimethylaminopyridine, N-methylmorpholine or a trialkylamine (for example triethylamine)] or in an aqueous organic medium in the presence of an alkaline condensation agent such as sodium bicarbonate, and the temperature used is between −40° and +40° C.

If a reactive ester of the general formula (XVI) is employed, the reaction is in general carried out in the presence of a trialkylamine (for example treithylamine) in an organic solvent such as dimethylformamide, at a temperature of between 0° and 40° C.

The cephalosporin derivatives of the general formulae (XII) and (XIV), in whch R₂ represents a radical of the general formula (V), can be obtained by esterification of the corresponding acid by any method which is in itself known for preparing an ester from an acid without affecting the remainder of the molecule.

In general, an alkali metal salt or a tertiary amine salt of a product of the general formula

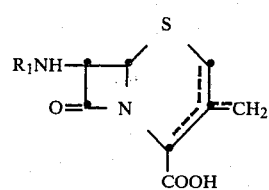
(XVII)

in which R₁ is defined as above, or

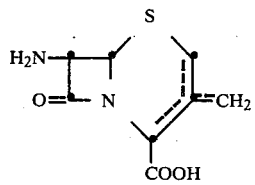
(XVIII)

[in which the position of the double bond is defined as for the product of the general formulae (XII) and (XIV) and, where appropriate, the amine group of the radical R₁ is protected] is reacted with a halide of the general formula

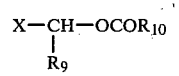
(XIX)

in which R₉ and R₁₀ are defined as above and X represents a halogen atom, in an inert solvent such as dimethylformamide, at a temperature of between 0° and 30° C.

The products of the general formula (XIX) can be prepared in accordance with the method described in German Patent Application 2,350,230.

The introduction of the protective groups R₁ and/or R₂ of the products of the general formula (XII), for which purpose R₁ and R₂ are defined as above in (a) [with the exception of R₁ representing a radical of the general formula (II) and R₂ representing a radical of the general formula (V)] and of the products of the general formula (XIV), for which purpose R₂ is defined as above in (a) [except for representing a radical of the general formula (V)] can be effected into a cephalosporin, respectively of the general formula (XIV), (XVII) or (XVIII), by application of the methods described in the following publications:

if R₁ is a trityl radical: by analogy with the method described by J. C. Sheehan et al., J. Amer. Chem. Soc., 84, 2983 (1962);

if R₁ is a formyl radical: according to J. C. Sheehan et al., J. Amer. Chem. Soc. 80, 1156 (1958);

if R₁ is acetyl, chloroacetyl, trichloroacetyl, phenylacetyl, phenoxyacetyl or benzoyl: according to E. H. Flynn, Cephalosporins and Penicillins, Academic Press (1972);

if R₁ is a tert.-butoxycarbonyl radical: according to L. Moroder et al., Hoppe Seyler's Z. Physiol. Chem. 357, 165o (1976);

if R₁ is 2,2,2-trichloro-1,1-dimethyl-ethoxycarbonyl: according to J. Ugi et al., Angew, Chem. Int. Ed. Engl. 17(5), 361 (1978);

if R₁ is 2,2,2-trichloro-ethoxycarbonyl, 2-chloro-1,1-dimethyl-ethoxycarbonyl, 2-cyano-1,1-dimethyl-ethoxycarbonyl, 2-trimethylsilyl-ethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by the action of a chloroformate in an aqueous organic medium in the presence of an alkali metal bicarbonate, or according to Belgian Patent No. 788,885;

if R₁ is diphenylmethoxycarbonyl: by the action of the corresponding azidoformate in an aqueous organic medium, in the presence of an alakali metal bicarbonate;

if R₁ is 2-(biphenyl-4-yl)-isopropoxycarbonyl: by analogy with the method described in Helv. Chim. Acta, 51, 924 (1968);

if R₁ is quinol-8-yl-oxycarbonyl or allyloxycarbonyl: by the action of the corresponding carbonate in a basic aqueous organic medium;

if R₁ is o-nitrophenylthio or p-nitrophenylthio: by analogy with the method described by L. Zervas et al., J. Amer. Chem. Soc. 85, 3660 (1963);

if R₁NH is replaced by dimethylaminomethyleneimino: by analogy with the method described by J. F. Fitt, J. Org. Chem. 42(15), 2639 (1977);

if R₁NH is replaced by 4-nitro-benzylideneimino or 3,4-dimethoxy-benzylideneimino: according to the method described by R. A. Sirestone, Tetrahedron Lett., 375 (1972);

if R₂ is methoxymethyl: according to S. Seki et al., Tetrahedron Lett., 33, 2915 (1977);

if R₂ is tert.-butyl: according to R. J. Stedman, J. Med. Chem., 9, 444 (1966);

if R₂ is benzhydryl: according to Netherlands Patent Application 73/03263; and if R₂ is p-nitrobenzyl or p-methoxybenzyl: according to R. R. Chauvette et al., J. Org. Chem., 38(17), 2994 (1973).

The cephalosporin derivatives of the general formula (XII), in which R₁ and R₂ are defined as above in (b), can be prepared by acylation of a 7-aminocephalosporin of the general formula (XIV) according to the methods described in U.S. Pat. No. 4,065,620.

The acids of the general formula (XV), in which R₅ is hydrogen or alkyl, can be prepared according to the method described in Belgian Pat. No. 850,662.

The products of the general formula (XV), in which R₅ is a vinyl radical, can be prepared according to the method described in Belgian Pat. No. 869,079.

The products of the general formula (XV), in which R₅ is a cyanomethyl radical, can be prepared according to the method described in German Patent Application 2,812,625.

The acids of the general formula (XV), in which R₅ is a protective radical, can be prepared by protection of the oxime of such an acid, in which R₅ is hydrogen, by any known method which does not adversely affect the remainder of the molecule. In particular, protection is effected by the trityl or tetrahydropyranyl groups, which can be removed by acidolysis, for example with trifluoroacetic acid, (aqueous or non-aqueous) formic acid or p-toluenesulphonic acid. Protection can also be effected by the 2-methoxy-prop-2-yl group, which can be removed by application of the method described in Belgian Patent. 875,379.

The novel products of the general formula (I) are useful as intermediates for the preparation of 3-thiovinyl-cephalosporins of the general formula

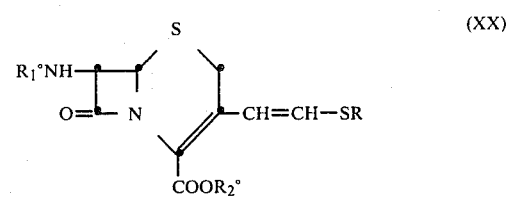

(XX)

in which (α) the symbol R is chosen from amongst the following meanings:

(1) alkyl, L-2-amino-2-carboxy-ethyl and phenyl, (2) pyrid-2-yl, pyrid-3-yl or pyrid-4-yl and their N-oxides, in the (3) pyrimidin-2-yl; pyridazin-3-yl substituted in the 6-position (by an alkyl, methoxy, amino or acylamino radical), its N-oxide, and tetrazolo[4,5-b]pyridazin-6-yl, (4) 5,6-dioxo-1,4,5,6-tetrahydro-1,2,4-triazin-3-yl substituted in the 4-position; 1,3,4-triazol-5-yl or 2-alkoxycarbonyl-1,3,4-triazol-5-yl, in each case substituted in the 1-position (a) by an alkyl radical containing 1 to 4 carbon atoms which is unsubstituted or substituted by an alkoxy, alkylthio, phenyl, formyl, carbamyl, alkylcarbamyl, dialkylcarbamyl, acyl, alkoxycarbonyl or thiazolidin-2-yl radical, (b) by an allyl, 2,3-dihydroxypropyl, 1,3-dihydroxyprop-2-yl, 2-formyl-2-hydroxy-ethyl radical, 3-formyloxy-2-hydroxy-propyl, bis-2,3-formyloxypropyl or bis-1,3-formyloxy-prop-2-yl.

(c) by an alkyl radical which contains 2 to 4 carbon atoms and is substituted by hydroxyl, carbamyloxy, acyloxy (of which the acyl part can be substituted by an amino, alkylamino or dialkylamino radical), alkylsulphinyl, alkylsulphonyl, amino, alkylamino, dialkylamino, sulphoamino, alkylsulphonylamino, sulphamylamino, acylamino (of which the acyl part is optionally substituted by hydroxyl, amino, alkylamino or dialkylamino), alkoxycarbonylamino, ureido, alkylureido or dialkylureido (d) by a radical corresponding to one of the general formulae:

(XXIa)

or

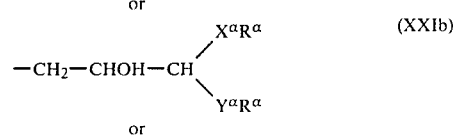

(XXIb)

or

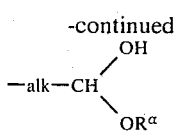
(XXIc)

in which alk is an alkylene radical containing 1 to 4 carbon atoms, $X^\alpha$ and $Y^\alpha$ are identical and represent oxygen or sulphur atoms and $R^\alpha$ represents an alkyl radical, or $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) by an alkyl radical containing 1 to 5 carbon atoms, substituted by an alkoxyimino or hydroxyimino radical, (5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl, (6) 1,3,4-triazol-5-yl, 1,2,3-triazol-5-yl or 1-alkyl-1,2,4-triazol-5-yl, which is unsubstituted or substituted in the 3-position by alkoxycarbonyl, (7) a. 1,3,4-thiadiazol-5-yl which is unsubstituted or substituted by an alkyl, trifluoromethyl, alkoxy, alkylthio, hydroxyalkylthio, of which the alkyl part contains 2 to 4 carbon atoms, alkylsulphonyl, hydroxyl, hydroxyalkyl, carboxyl, carboxyalkyl, amino, alkylamino, dialkylamino, aminoalkyl, alkylaminoalkyl, dialkylaminoalkyl, acylamino or acylamioalkyl radical, or b. 1,2,4-thiadiazol-5-yl substituted by an alkyl or alkoxy radical, (8) a. 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or b. oxazol-2-yl or 4-alkyl-oxazol-2-yl, or (9) tetrazol-5-yl which is unsubstituted or substituted in the 1-position by a. an alkyl radical containing 1 to 4 carbon atoms, which is unsubstituted or substituted by alkoxy, sulpho, carboxyl, formyl or sulphamyl, b. an alkyl radical which contains 2 to 4 carbon atoms and is substituted by hydroxyl, amino, alkylamino, dialkylamino, acylamino, carboxyalkylamino, sulphamylamino, sulphoamino, ureido, alkylureido or dialkylureido, c. an alkyl radical which contains 1 to 5 carbon atoms and is substituted by hydroxyimino or alkoxyimino, d. a phenyl, 2,3-dihydroxypropyl, 1,3-dihydroxyprop-2-yl, 2-formyl-2-hydroxy-ethyl radical, 3-formyloxy-2-hydroxy-propyl, bis-2,3-formyloxy-propyl or bis-1,3-formyloxy-prop-2-yl or e. a radical of the general formula (XXIa), in which $R^\beta$ is a hydrogen atom or a radical of the general formula (XXIb), the symbol $R°_1$ represents a radical of the general formula (II), in which $R_5$ is hydrogen, alkyl, vinyl or cyanomethyl and $R_6$ represents a hydrogen atom, and the symbol $R°_2$ represents a hydrogen atom or a radical of the general formula (V) or ($\beta$) the symbol R represents an alkyl or phenyl radical, the symbol $R°_1$ is defined like $R_1$ above in (b), or represents an azidoacetyl or cyanoacetyl radical or a radical of the general formula (VI), in which Ar is substituted phenyl [the substituents being trifuloromethyl, cyano or nitro radicals, of which at least one is located in the meta: or para-position] or a radical of the general formula (VIII) [in which Ar is defined as above and B is amino, azido, cyano or carbamyl] or a 2-(3-sydnone)-alkanoyl radical (of which the alkanoyl part contains 1 to 3 carbon atoms) or a radical of the general formula

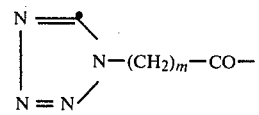
(XXII)

in which m is 0 to 2, and
the symbol $R°_2$ is defined like $R_1$ above in (b) or represents a hydrogen atom.

It is to be understood that in the products of the general formula (XX), the substituent in the 3-position of the bicyclooctene exhibits the E or Z stereoisomeric configuration and, if $R°_1$ is a radical of the general formula (II), this radical can be in the syn or anti forms. The products of the general formula (XX) also exist in the form of mixtures of these isomeric forms.

The products of the general formula (XX) can be obtained from the products of the general formula (I) by employing the following procedures:

The products of the general formula

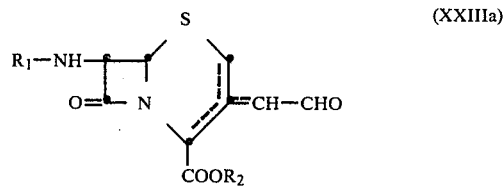
(XXIIIa)

[in which $R_1$ and $R_2$ are defined as above and which are in the 3-(2-oxoethyl)-bicyclooct-2-ene or 3-oxoethylidenebicyclooctane form] are prepared by hydrolysis, in an acid medium, of the enamine of the general formula (I) or of a mixture of its isomers.

Preferably, an enamine of the general formula (I) in which $R_3$ and $R_4$ represent a methyl radical is hydrolysed.

The procedure is generally carried out in an organic acid (for example formic acid or acetic acid) or an inorganic acid (for example hydrochloric acid or sulphuric acid) in the presence or absence of a solvent, in an aqueous or organic medium, at a temperature of between $-20°$ C. and the reflux temperature of the reaction mixture, after which, if appropriate, the mixture is treated with an inorganic base (an alkali metal bicarbonate) or an organic base (a tertiary amine or pyridine).

If the process is carried out in an organic medium, the hydrolysis is effected by adding water to the reaction mixture.

If the process is carried out in the presence of a solvent, it is not necessary for the solvent to be miscible with the aqueous acid phase. Where it is not miscible, contact is effected by vigorous stirring.

Amongst the solvents which can be used there may be mentioned the chlorinated solvents, ethyl acetate, tetrahydrofurane, acetonitrile, dimethylforamide and the alcohols.

To carry out this reaction is is not absolutely necessary to have purified the intermediate of the general formula (I).

The products of the general formula

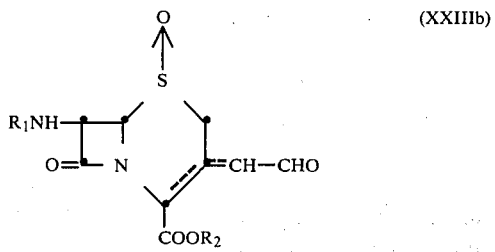

(XXIIIb)

in which $R_1$ and $R_2$ are defined as above and which are in the 3-(2-oxoethyl)-bicyclooct-2-ene or 3-oxoethylidenebicyclooctane form can be obtained by oxidation of the products of the general formula (XXIIIa) by application of the method described in German Patent Application 2,637,176.

The products of the general formula

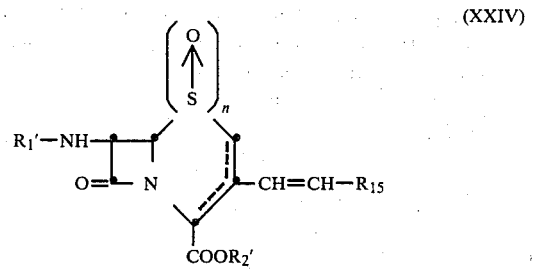

(XXIV)

[in which $R_1'$ is defined like $R_1$ above and $R'_2$ has the definition corresponding to $R_2$ or represents hydrogen, or $R_1'$ is a radical of the general formula (II) in which $R_6$ is hydrogen and $R_2'$ is defined like $R_2$ in a ) or represents hydrogen, it being understood that if n=0 the product is in the bicylooct-2-ene or bicyclooct-3-ene form and if n=1 the product is in the bicyclooct-2-ene form, the substituent on the carbon atom in the 3-position of the bicyclooctene exhibits the E or Z steroisomeric configuration and the symbol $R_{15}$ represents a radical of the general formula $$R'_{15}\text{-}SO_2O\text{-} \qquad (XXV)$$

or $$R_{15}''\text{-}COO\text{-} \qquad (XXVI)$$

in which $R_{15}'$ represents an alkyl, trifluoromethyl or trichloromethyl radical, or a phenyl radical which is unsubstituted or substituted by a halogen atom or by an alkyl or nitro radical and $R''_{15}$ is defined like $R_{15}$ or represents an acylmethyl, 2-acylethyl, 2-acylpropyl, alkoxycarbonylmethyl, 2-alkoxycarbonylethyl or 2-alkoxycarbonylpropyl radical] can be prepared by the action of an activated form of an acid $R_{15}'$ $SO_3H$ or $R_{15}'$ COOH, of the type

| | |
|---|---|
| $(R_{15}'\ SO_2)_2O$ | (XXVII) |
| ti $R_{15}'\ SO_2$ Hal | (XXVIII) |
| $(R_{15}'\ CO)_2O$ | (XXIX) |
| $R''_{15}\ CO\ Hal$ | (XXX) |

[in which formulae $R_{15}'$ and $R_{15}'$ are defined as above and Hal represents a halogen atom] on a product of the general formula (XXIIIa) or (XXIIIb) or on a mixture of these isomers, followed, where appropriate, by reduction of the sulphoxide obtained and, where necessary, by the removal of the protective groups of the amine group of the radical of the general formula (II) and/or, if appropriate, of the protective groups of the acid group, if it is desired to obtain a product of the general formula (XXIV) in which the amine and/or acid groups are free.

It is to be understood that if $R_1$ is a radical of the general formula (II), in which $R_5$ is a hydrogen atom, it is necessary that the oxime should be protected. The protection, and the removal of the protective group, are carried out in accordance with the methods described above.

In general, the process is carried out in the presence of a tertiary base of the type

(XXXI)

where $X_1$, $Y_1$ and $Z_1$ represent alkyl or phenyl radicals or optionally 2 of them form a ring with the nitrogen atom to which they are bonded (for example in the presence of triethylamine or of N,N-dimethylaniline), in a chlorinated organic solvent (for example methylene chloride), in an ester (for example ethyl acetate), in an ether (for example dioxane or tetrahydrofurane), in an amide (for example dimethylacetamide or dimethylformamide), in acetonitrile or N-methylpyrrolidone, or directly in a basic solvent such as pyridine, or in an aqueous organic medium in the presence of an alkaline condensation agent (for example an alkali metal bicarbonate, sodium hydroxide or potassium hydroxide) at a temperature of between $-78°$ C. and the reflux temperature of the reaction mixture.

Where appropriate, the reaction is carried out under nitrogen.

For carrying out this reaction it is not absolutely necessary to have purified the intermediate of the general formulae (XXIIIa) and (XXIIIb).

The reduction of the S-oxide can be carried out under the conditions described in German Patent Application 2,637,176.

Where necessary, the removal of the protective radicals from the amine group of the radical of the general formula (II), and from the acid group, can be effected simulaneously or successively.

By way of example:

1. The removal of the protective groups from amines is effected as follows:

in the case of a tert.-butoxycarbonyl, trityl, p-methoxybenzyloxycarbonyl or formyl radical: by treatment in an acid medium. Preferably, trifluoroacetic acid is used and the process is carried out at a temperature of between 0° and 20° C., or anhydrous or aqueous formic acid is used, or para-toluenesulphonic acid or methanesulphonic acid in acetone or acetonitrile at a temperature of between 20° C. and the reflux temperature of the reaction mixture. Under these conditions, the product of the general formula (I) can be obtained in the form of a trifluoroacetate, a solvate with formic acid, a dimethylsulphonate or a para-toluenesulphonate, from which the amine group can be liberated by any method which is in itself known for obtaining an amine from one of its salts without affecting the remainder of the molecule. In particular, this is effected by bringing into contact with an ion exchange resin or by the action of an organic base;

in the case of a 2,2,2-trichloro-ethoxycarbonyl or p-nitrobenzyloxycarbonyl radical: by reduction (especially by treatment with zinc in acetic acid);

in the case of a chloroacetyl or trichloroacetyl radical: by application of the method described in the French patent published uner No. 2,243,199;

in the case of a benzyl, dibenzyl or benzyloxycarbonyl radical: by catalytic hydrogenation;

in the case of a trifluoroacetyl radical: by treatment in a basic medium.

2. The removal of the protective groups from the carboxyl radical is effected as follows:

in the case of a tert.-butyl p-methoxybenzyl or benzhydryl group: by treatment in an acid medium, under the conditions described above for the removal of a protective trityl radical rom the amino group; in the case of the benzhydryl radical, the process can be carried out in the presence of anisole;

in the case of a methoxymethyl group: by treatment in a dilute acid medium;

in the case of a p-nitrobenzyl group: by reduction (especially by treatment with zinc in acetic acid, or by hydrogenolysis).

It is also possible to obtain the products of the general formula

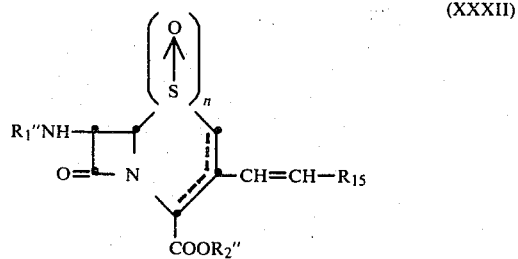

(XXXII)

in which $R_{15}$ and n are defined as above, if $n=0$, the product is in the bicyclooct-2-ene or bicyclooct-3-ene form and if $n=1$, the product is in the bicyclooct-2-ene form, the substituent on the carbon atom in the 3-position of the bicyclooctane exhibits the E or Z stereoisomeric configuration, and $R_1'$ represents (a₁) a radical of the general formula (II) [in which $R_6$ is defined as above in a) or represents a hydrogen atom, or (b₁) an azidoacetyl or cyanoacetyl radical, or a radical of the general formula (VI) in which Ar is substituted phenyl [the substituents being trifluoromethyl, cyano or nitro radicals, of which at least one is located in the meta- or in the para-position] or a radical of the general formula (VIII) [in which Ar is defined as above and B is amino, azido, cyano or carbamyl] or a 2(3-sydnone)-alkanoyl radical (of which the alkanoyl part contains 1 to 3 carbon atoms) or a radical of the general formula (XXII) and $R''_2$ assumes the corresponding definitions of $R_2$ or $R°_2$, by proceeding as follows:

A 7-amino-cephalosporin of the general formula

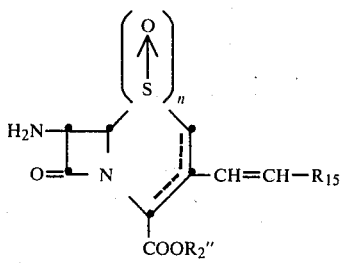

(XXXIII)

[in which $R_2''$, $R_{15}$ and n are defined as above and the position of the double bond as well as the configuration of the substituent in the 3-position are defined as for the product of the general formula (XXIV)] by elimination of the radical $R_1'$ or if appropriate by simultaneous elimination of the radicals $R_1'$ and $R_2'$ from a product of the general formula (XXIV) [in which $R_1'$ is defined like $R_1$ above in a), with the exception of representing a radical of the general formula (II), or represents a 5-amino-adipyl radical of which the amine group and acid group are protected, or radicals of the general formula (VI) or (VII) as defined for $R_1$ in b), and $R_2'$ has the corresponding definitions].

The removal of the protective radical $R_1'$ is effected by any known method for liberating an amine group without affecting the remainder of the molecule.

By way of example, the following methods may be mentioned:

if $R_1'$ represents trityl, benzhydryl, trichloroacetyl, chloroacetyl, tert.-butoxycarbonyl, trichloroethoxycarbonyl, benzyloxycarbonyl, p-methoxybenzyloxycarbonyl and p-nitrobenzyloxycarbonyl: according to the methods mentioned above for liberating the amino radical of the product of the general formula (XXIV);

if $R_1'$ represents formyl, 2-chloro-1,1-dimethylethoxycarbonyl, 2-cyano-1,1-dimethyl-ethoxycarbonyl, 3,5-dimethoxy-benzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, and if $R_1'NH$- is replaced by dimethylaminomethyleneimino, 3,4-dimethoxybenzylideneimino or 4-nitrobenzylideneimino: by hydrolysis in an acid medium;

if $R_1'$ represents 2,2,2-trichloroethyl or 2,2,2-trichloro-1,1-dimethyl-ethoxycarbonyl: by treatment with zinc in acetic acid;

if $R_1'$ represents acetyl, benzoyl, phenylacetyl, phenoxyacetyl or protected 5-amino-adipyl: according to the method described in Belgian Patent No. 758,800;

if $R_1'$ represents trimethylsilylethoxycarbonyl: according to the method described by H. GERLACH. Helv. Chim. Acta 60 (8), 3039 (1977); and if $R_1'$ represents p-nitrobenzyloxycarbonyl: by hydrogenolysis in the presence of palladium.

The products of the general formula (XXXII) are thus prepared by the action of an acid, represented by the general formula $R_1'OH$ (XXIV)

in which $R_1'$ is defined as above, or by the action of a reactive derivative of this acid, on the 7-amino-cephalosporin of the general formula (XXXIII) or, where appropriate, on a mixture of the isomers of this product, followed, if appropriate, by the reduction of the oxide obtained and then, if appropriate, by the removal of the protective radicals.

The process is carried out analogously to the method described above for obtaining a product of the general formula (XII) from products of the general formulae (XIV) and (XV), or in accordance with the methods mentioned in U.S. Pat. No. 4,065,620.

Where necessary, the reduction of the oxide as well as the removal of the protective radicals from the amine group and from the acid group can be effected under the conditions described for obtaining the product of the general formula (XXIV).

I. The 3-thiovinyl-cephalosporins of the general formula (XX) in which R does not contain a substituent of the general formula (XXIc), can be prepared by the action of a thiol of the general formula

R-SH                                                                                      (XXXV)

(or of one of its alkali metal salts or alkaline earth metal salts), in which R, which is defined as above in α) or in β) with the exception of containing a substitutent of the general formula (XXIc), is optionally protected, on a cephalosporin derivative (or on a mixture of the isomers) of the general formula

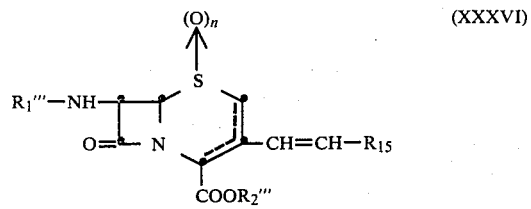

]in which n and $R_{15}$ are defined as above, $R_1'''$ is defined like $R_1'$ or assumes the meanings given above for $R_1$ in b) and $R_2'''$ has the corresponding definition of $R_2''$ or of $R_2$], followed by reduction of the sulphoxide obtained (if n=1) and then, if appropriate, by removal of the protective radicals.

If it is desired to obtain a product of the general formula (XX) in which R contains a formyl or acylalkyl radical, a thiol of the general formula (XXXV), in which R is protected in the form of an acetal (as defined by the general formulae (XXIa) and (XXIb) is employed).

It is to be understood that if the radical R of the product of the general formula (XXXV) is prone to interfere with the reaction, it is preferable to protect this group by any method which is in itself known and which does not adversely affect the remainder of the molecule.

IF an amino or alkylamino group is concerned, the protection is effected by a radical such as $R_6$ defined above.

If a carboxyl group is concerned, the protection is effected by methoxymethyl, tert.-butyl, benzhydryl, p-nitrobenzyl or p-methoxybenzyl radicals.

If hydroxyl groups are concerned, protection is effected by trityl, tetrahydropyranyl or 2-methoxy-prop-2-yl radicals or, where 2,3-dihydroxypropyl or 1,3-dihyroxyprop-2-yl radicals are concerned, protection is effected as a cyclic acetal in the form of 2,2-dimethyldioxolan-4-yl-methyl or 2,2-dimethyl-dioxan-5-yl radicals.

Furthermore it is to be understood that if the radical R of the product of the general formula (XXXV) contains a a hydroxyl, sulpho, sulphinyl or sulphonyl radical, it is preferable to employ a product of the general formula (XXXVI) in which n=0.

It is also to be understood that if in the general formula (XXXVI) the radical $R_1'''$ represents a radical of the general formula (II), in which $R_5$ is a hydrogen atom, it is necessary to protect the oxime under the conditions described above.

The reaction of the products of the general formulae (XXXV) and (XXXVI) is in general carried out in the presence of a base such as a pyridine or a tertiary organic base of the general formula (XXXI). For example, diisopropylethylamine or diethylphenylamine are used.

If a salt of the thiol of the general formula (XXXV) is used, it is not necessary to work in the presence of an organic base such as defined above.

Advantageously, the reaction is carried out in an organic solvent such as dimethylformamide, tetrahydrofuran or acetonitrile or in a mixture of the above-mentioned solvents.

It is also possible to carry out the reaction in the presence of an alkali metal bicarbonate in a solvent as defined above, optionally in the presence of water. The reaction is carried out at a temperature of between −20° C. and the reflux temperature of the reaction mixture, and the chosen temperature can be varied in accordance with the thiol employed. Equally, the reaction time can vary from 5 minutes to 48 hours, depending on the thiol employed.

Where appropriate, the reaction is carried out under nitrogen.

Preferably, if it is desired to use a bicyclooct-3-ene of the general formula (XXXVI), in which $R_1'''$ represents a radical of the general formula (II), a product in which $R_2'''$ is other than hydrogen is employed.

The reduction of the oxide and the removal of the amine, acid or oxime protective groups are effected in accordance with the methods described above.

The removal of the protective radicals from hydroxyl groups is effected under the conditions described above for the oxime protective radicals, namely:

by acidolysis, for example with trifluoroacetic acid, aqueous or non-aqueous formic acid, or paratoluenesulphonic acid, where the trityl, tetrahydropyranyl, 2,2-dimethyl-dioxolan-4-yl-methyl or 2,2-dimethyl-dioxan-5-yl radical is concerned. (When aqueous or non-aqueous formic acid is used, the liberation of the hydroxyl groups, which are protected in the form of a cyclic acetal, may field, at least in part, the corresponding mono- or di-formic esters, and these optionally may be separated by chromatography) or according to the method described in Belgian Patent No. 875,379, where the 2 -methoxy-prop-2-yl radical is concerned.

The removal of the groups of the general formula (XXIa) or (XXIb) (if it is desired to obtain a product of the general formula (XX) in which R contains a formyl or acylalkyl radical) is effected as follows:

in the presence of a sulphonic acid (for example methanesulphonic acid or p-toluenesulphonic acid) in an organic solvent (for example acetonitrile or acetone), optionally in the presence of water and optionally in the presence of an acetalisable reactant such as acetone, glyoxylic acid, benzaldehyde or pyruvic acid, at a temperature of between 20° C. and the reflux temperature of the reaction mixture, or, if the radical R is a 5,6-dioxo-1,4,5,6-tetrahydro--1,2,4-triazin-3-yl radical, by the action of aqueous formic acid (preferably containing less than 10% of water), in the presence or absence of silica, or by trans-acetalisation in the presence of an acetalisable reactant as defined above.

The thiols of the general formula (XXXV) (which can be employed in their tautomeric form) can be prepared by application of one of the following methods, depending on the meaning of the radical R:

if R is a pyrid-3-yl radical: according to the method described by H. M. WUEST and E. H. SAKAL, J. Am. Chem. Soc., 73, 1210 (1951);

if R is a pyrid-3-yl-1-oxide radical: according to the method described by B. BLANK et al., J. Med. Chem. 17, 1065 (1974);

if R is a pyrid-4-yl-1-oxide radical: according to the method described by R. A. Y. JONES et al., J. Chem. Soc. 2937 (1960);

if R is a pyridazin-3-yl radical substituted by alkyl or methoxy, or a N-oxide derivative of such a radical: according to the method described in Belgian Patent 787,635;

if R is a pyridazin-3-yl radical substituted by amino, or a N-oxide derivative of such a radical: according to the method described in Belgian Patent No. 579,291;

if R is a pyridazin-3-yl radical substituted by acylamino, or a N-oxide derivative of such a radical: by application of the methods described by M. KUMAGAI and M. BANDO, Nippon Kagaku Zasshi, 84, 995 (1963) and by T. HORIE and T. UEDA, Chem. Pharm. Bull., 11, 114 (1963);

if R is a tetrazolo[4,5-b]pyridazin-6-yl radical: according to the method described in Belgian Patent No. 804,251; and if R is a 5,6-dioxo-1,4,5,6-tetrahydro-1,2,4-triazin-3-yl radical substituted in the 4-position or a 2-alkoxycarbonyl-1,3,4-triazol-5-yl radical substituted in the 1-position by a radical $R^\gamma$ chosen from amongst:

(a) an allyl radical, or an alkyl radical (which has 1 to 4 carbon atoms and is itself optionally substituted by an alkoxy, alkylthio, phenyl, carbamyl, alkylcarbamyl, dialkylcarbamyl, acyl, alkoxycarbonyl or thiazolidin-2-yl radical), (b) a 2,3-dihydroxy-propyl radical or 1,3-dihydroxy-prop-2-yl radical (optionally protected in the form of the cyclic acetal).

(c) an alkyl radical [which has 2 to 4 carbon atoms and is itself substituted by hydroxyl, carbamyloxy, dialkylamino, alkylsulphinyl, alkylsulphonyl, alkylsulphonylamino, sulphamylamino, acylamino (which is optionally substituted), alkoxycarbonylamino, ureido, alkylureido or dialkylureido], (d) a radical of the general formula (XXIa) or (XXIb), or (e) a hydroxyiminoalkyl or alkoxyiminoalkyl radical: by reacting an alkyl oxalate with a thiosemicarbazide of the general formula:

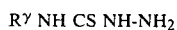 NH CS NH-NH   (XXXVa)

(in which $R^\gamma$ is defined as above), in the presence of an alkali metal alcoholate, for example sodium ethylate or sodium methylate, or potassium tert.-butylate, by applying the method described by M. PESSON and M. ANTOINE, Bull. Soc. Chim. France (1970), 1590.

It is not absolutely necessary to purify the product obtained (nor to liberate the protected radicals) in order to employ the product for the preparation of the products of the general formula (XX)

The thiosemicarbazide of the general formula (XXXVa) can be prepared in accordance with one of the methods described by K. A. JENSEN et al., Acta Chem. Scand., 22, 1 (1968), or by application of the method described by Y. KAZAROV and J. Y. POTOVSKII, Doklady Acad. Nauk. SSSR 134, 824 (1966), it being understood that if $R^\gamma$ contains an amino radical, the latter is protected.

The protection of the amino radical and the removal of the protective radical are carried out in accordance with the usual methods which do not adversely affect the remainder of the molecule. In particular, the tert.-butoxycarbonyl group, which can be removed by acid hydrolysis, is used.

If R is a 1,3,4-triazol-5-yl radical substituted in the 1-position by an alkyl, allyl or alkoxyalkyl radical, by an alkyl radical (having 1 to 4 carbon atoms) which is itself substituted as defined above in a), with the exception of a thiazolidin-2-yl radical, by a radical as defined above in c) or by an alkoxyiminoalkyl radical: by application of one of the methods described by M. PESSON and M. ANTOINE, Bull. Soc. Chim. France 1590 (1970).

If R is a 1,3,4-triazol-5-yl radical substituted in the 1-position by thiazolidin-2-yl alkyl or hydroxy iminoalkyl: by the respective action of cysteamine or hydroxylamine on a 1-dialkoxyalkyl-5-mercapto-1,3,4-triazole, which can be obtained by application of the method described by M. KANAOKA, J. Pharm. Soc. Japan, 75, 1149 (1955), from a 4-dialkoxyalkyl-thiosemicarbazide.

If R is a 1,3,4-triazol-5-yl radical substituted in the 1-position by 2,3-dihydroxypropyl or 1,3-dihydroxy-prop-2-yl (optionally protected in the form of a cyclic acetal), or R represents a radical of the general formula (II) or (III): by application of the method described by M. KANAOKA, J. Pharm. Soc. Japan, 75, 1149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by optionally substituted acyloxyalkyl: by acylation of, respectively, 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, of which the mercapto radical has beforehand been protected (for example according to the method of C. G. KRUSE et al., Tet. Lett. 1725 (1976)), by any method known for acylating an alcohol without affecting the remainder of the molecule, followed by liberation of the mercapto group in an acid medium.

If R is a 5,6-dioxo-1,4,5,6-tetrahydro-1,2,4-triazin-3-yl radical substituted in the 4-position or 2-alkoxycarbonyl-1,3,4-triazol-5-yl or 1,3,4-triazol-5-yl radical substituted in the 1-position by aminoalkyl or alkylaminoalkyl: by liberating the amine group of the corresponding product, protected, for example, by a tert.-butoxycarbonyl group.

If R is a 5,6-dioxo-1,4,5,6-tetrahydro-1,2,4-triazin-3-yl radical substituted in the 4-position or 2-alkoxycarbonyl-1,3,4-triazol-5-yl or 1,3,4-triazol-5-yl radical substituted in the 1-position by sulphoaminoalkyl: from the corresponding product substituted by a tert.-butoxycarbonylaminoalkyl radical, by analogy with the method described in Belgian Patent No. 847,237.

If R is a 1,4-dialkyl-1,4,5,6-tetrahydro-1,2,4-triazin-3-yl radical or 1-alkyl-5,6-dioxo-1,4,5,6-tetrahydro-1,2,4-triazin-3-yl radical: according to the method described in Belgian Patent No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: according to the method described by M. PESSON and M. ANTOINE, C. R. Acad. Sci., Ser C, 267, 25, 1726 (1968).

If R is a 1,2,3-triazol-5-yl radical: according to the method described in French Patent No. 2,215,942.

If R is a 1,3,4-triazol-5-yl radical: according to the method described by M. KANAOKA, J. Pharm. Soc. Jap. 75, 1149 (1955).

If R is a 1,3,4-thiadiazol-5-yl radical optionally substituted by alkyl, alkoxy, alkylthio, alkyl sulphonyl, amino, alkylamino, dialkylamino or acylamino: according to the methods described in Belgian Patent 830,821.

If R is a 1,3,4-thiadiazol-5-yl radical substituted by hydroxyalkyl, aminoalkyl, alkylaminoalkyl or dialkylaminoalkyl: according to the method described in German Patent Application 2,446,254.

If R is a 1,3,4-thiadiazol-5-yl radical substituted by a carboxyalkyl radical: by application of the method described in German Patent Application 1,953,861.

If R is a 1,3,4-thiadiazol-5-yl radical substituted by a trifluoromethyl radical: according to the method described in German Patent Application 2,162,575.

If R is a 1,3,4-thiadiazol-5-yl radical substituted by a carboxyl radical: according to the method des described in Japanese Patent Application 77/48,666.

If R is a 1,3,4-thiadiazol-5-yl radical substituted by an acylaminoalkyl radical: according to the method described in Japanese Patent Application 76/80,857.

If R is a 1,3,4-thiadiazol-5-yl radical substituted by a hydroxyalkylthio radical: by application of the method described by G. NANNINI, Arz. Forsch. 27 (2), 343 (1977).

If R is a 1,2,4-thiadiazol-5-yl radical substituted by alkyl or alkoxy: according to the method described in German Patent Application 2,806,226 or according to Chem. Ber. 90, 184 (1957).

If R is a 1,3,4-oxadiazol-5-yl radical as described in the definition of the general formula (XX) in 8a.: by application of the method described by E. HOGGARTH, J. Chem. Soc. 4811 (1952).

If R is an oxazol-2-yl or 4-alkyl-oxazol-2-yl radical: by application of the method described previously by C. BRADSHER, J. Org. Chem. 32, 2079 (1967).

If R is a tetrazol-5-yl radical optionally substituted in the 1-position by alkyl, hydroxyalkyl or phenyl: according to the methods described in Belgian Patent 830,821.

If R is a tetrazol-5-yl radical substituted in the 1-position by alkoxyalkyl: by addition reaction of sodium azide with an isothiocyanatoalkoxyalkyl derivative, in an organic solvent such as ethanol, at the reflux temperature of the reaction mixture.

The isothiocyanatoalkoxyalkyl derivative can be obtained by application of the method described by E. Schmidt et al., Chem. Ber. 73, 286 (1940).

If R is a tetrazol-5-yl radical substituted in the 1-position by a carboxyalkyl radical: according to the method described in Belgian Patent No. 858,112.

If R is a tetrazol-5-yl radical substituted in the 1-position by a sulphoalkyl radical: according to the method described in Belgian Patent No. 856,498 or described by D. A. BERGES et al., J. Het. Chem. 15, 981 (1978).

If R is a tetrazol-5-yl radical substituted in the 1-position by an aminoalkyl, alkylaminoalkyl or dialkylaminoalkyl radical: by application of the method described in German Patent Application 2,738,711.

If R is a tetrazol-5-yl radical substituted in the 1-position by a sulphamylalkyl, sulphamylaminoalkyl or sulphoaminoalkyl radical: according to the method described in Belgian Patent No. 856,636.

If R is a tetrazol-5-yl radical substituted by an acylaminoalkyl radical or a 1,3,4-thiadiazol-5-yl radical substituted by hydroxyl: according to the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (of which the mercapto radical has beforehand been protected), by treatment with an alkali metal isothiocyanate, with an alkyl isocyanate or with a dialkylcarbamyl halide, followed by liberation of the mercapto group under the conditions described in Belgian Patent No. 847,237.

If R is a tetrazol-5-yl radical substituted in the 1-position by a carboxyalkylaminoalkyl radical: according to the method described in German Patent Application 2,715,597.

If R is a tetrazol-5-yl radical substituted in the 1-position by a 2,3-dihydroxypropyl radical: according to the method described in U.S. Pat. No. 4,064,242.

If R is a tetrazol-5-yl radical substituted in the 1-position by a 1,3-dihydroxy-prop-2-yl radical: by addition reaction of sodium azide with a 2,2-dimethyl-1,3-dioxolan-5-yl isothiocyanate (followed, where appropriate, by liberation of the hydroxyl groups).

If R is a tetrazol-5-yl radical substituted in the 1-position by a radical of the general formula (XXIa) as defined in the definition of the general formula (XX) in 9e. or of the general formula (XXIb), or a radical defined above in 9c. for the general formula (XX): by the action of sodium azide on the corresponding isothiocyanate, by analogy with the method described by R. E. ORTH, J. Pharm. Sci. 52 (9), 909 (1963), it being understood that where R contains a hydroxyl or hydroxyiminoalkyl substituent, the alcohol or oxime function are protected, if appropriate, for example by a tetrahydropyranyl group.

II. The 3-thiovinyl-cephalosporins of the general formula (XX), in which R does not contain a substituent of the general formula (XXIc), can also be obtained as follows:

A product, or a mixture of isomers of the product, of the general formula (XXIV) [as defined for the preparation of the 7-amino-cephalosporin of the formula (XXXIII)] is treated with a thiol of the general formula (XXXV) (or with one of its alkali metal salts or alkaline earth metal salts), after which, if appropriate, the sulphoxide obtained (if n=1) is reduced and, if appropriate, the protective radicals of R are removed, to give a product of the general formula

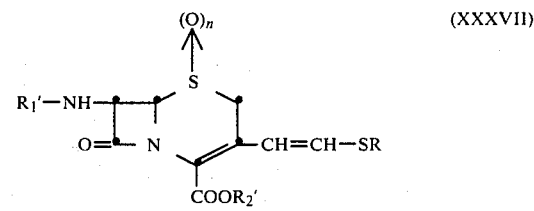

(XXXVII)

in which n is defined as above, $R'_1$ and $R'_2$ are defined as above for the preparation of the product of the general formula (XXXIII), and R assumes the corresponding definitions.

The reaction is carried out under the conditions described above for obtaining a product of the general formula (XX) from a product of the general formula (XXXVI) and from a thiol of the general formula (XXXV).

It is to be understood that the radical R of the thiol is (where necessary) protected as described above and that the removal of the protective radicals can be effected under the conditions described above. However, it is preferable to retain the protective groups until the product of the general formula (XX) is obtained.

A product of the general formula

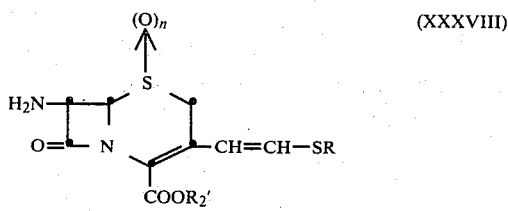
(XXXVIII)

in which R, R'$_2$ and n are defined as above, is prepared by elimination of the radical R'$_1$ from a product of the general formula (XXXVII) as defind above or, if appropriate, by simultaneous elimination of the protective radicals R'$_1$ and R'$_2$ from this product.

The process is carried out under the conditions described above for the preparation of a product of the general formula (XXXIII).

The 3-thiovinyl-cephalosporin of the general formula (XX), in which R, R°$_1$ and R°$_2$ are defined as above, is then prepared by acylation of a 7-amino-cephalosporin of the general formula (XXXVIII) by means of an acid represented by the general formula

R°$_1$—OH  (XXXIX)

[in which R°$_1$, which is defined as above, is optionally protected if it contains radicals which can interfere with the reaction], or by means of a reactive derivative of this acid, under the conditions described above for the preparation of the products of the general formula (XII), after which the oxide obtained (if n=1) is reduced and the protective radicals are removed.

It is to be understood that:
the amino or alkylamino radicals which are present in certain radicals R must be protected and
the carboxyl, hydroxyl, formyl or acylalkyl radicals contained in the radicals R can be protected.

The protection, and the removal of the protective radicals, are carried out under the conditions described above.

It is also to be understood that if R contains a hydroxyl, sulpho, sulphinyl or sulphonyl substituent, it is preferred to employ a product of the general formula (XXXVIII) in which n=0.

III. The 3-thiovinyl-cephalosporins of the general formula (XX), in which R does not contain a substituent of the general formula (XXIc), can also be obtained by the action of a thiolo-ester of the general formula

R'''$_1$—SR  (XL)

in which R'''$_1$ is defined as earlier and R is defined as above [it being understood that, if it contains an amino or alkylamino substituent, this substituent is protected, if it contains a hydroxyl or carboxyl substituent, this substituent is free or protected and if it contains a formyl or acylalkyl substituent, this substituent is protected in the form of an acetal of the general formula (XXIa) or XXIb)] on a 7-amino-cephalosporin of the general formula (XXXIII), followed by the reduction of the sulphoxide obtained if n=1, and, where necessary, by the removal of the protective radicals.

It is also to be understood that the radicals R'''$_1$ which contain a group which is prone to interfere with the reaction have been protected beforehand. The same is true of the oxime if R'''$_1$ represents a radical of the general formula (II), in which R$_5$ is a hydrogen atom.

Equally, as for the processes described above, if R contains a hydroxyl, sulpho, sulphinyl or sulphonyl substituent, it is preferred to employ a product of the general formula (XXXIII) in which n=0.

The protection, and the removal of the protective radicals, are carried out under the conditions described above.

The reaction of the thiolo-ester with the 7-aminocephalosporin of the general formula (XXXIII) is in general carried out in the presence of an acid acceptor such as an organic base, more especially in the presence of a pyridine or of a tertiary organic base of the general formula (XXXI), especially triethylamine, N,N-diisopropyl-N-ethylamine, diethylphenylamine or N-methylmorpholine.

The reaction is advantageously carried out in an organic solvent such as an amide (for example dimethylformamide or dimethylacetamide), an ether (for example tetrahydrofurane or dioxane), a chlorinated solvent (for example chloroform or methylene chloride), a ketone (for example acetone) or a nitrile (for example acetonitrile) or in a mixture of these solvents. It is also possible to carry out the reaction in the presence of an alkali metal bicarbonate in one of the abovementioned solvents, optionally in the presence of water.

The reaction is carried out at a temperature of between −20° C. and the reflux temperature of the reaction mixture. Optionally, the reaction is carried out under nitrogen.

The reduction of the S-oxide is carried out under the conditions described above.

The thiolo-esters of the general formula (XL) can be prepared by the action of an acid, or of a reactive derivative of an acid, of the general formula R'''$_1$—OH  (XXXIXa)

on a thiol of the general formula (XXXV) (or on an alkali metal salt or alkaline earth metal salt of this thiol), followed, where appropriate, by removal of the protective radicals.

In the general formula (XXXIXa), R'''$_1$ represents a radical of the general formula (II) in which R$_5$ is other than hydrogen, or is defined like R$_1$ in b.

It is to be understood that the amino or alkylamino substituents of R'''$_1$ or R are protected and that the hydroxyl or carboxyl substituents are free or protected.

It is also to be understood that the radical R is protected in the form of an acetal if it desired to prepare a product of the general formula (XX) in which R contains a formyl radical.

The reaction is carried out under the conditions described above for the preparation of a product of the general formula (XII) from a product of the general formula (XIV) and a reactive ester of the general formula (XVI).

If it is desired to obtain a product in which R contains a carboxyl or sulpho radical, it is preferable to treat the corresponding thiol with a reactive derivative of the acid R'''₁OH.

If it is desired to obtain a thiolo-ester in which R'''₁ is a radical of the general formula (II), as defined above for R⁰₁, it is possible to remove the tert.-butoxycarbonyl radical, protecting the aminothiazole, by treatment in an anhydrous acid medium. In this case, the product is obtained either in the form of a salt or in the form of a solvate with the acid employed. Preferably, trifluoroacetic acid is employed and the reaction is carried out at between 0° and 20° C. The trityl group protecting the oxime can be removed by acidolysis, for example with anhydrous trifluoroacetic acid.

Where necessary, the removal of the trityl group protecting a hydroxyl substituent of the thiolo-ester is effected under the conditions described above for the liberation of the oxime.

It is advantageous only to remove the protective groups after the reaction of the thiolo-ester with the 7-amino-cephalosporin.

IV. The 3-thiovinyl-cephalosporins of the general formula (XX), in which R⁰₁ represents a radical of the general formula (II), as defined above except for R₅ representing a vinyl radical, and R does not contain a substituent of the general formula (XXIc), can be obtained by proceeding as follows:

(1) (a) An acid halide of the general formula

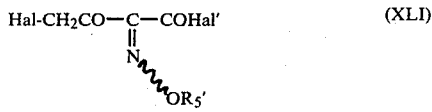

(XLI)

in which Hal and Hal' are chlorine or bromine atoms and R'₅ is an alkyl or cyanomethyl radical, is reacted with a 7-amino-cephalosporin of the general formula (XXXVIII), after which, where appropriate, the sulphoxide obtained (if n=1) is reduced, and the protective radicals are removed.

The reaction is in general carried out in an aqueous organic medium, for example water/ether (tetrahydrofurane or dioxane), water/ketone (acetone) or water/chlorinated solvent (chloroform or methylene chloride), in the presence of an alkaline condensation agent such as an alkali metal bicarbonate (for example sodium bicarbonate) at a temperature of between −40° and +40° C.

It is also possible to proceed by analogy with the method described in French Patent Application 2,399,418.

It is to be understood that if the radical R of the 7-amino-cephalosporin contains an amino or alkylamino radical, the latter is protected, and if the radical R contains a hydroxyl, carboxyl, formyl or acylalkyl radical, the latter is free or protected.

The protection, and the removal of the protective radicals, are effected under the conditions described above.

(b) Alternatively, a product of the general formula

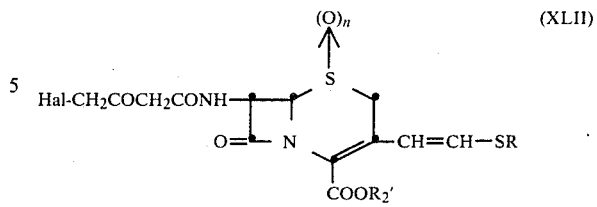

in which R, R'₂, Hal and n are defined as above, is treated with a nitrosylating agent by analogy with the method described in French Patent Application 2,399,418, after which, if appropriate, the sulphoxide is reduced and the protective radicals are removed.

It is to be understood that if the radical R of the product of the general formula (XLII) contains an amino, alkylamino or formyl radical, the latter is protected, and if the radical R contains a hydroxyl, carboxyl or acylalkyl substituent, the latter is free or protected.

(2) A thiourea of the general formula $$R'_6NH-CS-NH_2 \qquad (XLIII)$$

(in which R'₆ is defined like R₆ except for representing chloroacetyl or trichloroacetyl, or represents a hydrogen atom) is then reacted with the product of the general formula

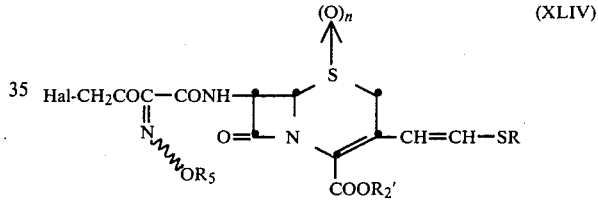

obtained above as described in (a) or (b), in which R₅, R, R'₂ and n are defined as above in IV and Hal represents a chlorine or bromine atom, followed, where appropriate, by the reduction of the sulphoxide and the removal of the protective radicals.

In general, the reaction is carried out in an aqueous, organic or aqueous-organic medium, for example in solvents or mixtures of solvents such as alcohols (methanol or ethanol), ketones (acetone), chlorinated solvents (chloroform or ethylene chloride), nitriles (acetonitrile), amides (dimethylformamide or dimethylacetamide), ethers (tetrahydrofurane or dioxane), esters (ethyl acetate) or acids (acetic acid or formic acid) in the presence or absence of a base such as sodium hydroxide, potassium hydroxide, the alkali metal carbonates and bicarbonates, the alkali metal salts of carboxylic acids (sodium formate or sodium acetate) or the tertiary amines (triethylamine, trimethylamine or pyridine), at a temperature of between −30° and 60° C.

If it is desired to obtain a product of the general formula (XX) in which R contains a formylalkyl or acylalkyl radical, this radical can be protected, as an acetal, in the form of a radical of the general formula (XXIa) or (XXIb), as defined above.

The reduction of the sulphoxide and the removal of the protective radicals is effected under the conditions described above.

The products of the general formula (XLI) can be obtained by halogenation of a product of the general formula

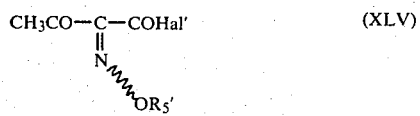 (XLV)

in which R′₅ and Hal′ are defined as above, by any method which is in itself known for the preparation of halogenated derivatives and which does not adversely affect the remainder of the molecule.

If it is desired to obtain a product of the general formula (XLI) in which Hal represents a bromine atom, the reaction is carried out with bromine in the presence of a catalyst, which is either an acid catalyst such as hydrobromic acid, hydrochloric acid or a sulphonic acid (methanesulphonic acid, anhydrous p-toluenesulphonic acid or benzenesulphonic acid) or in the presence of ultraviolet light.

If it is desired to obtain a product of the general formula (XLI) in which Hal is a chlorine atom, the reaction is carried out with chlorine in the presence of a catalyst as mentioned above, or with sulphuryl chloride.

The halogenation is carried out in an organic solvent, such as the chlorinated solvents (for example methylene chloride, chloroform, carbon tetrachloride, dichloroethane or trichloroethane) or the ethers (for example ethyl ether or dioxane), or in a mixture of these solvents, at a temperature of between −40° C. and the reflux temperature of the reaction mixture.

The products of the general formula (XLV) can be prepared from the corresponding esters in accordance with the method described in French Patent Application 2,414,508.

The esters themselves can be prepared by application of the method described by R. Bucourt et al., Tetrahedron, 34, 2233 (1978).

The products of the general formula (XLII) can be obtained from a 7-amino-cephalosporin of the general formula (XXXVIII) by the action of a product of the general formula Hal—CH₂—COCH₂—COHal (XLVI)

in which Hal is defined as above (which product may be formed in situ), by employing the conditions described above for condensing a product of the general formula (XLI) with a product of the general formula (XXXVIII), or by analogy with the method described in French Patent Application 2,399,418.

V. The 3-thiovinyl-cephalosporins of the general formula (XX) in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an alkyl radical containing 2 to 4 carbon atoms substituted by a carbamyloxy group or by an acyloxy group (of which the acyl part is optionally substituted by an amino, alkylamino or dialkylamino radical), and R°₁ and R°₂ have the corresponding definitions, which are functional derivatives of the product of the general formula (XX) in which R is a -Ⓡ-alk′-OH radical chosen from amongst 5,6-dioxo-4-hydroxyalkyl-1,4,5,6-tetrahydro-1,2,4-triazin-3-yl, 1-hydroxyalkyl-1,3,4-triazol-5-yl or 2-alkyloxycarbonyl-1-hydroxylalkyl-1,3,4-triazol-5-yl and R°₁ and R°₂ are defined as above, can be obtained from a product of the general formula

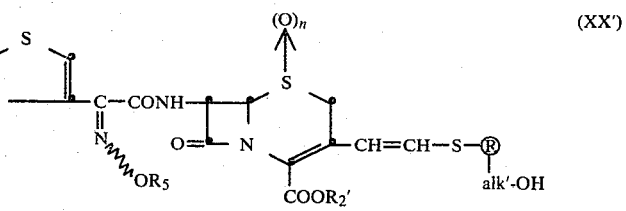 (XX′)

in which R₅, R₆, R′₂, Ⓡ-alk′-OH and n are defined as above, by any known method for obtaining an ester or a carbamate from an alcohol without affecting the remainder of the molecule, followed, where appropriate, by reduction of the sulphoxide obtained and removal of the protective radicals.

The esterification is carried out at a temperature of between −50° C. and the reflux temperature of the reaction mixture, especially by condensation of the anhydride of the acid (or of some other reactive derivative of the acid, for example the halide) in an inert organic solvent such as an ether (for example tetrahydrofurane), a chlorinated solvent (for example methylene chloride) or a mixture of these solvents, in the presence of a nitrogen-containing base such as pyridine, 4-dimethylamino-pyridine or a trialkylamine (triethylamine) or of an alkaline condensation agent (for example sodium bicarbonate) followed, where appropriate, by reduction of the S-oxide obtained and removal of the protective groups in accordance with the methods described above.

The carbamate is obtained by any known method which does not adversely affect the remainder of the molecule. In particular, the reaction of a chlorosulphonyl isocyanate or trichloroacetyl isocyanate in an inert organic solvent, for example tetrahydrofurane or acetonitrile, at a temperature of between −80° and 20° C., followed by removal of the protective groups, is employed. VI. The 3-thiovinyl-cephalosporins of the general formula (XX) in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an alkyl radical containing 2 to 4 carbon atoms substituted by sulphoamino, alkylsulphonylamino, sulphamylamino, acylamino (of which the acyl part is optionally substituted by hydroxyl, amino, alkyamino or dialkylamino), alkoxycarbonylamino, ureido, alkylureido or dialkylureido group, or represents a 1,3,4-thiadiazol-5-yl radical substituted by an acylamino or acylaminoalkyl radical, or represents a 1,3,4-oxadiazol-5-yl radical substituted by an acylaminoalkyl radical, or represents a tetrazol-5-yl radical substituted in the 1-position by an alkyl radical which contains 2 to 4 carbon atoms and is substituted by an acylamino, sulphamylamino, sulphoamino, ureido, alkylureido or dialkylureido group, and $R^o{}_1$ and $R^o{}_2$ have the corresponding definitions, which are all functional derivatives of the amine corresponding to them, can be obtained from a product of the general formula

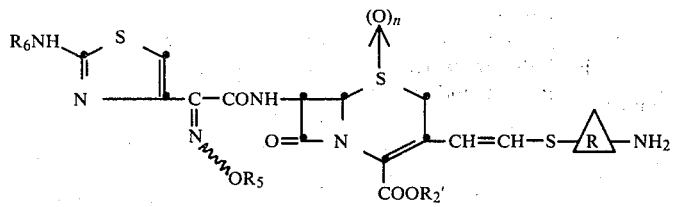

in which $R_5$, $R_6$, $R'_2$ nd n are defined as above, and —⟨R⟩—$NH_2$ represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by an aminoalkyl radical of which the alkyl part contains 2 to 4 carbon atoms, or a 1,3,4-thiadiazol-5-yl radical substituted by an amino or aminoalkyl radical, or a 1,3,4-oxadiazol-5-yl radical substituted by an aminoalkyl radical, or a tetrazol-5-yl radical substituted in the 1-position by an aminoalkyl radical of which the alkyl part contains 2 to 4 carbon atoms, by any method which is in itself known for forming an amide, sulphamide, carbamate or urea group without affecting the remainder of the molecule, followed, where appropriate, by reduction of the sulphoxide and removal of the protective groups.

It is to be understood that the products which contain a sulpho, sulphonyl or sulphamyl group are preferably prepared from a product of the general formula (XX)″ in which n=0.

Furthermore, if it is desired to prepare a product of which the radical R contains an amino or hydroxyl group, it is necessary to protect these radicals in the reactant used. Equally, if $R_5$ represents a hydrogen atom, it is necessary to protect the oxime.

If it is desired to prepare a product of the general formula (XX) in which the radical R contains an alkylsulphonylamino, sulphamylamino, acylamino (substituted or unsubstituted), alkoxycarbonylamino or dialkylureido substituent, the reaction is advantageously effected by treatment with, respectively, the corresponding chlorosulphonyl, acid chloride, chloroformate or dialkylcarbamyl chloride derivative, under the conditions described above for the reaction of the acid chloride of the general formula (XV) with the 7-aminocephalosporin of the general formula (XIV).

If it is desired to prepare a product of the general formula (XX) in which the radical R contains a sulphoamino, alkylsulphonylamino or (substituted or unsubstituted) acylamino substituent, the reaction can be effected by means of the anhydride of the corresponding acid, under the conditions described above for reacting the product of the general formula (XV) in the form of an anhydride.

If it is desired to obtain a product of the general formula (XX) in which R contains a (substituted or unsubstituted) acylamino radical, it is also possible to employ the corresponding acid, under the working conditions described above for the use of the acid of the general formula (XV).

If it is desired to obtain a product of the general formula (XX) in which R contains a ureido or alkylureido radical, the corresponding product of the general formula (XX)″ is treated, respectively, with an alkali metal isocyanate or an alkyl isocyanate, in an aqueous-organic medium or organic medium (for example in tetrahydrofurane) at a temperature of between −20° and 60° C.

The reduction, and the removal of the protective radicals, are carried out under the conditions described above. VII. The 3-thiovinyl-cephalosporins of the general formula (XX), in which R represents a 5,6-dioxo-1,4,5,6-tetrahydro-1,2,4-triazin-3-yl radical substituted in the 4-position, or a 1,3,4-triazol-5-yl or 2-alkoxycarbonyl-1,3,4-triazol-5-yl radical substituted in the 1-position, by a thiazolidin-2-yl-alkyl radical, by a radical of the general formula (XXIc) or by a hydroxyiminoalkyl or alkoxyiminoalkyl radical of which the iminoalkyl part contains 1 to 5 carbon atoms, or represents a tetrazol-5-yl radical substituted in the 1-position by a hydroxyiminoalkyl or alkoxyiminoalkyl radical of which the iminoalkyl part contains 1 to 5 carbon atoms and $R^o{}_1$ and $R^o{}_2$ have the corresponding definitions, which are addition reaction derivatives of the product of the general formula (XX) in which R is one of the heterocyclic radicals mentioned above, substituted by a formylalkyl radical (or by its hydrate form), can be obtained from a product of the general formula

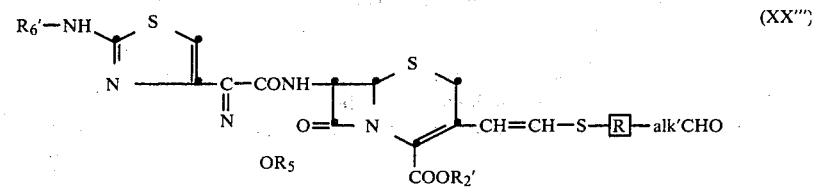

in which $R_5$ and $R'_2$ are defined as above, $R'_6$ is defined like $R_6$ or represents a hydrogen atom, and -⟨R⟩-alk′CHO represents a 5,6-dioxo-4-formylalkyl-1,4,5,6-tetrahydro-1,2,4-triazine-3-yl, 1-formylalkyl-1,3,4-triazol-5-yl, 2-alkoxycarbonyl-1-formylalkyl-1,3,4-triazol-5-yl or 1-formylalkyl-tetrazol-5-yl radical, by addition reaction with, respectively, cysteamine, an alcohol, hydroxylamine or an alkoxyamine, in accordance with the known methods for forming addition reaction derivatives of carbonyl groups, followed, where appropriate, by removal of the protective radicals.

The reaction is in general carried out in an organic solvent at a temperature of between 20° C. and the reflux temperature of the reaction mixture.

The organic solvents are chosen in accordance with the solubility of the products. If a product of the general formula (XX)''' in which R'$_6$ and R'$_2$ are other than hydrogen is employed, it is advantageous to use solvents such as tetrahydrofurane, acetonitrile, alcohols or ketones. If a product of the general formula (XX)''', in which R'$_6$ and R'$_2$ are hydrogen atoms, is employed, it is advantageous to carry out the reaction in solvents such as pyridine, dimethylsulphoxide or dimethylformamide.

If it is desired to prepare a product of the general formula (XX) in which the radical R contains a substituent of the general formula (XXIc), the reaction is carried out in an acid medium. VIII. The 3-thiovinyl-cephalosporins of the general formula (XX), in which R°$_2$ represents a radical of the general formula (V), in which R$_9$ and R$_{10}$ are defined as above, can also be obtained by esterification of a product of the general formula (XX), in which R°$_2$ represents a hydrogen atom, and in which the amine group has been protected beforehand, by any method which is in itself known for preparing an ester from an acid without affecting the remainder of the molecule.

In particular, the reaction is carried out under the conditions described above for the preparation of products of the general formula (XII) or (XIV) in which R$_2$ is a radical of the general formula (V).

The products of the general formulae (XXIV), (XXXII), (XXXIII), (XXXVI), (XXXVII), (XXXVIII), (XLII), or (XLIV), in which n=1, can be obtained by oxidation of the corresponding products in which n=0, in accordance with the method described in German Patent Application 2,637,176.

The isomers of the products of the general formulae (I), (XX), (XXII), (XXIII), (XXIV), (XXXII), (XXXIII), (XXXVI), (XXXVII), (XXXVIII), (XL), (XLI), (XLII), (XLIV) or (XLV) can be separated by chromatography or by crystallisation.

The novel products according to the invention, and the products of the general formula (XX), can optionally be purified by physical methods such as crystallisation or chromatography.

The cephalosporin derivatives of the general formula (XX) as defined in ($\alpha$), and their pharmaceutically acceptable salts, exhibit particularly valuable antibacterial properties. They exhibit a remarkable activity, in vitro and in vivo, against Gram-positive and Gram-negative germs:

In vitro, they have proved active at a concentration of between 0.5 and 15 $\mu$g/cc against strains of staphylococci sensitive to penicillin G (Staphylococcus aureus Smith), at a concentration of between 1 and 30 $\mu$g/cc, against strains of staphylococci resistant to penicillin G (Staphylococcus aureus MB 9), at a concentration of between 0.001 and 1 $\mu$g/cc against Escherichia coli, Monod strain, and at a concentration of between 0.06 and 30 $\mu$g/cc against Klebsiella pneumoniae. Furthermore, some of the compounds have proved active at a concentration of between 0.01 and 30 $\mu$g/cc against Proteus morganii and at a concentration of between 0.1 and 30 $\mu$g/cc against Enterobacter aerogenes.

In vivo, the compounds have proved active against experimental infections of mice with Staphylococcus aureus Smith (sensitive to penicillin G) at a dose of between 0.2 and 15 mg/kg per day, administered subcutaneously, and with Escherichia coli (Monod strain) at doses of between 0.001 and 10 mg/kg per day, administered subcutaneously.

Furthermore, the LD$_{50}$ of the products of the general formula (XX) is between 1.5 g/kg and doses greater than 2.5 g/kg, for subcutaneous administration to mice.

The derivatives of the cephalosporin of the general formula (XX), as defined in ($\beta$) are described, in respect of their antibacterial properties, or by way of intermediates for the preparation of antibiotic substances, in U.S. Pat. No. 4,065,620.

More especially interesting compounds are the products of the general formula (I) in which R$_1$ is defined as above in (a) or represents a radical of the general formula (VIII), where R$_1$NH- is replaced by a cyclic imide group of a dicarboxylic acid, as defined in (b), and R$_2$ has the corresponding definition, and the symbols R$_3$ and R$_4$ are alkyl radicals or form, together with the nitrogen atom to which they are attached, a saturated 5-membered or 6-membered heterocyclic radical optionally containing another hetero-atom chosen from amongst nitrogen, oxygen or sulphur, and optionally substituted by an alkyl radical.

Amongst these products, particularly preferred products are those of the general formula (I) in which:

(a) the symbol R$_1$ is a radical of the general formula (II) (in which R$_5$ is an alkyl or vinyl radical and R$_6$ is a trityl radical), a trityl radical, an acyl radical of the general formula (III) [in which R$_7$ is an alkyl radical (optionally substituted by a phenyl or phenoxy radical) or a phenyl radical], a radical of the general formula (IV) [in which R$_8$ is a branched unsubstituted alkyl radical, or a branched or straight alkyl radical substituted by a phenyl or nitrophenyl radical], and the symbol R$_2$ represents a pivalyloxymethyl, benzhydryl or p-nitrobenzyl radical, or (b) the symbol R$_1$ represents a radical of the general formula (VIII), in which Ar is a phenyl radical and B is an amino radical protected by an alkoxycarbonyl group, or R$_1$NH- represents a phthalimido radical, and the symbol R$_2$ represents a benzhydrydyl or nitrobenzyl radical, and the symbols R$_3$ and R$_4$ represent alkyl radicals containing 1 or 2 carbon atoms or form, together with the nitrogen atom to which they are attached, a morpholino radical, and more especially the following products:
2-benzhydryloxycarbonyl-7-tert.-butoxycarbonylamino-3-(2-dimethylamino-vinyl)-8-oxo-5-thia-1-aza-bicyclo[4.2.0]oct-2-ene, E-form,
2-benzhydryloxycarbonyl-3-(2-dimethylamino-vinyl)-8-oxo-7-tritylamino-5-thia-1-aza-bicyclo[4.2.0]oct-2-ene, E-form,
2-benzhydryloxycarbonyl-3-(2-dimethylaminovinyl)-8-oxo-7-phenylacetamido-5-thia-1-aza-bicyclo-[4.2.0]oct-2-ene, E-form, and
2-benzhydryloxycarbonyl-7-[2-methoxyimino-2-(2-tritylamino-thiazol-4-yl)-acetamido]-2-(2-dimethylaminovinyl)-8-oxo-5-thia-1-aza-bicyclo[4.2.0]oct-2-ene, syn isomer, E-form. I- The examples which follow and which are given without implying a limitation show how the invention can be put into practice.

In these examples, the products are named in accordance with the Chemical Abstracts nomenclature. It is to be understood that all the products according to the present invention exhibit the stereochemistry resulting from the partial general formula:

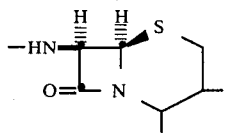

EXAMPLE 1

N,N,N',N'-Tetramethylformamidinium methylsulphate (0.85 g) is added dropwise, in the course of 1 minute, to a solution of potassium tert.-butylate (0.45 g) in anhydrous tetrahydrofurane (20 cc) under an atmosphere of dry nitrogen. The reaction mixture is stirred for 35 minutes at 25° C. and is then heated to the reflux temperature. A solution of 2-benzhydryloxycarbonyl-7-tert.-butoxycarbonylamino-3-methyl-8-oxo-5-thia-1-aza-bicyclo[4.2.0]oct-2-ene (0.96 g) in anhydrous N,N-dimethylformamide (20 cc) is added in the course of 2 minutes, and the mixture is then kept under reflux for 5 minutes. Thereafter the reaction mixture is poured into ethyl acetate (250 cc). The organic solution is washed with distilled water (2×100 cc) and with a half-saturated aqueous sodium chloride (2×100 cc) and is then dried over magnesium sulphate and filtered. After evaportion of the solvent under reduced pressure (20 mm Hg) at 30° C., an orange froth (1.05 g) is obtained.

Rf=0.29 [silica gel chromatographic plate; eluant: a 50:50 (by volume) mixture of cyclohexane and ethyl acetate].

The examination of the infrared and proton nuclear magnetic resonance spectra indicates that the material is principally 2-benzhydryloxycarbonyl-7-tert.-butoxycarbonylamino-3-(2-dimethylamino-vinyl)-8-oxo-5-thia-1-aza-bicyclo[4.2.0]oct-2-ene (E-form).

Infrared spectrum (CHBr$_3$): characteristic bands (cm$^{-1}$) at 3430, 3350, 2820, 1765, 1715, 1690, 1615, 1540, 1505, 1495, 1465, 1370, 1240, 940, 745 and 600.

UV and visible spectrum in ethanol: $\lambda_{max}$=390 mm; $\epsilon$=29,000 (c=2×10$^{-5}$ M).

Mass spectrum: molecular peak 535; characteristic fragments: m/e=378 and 379 (cleavage of the β-lactam).

Proton nuclear magnetic resonance spectrum (350 MHz, CDCl$_3$, δ in ppm, J in Hz): 1.48 (s, (CH$_3$)$_3$C-O-CO-, 9H); 2.89 (s, (CH$_3$)$_2$N-, 6H); 3.17 (AB, J=14, -S CH$_2$-cephem, 2H); 5.02 (d, J=4, H in the 6-position, 1H); 5.27 (dd, J=4 and 9, H in the 7-position, 1H); 5.60 (d, J=9, -OCONH-, 1H); 6.71 (d, J=14, -CH=CH-N<, 1H); 6.49 (d, J=14, -CH=CH-N<, 1H); 6.95 (s, -CH(C$_6$H$_5$)$_2$, 1H); 7.2 to 7.5 (hump, aromatics, 10H).

2-Benzhydryloxycarbonyl-7-tert.-butoxycarbonylamino-3-methyl-8-oxo-5-thia-1-aza-bicyclo[4.2.0]-oct-2-ene can be prepared in the following manner:

A solution of diphenyldiazomethane (116.5 g) in acetonitrile (800 cc) is added dropwise, in the course of 45 minutes, at a temperature of between 25° and 30° C., to a solution of 7-tert.-butyoxycarbonylamino-2-carboxy-3-methyl-8-oxo-5-thia-1-aza-bicyclo[4.2.0]oct-2-ene (188.6 g) in acetonitrile (2,100 cc). Thr reaction mixture is stirred for 16 hours at 22° C. and is then concentrated to dryness under reduced pressure (20 mm Hg) at 40° C. The residue is redissolved in ethyl acetate (2 liters) and the solution is washed with 2 N hydrochloric acid (700 cc) and then with a saturated aqueous sodium bicarbonate solution (70 cc) and a saturated aqueous sodium chloride solution (700 cc). The solution is dried over sodium sulphate, treated with decolorising charcoal, filtered, and then concentrated to dryness under reduced pressure (20 mm Hg) at 40° C. The residue is dissolved in boiling ethyl acetate (600 cc). Cyclohexane (1 liter) is added, and the mixture is heated to the reflux temperature and then allowed to cool. The crystals which have appeared are filtered off, washed with diethyl ether (3×250 cc) and then dried. 2-Benzhydryloxycarbonyl-7-tert.-butoxycarbonylamino-3-methyl-8-oxo-5-thia-1-aza-bicyclo[4.2.0]oct-2-ene (191 g) is obtained in the form of white crystals (m.p.=179° C.). On concentrating the mother liquor to 500 cc, a second fraction of product (32.6 g, m.p.=178° C.) is obtained.

7-tert.-Butoxycarbonylamino-2-carboxy-3-methyl-8-oxo-5-thia-1-aza-bicyclo[4.2.0]oct-2-ene can be obtained in the following manner:

7-Amino-2-carboxy-3-methyl-8-oxo-5-thia-1-aza-bicyclo[4.2.0]oct-2-ene (371 g) is dissolved in a solution of sodium bicarbonate (307 g) in a mixture of distilled water (2 liters) and dioxane (2 liters). A solution of di-tert.-butyl carbonate (421 g) in dioxane (2 liters) is added in the course of 10 minutes. The reaction mixture is stirred for 48 hours at 25° C. The suspension obtained is concentrated under reduced pressure (20 mm Hg) at 50° C. to a residual volume of about 2 liters, and is then diluted with ethyl acetate (1 liter) and distilled water (2 liters). The aqueous phase is decanted, washed with ethyl acetate (500 cc) and acidified to pH 2 with 6 N hydrochloric acid in the presence of ethyl acetate (1500 cc). The aqueous phase is extracted with ethyl acetate (2×1 liter). The combined organic phases are washed with a saturated sodium chloride solution (2×250 cc) and dried over sodium sulphate. After filtration, the solvent is evaporated under reduced pressure (20 mm Hg) at 50° C. 7-tert.-Butoxycarbonylamino-2-carboxy-3-methyl-8-oxo-5-thia-1-aza-bicyclo[4.2.0]oct-2-ene (486 g) is obtained in the form of yellow crystals (m.p.=190° C., with decomposition).

EXAMPLE 2

2-Benzhydryloxycarbonyl-7-tert.-butoxycarbonylamino-3-methyl-8-oxo-5-thia-1-aza-bicyclo[4.2.0]oct-2-ene (90.5 g) is dissolved in anhydrous N,N-dimethylformamide (400 cc). The solution obtained is heated to 80° C. under an atmosphere of nitrogen. A solution of bis-dimethylamino-tert-butoxymethane (36.1 g) in anhydrious N,N-dimethylformamide (60 cc), preheated to 80° C., is then added rapidly. The reaction mixture is kept at 80° C. for 5 minutes and then poured into ethyl acetate (3 liters). After addition of distilled water (1 liter), the organic phase is decanted, washed with distilled water (4×1 liter), dried over sodium sulphate and filtered in the presence of decolorising charcoal. It is then concentrated to dryness under reduced pressure (20 mm Hg) at 30° C. and a product (101 g) identical to that obtained in Example 1 is obtained in the form of an orange-coloured froth.

Rf=0.29; silica gel chromatographic plate [using a 50:50 (by volume) mixture of cyclohexane and ethyl acetate].

EXAMPLE 3 bis-Dimethylamino-tert.-butoxymethane (0.38 g) is added to a solution of 2-benzhydryloxycarbonyl-7-tert.-butoxycarbonylamino-3-methylene-8-oxo-5-thia-1-aza-bicyclo[4.2.0]octane (0.48 g) in anhydrous NN-dimethylformamide (25 cc) and the reaction mixture is kept at 25° C. under reduced pressure (400 mm Hg) for 15 minutes. It is then diluted with ethyl acetate (200 cc) and washed with a saturated aqueous sodium chloride solution (3×300 cc). The organic phase is decanted, dried over magnesium sulphate, filtered and concentrated to dryness under reduced pressure (20 mm Hg) at 30° C. A product (0.41 g) identical to that obtained in Example 1 is obtained in the form of an orange-coloured froth.

2-Benzhydryloxycarbonyl-7-tert.-butoxycarbonylamino-3-methylene-8-oxo-5-thia-1-aza-bicyclo[4.2.0]-octane can be prepared in the following manner:

2-Carboxy-7-tert.-butoxycarbonylamino-3-methylene-8-oxo-5-thia-1-aza-bicyclo[4.2.0]octane (21.3 g) is esterified with diphenyldiazomethane (11.2 g) in accordance with the procedure of Example 1. 2-Benzhydryloxycarbonyl-7-tert.-butoxycarbonylamino-3-methylene-8-oxo-5-thia-1-aza-bicyclo[4.2.0]octane (18.35 g) is obtained in the form of white crystals (m.p.=135°-7° C. after recrystallisation from ethyl acetate).

7-tert.-Butoxycarbonylamino-2-carboxy-3-methylene-8-oxo-5-thia-1-aza-bicyclo[4.2.0]octane can be prepared by electrochemical reduction of 3-acetoxymethyl-7-tert.-butoxycarbonylamino-2-carboxy-8-oxo-5-thia-1-aza-bicyclo[4.2.0]oct-2-ene (10 g) according to the process described in Japanese Patent No. 20,901/71. 7-tert.-butoxycarbonylamino-2-carboxy-3-methylene-8-oxo-5-thia-1-aza-bicyclo[4.2.0]octane (6 g) is obtained in the form of a beige froth, m.p.=180° C. (with decomposition) after recrystallisation from acetonitrile.

3-Acetoxymethyl-7-tert.-butoxycarbonylamino-2-carboxy-8-oxo-5-thia-1-aza-bicyclo[4.2.0]oct-2-ene can be obtained from 3-acetoxymethyl-7-amino-2-carboxy-8-oxo-5-thia-1-aza-bicyclo[4.2.0]oct-2-ene (13.1 g) according to the procedure described in Example 1. 3-Acetoxymethyl-7-tert.-butoxycarbonylamino-2-carboxy-8-oxo-5-thia-1-aza-bicyclo[4.2.0]oct-2-ene (11.8 g) is obtained in the form of a cream-coloured froth.

Rf=0.54 [silica gel chromatographic plate; eluant: a 60:20:2:2 (by volume) mixture of ethyl acetate, acetone, water and acetic acid].

EXAMPLE 4

A solution of 2-benzhydryloxycarbonyl-7-tert.-butoxycarbonylamino-3-methyl-8-oxo-5-thia-1-aza-bicyclo-[4.2.0]oct-3-ene (1.0 g) in anhydrous N,N-dimethylformamide (100 cc) is heated at 80° C. under a nitrogen atmosphere. bis-Dimethylamino-tert.-butoxymethane (0.86 cc) is then added rapidly. The reaction mixture is kept at 80° C. for 5 minutes and then poured into ethyl acetate (50 cc). After addition of distilled water (25 cc), the organic phase is decanted, washed with distilled water (4×25 cc), dried over magnesium sulphate and filtered. It is then concentrated to dryness under reduced pressure (20 mm Hg) at 30° C. and an orange-coloured froth (1.10 g) is obtained; its infrared and proton nuclear magnetic resonance spectra show that the product is principally 2-benzhydryloxycarbonyl-7-tert.-butoxycarbonylamino-3-(2-dimethylamino-vinyl)-8-oxo-5-thia-1-aza-bicyclo[4.2.0]oct-2-ene (E-form).

2-Benzhydryloxycarbonyl-7-tert.-butoxycarbonylamino-3-methyl-8-oxo-5-thia-1-aza-bicyclo[4.2.0]oct-3-ene can be prepared by esterification of 7-tert.-butoxycarbonylamino-2-carboxy-3-methyl-8-oxo-5-thia-1-aza-bicyclo[4.2.0]oct-3-ene (3.2 g) with diphenyldiazomethane (2.1 g) according to the procedure of Example 1. After recrystallisation from a 90:10 (by volume) mixture of cyclohexane and ethyl acetate, 2-benzhydryloxycarbonyl-7-tert.-butoxycarbonylamino-3-methyl-8-oxo-5-thia-1-aza-bicyclo[4.2.0]oct-3-ene (2.3 g) is obtained in the form of white crystals (m.p.=161° C.).

7-tert.-Butoxycarbonylamino-2-carboxy-3-methyl-8-oxo-5-thia-1-aza-bicyclo[4.2.0]oct-3-ene can be prepared by conversion of 7-tert.-butoxycarbonylamino-2-methoxycarbonyl-3-methyl-8-oxo-5-thia-1-aza-bicyclo-[4.2.0]oct-2-ene (8.28 g), using the method of R. B. Morin et al, J. Amer. Chem. Soc., 91(6), 1401 (1969). 7-tert.-Butoxycarbonylamino-2-carboxy-3-methyl-8-oxo-5-thia-1-aza-bicyclo[4.2.0]oct-3-ene (5.4 g) is obtained.

M.p.=200° C. (with decomposition) (after recrystallisation from ethyl acetate).

Rf=0.59 [silica gel chromatographic plate; eluant: a 60:20:1:1 mixture (by volume) of ethyl acetate, acetone, water and formic acid].

7-tert.-Butoxycarbonylamino-2-methoxycarbonyl-3-methyl-8-oxo-5-thia-1-aza-bicyclo[4.2.0]oct-2-end can be prepared by esterifying 7-tert.-butoxycarbonylamino-2-carboxy-3-methyl-8-oxo-5-thia-1-aza-bicyclo[4.2.0]oct-2-ene (16.7 g) (described in Example 1) with a solution of diazomethane in ether, according to the method of R. B. Morin, et al., J. Amer. Soc., 91(6), 1401 (1969). 7-tert.-Butoxycarbonylamino-2-methoxycarbonyl-3-methyl-8-oxo-5-thia-1-aza-bicyclo[4.2.0]oct-2-ene (13.6 g) is obtained in the form of white crystals (m.p.=148° C.).

Rf=0.45 [silica gel chromatographic plate; eluant: a 60:40 (by volume) mixture of cyclohexane and ethyl acetate].

EXAMPLE 5

A solution of 2-benzhydryloxycarbonyl-7-tert.-butoxycarbonylamino-3-methyl-8-oxo-5-thia-1-aza-bicyclo[4.2.0]oct-2-ene (4.8 g) in a mixture of anhydrous tetrahydrofurane (25 cc) and anhydrous N,N-dimethylformamide (25 cc) is heated at 80° C. in a nitrogen atmosphere. bis-Dimethylamino-tert.-butoxymethane (3.1 cc) is then added rapidly. The reaction mixture is kept at 80° C. for 10 minutes and then poured into ethyl acetate (400 cc). After addition of distilled water (100 cc), the organic phase is decanted, washed with distilled water (3×100 cc) and then with a saturated sodium chloride solution (100 cc), and dried over magnesium sulphate. The ethyl acetate is evaporated under reduced pressure (20 mm Hg) at 30° C. A product (5.35 g) identical to that obtained in Example 1 is obtained in the form of an orange-coloured froth.

EXAMPLE 6

2-Benzhydryloxycarbonyl-7-tert.-butoxycarbonylamino-3-methyl-8-oxo-5-thia-1-aza-bicyclo[4.2.-0]oct-2-ene (4.8 g) is dissolved in anhydrous N,N-dimethylformamide (50 cc) and the solution is heated to 80° C. under dry nitrogen. A solution of bis-dimethylamino-ethoxymethane (2.92 g) is anhydrous N,N-dimethylformamide (10 cc) is added. The reaction mixture is again brought to a temperature of 80° C. and kept at this value for 40 minutes. It is then diluted with ethyl acetate (200 cc) and this mixture is washed with distilled water (3×100 cc) and then with a saturated sodium chloride solution (100 cc). The organic phase is decanted, dried over magnesium sulphate, filtered and concentrated to dryness under reduced pressure (20 mm Hg) at 30° C. A product (5.15 g) identical to that obtained in Example 1 is obtained in the form of an orange-coloured froth.

EXAMPLE 7

A solution of dimethoxydimethylaminomethane in anhydrous N,N-dimethylformamide (12 cc) is added to a solution of 2-benzhydryloxycarbonyl-7-tert.-butoxycarbonylamino-3-methyl-8-oxo-5-thia-1-aza-bicyclo[4.2.0]-oct-2-ene (2.4 g) in anhydrous N,N-dimethylformamide (12 cc) at 25° C., under an atmosphere of dry nitrogen. The reaction mixture is heated at 80° C. for 3 hours 20 minutes and is then poured into a mixture of ethyl acetate (150 cc) and distilled water (150 cc). The aqueous phase is decanted and extracted with ethyl acetate (100 cc). The combined organic solutions are washed with distilled water (2×100 cc) and then dried over magnesium sulphate and filtered. Evaporation of the solvent under reduced pressure (20 mm Hg) at 30° C. gives a chestnut-coloured froth (2.7 g). Thin layer chromatography [silica gel; eluant: a 60:40 (by volume) mixture of cyclohexane and ethyl acetate] and the infrared spectrum indicate that the product is principally 2-benzhydryloxycarbonyl-7-tert.-butoxycarbonylamino-3-(2-dimethylamino-vinyl)-8-oxo-5-thia-1-aza-bicyclo[4.2.0]-oct-2-ene (E-form).

EXAMPLE 8

On treating 7-tert.-butoxycarbonylamino-2-methoxycarbonyl-3-methyl-8-oxo-5-thia-1-aza-bicyclo-[4.2.0]oct-2-ene (1.7 g) (described in Example 4) with bis-dimethylamino-tert.-butoxymethane (1.74 g) in anhydrous N,N-dimethylformamide (15 cc) in accordance with the procedure of Example 2, an orange-coloured froth (1.7 g) is obtained. The infrared and nuclear magnetic resonance spectra indicate that the product is principally 7-tert.-butoxycarbonylamino-3-(2-dimethylamino-vinyl)-2-methoxycarbonyl-8-oxo-5-thia-1-aza-bicyclo[4.2.0]oct-2-ene (E-form).

Infrared spectrum (CHCl$_3$): characteristic bands (cm$^{-1}$) at 2800, 1760, 1710, 1690 and 1610.

Proton nuclear magnetic resonance spectrum, characteristic signals of the E-isomer of bicyclooct-2-ene (350 MHz, CDCl$_3$, δ in ppm, J in Hz): 1.49 (s, 9H, (CH$_3$)$_3$CO-); 2.96 (s, 6H, (CH$_3$)$_2$N—CH=CH-); 3.76 (s, 3H, -CO$_2$C$\underline{H}_3$); 6.57 (d, J=14, 1H, -CH=C$\underline{H}$-N<); 6.87 (d, J=14, 1H, -C$\underline{H}$=CN-N<).

EXAMPLE 9

The procedure followed is as in Example 2, but starting from a solution of 7-tert.-butoxycarbonylamino-3-methyl-8-oxo-2-pivalyoxymethoxycarbonyl-5-thia-1-aza-bicyclo[4.2.0]oct-2-ene (1 g) in anhydrous N,N-dimethylformamide (10 cc) and bis-dimethylamino-tert.-butoxymethane (0.8 g). A crude product (0.75 g) is obtained in the form of a brown froth, of which the infrared and nuclear magnetic resonance spectra indicate that the product is principally 7-tert.-butoxycarbonylamino-3-(2-dimethylamino-vinyl)-pivalyoxymethyloxycarbonyl-5-thia-1-aza-bicyclo[4.2.0]oct-2-ene (a mixture of the Z- and E-forms).

Rf=0.36 [silica gel chromatographic plate; eluant: a 50:50 (by volume) mixture of cyclohexane and ethyl acetate]

Infrared spectrum (CHCl$_3$): characteristic bands (cm$^{-1}$) at 2810, 1770, 1760, 1720, 1705 and 1615.

Proten nuclear magnetic resonance spectrum (350 MHz, CDCl$_3$, δ in ppm, J in Hz): characteristic signals 3.0 (s, broad, (C$\underline{H}_3$)$_2$N-CH=CH-). Z- and E-isomers); 3.14 and 3.35 (AB, J=14, -S-CH$_2$-cephem, E-isomer); 5.06 (d, J=4, H in the 6-position, E-isomer); 5.13 (d, J=4, H in the 6-position, Z-isomer); 5.25 to 5.4 (hump, H in the 7-position and -CONH, Z- and E-isomers); 5.7 to 6.0 (2AB, -CO$_2$CH$_2$OCO-, Z- and E-isomers); 6.52 (d, J=14, CH=C$\underline{H}$-N<, E-isomer); 6.92 (d, J=14, -CH=C$\underline{H}$-N<, E-isomer); 6.24 (d, J=6.5, -CH=C$\underline{H}$-N<, Z-isomer); 6.72 (d, J=6.5, -C$\underline{H}$=CH-N<, Z-isomer).

7-tert.-Butoxycarbonylamino-3-methyl-8-oxo-2-pivalyloxymethoxycarbonyl-5-thia-1-aza-bicyclo[4.2.0]-oct-2-ene can be obtained according to the procedure of Example 1. Starting from 7-amino-3-methyl-8-oxo-2-pivalyloxymethoxycarbonyl-5-thia-1-aza-bicyclo[4.2.0]-oct-2-ene tosylate (6.9 g), 7-tert.-butoxycarbonylamino-3-methyl-8-oxo-2-pivalyloxymethoxycarbonyl-5-thia-1-aza-bicyclo[4.2.0]oct-2-ene (4.6 g) is obtained in the form of an oil which crystallises slowly (m.p.=97° C.).

7-Amino-3-methyl-8-oxo-2-pivalyloxymethoxycarbonyl-5-thia-1-aza-bicyclo[4.2.0]oct-2-ene tosylate can be prepared by application of the method described by M. Ogura et al., Chem. Pharm. Bull., 26(6), 1688 (1978).

EXAMPLE 10

2-Benzhydryloxycarbonyl-3-methyl-8-oxo-7-phthalimido-5-thia-1-aza-bicyclo[4.2.0]oct-2-ene (1.5 g) is treated, under nitrogen, with dimethoxydimethylaminomethane (0.71 g) in anhydrous N,N-dimethylformamide (13 cc) in accordance with the procedure of Example 7. A crude product (1.6 g), containing principally 2-benzhydryloxycarbonyl-3-(2-dimethylamino-vinyl)-8-oxo-7-phthalimido-5-thia-1-aza-bicyclo[4.2.0]oct-2-ene (E-form), is obtained in the form of an orange-coloured froth.

Rf=0.42 (Rf of the starting material=0.70) [silica gel chromatographic plate; eluant: a 50:50 (by volume) mixture of cyclohexane and ethyl acetate.

Infrared spectrum (CHCl$_3$): characteristic bands (cm$^{-1}$) at 2820, 1785, 1775, 1730, 1615, 1390, 695, 620 and 605.

Proton nuclear magnetic resonance spectrum (60 MHz, CDCl$_3$, δ in ppm, J in Hz): 2.9 (s, 6H, (CH$_3$)$_2$N-); 3.52 (AB, J=14, 2H, -S-CH$_2$-cephem); 5.26 (d, J=5, 1H, H in the 6-position); 6.8 (d, J=8, 1H, -CH=C$\underline{H}$-N<); 6.98 (s, 1H, (C$_6$H$_5$)$_2$C$\underline{H}$-O-); 7.2 to 7.8 (hump, 11H, (C$_6$H$_5$)$_2$CH-+-C$\underline{H}$=CH-N<); 7.8 to 8 (hump, 4H, aromatics: phthalimido).

2-Benzhydryloxycarbonyl-3-methyl-8-oxo-7-phthalimido-5-thia-1-aza-bicyclo[4.2.0]oct-2-ene can be prepared according to the method described in Japanese Patent Application 72/22,829.

EXAMPLE 11

2-Benzyhydryloxycarbonyl-3-methyl-8-oxo-7-phthalimido-5-thia-1-aza-bicyclo[4.2.0]oct-2-ene (1.5 g) is treated with bis-dimethylamino-tert.-butoxymethane (1.2 g) in anhydrous N,N-dimethylformamide (13 cc), following the procedure of Example 2. A crude product (1.6 g), of which the characteristics are identical to those of the product obtained in Example 10, is obtained in the form of an orange-coloured froth.

EXAMPLE 12

A solution of 2-benzhydryloxycarbonyl-7-(D-α-tert.-butoxycarbonylamino-phenylacetamido)-3-methyl-8-oxo-5-thia-1-aza-bicyclo[4.2.0]oct-2-ene (6.14 g) in anhydrous N,N-dimethylformamide (90 cc) is treated, at 80° C., with bis-dimethylamino-tert.-butoxymethane (3.49 g) in N,N-dimethylacetamide (30 cc) under nitrogen. Following the procedure of Example 2, a brown froth (6.27 g) is obtained, which consists essentially of 2-benzhydryloxycarbonyl-7-(D-α-tert.-butoxycarbonylamino-phenylacetamido)-3-(2-dimethylamino-vinyl)-8-oxo-5-thia-1-aza-bicyclo[4.2.0]oct-2-ene, E-form.

Rf=0.33 [slica gel chromatographic plate; using a 50:50 (by volume) mixture of cyclohexane and ethyl acetate].

Infrared spectrum (CHBr$_3$), characteristic bands (cm$^{-1}$) at 3420, 3310, 2800, 1760, 1710, 1690 and 1610.

2-Benzhydryloxycarbonyl-7-(D-α-tert.-butoxycarbonylamino-phenylacetamido)-3-methyl-8-oxo-5-thia-1-aza-bicyclo[4.2.0]oct-2-ene can be prepared according to the method described in German Patent Application 2,333,256.

EXAMPLE 13

A solution of 2-benzhydryloxycarbonyl-7-(D-α-tert.-butoxycarbonylamino-phenylacetamido)-3-methyl-8-oxo-5-thia-1-aza-bicyclo[4.2.0]oct-2-ene (6.13 g) in anhydrous N,N-dimethylformamide (50 cc) is heated at 80° C. under an atmosphere of dry nitrogen. A solution of bis-dimethylaminoethoxymethane (2.92 g) in anhydrous N,N-dimethylformamide (5 cc) is added rapidly. The reaction mixture is kept at 80° C. for 38 minutes and is then diluted with ethyl acetate (200 cc) and distilled water (100 cc). The organic phase is decanted, washed with distilled water (2×100 cc) and then with a saturated sodium chloride solution (150 cc), dried over magnesium sulphate and filtered. The ethyl acetate is evaporated in vacuo (20 mm Hg) at 30° C. 2-Benzhydryloxcarbonyl-7-(D-α-tert.-butoxycarbonylamino-phenylacetamido)-3-(2-dimethylamino-vinyl-8-oxo-5j-thia-1-aza-bicyclo[4.2.0]oct-2-ene, E-form (6 g) is obtained; its characteristics are identical to those of the product obtained in Example 12.

EXAMPLE 14

Following the procedure of Example 3, starting from 2-benzhydryloxycarbonyl-7-(D-α-tert.-butoxycarbonyl-amino-phenylacetamido)-3-methylene-8-oxo-5-thia-1-aza-bicyclo[4.2.0]octane (1.83 g), 2-benzhydryloxycarbonyl-3-(2-dimethylamino-vinyl)-7-D-α-tert.-butoxycarbonyl-amino-phenylacetamido-8-oxo-5-thia-1-aza-bicyclo[4.2.0]-oct-2-ene, E-form (1.84 g) are obtained in the form of an orange-coloured froth; its characteristics are identical to those of the product obtained in Example 12.

2-Benzhydryloxycarbonyl-7-(D-α-tert.-butoxy-carbonylamino-phenylacetamido)-3-methylene-8-oxo-5-thia-1-aza-bicyclo[4.2.0]octane can be prepared according to the method described by R. Scartazzini et al., Helv. Chim. Acta, 57 1919 (1974).

EXAMPLE 15

A solution of 3-methyl-2-(4-nitro-benzyloxy-carbonyl)-8-oxo-7-phenoxyacetamido-5-thia-1-aza-bicyclo[4.2.0]oct-2-ene (17 g) in anhydrous N,N-dimethylformamide (100 cc) is heated at 80° C. under dry nitrogen and then treated with bis-dimethylamino-tert.-butoxymethane (10.8 cc) for 1 minute at 80° C. The reaction mixture is then diluted with ethyl acetate (400 cc) and distilled water (250 cc). The organic phase is decanted, washed with distilled water (2×250 cc) and then with saturated aqueous sodium chloride solution (250 cc), dried and filtered. The residue obtained after evaporation of the solvent under reduced pressure (20 mm Hg) at 30° C. is redissolved in methylene chloride (50 cc) and the solution is poured dropwise into isopropyl ether (1600 cc). The precipitate formed is filtered off, washed with isopropyl ether (4×100 cc) and dried under reduced pressure (10 mm Hg) at 25° C. An ochre powder (8.6 g) is obtained, of which the infrared and nuclear magnetic resonance spectra indicate that it is principally 3-(2-dimethylamino-vinyl)-2-(4-nitrobenzyloxycarbonyl)-8-oxo-7-phenoxyacetamido-5-thia-1-aza-bicyclo[4.2.0]oct-2-ene (E-form).

Rf=0.3 [silica gel chromatographic plate; 40:60 (by volume) mixture of cyclohexane and ethyl acetate].

Proton nuclear magnetic resonance spectrum (350 MHz, CDCl$_3$, δ in ppm, J in Hz): 2.97 (s, 6H, —N(CH$_3$)$_2$); 3.23 (AB, J=15, 2H, —SCH$_2$—); 4.62 (s, 2H, C$_6$H$_5$OCH$_2$CO—); 5.15 (d, J=4.5, 1H, H in the 6-position); 5.31 (AB, J=14, 2H, —CO$_2$CH$_2$C$_6$H$_4$NO$_2$); 5.46 (dd, J=4.5 and 10, 1H, H in the 7-position); 6.55 and 6.9 (2d, J=14, —CH=CH—N<); 6.97 (d, 2H in the ortho positions of C$_6$H$_5$O—); 7.03 (t, 1H in the para-position of C$_6$H$_5$O—); 7.3 (t, 2H in the meta-positions of C$_6$H$_5$O—); 7.6 and 8.2 (2d, 2×2H, NO$_2$—C$_6$H$_4$—).

3-Methyl-2-(4-nitro-benzyloxycarbonyl)-8-oxo-7-phenoxyacetamido-5-thia-1-aza-bicyclo[4.2.0]oct-2-ene can be prepared according to the method described by E. H. Flynn, Cephalosporins and Penicillins, Academic Press, New York and London (1972), page 670.

EXAMPLE 16

A solution of 3-methyl-2-(4-nitro-benzyloxy-carbonyl)-8-oxo-7-phenoxyacetamido-5-thia-1-aza-bicyclo-[4.2.0]oct-2-ene (5.8 g) in anhydrous N,N-dimethylformamide (50 cc) is heated at 80° C. under an atmosphere of dry nitrogen. A solution of dimethoxydimethylaminomethane (2.8 g) in anhydorus N,N-dimethylformamide (20 cc) is added and the temperature is kept at 80° C. for 2 hours; after addition of triethylamine (5 cc), the reaction mixture is stirred for a further 30 minutes at 80° C. and is then poured into ethyl acetate (300 cc). The organic solution is washed with a half-saturated aqueous sodium chloride solution (4×300 cc), dried over magnesium sulphate in the presence of decolorising charcoal and then filtered. Evaporation of the solvent under reduced pressure (20 mm Hg) at 30° C. gives a gummy product (6.05 g).

A solution of the preceding product (5 g) in methylene chloride (25 cc) is added dropwise to isopropyl ether (800 cc). The product which has precipitated is filtered off, washed with isopropyl ether (2×100 cc) and dried in a desiccator under reduced pressure (10 mm Hg) at 25° C. A product (3.7 g) is obtained in the form of an ochre powder; the nuclear magnetic resonance and infrared spectra indicate that it is a mixture of isomers. This product is chromatographed on silica gel (400 g) (particle size 0.04–0.063 mm; column diameter 6 cm and column height 30 cm; operation under 40 kPa pressure of nitrogen) so as to give a purified sample of 3-(2-dimethylamino-vinyl)-2-(4-nitro-benzyloxycarbonyl)-8-oxo-7-phenoxyacetamido-5-thia-1-aza-bicyclo[4.2.0]oct-2-ene (E-form).

Rf=0.26 [silica gel chromatographic plate;eluant: a 50:50 (by volume) mixture of cyclohexane and ethyl acetate].

Infrared spectrum (CHBr$_3$): characteristic bands (cm$^{-1}$) at 2820, 1770, 1690, 1610, 1520, 1345 and 1240.

Proton nuclear magnetic resonance spectrum (350 MHz, CDCl$_3$, δ in ppm, J in Hz): 2.97 (s, —N(CH$_3$)$_2$, 6H); 3.23 (AB, J=15, —S—CH$_2$-cephem, 2H); 4.62 (s, C$_6$H$_5$O—C$\underline{H}_2$—CO—, 2H); 5.15 (d, J=4.5, H in the 6-position, 1H); 5.31 (AB, J=14, p.NO$_2$C$_6$H$_4$-CHOCO—, 2H); 5.46 (dd, J=4.5 and 10, H in the 7-position, 1H); 6.55 and 6.9 (2d, J=14, 2H trans-ethylenic, 2H); [6.97 (d, ortho, 2H); 7.03 (t, para, 1H); 7.30 (d, meta, 2H)]C$_6$H$_5$—O—; 7.5 to 7.7 (m, 3H, —CONH— and aromatics in the meta-position to the NO$_2$); 8.2 (d, 2H, aromatics in the ortho-position to the NO$_2$).

Mass spectrum (principal peaks): molecular peak M=538,m/e=348 and 347 (fragmentation of the β-lactam) m/e=493 [loss of —N(CH$_3$)$_2$], $m/e$=403 (loss of C$_6$H$_5$O—CH$_2$—CO—)→m/e=359 [loss of —N(CH$_3$)$_2$].

EXAMPLE 17

Following the procedure of Example 15, but starting from 3-methyl-2-(4-nitro-benzyloxycarbonyl)-8-oxo-7-phenoxyacetamido-5-thia-1-aza-bicyclo[4.2.0]oct-2-ene (2.44 g) and dimethylamino-dineopentyloxymethane (2.31 g), an ochre solid (1.05 g) is obtained; its characteristics are identical to those of the product obtained in Example 15.

EXAMPLE 18

A solution of 3-methyl-8-oxo-7-phenoxyacetamido-2-pivalyloxymethoxycarbonyl-5-thia-1-aza-bicyclo[4.2.0]-oct-2-ene (9.2 g) in anhydrous N,N-dimethylformamide (100 cc) is placed under a nitrogen atmosphere and heated to 80° C. bis-Dimethylamino-tert.-butoxymethane (6.2 cc) is added rapidly and the reaction mixture is kept at 80° C. for 5 minutes before being diluted with ethyl acetate (400 cc) and distilled water (100 cc). The organic phase is decanted and washed successively with distilled water (3×100 cc) and with saturated aqueous sodium chloride solution (150 cc), and is then dried over magnesium sulphate and filtered. Evaporation of the solvent under reduced pressure (20 mm Hg) at 30° C. gives a brown froth (5.5 g). This product is taken up in a 45:55 (by volume) mixture of cyclohexane and ethyl acetate (75 cc) and is chromatographed with the same eluant (4liters) on silica gel (0.04–0.63 mm, silica height 30 cm, column diameter 5 cm) under a nitrogen pressure of 40 kPa.

125 cc fractions are collected. Fractions 15 and 16 are concentrated to dryness under reduced pressure (20 mm Hg) at 30° C. 3-(2-Dimethylamino-vinyl)-8-oxo-7-phenoxyacetamido-2-pivalyloxymethoxycarbonyl-5-thia-1-aza-bicyclo[4.2.0]oct-2-ene (E-form) (0.45 g) is obtained.

Rf=0.23 [silica gel chromatographic plate; eluant: a 50:50 (by volume) mixture of cyclohexane and ethyl acetate].

Infrared spectrum (CHBr$_3$): characteristic bands (cm$^{-1}$) at 2820, 1760, 1740, 1695 and 1610.

Proton nuclear magnetic resonance spectrum (350 MHz, CDCl$_3$, δ in ppm, J in Hz): 1.21 (s, (CH$_3$)$_3$C—CO—, 9H); 3.00 (s, (CH$_3$)$_2$N—, 6H); 3.22 and 3.30 (AB, J=14, —S—CH$_2$-cephem, 2H); 4.55 (AB, J=14, C$_6$H$_5$O—C$\underline{H}_2$—CO—, 2H); 5.09 (d, J=4, H in the 6-position, 1 H); 5.36 (dd, J=9 and 4, H in the 7-position, 1H); 5.71 and 6.00 (AB, J=6,

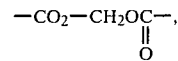

2H); 6.92 (d, J=9, aromatic ortho-positions, 2H); 7.01 (t, J=9, aromatic para-position, 1H); 7.29 (d, J=9, aromatic metapositions, 2H); 7.77 (d, J=9, —CONH—, 1H).

3-Methyl-8-oxo-7-phenoxyacetamido-2-pivalyloxymethoxycarbonyl-5-thia-1-aza-bicylco[4.2.0]oct-2-ene can be prepared according to German Patent Application 1,951,012.

EXAMPLE 19

Following the procedure of Example 7, but starting from 2-benzhydryloxycarbonyl-3-methyl-7-(4-nitrobenzyloxycarbonylamino)-8-oxo-5-thia-1-aza-bicyclo-[4.2.0]oct-2-ene (10 g) in anhydrous dimethylformamide (100 cc), treated with dimethoxydimethylaminomethane (4.8 cc), a crude product (10 g) consisting principally of 2-benzhydryloxycarbonyl-3-(2-dimethylamino-vinyl)-7-(4-nitro-benzyloxycarbonylamino)-8-oxo-5-thia-b-aza-bicyclo[4.2.0]oct-2-ene (E-form) (10 g) is obtained.

Rf=0.27 [silica gel chromatographic plate; eluant: a 50:50 (by volume) mixture of cyclohexane and ethyl acetate].

Infrared spectrum (CHCl$_3$): characteristic bands (cm$^{-1}$) at 2800, 1770, 1730, 1615, 1525 and 1350.

2-Benzhydryloxycarbonyl-3-methyl-7-(4-nitrobenzyloxycarbonylamino)-8-oxo-5-thia-1-aza-bicyclo[4.2.0]oct-2-ene can be prepared in the following manner:

7-ADCA (50 g) is acylated with para-nitrobenzyl chloroformate (50 g), by analogy with the method of working described by E. H. Flynn (Cephalosporins and Penicillins, page 664), to give crude 2-carboxy-3-methyl-(4-nitro-benzyloxycarbonylamino)-8-oxo-5-thia-1-aza-bicyclo[4.2.0]oct-2-ene (62.2 g) (yellow crystals).

This acid (38.5 g) is esterified according to Example 1, to give 2-benzhydryloxycarbonyl-3-methyl-7-(4-nitro-benzyloxycarbonylamino)-8-oxo-5-thia-1-aza-bicyclo[4.2.0]oct-2ene (36 g).

Rf=0.72 [silica gel chromatographic plate; eluant: a 50:50 (by volume) mixture of cyclohexane and ethyl acetate].

EXAMPLE 20 bis-Dimethylamino-tert.-butoxymethane (10 g) is added, under a dry nitrogen atmosphere, to a solution of 2-benzhydryloxycarbonyl-7-benzoylamino-3-methyl-8-oxo-5-thia-1-aza-bicyclo[4.2.0]oct-2-ene (24 g) in anhydrous N,N-dimethylformamide (100 cc). The reaction mixture is stirred at 25° C. for 23 hours and is then poured into a mixture of ethyl acetate (300 cc) and an aqueous saturated sodium chloride solution (700 cc). The aqueous phase is decanted and extracted with ethyl acetate (250 cc). The organic phases are combined, washed with 1 N aqueous hydrochloric acid (250 cc), with distilled water (500 cc) and with a saturated aqueous sodium chloride solution (300 cc) and then dried over magnesium sulphate in the presence of decolorising charcoal, and filtered. The solvent is evaporated under reduced pressure (20 mm Hg) at 30° C. The residue is dissolved in methylene chloride (200 cc) and fixed to silica (50 g). The powder obtained is placed in a column (height 60 cm, diameter 5 cm) containing silica gel (415 g) in a 95:5 (by volume) mixture of cyclohexane and ethyl acetate. Elution is carried out with the following mixtures of cyclohexane and ethyl acetate: 95:5 (by volume) (5 liters), 90:10 (by volume) (5 liters), 80:20 (by volume) (5 liters), 70:30 (by volume) (7.5 liters) (so as to elute the impurities) and 60:40 (by volume) (8 liters) the latter being collected and concentrated to dryness. 2-Benzhydryloxycarbonyl-7-benzoylamino-3-(2-dimethylamino- vinyl)-8-oxo-5-thia-1-aza-bicyclo[4.2.0]oct-2-ene (E-form) (10 g) is obtained in the form of a yellow solid.

Rf=0.24 [silica gel chromatographic plate; eluant: a 50:50 (by volume) mixture of cyclohexane and ethyl acetate].

Infrared spectrum (CHCl$_3$): characteristic bands (cm$^{-1}$) at 2800, 1760, 1740, 1660 and 1605.

Proton nuclear magnetic resonance spectrum (60 MHz, CDCl$_3$, δ in ppm, J in Hz): prinicipal signals 2.85 (s, 6H, (CH$_3$)$_2$N—CH=CH—); 5.1 (d, J=4 Hz, 1H, H in the 6-position); 5.65 (dd, J=9 and 4 Hz, 1H, H in the 7-position); 6.8 (s, 1H, —CH(C$_6$H$_5$)$_2$); 7.05 to 8.2 (hump, aromatics and —CONH—).

UV spectrum (C$_2$H$_5$OH, C=1.9 10$^{-5}$ M, 1=1cm); λ$_{max}$=392 mm, ε=16,000.

2 -Benzhydryloxycarbonyl-7-benzoylamino-3-methyl-8-oxo-5-thia-1-aza-bicyclo[4.2.0]oct-2-ene can be prepared according to the method described in Polish Patents 86,945 and 86,946.

EXAMPLE 21

Following the procedure described in Example 1, but replacing the N,N,N',N'-tetramethylformamidinium methylsulphate by N,N-dimethylmorpholinomethyleneimmonium methylsulphate (1 g), an orange froth (1.1 g) is obtained from 2-benzhydryloxycarbonyl-7-tert.-butoxy-carbonylamino-3-methyl-8-oxo-5 -thia-1-aza-bicyclo-[4.2.0]oct-2-ene (0.96 g). This crude product principally contains 2 -benzhydryloxycarbonyl-7-tert.- butoxycarbonylamino-3-(2-morpholino-vinyl)-8-oxo-5-thia-1-aza-bicyclo[4.2.0]oct-2-ene (E-form).

Rf=0.43 [silica gel chromatographic plate; eluant: a 50:50 (by volume) mixture of cyclohexane and ethyl acetate].

EXAMPLE 22

A solution of 2-benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene(syn isomer) (8.06 g) in anhydrous N,N-dimethylformamide (160 cc) is heated to 80° C. bis-Dimethylamino-tert.-butoxymethane (2.26 g) is added and the reaction mixture is kept at 80° C. for 5 minutes. It is then diluted with iced ethyl acetate (645 cc) and this mixture is washed with distilled water (4×250 cc) and then with a saturated aqueous sodium chloride solution (100 cc). The organic solution is dried over magnesium sulphate and filtered. Evaporation to dryness under reduced pressure (20 mm Hg) at 30° C. gives a brown froth (8.1 g), of which the infrared and nuclear magnetic resonance spectra show that it consists principally of the syn isomer, E-form, of 2-benzhydryloxycarbonyl-7-[2-methoxyimino-2-(2-tritylamino-thiazol-4-yl)-acetamido]-3-(2-dimethylamino-vinyl)-8-oxo-5-thia-1-aza-bicyclo[4.2.-0]oct-2-ene.

Rf=0.18 [silica gel chromatographic plate; eluant: a 50:50 (by volume) mixture of cyclohexane and ethyl acetate].

Infrared spectrum (solution in CHBr$_3$): characteristic bands at 1765 cm$^{-1}$ (carbonyl group of the β-lactam) and 1610 cm$^{-1}$ (double bond of the enamine).

Nuclear magnetic resonance spectrum (350 MHz, CDCl$_3$, δ in ppm, J in Hz): 2.87 (s, 6H, (CH$_3$)$_2$N—); 2.98 and 3.15 (AB, J=14, 2H, —S—CH$_2$-cephem); 4.08 (s, 3H, =NOCH$_3$); 5.12 (d, J=4, 1H, H in the 6-position); 5.51 (dd, J=4 and 8, 1H, H in the 7-position); 6.42 and 6.54 (AB, J=14, 2H, H, trans-vinyl); 6.83 (s, 1H, H of the thiazole ring); 6.94 (s, 1H, —COOCH(C$_6$H$_5$)$_2$); 7.01 (s broad, 1H, (C$_6$H$_5$)$_3$CNH—); 7.10 to 7.50 (15H aromatics); 7.53 (d, J=8, 1H, —CONH—).

2-Benzhydryloxycarbonyl-3-methyl-8-oxo-7-[2-methoxyimino-2-(2-tritylamino-thiazol-4-yl)-acetamido]-5-thia-1-aza-bicyclo[4.2.0]oct-2-ene, syn isomer, can be prepared in the following manner:

A solution of 2-(2-tritylamino-thiazol-4-yl)-2-methoxyimino-acetic acid (syn isomer) (7.2 g) in methylene chloride (22.4 cc) is added, in a single shot, to a solution of 7-amino-2-benzhydryloxycarbonyl-3-methyl-8-oxo-5-thia-1-aza-bicyclo[4.2.0]oct-2-ene (3.15 g) in methylene chloride (31.5 cc). The temperature rises from 8° to 14° C. The mixture is kept stirred for one hour 15 minutes, during which the temperature rises to 20° C., and is then washed with 0.5 N hydrochloric acid (10 cc), distilled water (10 cc) and a saturated sodium bicarbonate solution (20 cc). The insoluble matter formed is filtered off, and the organic phase is washed again with distilled water (2×20 cc), dried over magnesium sulphate, filtered and concentrated to dryness under reduced pressure (20 mm Hg) at 40° C. The residue is chromatographed on a column (diameter: 3 cm, height: 33 cm) containing silica gel (125 g), elution being carried out with a 20:80 (by volume) mixture of ethyl acetate and cyclohexane (1.2 liters) and then with a 40:60 (by volume) mixture (1 liter), and 50 cc fractions of eluate being collected. Fractions 31 to 44 are evaporated and 2-benzhydryloxycarbonyl-7-[2-methoxyimino-2(2-tritylamino-thiazol-4yl)-acetamido]-3-methyl-8-oxo-5-thia-1-aza-bicyclo[4.2.0]oct-2-ene, syn isomer (2.8 g) is obtained in the form of a pale yellow solid.

7-Amino-2-benzhydryloxycarbonyl-3-methyl-8-oxo-5-thia-1-aza-bicyclo[4.2.0]oct-2-ene can be prepared according to the method described in Netherlands Patent Application 73/03,263.

EXAMPLE 23 tert.-Butoxy-bis-dimethylaminomethane (0.7 cc) is added to a solution of 2-benzhydryloxycarbonyl-3-methyl-8-oxo-7-[2-(2-tritylamino-thiazol-4-yl)-2-vinyl-oxyimino-acetamido]-5-thia-1-aza-bicyclo[4.2.0]oct-2-ene, syn isomer (2.5 g) in dimethylformamide (40 cc) at 80° C., under nitrogen, and the mixture is then stirred for 10 minutes at 80° C. and poured into ethyl acetate (250 cc) and iced water (250 cc). The organic phase is decanted, washed with water (3×150 cc) and saturated aqueous sodium chloride (150 cc), dried over sodium sulphate, filtered and concentrated to dryness under 20 mm Hg (2.7 kPa) at 30° C. A brown froth (2.5 g) is obtained, which consists principally of 2-benzhydryloxycarbonyl-3-(2-dimethylamino-vinyl)-8-oxo-7-[2-(2-tritylamino-thiazol-4-yl)-2-vinyloxyimino-acetamido]-5-thia-1-aza-bicyclo[4.2.0]oct-2-ene, syn isomer, E-form.

Infrared spectrum (KBr): characteristic bands (cm$^{-1}$) at 1770, 1670, 1635, 1610, 1530, 1495, 1450, 1000, 945, 755 and 700.

Proton nuclear magnetic resonance spectrum (350 MHz, CDCl₃, δ in ppm, J in Hz): 2.90 (s, 6H, —N(CH₃)₂); 4.25 (dd, J=2 and 6,1H

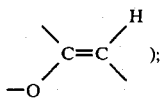

4.73 (dd, J=2 and 14, 1H,

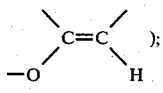

5.18 (d, J=4, 1H, H in the 6-position); 5.60 (dd, J=4 and 9, 1H, H in the 7-position); 6.53 and 6.75 (2d, J=16, 2H, —CH=CH—); 6.88 (s, 1H, —COOCH<); 7.10 (dd, J=6 and 14, 1H, =NOCH=).

2-Benzhydryloxycarbonyl-3-methyl-8-oxo-7-[2-(2-tritylamino-thiazol-4-yl)-2-vinyloxyimino-acetamido]-5-thia-1-aza-bicyclo[4.2.0]oct-2-ene, syn isomer, is prepared by condensing 2-(2-tritylamino-thiazol-4-yl)-2-vinyloxyimino-acetic acid, syn isomer (4.6 g) with the benzhydryl ester of 7-ADCA (3.8 g) in the presence of N,N'-dicyclohexylcarbondiimide (2.3 g) and of 4-dimethylamino-pyridine (0.05 g), in methylene chloride (40 cc), for 4 hours at between 5° C. and 20° C. After chromatography on silica gel (200 g) with methylene chloride, the expected product (5 g) is obtained in the form of a yellow froth.

Infrared spectrum (KBr): characteristic bands (cm⁻¹) at 3400, 1785, 1725, 1690, 1640, 1525, 1495, 1450, 1040, 1000, 940, 755 and 700.

Proton nuclear magnetic resonance spectrum (350 MHz, CDCl₃, δ in ppm, J in Hz): 2.12 (s, 3H, —CH₃); 3.22 and 3.49 (2d, J=18, 2H, —CH₂—); 4.25 (dd, J=2 and 6, 1H,

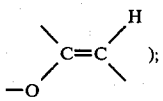

4.76 (dd, J=2 and 14, 1H,

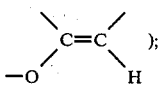

5.08 (d, J=4, 1H, H in the 6-position); 5.92 (dd, J=4 and 9, 1H, H in the 7-position); 6.83 (s, 1H, H of the thiazole); 6.93 (s, 1H, —COOCH<); 7.0 (s, 1H, —N-H—C(C₆H₅)₃).

2-(2-Tritylamino-thiazol-4-yl)-2-vinyloxyiminoacetic acid, syn isomer, is prepared according to Belgian Patent No. 869,079.

EXAMPLE 24 tert.-Butoxy-bis-dimethylaminomethane (10.8 cc) is added to a solution of a mixture (21.8 g) of 2-benzhydryloxycarbonyl-3-methyl-8-oxo-7-tritylamino-5-thia-1-aza-bicyclo[4.2.0]oct-2-ene (40%) and its oct-3-ene isomer (60%) in dry N,N-dimethylformamide (120 cc) heated to 80° C. under nitrogen. After 5 minutes at 80° C., the reaction mixture is poured into ethyl acetate (500 cc). Distilled water (250 cc) is added, the mixture is stirred, and the organic phase is decanted, washed with distilled water (3×250 cc), then dried over magnesium sulphate and concentrated under reduced pressure (40 mm Hg) at 40° C. Examination, by thin layer chromatography, of the residue shows the presence of unchanged starting material. The product is redissolved in dry N,N-dimethylformamide (100 cc), the solution is heated to 80° C. under nitrogen, and after addition of tert.-butoxybis-dimethylaminomethane (6 cc) the reaction mixture is kept at 80° C. for 5 minutes. It is then diluted with ethyl acetate (500 cc) and treated as above, to give an orange froth (24 g) consisting principally of 2-benzhydryloxycarbonyl-3-(2-dimethylamino-vinyl)-8-oxo-7-tritylamino-5-thia-1-aza-bicyclo[4.2.0]oct-2-ene (E-form).

Infrared spectrum (CHBr₃, characteristic bands in cm⁻¹): 3320, 2800, 1760, 1680, 1610, 1445, 760 and 705.

Proton nuclear magnetic resonance spectrum (CDCl₃, 350 MHz, δ in ppm, J in Hz): 2.84 (s, 6H, —N(CH₃)₂); 2.95 and 3.12 (2d, J=16, 2H, —SCH₂—); 3.36 (d, J=10, 1H, —NH—); 3.98 (d, J=4, 1H, H in the 6-position); 4.41 (dd, J=4 and 10, 1H, H in the 7 -position); 6.46 and 6.72 (2d, J=14, —CH=CH—); 6.82 (s, 1H,

CH(C₆H₅)₂;

7.2 to 7.6 (hump, 25 H aromatics).

The mixture of 2-benzhydryloxycarbonyl-3-methyl-8-oxo-7-tritylamino-5-thia-1-aza-bicyclo[4.2.0]oct-2-ene (40%) and its oct-3-ene isomer (60%) can be obtained in the following manner:

A solution of diphenyldiazomethane (12.3 g) in acetonitrile (200 cc) is added, in the course of 15 minutes, to a suspension of the preceding mixture in acetonitrile (500 cc), and the reaction mixture is then stirred for 2 hours at 25° C. The solvent is evaporated under reduced pressure (40 mm Hg) at 30° C. and the oily residue is redissolved in ethyl acetate (500 cc). The solution is washed successively with normal hydrochloric acid (until colourless), with a saturated sodium bicarbonate solution (3×100 cc), with water (100 cc) and with a saturated sodium chloride solution (100 cc), and is then dried and concentrated to dryness, to give a mixture (35.4 g) of 2-benzhydryloxycarbonyl-3-methyl-8-oxo-7-tritylamino-5-thia-1-aza-bicyclo[4.2.0]oct-2-ene (40 %) and its oct-3-ene isomer (60%), in the form of a cream-coloured froth.

Infrared spectrum (CHBr₃); characteristic bands (cm⁻¹) at 3340, 1765, 1730, 1620, 1590, 1490, 1445, 745 and 700.

Proton nuclear magnetic resonance spectrum (CDCl₃, 350 MHz, δ in ppm, J in Hz): 1.73 (s, —CH₃ of the oct-3-ene); 2.04, s, —CH₃ of the oct-2-ene); 3.05 and 3.30 (2d, AB, J=18, —SCH₂— of the oct-2-ene); 4.20 (2d, J=4, H in the 6-position of the oct-2-ene and oct-3-ene); 4.60 (2dd, J=4 and 10, H in the 7-position of the oct-2-ene and oct-3-ene); 4.80 (s, H in the 2-position of the oct-3-ene); 5.75 (s broad, H in the 4-position of oct-2-ene); 6.78 (s, —CO₂CH(C₆H₅)₂ of the oct-3-ene); 6.89 (s, —CO₂CH(C₆H₅)₂ of the oct-2-ene); 7.2 to 7.50 (aromatics).

The mixture of 2-carboxy-3-methyl-8-oxo-7-tritylamino-5-thia-1-aza-bicyclo[4.2.0]octene (40%) and its oct-3-ene isomer (60%) can be obtained in the following manner:

Triethylamine (55.6 cc) is added to a suspension of 7-amino-2-carboxy-3-methyl-8-oxo-5-thia-1aza-bicyclo[4.2.0]oct-2-ene (42.8 g) in dry N,N-dimethylformamide (250 cc), and after cooling the mixture to −20° C. a solution of chlorotriphenylmethane (55.8 g) in chloroform (250 cc) is added in the course of 2 hours. The reaction mixture is stirred for 24 hours at 25° C. and then poured into normal hydrochloric acid (400 cc). After filtration, the organic phase is separated off, concentrated to half its volume under reduced pressure (40 mm Hg) at 40° C., and taken up in ethyl acetate (400 cc). The aqueous phase is extracted with ethyl acetate (400 cc), and the combined organic phases are washed with normal hydrochloric acid (2×250 cc) and then extracted with a half-saturated sodium bicarbonate solution (4×500 cc). These combined aqueous phases are washed with ethyl acetate (300 cc), then acidified to pH 3 with 12 N hydrochloric acid and extracted with ethyl acetate (2×500 cc). The combined organic solutions are washed with a saturated sodium chloride solution (250 cc), dried over sodium sulphate and concentrated to dryness under reduced pressure (40 mm Hg) at 40° C. The residue is caused to solidify by adding isopropyl ether (250 cc). The solid is filtered off, washed with isopropyl ether (100 cc) and dried. A mixture (22.2 g) of 2-carboxy-3-methyl-8-oxo-7-tritylamino-5-thia-1-aza-bicyclo[4.2.0]oct-2-ene (40%) and its oct-3-ene isomer (60%) is obtained in the form of a cream-coloured solid.

Infrared spectrum (CHBr$_3$): characteristic bands (cm$^{-1}$) at 3320, 3300, 2400, 1765, 1730, 1625, 1595, 1490, 750 and 710.

Proton nuclear magnetic resonance spectrum (CDCl$_3$, 350 MHz, δ in ppm, J in Hz): 1.84 (s, —CH$_3$ of the oct-3-ene); 2.16 (s, —CH$_3$ of the oct-2-ene); 3.10 and 3.40 (2d, J=10, —SCH$_2$— of the oct-2-ene); 4.2 (2d, J=4, H in the 6-position of the oct-2-ene and oct-3-ene); 4.6 (2dd, J=4 and 10, H in the 7-position of the oct-2-ene and oct-3-ene); 4.73 (s, H in the 2-position of the oct-3-ene); 5.77 (s broad, H in the 4-position of the oct-3-ene; 7.2 to 7.5 (aromatics).

EXAMPLE 25

2-Benzhydryloxycarbonyl-3-methyl-8-oxo-7-phenylacetamido-5-thia-1-aza-bicyclo[4.2.0]oct-2-ene (4.6 g) (prepared according to Netherlands Patent Application 7,303,263) is dissolved in dimethylformamide (44 cc) at 80° C. A solution of ethoxy-bis-(dimethylamino)-methane (2.68 g) in dimethylformamide (2.67 cc) is added in the course of 30 minutes. The resulting solution is then poured into a mixture of water (100 cc), ice (100 cc) and ethyl acetate (300 cc). The organic phase is decanted, washed with water (2×200 cc) and then with a saturated sodium chloride solution (100 cc), dried over sodium sulphate, filtered and evaporated to dryness under reduced pressure (40° C., 20 mm Hg, 2.7 kPa). This gives 2-benzhydryloxycarbonyl-3-(2-dimethylamino-vinyl)-8-oxo-7-phenylacetamido-5-thia-1-aza-bicyclo[4.2.0]oct-2-ene, E-form (5.0 g) in the form of a brown oil.

Infrared spectrum (CHBr$_3$): characteristic bands in cm$^{-1}$ at 3320, 1680, 1755, 1620 and 1540.

Proton nuclear magnetic resonance spectrum (350 MHz, CDCl$_3$, δ in ppm, J in Hz): 2.72 (s, 6H, —N(CH$_3$)$_2$); 2.30 and 3.15 (2d, J=18, 2H, —SCH$_2$—); 3.65 (s, 2H,

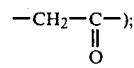

4.93 (d, J=4, 1H, H$_6$); 5.34 (dd, J=4 and 8, 1H, H$_7$); 6.01 (d, J=12, 1H, —C<u>H</u>=CH—N<); 6.11 (d, J=12, 1H, —CH=C<u>H</u>—N<); 6.66 (s, 1H, —CH< (benzhydryl)); 7.2 to 7.5 (m, 15H, aromatic); 7.56 (d, J=8, 1H, >NH).

EXAMPLE 26 bis-Dimethylamino-butoxymethane (7.8 g) is added, in the course of 30 seconds, to a solution of 2-benzhydryloxycarbonyl-3-methyl-8-oxo-7-phenoxyacetamido-5-thia-1-aza-bicyclo[4.2.0]oct-2-ene (21 g) in dimethylformamide (400 cc), which has been heated to 80° C. The solution becomes greenish brown. After 5 minutes at 80° C., the solution is poured into a mixture of water (500 cc), ice (500 g) and ethyl acetate (1500 cc). The organic phase is washed with water (2×1000 cc) and then with a saturated sodium chloride solution (500 cc), dried over magnesium sulphate and concentrated to dryness under reduced pressure (20 mm Hg, 2.7 kPa). The residue is dissolved in ethyl acetate (75 cc), the solution is poured into ethyl ether (250 cc) and the mixture is filtered; the filtrate is concentrated to dryness under reduced pressure (20 mm Hg, 2.7 kPa), the residue is dissolved in ethyl acetate (50 cc) and the solution is poured into isopropyl ether (250 cc). The precipitate formed is filtered off and then dried. This gives 2-benzhydryloxycarbonyl-3-(2-dimethylamino-vinyl)-8-oxo-7-phenoxyacetamido-5-thia-1-aza-bicyclo[4.2.0]oct-2-ene, E-form (11 g) in the form of a yellow solid.

Infrared spectrum (KBr): characteristic bands (cm$^{-1}$) at 3320, 1765, 1690, 1615, 1540, 1500, 1460, 1240, 760 and 705.

Proton nuclear magnetic resonance spectrum (350 MHz, CDCl$_3$, δ in ppm, J in Hz): 2.90 (s, 6H, —N(CH$_3$)$_2$; 2.93 and 3.18 (2d, J=14, 2H, —S—CH$_2$—); 4.62 (s broad, 2H, —OCH$_2$—CO—); 5.11 (d, J=4, 1H, H in the 6-position); 5.43 (dd, J=4 and 8, 1H, H in the 7-position); 6.42 (d, J=14, 1H, —CH=CH—N<); 6.57 (d, J=14, 1H, —C<u>H</u>=CH—N<); 6.85(s, 1H, —COOCH<); 7.92 (d, J=8, 1H, —CON<u>H</u>—).

II. The reference examples which follow show how the products of the invention can e used for the preparation of cephalosporins of the general formula (XX).

REFERENCE EXAMPLE 1

A. bis-(Dimethylamino)-ethoxymethane (0.91 g) is added to a solution of 2-benzhydryloxycarbonyl-7-[2-methoxyimino-2-(2-tritylamino-thiazol-4-yl)-acetamido]-3-methyl-8-oxo-5-thia-1-aza-bicyclo[4.2.0]oct-2-ene (syn isomer) (2.5 g) in dimethylformamide (50 cc), which has been heated to 80° C. The solution becomes brownish green. It is left at 80° C. for 20 minutes and then cooled rapidly and poured into ethyl acetate (200 cc) and the mixture is washed with water (three x 80 cc) and with a saturated sodium chloride solution (50 cc). The ethyl acetate phase contains, in solution, the intermediate product 2-benzhydryloxycarbonyl-3-(2-dimethylamino-vinyl)-8-oxo-7-[2-methoxyimino-2-2-tritylamino-thiazol-4-yl)-acetamido]-5-thia-1-aza-bicyclo-[4.2.0 oct-2-ene (described in Example 22), which can be used directly for the next stage. This solution is stirred at 20° C. for one hour in the presence of 1 N hydrochloric acid (37.5 cc). The aqueous phase is removed, and the organic phase is washed with a saturated sodium bicarbonate solution (20 cc) and then with a saturated sodium chloride solution (20 cc). The organic phase is dried over magnesium sulphate, filtered in the presence of decolorising charcoal and then concentrated to dryness under reduced pressure (20 mm Hg) at 40° C. The residue is dissolved in anhydrous pyridine (10 cc). The solution is cooled to 5° C. in an ice bath, tosyl chloride (0.87 g) is added and the reaction mixture is allowed to return to 20° C. After 1½ hours, the mixture is poured onto iced water (200 cc). The precipitaed formed is filtered off, washed with water (2×20 cc) and then dissolved in ethyl acetate (50 cc). This solution is washed with a saturated sodium bicarbonate solution (20 cc) and a saturated sodium chloride solution (20 cc), dried over magnesium sulphate, filtered in the presence of decolorising charcoal and concentrated to dryness under reduced pressure (20 mm Hg) at 40° C. The residue is dissolved in methylene chloride (13 cc) and the solution obtained is cooled to −10° C. in an ice/methanol bath. A solution of 85pure m-chloroperbenzoic acid (0.226 g) in methylene chloride (10 cc) is added in the course of 15 minutes. The reaction mixture is left at between −10° C. and +5° C. for 20 minutes and is then washed twice with a saturated sodium bicarbonate solution (20 cc), dried over magnesium sulphate, filtered in the presence of decolorising charcoal and concentrated to dryness under reduced pressure (20 mm Hg) at 40° C.

The residue is chromatographed over a column (diameter: 1.7 cm, height: 21 cm) containing silica gel (26g). Elution is carried out with ethyl acetate/cyclohexane mixtures (120, 240, 200 and 120 cc, with respective compositions of 20:80, 30:70, 40:60 and 60:40 by volume), and 20 cc fractions of eluate are collected. Fractions 17 to 34 ae evaporated and 2-benzhydryloxycarbonyl-7-[2-methoxyimino-2-(2-tritylaminothiazol-4l-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (0.88 g) is isolated.

B. A mixture of 2-benzhydryloxycarbonyl-7-[2-methoxyimino-2-(2-tritylamino-thiazol-4-yl)-acetamido]-8-oxo-5-oxide-3-(2-tosyloxy-vinyl)-5-thia-1-azabicyclo[4.2.0]oct-2-ene (syn isomer, mixture of the E- and Z-forms) (8,03 g), dimethylformamide (80 cc), methylmercaptan (1.59 g) and N-ethyl-N,N-diisopropylamine (1.53 cc) is heated in an autoclave at 40° C. for 5 hours. It is then diluted with ethyl acetate (500 cc), and this mixture is washed with water (3×250 cc), 0.1 N hydrochloric acid (100 cc), a 1% strength sodium bicarbonate solution (100 cc) and a half-saturated sodium chloride solution (2×200 cc), dried over sodium sulphate and concentrated to dryness under reduced pressure (20 mm Hg) at 20° C.

The residue is dissolved in a 50:50 (by volume) mixture of cyclohexane and ethyl acetate (100 cc) and the solution is chromatographed on a column (column diameter: 6 cm, height: 36 cm) of Merck silica gel (0.04–0.06 mm) (300 g). Elution is carried out with a 50:50 (by volume) mixture of cyclohexane and ethyl acetate (8 liters) under a pressure of 40 kPa, 125 cc fractions being collected. Fractions 25 to 57 are collected and evaporated to dryness under reduced pressure (20 mm Hg) at 20° C. 2-Benzhydryloxycarbonyl-7-[2-methoxyimino-2-(2-tritylamino-thiazol-4-yl)-acetamido]-3-(2-methylthio-vinyl)-8-oxo-5-oxide-5-thia-1-aza-bicyclo[4.2.0]oct-2-ene (syn isomer, mixture of the E- and Z-forms) (3.7 g) is obtained in the form of a cream-coloured froth.

Infrared spectrum (CHBr$_3$): characteristic bands (cm$^{-1}$) at 3380, 1800, 1720, 1680, 1515, 1370, 1205, 1045, 835, 750 and 740.

Proton nuclear magnetic resonance spectrum (350 MHz, CDCl$_3$, δ in ppm, J in Hz): 2.17 (s, 3H, —CH$_3$, E-form); 2.35 (s, 3H, —CH$_3$, Z-form); 3.23 and 3.98 (AB, J=18, 2H, —SCH$_2$—, E-form); 3.44 and 4.3 (AB, J=18, 2H, —SCH$_2$—, E-form); 3.44 and 4.3 (AB, J=18, 2H, —SCH$_2$—, Z-form); 4.09 (s, 3H, —OCH$_3$); 4.58 (d, J=9, 1H, H in the 6-position); 6.12 (dd, J=4 and 9, 1H, H in the 7-position); 6.17 (d, J=10, 1H, —CH═CH—S—CH$_3$, Z-form); 6.65 (d, J=15, 1H, —CH═CH—S—CH$_3$, E-form); 6.88 (d, J=10, 1H, ═CH—S—CH$_3$, Z-form); 7.15 (d, J=15, 1H, ═CH—S—CH$_3$, E-form); 6.72 (s, 1H, H in the 5-position of the thiazole); 6.98 (s, 1H, —COOCH<); 7.07 (s broad, 1H, (C$_6$H$_5$)$_3$CNH—).

A solution of 2-benzhydryloxycarbonyl-7-[2-methoxyimino-2-(2-tritylamino-thiazol-4-yl)-acetamido]-3-(2-methylthio-vinyl)-8-oxo-5-oxide-5-thia-1-aza-bicyclo-[4.2.0]oct-2-ene (syn isomer, mixture of the E- and Z-forms) (2.30 g) in methylene chloride (25 cc) and dimethylacetamide (1.04 cc) is treated with phosphorus trichloride (0.46 cc) at −10° C. for 30 minutes. The mixture is diluted with ethyl acetate (500 cc) and this mixture is washed with a 2% strength sodium bicarbonate solution (2×100 cc) and a half-saturated sodium chloride solution (2×100 c), dried over sodium sulphate, filtered and concentrated to dryness under reduced pressure (20 mm Hg) at 20° C.

The residue is dissolved in methylene chloride (10 c) and the solution is chromatographed on a column (column diameter: 4 cm, height: 20 cm) of Merck silica gel (0.04–0.06 mm) (150 g). Elution is carried out with a 60:40 (by volume) mixture of cyclohexane and ethyl acetate (2 liters) under a pressure of 40 kPa, 125 cc fractions being collected. Fractions 4 to 8 are concentrated under reduced pressure (20 mm Hg) at 20° C. and 2-benzhydryloxycarbonyl-7-[2-methoxyimino-2-(2-tritylamino-thiazol-4-yl)-acetamido]-3-(2-methylthiovinyl)-8-oxo-5-thia-1-aza-bicyclo[4.2.0]oct-2-ene (syn isomer, mixture of the E- and Z-forms) (1.32 g) is obtained in the form of a cream-coloured froth.

Infrared spectrum (CHBr$_3$): characteristic bands (cm$^{-1}$) at 3390, 1780, 1715, 1680, 1515, 1370, 1200, 1050, 1035, 750 and 740.

Proton nuclear magnetic resonance spectrum (350 MHz, CDCl$_3$, δ in ppm, J in Hz): 2.18 (s, 3H, —CH$_3$, E-form); 2.18 (s, 3H, —CH$_3$, E-form); 2.31 (s, 3H, —CH$_3$, Z-form); 3.44 (AB, J=18, 2H, —SCH$_2$—, E-form); 3.80 (AB, J=18, 2H, —SCH$_2$—, Z-form); 4.08 (s, 3H, —OCH$_3$); 5.06 (d, J=4, 1H, H in the 6-position); 5.80 (dd, J=4 and 9, 1H, H in the 7-position, E-form); 5.90 (dd, J=4 and 9, 1H, H in the 7-position, Z-form); 6.14 (d, J=11, 1H, —CH═CHS—, Z-form); 6.64 (d, J=16, 1H, —CH═CHS—, E-form); 6.70 (d, J=11, 1H, ═CHS—, Z-form); 6.79 (s, 1H, H in the 5-position of the thiazole); 6.93 (s, 1H, —COOCH<); 6.98 (d, J=16, 1H, ═CHS, E-form).

2-Benzhydryloxycarbonyl-7-[2-methoxyimino-2-(2-tritylamino-thiazol-4-yl)-acetamido]-3-(2-methylthiovinyl)-8-oxo-5-thia-1-aza-bicyclo[4.2.0]oct-2-ene (syn isomer, mixture of E- and Z-forms) (1.26 g) is dissolved in formic acid (35 cc), water (13 cc) is added and the mixture is heated at 50° C. for 15 minutes. It is then allowed to cool, filtered and concentrated to dryness under reduced pressure (20 mm Hg at 20° C.). The residue is triturated in diethyl ether (20 cc), filtered off, washed with ether (20 cc) and dried. 7-[2-(2-Aminothiazol-4-yl)-2-methoxyimino-acetamido]-2-carboxy-3-(2-methylthio-vinyl)-8-oxo-5-thia-1-aza-bicyclo[4.2.0]oct-2-ene (syn isomer, mixture of E- and Z-forms) (0.63 g) is obtained as a solvate with formic acid, in the form of a cream-coloured powder.

Rf=0.34 and 0.48 [silica gel chromatographic plate, solvent: a 60:20:1:1 (by volume) mixture of ethyl acetate, acetone, formic acid and water].

Infrared spectrum (KBr): characteristic bands ($cm^{-1}$) at 3320, 1770, 1675, 1530 and 1035.

Proton nuclear magnetic resonance spectrum (350 MHz, DMSO $d_6$, δ in ppm, J in Hz): E-form: 2.34 (s, 3H, —$SCH_3$); 3.61 and 3.77 (AB, J=18, 2H, —$SCH_2$—); 3.86 (s, 3H, —$OCH_3$); 5.14 (d, J=4, 1H, H in the 6-position); 5.62 (dd, J=4 and 9, 1H, H in the 7-position); 6.77 (s, 1H, H in the 5-position of the thiazole); 6.85 (d, J=16, 1H, —CH=CH—S—); 7.04 (d, J=16, 1H, =CH—S—); 9.57 (d, J=9, 1H, —CONH—). Z-form: in particular, the following signals are observed: 2.25 (s, 3H, —$SCH_3$), 6.74 (d, J=13, 1H, —CH=CH—S—$CH_3$) and 6.89 (d, J=13, 1H, =CHS—).

REFERENCE EXAMPLE 2

A solution of formic acid (50 cc) in water (500 cc) is added to a solution of 2-benzhydryloxycarbonyl-7-tert.-butoxycarbonylamino-3-(2-dimethylaminovinyl)-8-oxo-5-thia-1-aza-bicyclo[4.2.0]oct-2-ene (E-form) (113.7 g) (described, in particular, in Example 2) in tetrahydrofurane (1 liter). The homogeneous solution is stirred at 20° C. for 20 minutes and is then concentrated to a quarter of its volume under reduced pressure (20 mm Hg) at 20° C. The concentrate is taken up in ethyl acetate (2 liters) and this mixture is washed with a 5% strength sodium bicarbonate solution (2×500 cc), water (2×500 cc) and a saturated sodium chloride solution (2×500 cc), dried over sodium sulphate, filtered and evaporated to dryness at 20° C. under reduced pressure (20 mm Hg). A crude product (112.4 g) is obtained, which is dissolved in anhydrous pyridine (250 cc), and the solution is treated, at 5° C., with tosyl chloride (57.2 g). After 30 minutes at 5° C. and 1 hour at 20° C., the solution is poured into a mixture of water and crushed ice (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength sodium bicarbonate solution (2×750 cc) and water (4×750 cc), dried over sodium sulphate and concentrated to dryness under reduced pressure (20 mm Hg) at 20° C. A mixture (121 g) consisting principally of 2-benzhydryloxycarbonyl-7-tert.-butoxycarbonylamino-8-oxo-3-(2-tosyloxyvinyl)-5-thia-1-aza-bicyclo[4.2.0]oct-2-ene (a mixture of the E- and Z-forms) is obtained in the form of a crude brown froth.

A solution of 85% strength m-chloroperbenzoic acid (55.22 g) in methylene chloride (600 cc) is added dropwise in the course of 2 hours to a solution, cooled to −10° C., of 2-benzhydryloxycarbonyl-7-tert.-butoxycarbonylamino-8-oxo-3-(2-tosyloxyvinyl)-5-thia-1-aza-bicyclo[4.2.0]oct-2-ene (or oct-3-ene) (a mixture of the E- and Z-forms) (180.56 g) in methylene chloride (1.4 liters). The mixture is washed with a 5% strength solution of sodium bicarbonate (1.5 liters) and with water (2×1.5 liters), dried over sodium sulphate and concentrated at 20° C. under reduced pressure (20 mm Hg) to a volume of 300 cc. This solution is chromatographed on a column (column diameter: 9.2 cm; height: 145 cm) of Merck silica gel (0.05–0.2 mm) (3 kg). Elution is carried out successively with an 80:20 (by volume) mixture (15 liters) and a 70:30 (by volume) mixture (32 liters) of cyclohexane and ethyl acetate, 600 cc fractions being collected. Fractions 27 and 28 are collected and concentrated to dryness and 2-benzhydryloxycarbonyl-7-tert.-butoxycarbonylamino-8-oxo-5-oxide-3-(2-tosyloxyvinyl)-5-thia-1-aza-bicyclo-[4.2.0]oct-2-ene (Z-form) (5.56 g) is obtained.

Infra-red spectrum ($CHBr_3$): characteristic bands ($cm^{-1}$) at 3420, 1800, 1720, 1505, 1380, 1370, 1195, 1180, 1050, 1010 and 730.

Proton nuclear magnetic resonance spectrum (350 MHz, $CDCl_3$, δ in ppm, J in Hz): 1.49 (s, 9H, —C($CH_3$)$_3$); 2.44 (s, 3H, —$CH_3$); 3.36 and 4.04 (2 d, J=19, 2H, —$SCH_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —CH=CH—$OSO_2$—); 6.46 (d, J=7, 1H, =CH—$OSO_2$—); 6.89 (s, 1H, —COOCH<); 7.77 (d, J=9, 2H, H in the ortho-position of the tosyl group).

A mixture (26 g) of the Z- and E-forms is obtained from fractions 29 to 34.

Finally, the E-form of the product (43 g) is obtained from fractions 35 to 58.

Infra-red spectrum ($CHBr_3$): characteristic bands ($cm^{-1}$) at 3420, 1800, 1720, 1505, 1380, 1370, 1195, 1180, 1075, 935 and 745.

Proton nuclear magnetic resonance spectrum (350 MHz, $CDCl_3$, δ in ppm, J in Hz): 1.48 (s, 9H, ($CH_3$)$_3$C—); 2.46 (s, 3H, —$CH_3$); 3.16 and 3.81 (2 d, J=18, 2H, —$SCH_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —CH=CH—$OSO_2$—); 6.83 (s, 1H, —COOCH<); 7.08 (d, J=13, 1H, =CH $OSO_2$—); 7.73 (d, J=9, 2H, H in the ortho-position of the tosyl group).

A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (Z-form) (5.44 g), dimethylformamide (40 cc), 1-methyl-2-mercapto-tetrazole (1.88 g) and N-ethyl-N,N-diisopropylamine (2.8 cc) is heated at 60° C. for 1 hour, whilst stirring. The mixture is then diluted with ethyl acetate (250 cc) and washed successively with water (3×100 cc), 0.1 N hydrochloric acid (100 cc), a 2% strength sodium bicarbonate solution (2×100 cc) and a half-saturated sodium chloride solution (2×100 cc), dried over sodium sulphate, filtered and concentrated to dryness under reduced pressure (20 mm Hg at 20° C.). The residue is fixed on silica gel (20 g) and charged onto a column (column diameter: 3 cm, height: 12 cm) of Merck silica gel (0.05–0.2 mm) (80 g). Elution is carried out successively with the following mixtures of cyclohexane and ethyl acetate: 90:10 (by volume) (250 cc), 80:20 (by volume) (500 cc), 70:30 (by volume) (1,000 cc), 60:40 (by volume) (2,000 cc) and 40:60 (by volume) (2,000 cc), 125 cc fractions being collected. Fractions 34 to 45 are collected and concentrated to dryness and 2-benzhydryloxycarbonyl-7-tert.-butoxycarbonylamino-3-[2-(1-methyltetrazol-5-yl)-thiovinyl]-8-oxo-5-oxide-5-thia-1-aza-bicyclo[4.2.0]oct-2-ene (Z-form) (3.44 g) is obtained in the form of a light brown froth.

Infra-red spectrum ($CHBr_3$): characteristic bands ($cm^{-1}$) at 3410, 1800, 1720, 1500, 1370, 1230, 1045, 755 and 740.

Proton nuclear magnetic resonane spectrum (350 MHz, CDCl$_3$, δ in ppm, J in Hz): 1.48 (s, 9H, (CH$_3$)$_3$C—); 3.81 (s, 3H, >NCH$_3$); 3.38 and 4.03 (2d, J=18, 2H, —SCH$_2$—); 4.58 (d, J=4.5, 1H, H in the 6-position); 5.75 (d, J=9, 1H, —CONH—); 5.85 (dd, J=4.5 and 9, 1H, H in the 7-position); 6.70 (d, J=9.5, 1H, —C<u>H</u>=CH—S—); 6.79 (d, J=9.5, 1H, =CHS—); 6.98 (s, 1H, —COOCH<).

A mixture of 2-benzhydryloxycarbnyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (Z-form) (3.11 g), acetonitrile (50 cc) and p-toluene-sulphonic acid monohydrate (1.9 g) is stirred for 16 hours at 25° C. It is then concentrated under reduced pressure (20 mm Hg) at 20° C., and the residue is stirred in the presence of ethyl acetate (100 cc) and a 5% strength sodium bicarbonate solution (100 cc). The organic phase is decanted, washed with a 5% strength sodium bicarbonate solution (50 cc) and a half-saturated sodium chloride solution (2×50 cc), dried over sodium sulphate, filtered and concentrated to dryness under reduced pressure (20 mm Hg at 20° C.). This gives 7-amino-2-benzhydryloxycarbonyl-3-[2-(1-methyl-tetrazol-5-yl)-thiovinyl]-8-oxo-5-oxide-5-thia-1-aza-bicyclo[4.2.0]-oct-2-ene (Z-form) (1.55 g) in the form of a crude brown froth.

Rf=0.21 [silica gel chromatographic plate, solvent: and 85:15 (by volume) mixture of dichloroethane and methanol].

Dicyclohexylcarbodiimide (0.71 g) is added to a solution, cooled to 4° C., of syn-2-methoxyimino-2-(2-tritylamino-thiazol-4-yl)-acetic acid (2.89 g) in methylene chloride (10 cc). The solution is stirred for 40 minutes at 4° C. and then for 30 minutes at 20° C., and is filtered.

To this filtered solution, cooled to −30° C., is added a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (Z-form) (1.55 g) in methylene chloride (13 cc) containing triethylamine (0.46 cc). The cooling bath is removed and the mixture is stirred for 1 hour 50 minutes at 20° C. It is then concentrated under reduced pressure (20 mm Hg) at 20° C. and the residue is taken up in ethyl acetate (100 cc). This organic phase is washed with water (3×50 cc), 0.05 N hydrochloric acid (50 cc), a 1% strength sodium bicarbonate solution (50 cc) and half-saturated aqueous sodium chloride (2×50 cc), dried over sodium sulphate, filtered and concentrated to dryness under reduced pressure (20 mm Hg) at 20° C. The concentrate is redissolved in a 10:90 (by volume) mixture of cyclohexane and ethyl acetate (25 cc) and the solution if chromatographed on a column (column diameter: 5 cm, height: 33 cm) of Merck silica gel (0.04–0.06 mm) (300 g). Elution is carried out with a 10:90 (by volume) mixture of cyclohexane and ethyl acetate (3 liters) under a nitrogen pressure of 0.4 bar, 110 cc fractions being collected. After concentrating fractions 9 to 17 to dryness, and drying this product, 2-benzhydryloxycarbonyl-7-[2-methoxyimino-2-(2-tritylamino-thiazol-4-yl)-acetamido]- 3-[(1-methyl-tetrazol-5-yl)-thiovinyl]-8-oxo-5-oxide- 5-thia-1-aza-bicyclo[4.2.0]oct-2-ene (syn isomer, Z-form) (0.98 g) is obtained in the form of a yellow froth.

Infra-red spectrum (CHBr$_3$): characteristic bands (cm$^{-1}$) at 3380, 1805, 1725, 1680, 1515, 1050, 755 and 740.

Proton nuclear magnetic resonance spectrum (350 MHz, CDCl$_3$, δ in ppm, J in Hz): 3.81 (s, 3H, >NCH$_3$); 3.89 and 4.01 (2 d, J=19, 2H, —S—CH$_2$—); 4.10 (s, 3H, —OCH$_3$); 4.66 (d, J=4, 1H, H in the 6-position); 6.24 (dd, J=4 and 10, 1H, H in the 7-position); 6.72 and 6.76 (2 d, J=10, 2H, —C<u>H</u>=C<u>H</u>S—); 6.98 (s, 1H,

—COOCH—);
      |

6.72 (s, 1H, H in the 5-position of the thiazole); 7.07 (s, 1H, (C$_6$H$_5$)$_3$C—N<u>H</u>—).

Phosphorus trichloride (0.17 cc) is added to a solution, cooled to −10° C., of 2-benzhydryloxycarbonyl-7-[2-methoxyimino-2-(2-tritylamino-thiazol-4-yl)-acetamido]- 3-[2-(1-methyl-tetrazol-5-yl)-thiovinyl]-8-oxo-5-oxide- 5-thia-1-aza-bicyclo[4.2.0]oct-2-ene (syn isomer, Z-form) (0.93 g) in methylene chloride (10 cc) and dimethylacetamide (0.39 cc) and the mixture is stirred for 45 minutes at the same temperature. It is then diluted with ethyl acetate (200 cc) and this mixture is washed with 2% strength sodium bicarbonate solution (2×50 cc) and a saturated sodium chloride solution (2×50 cc), dried over sodium sulphate, filtered and concentrated to dryness under reduced pressure (20 mm Hg) at 20° C. The residue is fixed on Merck silica gel (0.05–0.2 mm) (5 g) and the powder is charged onto a column (diameter: 2 cm, height: 8 cm) of Merck silica gel (0.05–0.2 mm) (15 g). Elution is carried out successively with the following mixtures of cyclohexane and ethyl acetate: 75:25 (by volume) (100 cc), 50:50 (by volume) (250 cc) and 25:75 (by volume) (250 cc), 60 cc fractions being collected. Fractions 3 to 7 are concentrated to dryness under reduced pressure (20 mm Hg) at 25° C. and 2-benzhydryloxycarbonyl-7-[2methoxyimino-2-(2-trityl-amino-thiazol-4-yl)-acetamido]-3-[2-(1-methyl-tetrazol-5-yl)-thiovinyl]-8-oxo-5-thia-1-aza-bicyclo[4.2.0]oct-2-ene (syn isomer, Z-form) (0.74 g) is obtained in the form of a yellow froth.

Infra-red spectrum (CHBr$_3$): characteristic bands (cm$^{-1}$) at 3400, 1790, 1725, 1685, 1515, 1370, 1050, 755 and 740.

Proton nuclear magnetic resonance spectrum (350 MHz, CDCl$_3$, δ in ppm, J in Hz): 3.56 and 3.69 (2 d, J=17.5, 2H, —SCH$_2$—; 3.81 (s, 3H, >NCH$_3$); 4.09 (s, 3H, —OCH$_3$); 5.13 (d, J=4, 1H, H in the 6-position); 5.99 (dd, J=4 and 10, 1H, H in the 7-position); 6.76 (AB, J=11, 2H, —CH=CH S—); 6.9 (d, J=10, 1H, —CONH—); 6.97 (s, 1H,

—COOCH—);
      |

7.01 (s, 1H, (C$_6$H$_5$)$_3$CNH—).

2-Benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-thia-1-aza-bicyclo-[4.2.0]oct-2-ene (syn isomer, Z-form) (0.67 g) is dissolved in trifuloracetic acid (3.6 cc) and anisole (0.07 cc). The mixture is stirred for 1 hour at 5° C. and then for 30 minutes at 20° C., and is concentrated to dryness under reduced pressure (20 mm Hg) at 20° C. The residue is redissolved in trifluoroacetic acid (2 cc) and the solution is poured, with stirring, into ethyl ether (10 cc). After filtering and drying, 7-[2-(2-amino-thiazol-4-yl)-2-methoxyimino-acetamido]-2-carboxy-3-[2-(1-methyltetrazol-5-yl)-thiovinyl]-8-oxo-5-thia 1-aza-bicyclo[4.2.-0]oct-2-ene (syn isomer, Z-form) trifuloroacetate (0.33 g) is obtained.

Rf=0.50 [silica gel chromotographic plate, solvent: a 50:20:10:10 (by volume) mixture of ethyl acetate, acetone, acetic acid and water].

Infra-red spectrum (KBr): characteristic bands ($cm^{-1}$) at 3300, 1785, 1675, 1180, 1140 and 1050.

Proton nuclear magnetic resonance spectrum (350 MHz, DMSO $d_6$, δ in ppm, J in Hz): 3.8 and 3.85 (AB, J=17.5, 2H, —$SCH_2$—); 3.93 (s, 3H, >$NCH_3$); 4.0 (s, 3H, —$OCH_3$); 5.26 (d, J=4, 1H, H in the 6-position); 5.85 (dd, J=4 and 10, H in the 7-position); 6.75 (d, J=11, 1H, —C$\underline{H}$=CH—S—); 6.87 (s, 1H, H in the 5-position of the thiazole); 6.91 (d, J=11, 1H, =CH—S—); 9.34 (d, J=10, 1H, —CONH—).

REFERENCE EXAMPLE 3

A solution of 2-benzhydryloxycarbonyl-7-tert.-butoxycarbonylamino-8-oxo-5-oxide-3-(2-tosyloxyvinyl)-5-thia-1-aza-bicylco[4.2.0]oct-2-ene (mixture of the E- and Z-forms) (4.06 g) (obtained as described in Reference Example 2 ) in acetonitrile (150 cc) is stirred with p toluenesulphonic acid monohydrate (2.28 g) at 20° C. for 16 hours. The mixture is concentrated under reduced pressure (20 mm Hg) at 20° C. to a volume of 10 cc and is diluted with ethyl acetate (150 cc), and this mixture is washed with a 2% strength sodium bicarbonate solution (100 cc) and then with saturated aqueous sodium chloride (2×150 cc), dried over sodium sulphate and concentrated to dryness under reduced pressure (20 mm Hg) at 20° C. 7-Amino-2-benzhydryloxycarbonyl-8-oxo-5-oxide-3-(2-tosyl-oxyvinyl) -5-thia-1-aza-bicyclo[4.2.0]oct-2-ene (mixture of the E- and Z-forms) (3.5 g) is obtained in the form of a crude brown solid.

Infra-red spectrum (KBr): characteristic bands ($cm^{-1}$) at 3430, 3360, 1780, 1725, 1370, 1180, 1170, 1070, 745 and 700.

Proton nuclear magnetic resonance spectrum (350 MHz, $CDCl_3$, δ in ppm, J in Hz): 2.43 (s, 3H, —$CH_3$); 3.12 and 3.75 (2 d, J=18, 2H, —$SCH_2$—); 4.36 (d, J=4, 1H, H in the 6-position); 4.74 (d, J=4, 1H, H in the 7-position); 6.87 (d, J=12, 1H, —C$\underline{H}$=CH—$OSO_2$—); 6.90 (s, 1H, COOCH<); 6.99 (d, J=12, 1H, =CH—$OSO_2$—); 7.40 and 7.71 (2 d, J=9, —$C_6H_4$—).

Dicyclohexylcarbodiimide (1.85 g) is added, with stirring, to a solution, cooled to +4° C., of syn-2-methoxyimino-2-(2-tritylamino-thiazol-4-yl)-acetic acid (7.97 g) in methylene chloride (100 cc). The solution is stirred for 40 minutes at +4° C. and then for 30 minutes at 20° C., and is filtered.

A solution of crude 7-amino-2-benzhydryloxy-carbonyl-8-oxo-5-oxide-3-(2-tosyloxyvinyl)-5-thia-1-aza-bicyclo[4.2.0]oct-2-ene (mixture of the E- and Z-forms) (3.47 g) in methylene chloride (30 cc) containing triethylamine (0.84 cc) is added rapidly to the preceding filtered solution, cooled to −30° C. The cooling bath is removed at the end of the addition and the reaction mixture is stirred for 1 hour 50 minutes at 20° C. It is then concentrated to dryness at 20° C. under reduced pressure (20 mm Hg) and the residue is taken up in ethyl acetate (250 cc). The organic phase is washed with water (3×100 cc), 0.05 N hydrochloric acid (100 cc), a 1% strength sodium bicarbonate solution (100 cc) and half-saturated aqueous sodium chloride (2×100 cc), dried over sodium sulphate, filtered and concentrated to dryness under reduced pressure (20 mm Hg at 20° C.).

The residue is taken up in ethyl acetate (20 cc), cyclohexane (20 cc) is added, the mixture is filtered and the solution is chromatographed on a column (column diameter: 6 cm, height: 30 cm) of Merck silica gel (0.04–0.06 mm) (300 g). Elution is carried out with a 40:60 (by volume) mixture of cyclohexane and ethyl acetate (4 liters) under a pressure of 40 kPa, 125 cc fractions being collected. Fractions 6 to 25 are concentrated under reduced pressure (20 mm Hg at 20° C.) and 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, mixture of the E- and Z-forms) (4.8 g) is obtained in the form of a cream-coloured froth.

On carrying out a second chromatography identical to the above, the Z-isomer (1.21 g) is obtained from fractions 12 to 16 and the E-isomer (1.49 g) from fractions 22 to 40; fractions 17 to 21 contain a mixture of the E- and Z-isomers (0.8 g).

Z-isomer:

Infra-red spectrum ($CHBr_3$): characteristic bands ($cm^{-1}$) at 3380, 1800, 1720, 1680, 1510, 1375, 1190, 1175, 1045, 1000 and 735.

Proton nuclear magnetic resonance spectrum (350 MHz, $CDCl_3$, δ in ppm, J in Hz): 2.03 (s, 3H, —$C_6H_4$—$CH_3$); 3.36 and 4.07 (2d, J=19, 2H, —$SCH_2$—); 4.09 (s, 3H, —$OCH_3$); 4.52 (d, J=4, 1H, H in the 6-position); 6.16 (dd, J=4 and 9, 1H, H in the 7-position); 6.43 (AB, J=8, 2H, —C$\underline{H}$=C$\underline{H}$—); 6.86 (s, 1H, >CHO-CO—); 6.71 (s, 1H, H in the 5-position of the thiazole); 7.75 (d, J=9, 2H, H in the ortho-position of the tosyl group). E-isomer:

Infra-red spectrum ($CHBr_2$): characteristic bands ($cm^{-1}$) at 3380, 1800, 1725, 1685, 1515, 1380, 1190, 1180, 1070, 1050, 755 and 735.

Proton nuclear magnetic resonance spectrum (350 MHz, $CDCl_3$, δ in ppm, J in Hz): 2.45 (s, 3H, —$C_6H_4C\underline{H}_3$); 3.19 and 3.77 (2 d, J=18, 2H, —$SCH_2$—); 4.08 (s, 3H, —$OCH_3$); 4.6 (d, J=4, H in the 6-position); 6.18 (dd, J=4 and 9, 1H, H in the 7-position); 6.72 (s, 1H, H in the 5-position of the thiazole); 6.93 (d, J=12, 1H, —CH=CH—$OSO_2$—); 7.11 (d, J=12, 1H, —CH=CH—$OSO_2$—); 6.90 (s, 1H, —COOCH<); 7.73 (d, J=9, 2H, H in the ortho-position of the tosyl group).

2-Benzhydryloxycarbonyl-7-[2-methoxyimino-2-(2-tritylamino-thiazol-4-yl)-acetamido]-3-(2-tosyloxyvinyl)-8-oxo-5-oxide-5-thia- 1 -aza-bicyclo[4.2.0]oct-2-ene (syn isomer, E-form) (3 g) is dissolved in methylene chloride (30 cc); N, N-dimethylacetamide (1.2 cc) is added. The solution is placed under an atmosphere of dry nitrogen, cooled to −10° C., and treated with phosphorous trichloride (0.9 g). The reaction mixture is then stirred for 90 minutes at a temperature of between −10° and −5° C., after which it is diluted with ethyl acetate (250 cc), and this mixture is washed with a saturated aqueous sodium bicarbonate solution (150 cc) and a saturated sodium chloride solution (2×100 cc). After drying over magnesium sulphate and filtering, the organic solution is concentrated to dryness under reduced pressure (20 mm Hg) at 30° C; the residue is taken up in methylene chloride (20 cc) and the solution is chromatographed on a column (height: 25 cm, diameter: 5 cm) containing silica (0.40–0.063 mm) (240 g). Elution is carried out with a 60:40 (by volume) mixture of cyclohexane and ethyl acetate (2 liters), 100 cc fractions being collected. Fractions 8 to 13 are concentrated to dryness under reduced pressure (20 mm Hg) at 30° C. 2-Benzhydryloxycarbonyl-7-[2-methoxyimino-2-(2- tritylamino-thiazol-4-yl)-acetamido]-3-(2-tosyloxyvinyl)-8-oxo-5-thia-1-aza-bicyclo[4.2.0]oct-2-ene (syn isomer, E-form) (1.7 g) is obtained.

Rf=0.52; silica gel chromatographic plate; eluant: a 50:50 (by volume) mixture of cyclohexane and ethyl acetate.

Infra-red spectrum(CHBr$_3$): characteristic bands (cm$^{-1}$) at 3400, 1790, 1725, 1685, 1520, 1375, 1190, 1180, 1075, 1050, 755 and 740.

Proton nuclear magnetic resonance spectrum (350 MHz, CDCl$_3$, δ in ppm, J in Hz): 2.42 (s, 3H, —CH$_3$ of the tosyl group); 3.33 and 3.42 (AB, J=19, 2H, —SCH$_2$-); 4.07 (s, 3H, —OCH$_3$); 5.03 (d, J=4, 1H, H in the 6-position); 5.87 (dd, J=4 and 9, 1H, H in the 7-position); 6.71 (s, 1H, H in the 5-position of the thiazole); 6.87 (s, 1H, —CO$_2$CH<); 6.87 (d, J=10, 1H, —CH═CH—OSO$_2$-); 7.0 (s broad, 1H, NH— of the thiazole); 7.78 (d, J=9, 1H, —CONH-).

2-Benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) 1.5 g) is dissolved in a mixture of formic acid (30 cc) and distilled water (10 cc). The solution is heated at 50° C. for 30 minutes. After cooling, the precipitate is filtered off and the filtrate is concentrated to dryness under reduced pressure (10 mm Hg) at 30° C. The residue is triturated with diethyl ether (50 cc). The solidifed product is filtered off, washed with diethyl ether (2×25 cc) and then dried under reduced pressure (5 mm Hg) at 25° C. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]-oct-2-ene (syn isomer, E-form) (0.75 g) is obtained as a solvate with formic acid.

Rf=0.57; silica gel chromatographic plate; eluant: a 50:20:10:10 (by volume) mixture of ethyl acetate, acetone, water and acetic acid.

Infra-red spectrum (KBr)- characteristic bands (cm$^{-1}$) at 3400, 3340, 3000, 2820, 2200, 1775, 1720, 1670, 1630, 1370, 1190, 1165 and 1070.

Proton nuclear magnetic resonance spectrum (350 MHz, DMSO d$_6$, δ in ppm, J in Hz): 2.42 (s, 3H, -CH$_3$ of the tosyl group); 3.55 and 3.78 (AB J=19, 2H, —SCH$_2$-); 3.83 (s, 3H, —OCH$_3$); 5.14 (d, J=4, 1H, H in the 6-position); 5.75 (dd, J=4 and 9, 1H, H in the 7-position); 6.65 (d, J=12, 1H, —CH═CH—OSO$_2$-); 6.73 (s, 1H, H in the 5-position of the thiazole); 7.18 (s broad, —NH$_3$+); 9.58 (d, J=9, 1H, —CONH—).

A solution of the formic acid solvate of 7-[2-(2-amino-thiazol-4-yl)-2-methoxyimino-acetamido]-2-carboxy-8-oxo-3-(2-tosyloxyvinyl)-5-thia-1-aza-bicyclo-[4.2.0]oct-2-ene (syn isomer, E-form) (0.1 g) and of thiophenol (0.02 g) in anhydrous N,N-dimethylformamide (1 cc) is cooled to 0° C. A solution of N,N-diisopropyl N-ethylamine (0.069 g) in N,N-dimethylformamide (3 cc) is added dropwise. The reaction mixture is heated again and stirred for 1 hour at 25° C. Evaporation of the solvent under reduced pressure (10 mm Hg) at 30° C. gives a residue (0.19 g), the chromatographic examination of which [silica gel chromatographic plate; eluant: a 50:20:10:10 (by volume) mixture of ethyl acetate, acetone, water and acetic acid] shows the formation of 7-[2-(2-amino-thiazol-4-yl)-2-methoxyiminoacetamido]-2-carboxy-8-oxo-3-(2-phenylthiovinyl)-5-thia-1-aza-bicyclo[4.2.0]oct-2-ene (syn isomer, E-form): Rf=0.62.

REFERENCE EXAMPLE 4

A mixture of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (40.73 g) (obtained as described in Reference Example 2), dimethylformamide (300 cc), 1-methyl-5-mercapto-tetrazole (13.94 g) and N-ethyl N,N-diisopropylamine (20.9 cc) is heated at 60° C. for 1½ hours whilst stirring under nitrogen. The mixture is then diluted with ethyl acetate (2 liters) and washed successively with water (3×1 liter), 0.1 N hydrochloric acid (1 liter), a 1% strength sodium bicarbonate solution (1 liter) and a half-saturated sodium chloride solution (2×1 liter), dried over sodium sulphate, filtered and concentrated to dryness at 30° C. under reduced pressure (20 mm Hg). 2-Benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (35.7 g) is obtained in the form of a brown froth.

Infra-red spectrum (CHBr$_3$): characteristic bands (cm$^{-1}$) at 3410, 1800, 1715, 1505, 1370, 1050, 945, 760 and 745.

Proton nuclear magnetic resonance spectrum (350 MHz, CDCl$_3$, δ in ppm, J in Hz): 1.47 (s, 9H, (CH$_3$)$_3$C—); 3.32 and 4.15 (2 d, J=17.5, 2H, —SCH$_2$—); 3.94 (s, 3H, >NCH$_3$); 4.56 (d, J=4, 1H, H in the 6-position); 5.72 (d, J=10, 1H, —CONH—); 5.83 (dd, J=4 and 10, 1H, H in the 7-position); 6.97 (s, 1H, —COOCH<); 7.05 (d, J=16, 1H, —CH═CHS—); 7.58 (d, J=16, 1H, ═CHS—).

A mixture of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (34.87 g), acetonitrile (560 cc) and p-toluenesulphonic acid monohydrate (21.31 g) is stirred for 16 hours at 25° C. The mixture is then concentrated at 20° C. under reduced pressure (20 mm Hg) and the residue is taken up in ethyl acetate (1 liter). This mixture is neutralised by stirring with a 5% strength sodium bicarbonate solution (500 cc) and the organic phase is decanted, washed with a half-saturated sodium chloride solution (3×500 cc), dried over sodium sulphate, filtered and concentrated to dryness under reduced pressure (20 mm Hg) at 20° C. 7-Amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form (19.59 g) is obtained in the form of a crude brown froth.

Rf=0.27 [silica gel chromatographic plate, solvent: an 85:15 (by volume) mixture of dichloroethane and methanol].

Dicyclohexylcarbodiimide (8.90 g) is added to a solution, cooled to 4° C., of syn-2-methoxyimino-2-(2-tritylamino-thiazol-4-yl)-acetic acid (36.59 g) in methylene chloride (135 cc). After stirring for 40 minutes at 4° C. and 30 minutes at 20° C., the solution is filtered.

To this filtered solution, cooled to −30° C., is added, with stirring, a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form (19.59 g) in methylene chloride (165 cc) containing triethylamine (5.8 cc. The cooling bath is removed and stirring is continued for 1½ hours. The mixture is then concentrated at 20° C. under reduced pressure (20 mm Hg), the residue is taken up in ethyl acetate (1 liter) and the solution is washed successively with water (2×500 cc), 0.1 N hydrochloric acid (500 cc), a 2% strength sodium bicarbonate solution (2×250 cc) and a half-saturated sodium chloride solution (2×500 cc), dried over sodium sulphate and concentrated to dryness at 20° C. under reduced pressure (20 mm Hg). The residue is fixed on Merck silica gel (0.05-0.2 mm) (100 g) and the powder is obtained is deposited on a column (column diameter: 6 cm, height: 61 cm) of Merck silica gel (0.05-0.2 mm) (700 g). Elution is carried out successively with the following mixtures of cyclohexane and ethyl acetate: 80:20 (by volume) (1.5 liters), 70:30 (by volume (1.5 liters), 60:40 (by volume) (3 liters), 50:50 (by volume) (3 liters), 40:60 (by volume) (6 liters) and 30:70 (by volume) (7.5 liters), 600 cc fractions being collected. After evaporating fractions 27 to 37 to dryness at 20° C. under reduced pressure (20 mm Hg), and drying the residue, 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo-[4.2.0]oct-2-ene (syn isomer, E-form) (15.52 g) is obtained.

Infra-red spectrum (CHBr$_3$): characteristic bands (cm$^{-1}$) at 3390, 1805, 1725, 1685, 1520, 1375, 1210, 1050, 945, 755 and 740.

Proton nuclear magnetic resonance spectrum (350 MHz, CDCl$_3$, δ in ppm, J in Hz): 3.28 and 4.06 (2 d, J=17.5, 2H, —SCH$_2$—); 3.91 (s, 3H, >NCH$_3$); 4.06 (s, 3H, —OCH$_3$); 4.60 (d, J=4, 1H, H in the 6-position); 6.14 (dd, J=4 and 10, 1H, H in the 7-position); 6.71 (s, 1H, H in the 5-position of the thiazole); 6.94 (s, 1H,

6.99 (d, J=16, 1H, —C$\underline{H}$=CHS—); 7.56 (d, J=16,1H, =CHS—).

Phosphorus trichloride (2.8 cc) is added to a solution, cooled to −10° C., of 2-benzhydryloxycarbonyl-7-[2-methoxyimino-2-(2-tritylamino-thiazol-4-yl)-acetamido]-3-[2-(1-methyl-tetrazol-5-yl)-thiovinyl]-8-oxo-5-oxide-5-thia-1-aza-bicyclo[4.2.0]oct-2-ene (syn isomer, E-form (15.11 g) in methylene chloride (160 cc) and dimethylacetamide (6.4 cc), and the mixture is stirred for 1 hour at the same temperature. It is then concentrated to about 20 cc (at 20° C. under 25 mm Hg), this material is diluted with ethyl acetate (1 liter) and the solution is washed successively with a 5% strength sodium bicarbonate solution (2×500 cc) and a half-saturated sodium chloride solution (2×500 cc). After drying over sodium sulphate and filtering, the solution is concentrated at 20° C. under reduced pressure (20 mm Hg). The residue is fixed on Merck silica gel (0.05-0.2 mm) (50 g) and the powder obtained is deposited on a column (diameter: 6 cm, height: 37 cm) of Merck silica gel (0.05-0.2 mm) (250 g). Elution is carried out successively with the following mixtures of cyclohexane and ethyl acetate: 75:25 (by volume) (1 liter), 50:50 (by volume) (2 liters) and 25:75 (by volume) (2 liters), 600 cc fractions being collected. After evaporation of fractions 4 to 6 at 25° C. under reduced pressure (20 mm Hg), 2-benzhydryloxycarbonyl-7-[2-methoxyimino-2-(2-tritylamino-thiazol-4-yl)-acetamido]-3-[2-(1-methyltetrazol-5-yl)-thiovinyl]-8-oxo-5-thia-1-aza-bicyclo-[4.2.0]oct-2-ene (syn isomer, E-form) is obtained in the form of a yellow froth (9.8 g).

Infra-red spectrum (CHBr$_3$): characteristic bands (cm$^{-1}$) at 3390, 1785, 1720, 1680, 1515, 1370, 1205, 1040, 940, 760 and 735.

Proton nuclear magnetic resonance spectrum (350 MHz, CDCl$_3$, δ in ppm, J in Hz): 3.60 and 3.70 (AB, J=18, 2H, -SCH$_2$-); 3.95 (s, 3H, >NCH$_3$); 4.10 (s, 3H, —OCH$_3$); 5.10 (d, J=4, 1H, H in the 6-position); 5.95 (dd, J=4 and 10, 1H, H in the 7-position); 6.72 (s, 1H, H in the 5-position of the thiazole); 6.95 (s, 1H, —COO-CH<); 7.02 (d, J=16, 1H, —C$\underline{H}$=CHS—); 7.04 (d, J=10, 1H, —CONH—); 7.05 (s, 1H, >NH); 7.37 (d, J=16,=CHS—).

2-Benzhydryloxycarbonyl-7-[2-methoxyimino-2-(2-tritylamino-thiazol-4-yl)-acetamido]-3-[2-(1-methyltetrazol-5-yl)-thiovinyl]-8-oxo-5-thia-1-aza-bicyclo-[4.2.0]oct-2-ene (syn isomer, E-form) (9.32 g) is dissolved in trifluoroacetic acid (50 cc) and anisole (1 cc). The mixture is stirred for 1 hour at 4° C. and 30 minutes at 20° C. and is then concentrated at 20° C. under reduced pressure (0.05 mm Hg). The concentrate is taken up in ethyl acetate (2×200 cc), the mixture being evaporated each time at 20° C. under reduced pressure (20 mm Hg). The residue is triturated in diethyl ether (100 cc). After filtration and drying, a cream-coloured solid (4.87 g) containing 80% of the expected product and 20% of the N-tritylated product (the percentages being based on nuclear magnetic resonance measurements) is obtained.

The two constituents are separated as follows:

The above solid is dissolved in trifluoroacetic acid (35 cc) and the solution obtained is poured, with stirring, into diethyl ether (175 cc). After filtration and drying, 7-[2-(2-amino-thiazol-4-yl)-2-methoxyimino-acetamido]-2-carboxy -3-[2-(1-methyl-tetrazol-5-yl)-thiovinyl]-8-oxo-5-thia-1-aza-bicyclo[4.2.0]oct-2-ene (syn isomer, E-form) trifluoroacetate (4.57 g) is obtained.

Rf=0.49 [silica gel chromatographic plate, solvent: a 50:20:20:10:10 (by volume) mixture of ethyl acetate, acetone, acetic acid and water].

Infra-red spectrum (KBr): characteristic bands (cm$^{-1}$) at 3320, 1780, 1675, 1200, 1140, 1040 and 950.

Proton nuclear magnetic resonance spectrum (350 MHz, DMSO d$_6$, δin ppm, J in Hz): 3.66 and 3.86 (2 d, J=17, 2H, —SCH$_2$—); 3.90 (s, 3H, >NCH$_3$); 4.0 (s, 3H, —OCH$_3$); 5.20 (d, J=4, 1H, H in the 6-position); 5.80 (dd, J=4 and 9, 1H, H in the 7-position); 6.89 (s, 1H, H in the 5-position of the thiazole); 7.0 (d, J=16, 1H, —C$\underline{H}$=CHS—); 7.1 (d, J=16, 1H, =CHS—); 9.7 (d, J=9, 1H, —CONH—).

REFERENCE EXAMPLE 5

A mixture of 2-benzhydryloxycarbonyl-7-[2-methoxyimino-2-(2-tritylamino-thiazol-4-yl)-acetamido]-8-oxo-3-(2-tosyloxy-vinyl)-5-thia-1-aza-bicyclo[4.2.0]-oct-2-ene (syn isomer, E-form) (0.57 g) (obtained as described in Reference Example 3), dimethylformamide (15 cc) and 1-(2-hydroxyethyl)-5-mercapto-tetrazole (0.17 g) is heated to 60° C. under nitrogen. A solution of N-ethyl-N,N-diisopropylamine (0.1 cc) in dimethylformamide (5 cc) is added dropwise to this mixture in the course of 15 minutes, whilst stirring. After 3½ hours at 60° C., the mixture is diluted with ethyl acetate (100 cc) and this mixture is washed with distilled water (5×50 cc), dried over sodium sulphate, filtered and concentrated to dryness under reduced pressure (20 mm Hg) at 20° C. The residue is dissolved in methylene chloride (5 cc) and the solution is chromatographed on a column (column diameter: 2 cm, height: 15 cm) of Merck silica gel (0.04-0.06 mm) (80 g). Elution is carried out with a 25:75 (by volume) mixture of cyclohexane and ethyl acetate (300 cc) under a pressure of 40 kPa, 60 cc fractions being collected.

In fraction 1, some starting material (0.06 g) is obtained. Fractions 2 to 4 are concentrated to dryness under reduced pressure (20 mm Hg at 20° C.) and 2-benzhydryloxycarbonyl-3-{2-[1-(2-hydroxyethyl)tetrazol-5-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (0.4 g) is obtained.

Infrared spectrum (KBr): characteristic bands (cm$^{-1}$) at 3400, 1785, 1720, 1580, 1525, 1370, 1210, 1035, 940, 755 and 700.

Proton nuclear magnetic resonance spectrum (350 MHz, CDCl$_3$, δ in ppm, J in Hz): 3.57 and 3.67 (AB, J=18, 2H, —SCH$_2$—); 4.07 (s, 3H, —OCH$_3$); 4.1 and 4.35 (2t, 4H, —CH$_2$CH$_2$O—); 5.09 (d, J=4, 1H, H in the 6-position); 5.94 (dd, J=4 and 9, 1H, H in the 7-position); 6.74 (s, 1H, H in the 5-position of the thiazole); 6.95 (s, 1H, —COOCH<); 6.97 (s, 1H, (C$_6$H$_5$)$_3$CNH—); 7.00 (d, J=16, 1H, —C$\underline{H}$=CHS—).

2-Benzhydryloxycarbonyl-3-{2-[1-(2-hydroxyethyl)-tetrazol-5-yl]-thiovinyl}-7-[2-methoxyimino-2-(2-tritylamino-thiazol-4-yl)-acetamido]-8-oxo-5-thia-1-azabicyclo[4.2.0]oct-2-ene (syn isomer, E-form) (0.39 g) is dissolved in formic acid (7 cc), and the solution is diluted with water (4 cc) and heated for 30 minutes at 50° C. It is then allowed to cool, filtered, and concentrated to dryness under reduced pressure (0.05 mm Hg) at 20° C. The residue is triturated in diisopropyl (10 cc) and after filtration and drying the formic acid solvate of 7-[2-(2-amino-thiazol-4-yl)-2-methoxyiminoacetamido]-2-carboxy-3-{2-[1-(2-hydroxyethyl)-tetrazol-5-yl]-thiovinyl}-8-oxo-5-thia-1-aza-bicyclo[4.2.0]oct-2-ene (syn isomer, E-form) is obtained in the form of a pale yellow solid.

The preceding product (0.9 g) (in the form of the solvate) is treated with ethanol (50 cc) under reflux, a small amount of insoluble matter is removed by filtration and the filtrate is allowed to cool for 2 hours at 20° C. and 2 hours at 4° C. and is then filtered. The preceding product (0.41 g) is obtained in the form of its internal salt.

Infrared spectrum (KBr): characteristic bands (cm$^{-1}$) at 3350, 1770, 1720, 1675, 1530, 1390, 1040 and 940.

Proton nuclear magnetic resonance spectrum (350 MHz, DMSO d$_6$, δ in ppm, J in Hz): 3.63 and 3.87 (AB, J=19, 2H, —SCH$_2$—); 3.77 and 4.41 (2t, 4H, —CH$_2$CH$_2$O—); 3.84 (s, 3H, —OCH$_3$); 5.19 (d, J=4, 1H, H in the 6-position); 5.89 (dd, J=4 and 9, 1H, H in the 7-position); 6.73 (s, 1H, H in the 5-position of the thiazole); 6.94 (d, J=16, 1H, —C$\underline{H}$=CHS—); 7.25 (d, J=16, 1H, =CHS—); 9.61 (d, J=9, 1H, —CONH—).

REFERENCE EXAMPLE 6

A mixture of 2-benzhydryloxycarbonyl-7-tert.-butoxycarbonylamino-8-oxo-5-oxide-3-(2-tosyloxy-vinyl)-5-thia-1-aza-bicyclo[4.2.0]oct-2-ene (mixture of the and Z-forms) (13.58 g) (obtained as described in reference example 2), dimethylformamide (40 cc), trimethylchlorosilane (0.13 cc), 2-methyl-5-mercapto-1,3,4-thiadiazole (2.91 g) and N-ethyl-N,N-diisopropylamine (3.85 cc) is stirred at 20° C. for 17 hours under nitrogen. The mixture is diluted with ethyl acetate (500 cc) and this mixture is washed successively with water (4×250 cc), 0.1 N hydrochloric acid (250 cc), a 2% strength sodium bicarbonate solution (2×250 cc), water (500 cc) and saturated aqueous sodium chloride (2×250 cc), dried over sodium sulphate, filtered and concentrated to dryness under reduced pressure (20 mm Hg at 20° C.). The residue is fixed on Merck silica gel (0.05–0.2 mm) (50 g) and the powder is deposited on a column (column diameter: 4 cm, height: 47 cm) of Merck silica gel (0.05–0.2 mm) (200 g). Elution is carried out with the following mixtures of cyclohexane and ethyl acetate: 80:20 (by volume) (500 cc), 60:40 (by volume) (2000 cc) and 40:60 (by volume) (8000 cc), 125 cc fractions being collected. Fractions 38 to 80 are collected and concentrated to dryness at 20° C. under reduced pressure (20 mm Hg). 2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (mixture of The E- and Z-forms) (7.91 g) is obtained in the form of a light brown froth.

Infrared spectrum (CHBr$_3$): characteristic bands (cm$^{-1}$) at 3420, 1805, 1720, 1505, 1370, 1050, 940, 940, 760 and 745.

Proton nuclear magnetic resonance spectrum (350 MHz, CDCl$_3$, δ in ppm, J in Hz): E-form: 1.5 (s, 9H, (CH$_3$)$_3$C—); 2.75 (s, 3H, —CH$_3$); 3.30 and 4.15 (2d, J=18, 2H, —SCH$_2$—); 4.55 (d, J=4.5, 1H, H in the 6-position); 5.7 to 5.9 (mt, 2H, —CONH— and H in the 7-position); 6.97 (s, 1H, —COOCH<); 7.15 (d, J=16, 1H, —C$\underline{H}$=CHS—); 7.53 (d, J=16, 1H, =CHS—). Z-form: 1.5 (s, 9H, (CH$_3$)$_3$C—); 2.74 (s, 3H, —CH$_3$); 3.45 and 4.11 (2d, J=18, 2H, —SCH$_2$—); 4.55 (d, J=4.5, 1H, H in the 6-position); 5.7 to 5.9 (mt, 2H, —CONH— and H in the 7-position); 6.78 (d, J=10, 1H, —C$\underline{H}$=CHS—); 6.88 (d, J=10, 1H, =CHS—); 6.95 (s, 1H, —COOCH<).

A mixture of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]-oct-2-ene (mixture of the E- and Z-forms) (7.67 g), acetonitrile (120 cc) and p-toluenesulphonic acid monohydrate (4.57 g) is stirred for 16 hours at 20° C. It is then diluted with ethyl acetate (300 cc) and this mixture is washed with a saturated sodium bicarbonate solution (200 cc) and a half-saturated sodium chloride solution (3×200 cc), dried over sodium sulphate, filtered and concentrated to dryness under reduced pressure (20 mm Hg) at 20° C. This gives 7-amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (4.32 g) in the form of a crude brown froth.

Rf=0.17; [silica gel chromatographic plate, eluant: an 85:15 (by volume) mixture of methylene chloride and methanol].

Dicyclohexylcarbodiimide (1.90 g) is added to a solution, cooled to 5° C., of 2-syn-methoxyimino-2-(2-tritylamino-thiazol-4-yl)-acetic acid (7.81 g) in methylene chloride (30 cc). The solution is stirred for 40 minutes at 5° C. and then for 30 minutes at 20° C., after which it is filtered.

To this solution, cooled to −30° C., is added a solution of 7-amino-2-benzhydryloxycarbonyl-3-[2-(2-methyl-1,3,4-thiadiazol-5-yl)-thiovinyl]-8-oxo-5-oxide-5-thia-1-aza-bicyclo[4.2.0]oct-2-ene (mixture of the E- and Z-forms) (4.32 g) in methylene chloride (25 cc) containing triethylamine (1.25 cc). The cooling bath is removed and the mixture is stirred for 1 hour 50 minutes at 20° C. It is then concentrated under reduced pressure (20 mm Hg) at 20° C., the residue is taken up in ethyl acetate (300 cc) and the solution is washed successively with water (3×100 cc), 0.1 N hydrochloric acid (100 cc), a 1% strength sodium bicarbonate solution (100 cc) and half-saturated aqueous sodium chloride (2×100 cc), dried over sodium sulphate and concentrated to dryness under reduced pressure (20 mm Hg) at 20° C. The residue is fixed on Merck silica gel (0.05–0.2 mm) (30 g) and the powder is deposited on a column (column diameter: 3 cm, height: 54 cm) of Merck silica gel (0.05–0.2 mm) (130 g). Elution is carried out successively with the following mixtures of cyclohexane and ethyl acetate: 80:20 (by volume) (500 cc), 60:40 (by volume) (1000 cc), 40:60 (by volume) (2000 cc) and 20:80 (by volume) (3000 cc), 125 cc fractions being collected. After evaporation of fractions 32 to 49 under reduced pressure (20 mm Hg at 20° C.), 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, mixture of the E- and Z-forms) (3.12 g) is obtained in the form of a light brown froth.

Infrared spectrum (CHBr$_3$): characteristic bands (cm$^{-1}$) at 3390, 1805, 1725, 1685, 1520, 1375, 1050, 940, 755 and 740.

Proton nuclear magnetic resonance spectrum (350 MHz, CDCl$_3$, δ in ppm. J in Hz): the following principal signals are observed: 2.74 and 2.75 (2s, total 3H, —CH$_3$); 4.09 (s, 3H, =NOCH$_3$); 6.73 (s, 1H, H in the 5-position of the thiazole).

Phosphorus trichloride (0.54 cc) is added to a solution, cooled to −10° C., of 2-benzhydryloxycarbonyl-7--[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, mixtures of the E- and Z-forms) (2.99 g) in methylene chloride (30 cc) and dimethylacetamide (1.25 cc). The mixture is stirred for 30 minutes at this temperature and is then diluted with ethyl acetate (500 cc), and this mixture is washed successively with a 2% strength sodium bicarbonate solution (2×100 cc) and a half-saturated sodium chloride solution (2×200 cc), dried over sodium sulphate, filtered and concentrated under reduced pressure (20 mm Hg) at 20° C. The residue is fixed on Merck silica gel (0.05–0.2 mm) (10 g) and the powder is deposited on a column (column diameter: 3 cm, height: 23 cm) of Merck silica gel (0.05–0.2 mm) (50 g). Elution is carried out successively with the following mixtures of cyclohexane and ethyl acetate: 75:25 (by volume) (500 cc), 50:50 (by volume) (750 cc), and 25:75 (by volume) (1000 cc), 125 cc fractions being collected. Fractions 9 to 14 are concentrated to dryness under reduced pressure (20 mm Hg at 20° C.); 2-benzhydryloxycarbonyl-7-[2-methoxyimino-2-(2-tritylamino-1,3-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) (1.55 g) is obtained in the form of a yellow froth.

Infrared spectrum (CHBr$_3$): characteristic bands (cm$^{-1}$) at 3400, 1790, 1720, 1685, 1515, 1370, 1045, 755 and 740.

Proton nuclear magnetic resonance spectrum (350 MHz, CDCl$_3$, δ in ppm, J in Hz): the following principal signals are observed: 2.77 (s, 3H, —CH$_3$); 4.09 (s, 3H, =NOCH$_3$); 6.77 (s, 1H, H in the 5-position of the thiazole).

2-Benzhydryloxycarbonyl-7-[2-methoxyimino-2-(2-tritlylamino-thiazol-4-yl)-acetamido]-3-[2-(2-methyl-1,3,4-thiadiazol-5-yl)-thiovinyl]-8-oxo-5-thia-1-azabicyclo[4.2.0]oct-2-ene (syn isomer, mixture of the E- and Z-forms) (1.47 g) is dissolved in trifluoroacetic acid (8 cc) and anisole (0.15 cc). The mixture is stirred for 1 hour at 5° C. and 30 minutes at 20° C. and is then poured, with stirring, into diethyl ether (35 cc). The product is filtered off and dried, and 7-[2-(2-aminothiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, mixture of the E- and Z-forms) (1 g) is obtained in the form of the trifluoroacetate.

Rf=0.50 [silica gel chromatographic plate, solvent: a 50:20:10:10 (by volume) mixture at ethyl acetate, acetone, acetic acid and water].

Infrared spectrum (KBr): characteristic bands (cm$^{-1}$) at 3380, 3300, 1780, 1675, 1200, 1140, 1050 and 945.

Proton nuclear magnetic resonance spectrum (350 MHz, CDCl$_3$, δ in ppm, J in Hz): E-form: 2.74 (s, 3H, —CH$_3$); 3.69 and 3.83 (2d, J=17, 2H, —SCH$_2$—); 3.91 (s, 3H, —OCH$_3$); 5.23 (d, J=4, 1H, H in the 6-position); 5.82 (dd, J=4 and 10, 1H, H in the 7-position); 6.85 (s, 1H, H in the 5-position of the thiazole); 7.16 and 7.32 (2d, J=16, 2H, —CH=CHS—); 9.75 (d, J=10, 1H, —CONH—). Z-form: 3.88 and 3.92 (2d, J=17, 2H, —SCH$_2$); 6.91 (AB limit, 2H, —CH=CH—).

REFERENCE EXAMPLE 7

2-(2-Tritylamino-thiazol-4-yl)-2-trityloxyiminoacetic acid (syn isomer) (6.2 g) is added to a solution of 7-amino-2-benzhydryloxycarbonyl-3-[2-(1-methyl-tetrazol-5-yl)-thiovinyl]-8-oxo-5-oxide-5-thia-1-aza-bicyclo[4.2.0]oct-2-ene (E-form) (4.4 g) (described in Reference Example 4) in methylene chloride (100 cc), the mixture is cooled to 4° C. and 4-dimethylaminopyridine (0.1 g) and dicyclohexycarbodimide (1.89 g) are introduced successively, whilst stirring. The cooling bath is removed and the mixture is stirred for 1½ hours at 20° C. It is then filtered and the filtrate is concentrated at 20° C. under reduced pressure (20 mm Hg), the residue is taken up in ethyl acetate (500 cc) and the solution is washed with 1 N hydrochloric acid (250 cc), a 2% strength sodium bicarbonate solution (2×100 cc), water (2×100 cc) and a saturated sodium chloride solution (100 cc), dried over sodium sulphate and concentrated to dryness at 20° C. under reduced pressure (20 mm Hg). The residue is fixed on Merck silica gel (0.05–0.2 mm) (20 g) and the powder is charged onto a column (column diameter: 2.6 cm, height: 30 cm) of silica gel (70 g) which has been prepared with an 80:20 (by volume) mixture of cyclohexane and ethyl acetate; elution is carried out successively with the following mixtures of cyclohexane and ethyl acetate: 80:20 (by volume) (500 cc), 70:30 (1,000 cc) and 60:40 (1,200 cc), 60 cc fractions being collected.

Fractions 33 to 42 are evaporated to dryness under reduced pressure (20 mm Hg) at 20° C.; 2-benzhydryloxycarbonyl-3-[2-(1-methyl-tetrazol-5-yl)-thiovinyl]-8-oxo-5-oxide-7-[2-(2-tritylamino-thiazol-4-yl)-2-trityloxyimino-acetamido]-5-thia-1-aza-bicyclo[4.2.0]-oct-2-ene (syn isomer, E-form) (2 g) is obtained in the form of a cream-coloured powder.

Infra-red spectrum (CHBr$_3$): characteristic bands (cm$^{-1}$) at 3390, 1800, 1720, 1680, 1655, 1525, 1490, 1450, 750 and 700.

Proton nuclear magnetic resonance spectrum (350 MHz, CDCl$_3$, δ in ppm, J in Hz): 3.72 and 3 (2d, J=18, 2H, —S—CH$_2$—); 3.96 (s, 3H, >NCH$_3$); 4.44 (d, J=4, 1H, H in the 6-position); 5.35 (dd, J=4 and 9, 1H, H in the 7-position); 6.40 (s, 1H, H in the 5-position of the thiazole); 6.95 (d, J=16, 1H, —CH=CHS—); 6.97 (s, 1H,

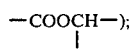

7.60 (d, J=16, 1H, =CHS—).

Phosphorus trichloride (0.302 cc) is added, whilst stirring, to a solution, cooled to −10° C., of 2-benzhydryloxycarbonyl-3-[2-(1-methyl-tetrazol-5-yl)-thiovinyl]-8-oxo-5-oxide-7-[2-(2-tritylamino-thiazol-4-yl)-2-trityloxyimino-acetamido]-5-thia-1-aza-bicyclo[4.2.0]oct-2-ene (syn isomer, E-form) (2 g) in methylene chloride (17 cc) and dimethylacetamide (0.64 cc). After 10 minutes at the same temperature, the mixture is diluted with ethyl acetate (500 cc) and the solution is washed with a 5% strength sodium bicarbonate soltuion (2×100 cc) and a saturated sodium chloride solution (2×100 cc), dried over sodium sulphate, filter concentrated to dryness at 20° C. under reduced pressure (20 mm Hg). The residue is taken up in methylene chloride (10 cc) and the solution is chromatographed on a column (column diameter: 4 cm, height: 20 cm) of silica gel (0.04–0.06 mm) (150 g), which has been prepared with a 65:35 (by volume) mixture of cyclohexane and ethyl acetate. Elution is carried out with 2 liters of the same mixture under a pressure of 40 kPa, 120 cc fractions being collected.

Fractions 6 to 21 are concentrated to dryness under reduced pressure (20 mm Hg) at 20° C.; 2-benzhydrylo xycarbonyl-3-[2-(1-methyl-tetrazol-5-yl)-thiovinyl]-8-oxo-7-[2-(2-tritylamino-thiazol-4-yl)-2-trityloxyimino-acetamido]-5-thia-1-aza-bicyclo[4.2.0]oct-2-ene (syn isomer, E-form) (0.85 g) is obtained in the form of a cream-coloured powder.

Infra-red spectrum (CHBr₃): characteristic bands (cm⁻¹) at 3400, 1790, 1715, 1690, 1510, 1490, 1450, 950, 750 and 710.

Proton nuclear magnetic resonance spectrum (350 MHz, CDCl₃, δ in ppm, J in Hz): 3.43 and 3.50 (2d, J=18, 2H, —S—CH₂—); 3.94 (s, 3H, >NCH₃); 5.09 (d, J=4, 1H, H in the 6-position); 6.10 (dd, J=4 and 9, 1H, H in the 7-position); 6.41 (s, 1H, H in the 5-position of the thiazole); 6.71 (s, 1H, (C₆H₅)₃ CNH—); 6.95 (s, 1H,

6.97 (d, J=16, 1H, —CH=CHS—).

A solution of 2-benzhydryloxycarbonyl-3-[2-(1-methyl-tetrazol-5-yl)-thiovinyl]-8-oxo-7-[2-(2-tritylamino-thiazol-4-yl)-2-trityloxyimino-acetamido]-5-thia-1-aza-bicyclo[4.2.0]oct-2-ene (syn isomer, E-form) (0.85 g) in tetrahydrofurane (10 cc) is treated with 50% strength by volume aqueous formic acid (10 cc) for 30 minutes at 50° C. The mixture is concentrated to dryness under reduced pressure (20 mm Hg) at 20° C., the residue is taken up in ethanol (20 cc) at 60° C., the solution is allowed to cool, and the crystals which have appeared are filtered off, washed with diethyl ether (2×10 cc) and dried. 7-[2-(2-Amino-thiazol-4-yl)-2-hydroxyimino-acetamido]-2-carboxy-3-[2-(1-methyl-tetrazol-5-yl)-thiovinyl]-8-oxo-5-thia-1-aza-bicyclo[4.2.0]oct-2-ene (syn isomer, E-form (0.24 g) is obtained in the form of a yellow powder.

Infra-red spectrum (KBr): characteristic bands (cm⁻¹) at 3440, 3360, 3200, 1785, 1720, 1680, 1610 and 1405.

Proton nuclear magnetic resonance spectrum (350 MHz, DMSO d₆, δ in ppm, J in Hz): 3.65 and 3.91 (2d, J=18, 2H, —S—CH₂—); 4.97 (s, 3H, >NCH₃); 5.25 (d, J=4, 1H, H in the 6-position); 5.90 (dd, J=4 and 9, 1H, H in the 7-position); 6.76 (s, 1H, H in the 5-position of the thiazole); 6.96 (d, J=14, 1H, —CH=CHS—); 7.07 (d, J=14, 1H, =CHS—); 9.50 (d, J=9, 1H, —CONH—).

REFERENCE EXAMPLE 8

2-Mercapto-pyridine-N-oxide (0.43 g) and N,N-diisopropylethylamine (0.6 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer, E-form) (3.4 g) (obtained as described in reference example 3) in dry N,N-dimethylformamide (85 cc) and the mixture is stirred for 30 minutes at 25° C. A further amount of 2-mercaptopyridine-N-oxide (0.43 g) and of N,N-diisopropylethylamine (0.6 cc) is added and the mixture is stirred for a further 10 minutes at 25° C., after which it is diluted with ethyl acetate (250 cc). The mixture is washed with water (2×200 cc) followed by 0.1 N hydrochloric acid (200 cc) and a saturated sodium chloride solution (200 cc); after drying over magnesium sulphate, the solvent is evaporated under reduced pressure (30 mm Hg) at 40° C. The residue (3.5 g) is added to a further amount (0.5 g) of product obtained in the same way and the mixture is chromatographed over Merck silica gel (0.04–0.06 mm) (column diameter: 5 cm), elution being carried out with 10 liters of a 98:2 (by volume) mixture of ethyl acetate and methanol under a pressure of 50 kPa, and 120 cc fractions being collected. Unchanged starting material (1.1 g) is recovered from fractions 2 to 4. Fractions 45 to 75 are concentrated to dryness under reduced pressure (30 mm Hg) at 40° C. and 2-benzhydryloxycarbonyl-7-[2-methoxyimino-2-(2-tritylamino-thiazol-4-yl)-acetamido]-8-oxo-3-[2-(pyrid-2-1-1-oxide)-thiovinyl]-5-thia-1-aza-bicyclo[4.2.0]oct-2-ene (syn isomer, E-form) (1.6 g) is obtained in the form of a grey froth.

Infra-red spectrum (CHBr₃): characteristic bands (cm⁻¹) at 3390, 1780, 1720, 1680, 1585, 1510, 1465, 1420, 1040, 945 and 750.

Proton nuclear magnetic resonance spectrum (350 MHz, CDCl₃, δ in ppm, J in HZ): 3.60 and 3.69 (AB, J=18, 2H, —SCH₂—); 4.08 (s, 3H, =NOCH₃); 5.12 (d, J=4, 1H, H in the 6-position); 5.97 (dd, J=4 and 9, 1H, H in the 7-position); 6.57 (d, J=16, 1H, —CH=CHS—); 6.76 (s, 1H, H of the thiazole); 7.0 (s, 2H, —CH(C₆H₅)₂ and (C₆H₅)₃CNH—); 7.1 to 7.5 (hump, aromatic); 8.25 (d, J=9, 1H, —CONH—).

2-Benzhydryloxycarbonyl-7-[2-methoxyimino-2-(2-tritylamino-thiazol-4-yl)-acetamido]-8-oxo-3-[2-(pyrid-2-yl-1-oxide)-thiovinyl]-5-thia-1-aza-bicyclo[4.2.0]oct-2-ene (syn isomer, E-form) (2.3 g) is dissolved in formic acid (54 cc). The solution is diluted with distilled water (21 cc) and stirred for 20 minutes at 50° C. It is then filtered hot and the solvents are evaporated under reduced pressure (10 mm Hg) at 40° C. The residue is triturated with ethanol (50 cc). The mixture is evaporated to dryness under reduced pressure (30 mm Hg) at 40° C. The operation is repeated once. The residue is taken up in ethanol (50 cc) and the solid is filtered off, washed with ethanol (15 cc) and then with ethyl ether (2×25 cc) and is dried under reduced pressure (10 mm Hg) at 25° C. 7-[2-(2-Amino-thiazol-4-yl)-acetamido[-2-carboxy-8-oxo-3-[2-(pyrid-2-yl-1-oxide)-thiovinyl]-5-thia-1-aza-bicyclo[4.2.0]oct-2-ene (syn isomer, E-form) (0.98 g) is obtained in the form of a grey powder.

Infra-red spectrum (KBr), characteristic bands (cm$^{-1}$) at 3330, 1770, 1670, 1540, 1470, 1420, 1040, 950 and 760.

Proton nuclear magnetic resonance spectrum (350 MHz, DMSO d$_6$, δ in ppm, J in Hz): 3.75 and 4.16 (AB, J=18, 2H, —SCH$_2$—); 3.88 (s, 3H, =NOCH$_3$); 5.24 (d, J=4, 1H, H in the 6-position); 5.73 (dd, J=4 and 9, 1H, H in the 7-position); 6.78 (s, 1H, H of the thiazole); 7.05 and 7.32 (AB, J=16, 2H, —CH=CH—S—); 7.63 (d, J=7, 1H, H in the 3-position of the pyridine group); 7.1 to 7.5 (hump, 4H, H in the 4- and 5-position of pyridine +—NH$_2$); 7.63 (d, J=7, 1H, H in the 3-position of pyridine); 8.32 (d, J=6, 1H, H in the 6-position of pyridine); 9.64 (d, J=9, 1H, —CONH—).

REFERENCE EXAMPLE 9

3-Mercapto-6-methyl-pyridazine-1-oxide (0.738 g) and N,N-diisopropylethylamine (0.89 cc) are added successively at 22° C., under a nitrogen atmosphere and with stirring, to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo-[4.2.0]oct-2-ene (syn isomer, E-form) (4.9 g) (obtained as described in reference example 3) in dimethylformamide (40 cc). The mixture is stirred for 15 minutes at 25° C. and is then diluted with ethyl acetate (600 cc) washed successively with water (2×120 cc), 0.1 N hydrochloric acid (120 cc), a 2% strength sodium bicarbonate solution (2×120 cc), and a half-saturated sodium chloride solution (2×120 cc), dried over sodium sulphate, filtered and concentrated to dryness at 20° C. under reduced pressure (20 mm Hg). The residue is taken up in ethyl acetate (10 cc) and the solution is filtered over a column (column diameter: 2.4 cm) of Merck silica gel (0.05 -0.2 mm) (50 g). Elution is carried out with ethyl acetate (500 cc), successively collecting a colourless fraction 1 (100 cc), a pale yellow fraction 2 (20 cc) and a fraction 3 (360 cc). The latter is concentrated to dryness at 20° C. under reduced pressure (20 mm Hg). This gives 2-benzhydryloxycarbonyl-7-[2-methoxyimino-2-(2-tritylaminothiazol-4-yl)-acetamido]-3-[2-(6-methyl-pyridazin-3-yl-1-oxide)-thiovinyl]-8-oxo-5-thia-1-aza-bicyclo[4.2.0]oct-2-ene (syn isomer, E-form) (4 g) in the form of a brownish-orange froth.

Infra-red spectrum (KBr): characteristic bands (cm$^{-1}$) at 3400, 1780, 1720, 1680, 1530, 1495, 1450, 1330, 1210, 1050, 1040, 1000, 945, 810, 755 and 700.

Proton nuclear magnetic resonance spectrum (350 MHz, CDCl$_3$, δ in ppm, J in Hz): 2.45 (s, 3H, —CH$_3$); 3.62 and 3.77 (2d, J=18, 2H, —SCH$_2$—); 4.09 (s, 3H, —OCH$_3$); 5.08 (d, J=4, 1H, H in the 6-position); 5.93 (dd, J=4 and 9, 1H, H in the 7-position); 6.03 ( s, 1H, (C$_6$H$_5$)$_3$CNH—); 6.76 (s, 1H, H of the thiazole); 6.95 (s, 1H,

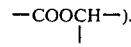

—COOCH—).

A solution of 2-benzhydryloxycarbonyl-7-[2-methoxyimino-2-(2-tritylamino-thiazol-4-yl)-acetamido]-3-[2-(6-methyl-pyridazin-3-yl-1-oxide)-thiovinyl]-8-oxo-5-thia-1-aza-bicyclo[4.2.0]oct-2-ene (syn isomer, E-form) (3.9 g) in a mixture of formic acid (60 cc) and distilled water (25 cc) is stirred at 50° C. for 30 minutes. The mixture is then cooled to about 20° C. and filtered, and the filtrate is concentrated to dryness at 30° C. under reduced pressure (0.05 mm Hg). The residue is taken up in ethanol (50 cc), the mixture is concentrated to dryness at 20° C. under reduced pressure (20 mm Hg) and this operation is repeated twice. The solid which remains is treated with ethanol (40 cc) under reflux for 5 minutes and the suspension is then cooled to about 20° C. and filtered. After drying, 7-[2-(2-amino-thiazol-4-yl)-2-methoxyimino-acetamido]-2-carboxy-3-[2-(6-methyl-pyridazin-3-yl-1-oxide)-thiovinyl]-8-xo-5-thia-1-aza-bicyclo[4.2.0]oct-2-ene (syn isomer, E-form) (1.96 g) is obtained in the form of a yellow powder.

Infra-red spectrum (KBr): characteristic bands (cm$^{-1}$) at 3420, 3320, 3230, 1765, 1675, 1655, 1620, 1535, 1325, 1210, 1040, 1000 and 810.

Proton nuclear magnetic resonance spectrum (350 MHz, DMSO d$_6$, δ in ppm, J in Hz): 2.33 (s, 3H, —CH$_3$); 3.70 and 3.97 (2d, J=18, 2H, —SCH$_2$—); 3.86 (s, 3H, —OCH$_3$); 5.23 (d, J=4, 1H, H in the 6-position); 5.81 (dd, J=4 and 9, 1H, H in the 7-position); 6.76 (s, 1H, H of the thiazole); 7.18 to 7.20 (hump, 5H, —CH=CH— and —NH$_3$+); 7.31 and 7.86 (2d, J=7, H of the pyridazine); 9.62 (d, J=9, 1H, —CONH—).

REFERENCE EXAMPLE 10

5,6-Dioxo-4-methyl-3-thioxo-perhydro-1,2,4-triazine (0.7 g) and N,N-diisopropylethylamine (0.77 cc) are added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (4 g) (obtained as described in reference example 3) in dry N,N-dimethylformamide (40 cc). The reaction mixture is heated for 90 minutes at 60° C. and is then diluted with ethyl acetate (200 cc) and washed with distilled water (4×100 cc). After drying over magnesium sulphate, filtering and evaporating to dryness under reduced pressure (30 mm Hg) at 40° C., the residue is chromatographed over Merck silica gel (0.04–0.06 mm) (column diameter: 4 cm), elution being carried out under 50 kPa with ethyl acetate (3 liters ) and 100 cc fractions being collected; fractions 11 to 29 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (2.8 g) is obtained.

Infra-red spectrum (CHBr$_3$): characteristic bands (cm$^{-1}$) at 3360, 3200, 2820, 1795, 1710, 1680, 1590, 1515, 1490, 1450, 1040 and 760.

Proton nuclear magnetic resonance spectrum (350 MHz, CDCl$_3$, δ in ppm, J in Hz): 3.30 (s, 3H, —CH$_3$ of the triazine); 3.30 and 4.0 (AB, J=18, —S(O)CH$_2$—); 3.88 (s, 3H, =NOCH$_3$); 4.65 (d, J=4, 1H, H in the 6-position); 6.02 (dd, J=4 and 9, 1H, H in the 7-position); 6.32 (d, J=16, 1H, —CH=CH—S—); 6.68 (s, 1H, H of the thiazole); 6.92 (s, 1H, —CH(C$_6$H$_5$)$_2$); 7.15 to 7.55 (hump, aromatic+—CONH—+(C$_6$H$_5$)$_3$CNH—+—CH=CHS—).

Phosphorus trichloride (0.53 cc) is added to a solution, cooled to −30° C., of 2-benzhydryloxycarbonyl -3-[2-(5,6-dioxo-4-methyl-1,4,5,6-tetrahydro-1,2,4-triazin-3-yl)-thiovinyl]-7-[2-methoxyimino-2-(2-tritylaminothiazol-4-yl)-acetamido]-8-oxo-5-oxide-5-thia-1-aza-bicyclo]4.2.0]oct-2-ene (syn isomer, E-form) (2.8 g) in methylene chloride (30 cc) and N,N-dimethylacetamide (1.1 cc) and the reaction mixture is stirred for 2 hours at between $-15°$ and $-10°$ C., after which it is diluted with ethyl acetate (250 cc). It is washed with a saturated sodium bicarbonate solution ($2\times100$ cc) and then with a saturated sodium chloride solution (250 cc), dried over magnesium sulphate and filtered, and the solvent is evaporated under reduced pressure (30 mm Hg) at 40° C. The residue is chromatographed over silica gel (0.04–0.06 mm) (120 g) (column diameter: 4 cm, height: 20 cm), elution being carried out with a 20:80 (by volume) mixture of cyclohexane and ethyl acetate (2 liters) under a pressure of 50 kPa, and 100 cc fractions being collected. Fractions 4 to 16 are concentrated to dryness under reduced pressure (30 mm Hg) at 40° C. 2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.75 g) is obtained in the form of a cream-coloured solid.

Infra-red spectrum (CHBr$_3$): characteristic bands (cm$^{-1}$) at 3380, 1785, 1710, 1680, 1515, 1490, 1445, 1040, 940, 755 and 740.

Proton nuclear magnetic resonance spectrum (350 MHz, CDCl$_3$, δ in ppm, J in Hz): 3.41 (s, 3H, —CH$_3$ of the triazine); 3.58 and 3.68 (AB, J=18, 2H, —SCH$_2$—); 4.04 (s, 3H, =NOCH$_3$); 5.10 (d, J=4, 1H, H in the 6-position); 5.95 (dd, J=4 and 9, 1H, H in the 7-position); 6.74 (s, 1H, H of the thiazole); 6.84 (d, J=17, 1H, —C$\underline{H}$=CH—S—); 6.96 (s, 1H, —CH(C$_6$H$_5$)$_2$); 7.03 (d, J=9, 1H, —CONH—); 7.15 to 7.55 (hump, aromatics+(C$_6$H$_5$)$_3$CNH—+—CH=C$\underline{H}$S—); 10.8 (s, 1H, —NH— of the triazine).

2-Benzhydryloxycarbonyl-3-[2-(5,6-dioxo-4-methyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.7 g) is dissolved in formic acid (24 cc); after addition of distilled water (16 cc), the reaction mixture is heated for 25 minutes at 50° C. and is then filtered hot and concentrated to dryness under reduced pressure (10 mm Hg) at 40° C. The solid is triturated with ethanol (40 cc) and the mixture is evaporated to dryness under reduced pressure (30 mm Hg) at 40° C.; this operation is repeated once, and the residue obtained is then taken up in ethanol (30 cc). The insoluble matter is filtered off, washed with ethanol (10 cc) and ether ($2\times50$ cc) and dried under reduced pressure (10 mm Hg) at 25° C. 7-[2-(2-Aminothiazol-4-yl)-2--methoxyimino-acetamido]-2-carboxy-3-[2-(5,6-dioxo-4-methyl-1,4,5,6-tetrahydro-1,2,4-triazin-3-yl)-thiovinyl]-8-oxo-5-thia-1-aza-bicyclo[4.2.0]oct-2-ene (syn isomer, E-form) (0.85 g) is obtained in the form of a cream-coloured solid.

Rf=0.37; silica gel chromatographic plate; eluant: 3:2:2 (by volume) ethyl acetate/water/acetic acid.

Infra-red spectrum (KBr): characteristic bands (cm$^{-1}$) at 3300, 3260, 2600, 1770, 1705, 1680, 1630, 1585, 1530, 1375, 1040 and 950.

Proton nuclear magnetic resonance spectrum (350 MHz, DMSO d$_6$, δ in ppm, J in Hz): 3.35 (s, 3H, —CH$_3$ of the triazine); 3.65 and 3.88 (AB, J=18, 2H, —SCH$_2$—); 3.87 (s, 3H, =NOCH$_3$); 5.22 (d, J=4, 1H, H in the 6-position); 5.80 (dd, J=4 and 9, 1H, H in the 7-position); 6.75 (s, 1H, H of the thiazole); 6.83 (d, J=16, —CH=C$\underline{H}$—S—); 7.11 (d, J=16, 1H, —C$\underline{H}$=CH—S—); 7.20 (s broad, 3H, —NH$_3$$^+$); 9.58 (d, J=9, 1H, —CONH—).

REFERENCE EXAMPLE 11

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.8 g) (obtained as described in reference example 3), dimethylformamide (58 cc), 4-(2-methoxyethyl)-5,6-dioxo-3-thioxoperhydro-1,2,4-triazine (1.3 g) and diisopropylethylamine (0.819 mg) is stirred at 60° C. for 80 minutes, under nitrogen. The mixture is cooled to 20° C. and diluted with ethyl acetate (300 cc), and the organic phase is washed 4 times with water (a total of 100 cc), dried over magnesium sulphate, filtered and concentrated to dryness at 20° C. under reduced pressure (20 mm Hg). The residue, dissolved in ethyl acetate (250 cc) is filtered over a column of silica gel (32 g) and eluted with ethyl acetate (500 cc). The eluate is evaporated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (5.4 g) in the form of a beige solid.

Infra-red spectrum (KBr): characteristic bands (cm$^{-1}$) at 3400, 2830, 1800, 1720, 1690, 1590, 1525, 1495, 1450, 1370, 1210, 1110, 1040, 945, 755 and 700.

Proton nuclear magnetic resonance spectrum (350 MHz, CDCl$_3$, δ in ppm, J in Hz): 3.32 (s, 3H, —CH$_2$OCH$_3$); 3.60 (t, J=5, 2H, —CH$_2$O—); 4.05 (t, J=5, 2H, —CH$_2$N<); 3.34 and 4.1 (dd, J=18, 2H, —S(O)CH$_2$—); 4.00 (s, 3H, =NOCH$_3$); 4.66 (d, J=4, 1H, H in the 6-position); 6.08 (dd, J=4 and 9, 1H, H in the 7-position); 6.71 (s, 1H, H of the thiazole); 6.85 (d, J=16, 1H, —C$\underline{H}$=CHS—); 6.97 (s, 1H, —COOCH<).

Dimethylacetamide (2.06 cc), followed by phosphorus trichloride (0.91 cc) is added to a solution, cooled to $-10°$ C., of 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (5.3 g) in methylene chloride (53 cc). The solution is stirred for 2 hours at $-10°$ C. and is then diluted with ethyl acetate (750 cc); this solution is washed with a saturated sodium bicarbonate solution ($2\times100$ cc), and a saturated sodium chloride solution ($2\times100$ cc), dried over magnesium sulphate and concentrated to 50 cc under reduced pressure (20 mm Hg) at 20° C., and isopropyl ether (200 cc) is added. The solid formed is isolated by filtration, washed with isopropyl ether (20 cc) and dried. This gives a cream-coloured solid (4.2 g). This solid, dissolved in a 70:30 (by volume) mixture of ethyl acetate and cyclohexane, is chromatographed over a column (column diameter 6 cm, height 20 cm) of Merck silica gel (0.04–0.06 mm). Elution is carried out with a 70:30 (by volume) mixture of ethyl acetate and cyclohexane (1,500 cc) under a pressure of 40 kPa, 75 cc fractions being collected. Fractions 9 to 19 are concentrated to dryness under reduced pressure (20 mm Hg) at 20° C. This gives 2-benzhydryloxycarbonyl-3-{2-[5,6-dioxo-4-(2-methoxyethyl)-1,4,5,6-tetrahydro-1,2,4-triazin-3-yl]-thiovinyl}-7-[2-methoxyimino-2-(2-tritylamino-thiazol- 4-yl)-acetamido]-8-oxo-5-thia-1-aza-bicyclo[4.2.0]oct-2-ene (syn isomer, E-form) (2.9 g) in the form of a cream-coloured solid.

Infra-red spectrum (KBr): characteristic bands (cm$^{-1}$) at 3400, 2820, 1785, 1720, 1690, 1590, 1525, 1495, 1450, 1370, 1210, 1110, 1040, 945, 755 and 705.

Proton nuclear magnetic resonance spectrum (350 MHz, CDCl$_3$, δ in ppm, J in Hz): 3.34 (s, 3H, —CH$_2$OCH$_3$); 3.65 (t, J=5, 2H, —CH$_2$O—); 4.11 (t, J=5, 2H, —CH$_2$N<); 3.60 and 3.68 (2d, J=18, 2H, —SCH$_2$—); 4.06 (s, 3H, =NOCH$_3$); 5.11 (d, J=4, 1H, H in the 6-position); 5.95 (dd, J=4 and 9, 1H, H in the 7-position); 6.76 (s, 1H, H of the thiazole); 6.86 (d, J=16, 1H, —CH=CHS—); 6.93 (d, J=9, 1H, —CONH—); 6.97 (s, 1H,

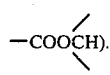

2-Benzhydryloxycarbonyl-3-{2-[5,6-dioxo-4-(2-m ethoxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.8 g) is dissolved in formic acid (50 cc), water (25 cc) is added and the mixture is heated for 15 minutes at 50° C., with stirring. The mixture is then diluted with water (25 cc), cooled, filtered and concentrated to dryness at 40° C. under 0.05 mm Hg. The residue is taken up three times in ethanol (50 cc), and each time the mixture is evaporated to dryness under reduced pressure (0.05 mm Hg). The residue is taken up in ethanol (200 cc) under reflux, the mixture is filtered hot on a glass frit, the residue is again taken up in ethanol (100 cc) under reflux and the mixture again filtered hot, the two combined filtrates are concentrated to 20 cc and cooled to 0° C., and the solid obtained is filtered off and dried. This gives 7-[2-(2-amino-thiazol-4-yl)-2-methoxyimino-acetamido]-2-carboxy-3-{2-[5,6-dioxo-4-(2-methoxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (1.45 g), in the form of a yellow solid.

Infra-red spectrum (KBr): characteristic bands (cm$^{-1}$) at 3480, 2830, 1775, 1710, 1680, 1635, 1590, 1535, 1380, 1110, 1040 and 940.

Proton nuclear magnetic resonance spectrum (350 MHz, DMSO d$_6$, δ in ppm, J in Hz): 3.36 (s, 3H, —CH$_2$OCH$_3$); 3.56 (t, J=5, 2H, —CH$_2$O—); 4.10 (t, J=5, 2H, —CH$_2$N<); 3.62 and 3.73 (2d, J=18, 2H, —SCH$_2$—); 3.96 (s, 3H, =NOCH$_3$); 5.18 (d, J=4, 1H, H in the 6-position); 5.81 (dd, J=4 and 9, 1H, H in the 7-position); 6.78 (s, 1H, H of the thiazole); 6.87 (d, J=15, 1H, —CH=CH—S—); 7.29 (d, J=15, 1H, —CH=CH—S—); 6.70 (s broad, 3H, —NH$_3$+); 9.55 (d, J=9, 1H, —CONH—); 12.64 (s, 1H, =N NHCO— or

=N—N=C—).
       |
       OH 4-(2-Methoxyethyl)-5,6-dioxo-3-thioxo-perhydro-1,2,4-triazine can be prepared in accordance with Belgian Patent No. 830,455.

REFERENCE EXAMPLE 12

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (10 g) (obtained as described in reference example 3), dimethylformamide (50 cc), 4-(2,2-dimethoxyethyl)-5,6-dioxo-3-thioxo-perhydro-1,2,4-triazine (2.56 g) and N,N-diisopropylethylamine (1.9 cc) is stirred at 60° C. under nitrogen for 2 hours 30 minutes. It is then diluted with ethyl acetate (600 cc) and this mixture is washed with water (2×125 cc), 1 N hydrochloric acid (150 cc), a half-saturated sodium bicarbonate solution (2×150 cc) and a half-saturated sodium chloride solution (2×150 cc), dried over sodium sulphate, filtered and concentrated to dryness under reduced pressure (20° C. 20 mm Hg; 2.7 kPa). The residue, dissolved in methylene chloride (30 cc), is chromatographed over a column (column diameter: 7 cm, height: 35 cm) of Merck silica gel (0.02–0.06 mm). Elution is carried out with a 40:60 (by volume) mixture of cyclohexane ethyl acetate (7 liters) under a pressure of 40 kPa, 100 cc fractions being collected. Fractions 27 to 46 are concentrated to dryness at 20° C. under reduced pressure (20 mm Hg; 2.7 kPa). 2-Benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.5 g) (obtained in the form of a beige-coloured froth).

Infra-red spectrum (KBr): characteristic bands in cm$^{-1}$ at 3380, 3250, 1795, 1720, 1685, 1520, 1490, 1445, 1040, 940, 760 and 700.

Proton nuclear magnetic resonance spectrum (350 MHz, CDCl$_3$, δ in ppm, J in Hz): 3.34 and 4.12 (2d, J=18, 2H, —SCH$_2$—); 3.40 (s, 6H, —CH(OCH$_3$)$_2$); 3.94 to 4.06 (m, 5H, —OCH$_3$ and >NCH$_2$—); 4.60 to 4.68 (m, 2H, H in the 6-position and —CH(OCH$_3$)$_2$); 6.07 (dd, J=4 and 9, 1H, H in the 7-position); 6.70 (s, 1H, H of the thiazole); 6.82 (d, J=16, 1H, —CH=CHS—); 6.96 (s, 1H,

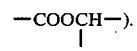

A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.5 g) and dimethylacetamide (3 cc) in methylene chloride (100 cc) is treated with phosphorus trichloride (1.40 cc) at −10° C., whilst stirring; phosphorous trichloride (0.7 cc) is added after 1 hour 30 minutes and the same amount is added again after a further 2 hours. The mixture is diluted with ethyl acetate (600 cc) and this mixture is washed with a half-saturated sodium bicarbonate solution (2×150 cc) and a half-saturated sodium chloride solution (2×150 cc), dried over sodium sulphate, filtered and concentrated to dryness at 20° C. under a pressure of 20 mm Hg (2.7 kPa). The residue is taken up in ethyl acetate (50 cc) and the solution is chromatographed over a column (column diameter: 3 cm, height: 25 cm) of Merck silica gel (0.05–0.2 mm) (100 g). Elution is carried out with ethyl acetate (1 liter), 200 cc fractions being collected. Fractions 3, 4 and 5 are concentrated to dryness (20 mm Hg; 2.7 kPa) at 20° C. 2-Benzhydryloxycarbonyl-3-{2-[4-(2,2-dimethoxyethyl)-5,6-dioxo-1,4,5,6-tetrahydro-1,2,4-triazin-3- yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (7.5 g) is obtained in the form of an orange-coloured froth.

Infra-red spectrum (CHBr$_3$): characteristic bands in cm$^{-1}$ at 3380, 1780, 1720, 1680, 1515, 1490, 1445, 755 and 740.

Proton nuclear magnetic resonance spectrum (350 MHz, CDCl$_3$, δ in ppm, J in Hz): 3.40 (s, 6H, —CH(OC$\underline{H}_3$)$_2$); 3.54 and 3.66 (2d, J=18, 2H, —SCH$_2$—); 3.98 (d, J=5, 2H, >NCH$_2$—); 4.02 (s, 3H, =NOCH$_3$); 4.65 (t, J=5, 1H, —C$\underline{H}$(OCH$_3$)$_2$); 5.08 (d, J=4, 1H, H in the 6-position); 5.92 (dd, J=4 and 9, 1H, H in the 7-position); 6.73 (s, 1H, H of the thiazole); 6.83 (d, J=16, 1H, —C$\underline{H}$=CHS—); 6.95 (s, 1H, —COOCH<).

1. (a) A solution of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.05 g) in 98% strength formic acid (20 cc) is kept at 50° C. for 30 minutes. The mixture is then concentrated to dryness at 50° C. under a pressure of 0.05 mm Hg (0.007 kPa), the residue is taken up in acetone (50 cc), this mixture is concentrated to dryness at 30° C. under reduced pressure (20 mm Hg; 2.7 kPa) and this operation is repeated a second time.

The solid obtained is treated with acetone (50 cc) at 60° C. for 10 minutes whilst stirring, the cooled suspension is filtered and the residue is dried, giving 7-[2-(2-amino-thiazol-4-yl)-2-methoxyimino-acetamido]-2-carboxy-3-{2-[5,6-dioxo-4-formylmethyl-1,4,5,6-tetrahydro-1,2,4-triazin-3-yl]-thiovinyl}-8-oxo-5-thia-1-aza-bicyclo[4.2.0]oct-2-ene (syn isomer, E-form) (0.51 g).

Infra-red spectrum (KBr): characteristic bands in cm$^{-1}$ at 3500, 2300, 1770, 1715, 1680, 1540, 1050 and 950.

Proton nuclear magnetic resonance spectrum (350 MHz, CF$_3$COOD, δ in ppm, J in Hz): 3.87 (AB limit, 2H, —SCH$_2$—); 4.30 (s, 3H, —OCH$_3$); 5.20 (s broad, 2H, >NCH$_2$—); 5.38 (d, J=4, 1H, H in the 6-position); 6.03 (d, J=4, 1H, H in the 7-position); 7.22 (d, J=16, 1H, —C$\underline{H}$=CHS—); 7.50 (s, 1H, H of the thiazole); 7.72 (d, J=16, 1H, =CHS—); 9.74 (s broad, 1H, —CHO).

Proton nuclear magnetic resonance spectrum (350 MHz, CF$_3$COOD+D$_2$O, δ in ppm, J in Hz): 3.82 (AB limit, 2H, —SCH$_2$—); 4.26 (s, 1H, —OCH$_3$); 5.10 (s broad, 2H, >NCH$_2$—); 5.31 (d, J=4, 3H, H in the 6-position); 5.96 (d, J=4, 1H, H in the 7-position); 7.06 (d, J=16, 1H, —C$\underline{H}$=CHS—); 7.43 (s, 1H, H of the thiazole); 7.56 (d, J=16, 1H, =CHS—); 9.67 (s broad, 1H, —CHO). (b) It is also possible to proceed as follows:

A mixture of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1 g), pure formic acid (40 cc), water (1.27 cc) and Merck silica gel (0.05-0.2 mm) (6 g) is heated at 50° C. for 30 minutes, whilst stirring. The mixture is concentrated to dryness at 30° C. under 20 mm Hg (2.7 kPa) and the powder obtained is deposited on a column (column diameter: 2 cm, height: 17 cm) of Merck silica gel (0.05-0.2 mm) (20 g). Elution is carried out with a 3:1:1 (by volume) mixture of ethyl acetate/formic acid/water, 10 cc fractions being collected. Fractions 3 to 26 are concentrated to dryness at 27° C. under 0.05 mm Hg (0.007 kPa). The yellow solid obtained is triturated in ether (60 cc), the mixture is filtered, the residue is dried and 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (syn isomer, E-form) (0.4 g) is obtained, the nuclear magnetic resonance characteristics and infra-red characteristics of this product being identical to those of the product described in (a). 2.

A mixture of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)thiovinyl]-8-oxo-5-thia-1-aza-bicyclo[4.2.0]oct-2-ene (syn isomer, E-form) (0.297 g), water (10 cc) and sodium bicarbonate (0.042 g) is stirred under nitrogen until all has dissolved, and the solution is filtered and lyophilised. The sodium salt of 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) as the aldehyde hydrate (0.28 g) is obtained.

Infra-red spectrum (KBr): characteristic bands in cm$^1$ at 3420, 3200, 1760, 1710, 1670, 1600, 1530, 1040 and 945.

Proton nuclear magnetic resonance spectrum (350 MHz, DMSO d$_6$+D$_2$O, δ in ppm, J in Hz): 3.54 (AB limit, 2H, —SCH$_2$—); 5.06 (d, J=4, 1H, H in the 6-position); 5.08 (s, 1H, —C$\underline{H}$(OH)$_2$); 5.63 (d, J=4, 1H, H in the 7-position); 6.44 (d, J=16, 1H, —C$\underline{H}$=CHS—); 6.76 (s, 1H, H of the thiazole); 7.24 (d, J=16, 1H, =CHS—); 9.60 (s, 0.05H, —CHO).

The nuclear magnetic resonance spectrum of this sodium salt, as the aldehyde hydrate, recorded in CF$_3$COOD, shows that in solution in this solvent the product is in the aldehyde form [spectrum identical to that described in 1. (a)].

4-(2,2-Dimethoxyethyl)-5,6-dioxo-3-thioxo-perhydro-1,2,4-triazine can be prepared as follows:

A solution of sodium methylate is prepared by dissolving sodium (4.15 g) in methanol (140 cc), and 4-(2,2-dimethoxyethyl)-thiosemicarbazide (32.3 g) and ethyl oxalate (26.3 g) are added. The mixture is refluxed, with stirring, for 4 hours and is then allowed to cool. After standing overnight, the suspension obtained is filtered and the precipitate is washed with ether (3×25 cc). The solid is dissolved in water (40 cc) and after cooling to about 4° C. the solution is acidified to pH 3 by means of 4 N hydrochloric acid and left at 4° C. for 30 minutes. After filtering and drying, 4-(2,2-dimethoxyethyl)-5,6-dioxo-3-thioxo-perhydro-1,2,4-trizine (12 g) is obtained in the form of a white solid. Instantaneous m.p. (Kofler)=172° C. (with decomposition).

Infra-red spectrum (KBr): characteristic bands in cm$^1$ at 3280, 3250, 1695, 1380, 1130 and 1050.

Proton nuclear magnetic resonance spectrum (80 MHz, DMSO d$_6$, δ in ppm, J in Hz): 3.30 (s, 6H, —CH(OC$\underline{H}_3$)$_2$); 4.38 (d, J=5.5, 2H, >NCH$_2$—); 4.94 (t, J=5.5, 1H, —C$\underline{H}$(OCH$_3$)$_2$).

4-(2,2-Dimethoxyethyl)-thiosemicarbazide can be prepared as follows:

2,2-Dimethoxyethyl isothiocyanate (37.7 g) is added in the course of 1 hour to a solution of hydrazine hydrate (14.35 g) in ethanol (40 cc), whilst stirring at a temperature of between 5° and 9° C. After 12 hours at 4° C., the mixture is concentrated to dryness at 20° C. under reduced pressure (20 mm Hg; 2.7 kPa). The yellow syrup obtained crystallises after seeding. The solid is dissolved in hot methanol (50 cc) and the solution is filtered and diluted with diethyl ether (200 cc). After about ten hours at 4° C., the mixture is filtered and 4-(2,2-dimethoxyethyl)-thiosemicarbazide (32.3 g) is obtained in the form of a white solid.

Instantaneous m.p. (Kofler)=69° C.

REFERENCE EXAMPLE 13

2-Benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) is prepared as described in Example 12 from the tosylate (15.06 g) and 4-(2,2-diethoxyethyl)-5,6-dioxo-3-thioxo-perhydro-1,2,4-triazine (8 g) in the presence of N,N-diisopropylethylamine (2.85 cc) in dimethylformamide (75 cc). Chromatography is carried out on a column (column diameter: 5 cm, height: 40 cm) of Merck silica gel (0.05-0.2 mm) (250 g), elution being effected with a 30:70 (by volume) mixture of cyclohexane and ethyl acetate (5 liters). The expected product (8.35 g) is obtained in the form of a brown-red froth.

Proton nuclear magnetic resonance spectrum (350 MHz, CDCl$_3$, δ in ppm, J in Hz): 1.15 (t, J=7, 6H, —CH$_3$); 3.38 (d, J=18, 1H, —SCH—); 3.50 and 3.72 (2 q AB, J=9 and 7, 4H, —OCH$_2$—); 3.90 to 4.20 (hump, 6H, >NCH$_2$—, —OCH$_3$ and —SCH—); 4.65 (d, J=4, 1H, H in the 6-position); 4.72 (t, J=5, 1H, —CH(O Et)$_2$); 6.04 (dd, J=4 and 9, 1H, H in the 7-position); 6.70 (s, 1H, H of the thiazole); 6.85 (d, J=16, 1H, —CH=CHS—); 6.97 (s, 1H,

11.94 (s broad, 1H, =NNHCO— or =N

A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (8.30 g) in methylene chloride (100 cc) and dimethylacetamide (2.88 cc) is treated with phosphorus trichloride (1.33 cc) at −10° C. for 2 hours. The product is treated as described in Reference Example 12 1.(a), by chromatography on a colum. (column diameter: 4 cm, height: 44 cm) of Merck silica gel (0.05-0.2 mm) (200 g) and elution with a 30:70 (by volume) mixture of cyclohexane and ethyl acetate (2 liters). 2-Benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.3 g) is obtained in the form of a yellow-orange froth. The product is purified by dissolving it in ethyl acetate (20 cc) and adding isopropyl ether (100 cc); this gives a cream-coloured solid (4.5 g).

Infra-red spectrum (CHBr$_3$): characteristic bands in cm$^1$ at 3390, 1785, 1720, 1685, 1585, 1515, 1495, 1445, 1050, 940, 750 and 740.

Proton nuclear magnetic resonance spectrum (350 MHz, CDCl$_3$, δ in ppm, J in Hz): 1.18 (t, J=7, 6H, —CH$_3$); 3.52 and 3.75 (2 q AB, J=7 and 10, 4H, —OCH$_2$—); 3.60 (d, J=18, 1H, —SCH=); 3.97 to 4.06 (hump, 6H, —OCH$_3$, >NCH$_2$—, —SCH=); 4.76 (t, J=5, 1H, —CH(O Et)$_2$); 5.09 (d, J=4, 1H, H in the 6-position); 5.92 (dd, J=4 and 9, 1H, H in the 7-position); 6.75 (s, 1H, H of the thiazole); 6.85 (d, J=16, 1H, —CH=CHS—); 6.92 (d, J=9, 1H, —CONH—); 6.92 (s, 1H,

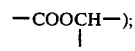

11.30 (s broad, 1H, =NNHCO— or =N

A solution of 2-benzhydryloxycarbonyl-3-{2-[4-(2,2-diethoxyethyl)-5,6-dioxo-1,4,5,6-tetrahydro-1,2,4-triazin-3-yl]-thiovinyl}-7-[2-methoxymino-2-(2-tritylamino-thiazol-4-yl)-acetamido]-8-oxo-5-thia-1-azabicyclo[4.2.0]oct-2-ene (syn isomer, E-form) (1 g) in pure formic acid (25 cc) is heated at 50° C. for 30 minutes. It is then concentrated to dryness at 40° C. under 20 mm Hg (2.7 kPa), the residue is taken up in acetone (20 cc), the mixture is concentrated to dryness at 20° C. under 20 mm Hg (2.7 kPa), the operation is repeated twice, the residue is triturated in acetone (40 cc), this mixture is heated under reflux for 10 minutes, whilst stirring, and the suspension is cooled and filtered. A yellow powder (0.6 g) is obtained, which is purified as follows:

The preceding product (50 mg) is dissolved in pure formic acid (5 cc), Merck silica gel (0.05-0.2 mm) (2.5 g) is added and the mixture is concentrated to dryness at 30° C. under 0.05 mm Hg (0.007 kPa). The powder is deposited on a column (column diameter: 2.5 cm, height: 3 cm) of silica gel (5 g) and elution is carried out with a 3:2:2 (by volume) mixture of ethyl acetate/acetic acid/water (100 cc), 10 cc fractions being collected. Fractions 2 to 7 are concentrated to dryness (30° C., under 0.05 mm Hg; 0.007 kPa) and 7-[2-(2-amino-thiazol-4-yl)-2-methoxyimino-acetamido]-2-carboxy-3-[2-(5,6-dioxo-4-formylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (30 mg) is obtained in the form of a cream-coloured powder, of which the infra-red characteristics and nuclear magnetic resonance characteristics are identical to those of the product of Reference Example 12.

4-(2,2-Diethoxyethyl)-5,6-dioxo-3-thioxo-perhydro-1,2,4-trianzine can be prepared as follows:

4-(2,2-Diethoxyethyl)-thiosemicarbazide (18.6 g) and diethyl oxalate (13.15 g) are added successively to a solution of sodium (2.07 g) in dry methanol (70 cc) and the mixture is refluxed under nitrogen for 4 hours. The cooled mixture is diluted with water (300 cc) and ethyl acetate (150 cc) and then acidified to pH=2 with concentrated hydrochloric acid whilst cooling to 4° C. The mixture is allowed to settle out, the aqueous phase is extracted with ethyl acetate (3×100 cc), and the organic phase is washed with a saturated sodium chloride solution (3×100 cc), dried over sodium sulphate, filtered and concentrated to dryness at 20° C. under 20 mm Hg (2.7 kPa). A thick yellow oil (22.6 g) consisting principally of 4-(2,2-diethoxyethyl)-5,6-dioxo-3-thioxoperhydro-1,2,4-triazine is obtained.

4-(2,2-Diethoxyethyl)-thiosemicarbazide can be prepared as follows:

Hydrazine hydrate (27.3 cc) is added over the course of 1 hour to a solution of 2,2-diethoxyethyl isothiocyanate (94 g) in ethanol (150 cc), at 4° C. The mixture is stirred for a further 20 minutes at 4° C. and is then filtered; the desired product (86 g) is obtained as a white solid, m.p.=96° C.

REFERENCE EXAMPLE 14

4-Carbamylmethyl-5,6-dioxo-3-thioxo-perhydro-1,2,4-trrazine (1.5 g) and N,N-diisopropylethylamine (0.65 cc) are added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-azabicyclo[4.2.0]oct-2-ene (syn isomer, E-form) (3.7 g) (obtained as described in reference example 3) in dry N,N-dimethylformamide (70 cc). The reaction mixture is heated for 3 hours at 60°-65° C. under nitrogen, then diluted with ethyl acetate (300 cc), and washed with distilled water (3×100 cc). After drying over magnesium sulphate and filtration, the solvent is evaporated under reduced pressure (35 mm Hg; 9.4 kPa) at 40° C., and the expected crude product (3.1 g) is obtained.

The crude product (3.7 g) obtained in accordance with the working method described above is chromatographed on a column (column diameter: 4 cm, height: 30 cm) of Merck silica gel (0.04–0.06 mm), elution being carried out under a pressure of 40 kPa with ethyl acetate, and 200 cc fractions being collected. Fractions 11 to 32 are evaporated to dryness under reduced pressure (35 mm Hg; 9.4 kPa) at 40° C. This gives 2-benzhydryloxycarbonyl-3-[2-(4-carbamylmethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g).

Infra-red spectrum (CHBr₃): characteristic bands in cm⁻¹ at 3450, 3390, 3190, 2820, 1780, 1720, 1685, 1590, 1475, 1450, 1050, 945, 755 and 700.

Proton nuclear magnetic resonance spectrum (350 MHz, CDCl₃, δ in ppm, J in Hz): 3.62 and 3.88 (AB, J=16, 2H, —SCH₂—); 3.83 (s, 3H, =NOCH₃); 4.41 (s broad, 2H, —CH₂ CONH₂); 5.22 (d, J=5, 1H, H in the 6-position); 5.75 (dd, J=5 and 9, 1H, H in the 7-position); 6.71 (s, 1H, H of the thiazole); 6.85 and 6.95 (AB, J=16, —CH=CH—S—); 6.94 (s, 1H, —CH(C₆H₅)₂); 7.15 to 7.50 (Mt. 25H, aromatics); 7.71 and 8.80 (2s, 2×1H, —CONH₂); 9.58 (d, J=9, 1H, —CONH—C₇); 12.65 (s, 1H,

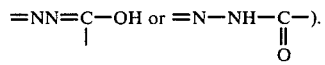

2-Benzhydryloxycarbonyl-3-[2-(4-carbamylmethyl-5,6-dioxo-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.7 g) is dissolved in formic acid (47 cc). After addition of distilled water (30 cc), the reaction mixture is heated for 30 minutes at 50° C. and then diluted with distilled water (17 cc) and filtered. The filtrate is concentrated under reduced pressure (5 mm Hg; 0.67 kPa) at 40° C. The residue is triturated with anhydrous ethanol (50 cc), which is evaporated under reduced pressure (30 mm Hg; 4 kPa) at 40° C.; this operation is repeated twice more. The residue is taken up in anhydrous ethanol (50 cc). The insoluble matter is filtered off and washed with anhydrous ethanol (25 cc) and ether (2×50 cc) and then dried under reduced pressure (5 mm Hg; 0.67 kPa) at 20° C. This gives 7-[2-(2-amino-thiazol-4-yl)-2-methoxyiminoacetamido]-3-[2-(4-carbamylmethyl-5,6-dioxo-1,4,5,6-tetrahydro-1,2,4-triazin-3-yl)-thiovinyl]-2-carboxy-8-oxo-5-thia-1-aza-bicyclo[4.2.0]oct-2-ene (syn isomer, E-form) (1.3 g) in the form of a beige powder.

Infra-red spectrum (KBr): characteristic bands in cm⁻¹ at 3410, 3320, 3200, 3100, 2000, 1770, 1710, 1680, 1630, 1590, 1380, 1040 and 945.

Proton nuclear magnetic resonance spectrum (350 MHz, DMSO d₆, δ in ppm, J in Hz): 3.63 and 3.83 (AB, J=18, 2H, —SCH₂—); 3.87 (s, 3H, =NOCH₃); 4.45 (s broad, 2H, —CH₂—CONH₂); 5.20 (d, J=4, 1H, H in the 6-position); 5.78 (dd, J=4 and 9, 1H, H in the 7-position); 6.75 (s, 1H, H of the thiazole); 6.90 and 7.08 (2d, J=16, 2×1H, —CH=CH—S—); 7.32 (s broad, 2H, —NH₂ of the thiazole); 7.70 (s broad, 2H, -CONH₂); 9.60 (d, J=9, 1H, —CONH—C₇);

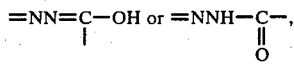

δ>12 ppm.

4-Carbamylmethyl-5,6-dioxo-3-thioxo-perhydro-1,2,4-triazine can be prepared in the following manner:

4-Ethoxycarbonylmethyl-thiosemicarbazide (8.33 g) (GANTE and LANTSCH, Chem. Ber., 97, 989 (1964) are suspended in a saturated solution (250 cc) of ammonia in ethanol, and the reaction mixture is stirred at 25° C. for 22 hours. The insoluble matter is filtered off and washed with alcohol (2×25 cc) and ether (2×50 cc); after drying, 4-carbamylmethyl-thiosemicarbazide (6.2 g), m.p.=188° C., is obtained.

4-Carbamylmethyl-5,6-dioxo-3-thioxo-perhydro-1,2,4-triazine (3.8 g) is obtained by condensing 4-carbamylmethyl-thiosemicarbazide (6.8 g) and ethyl oxalate (6.7 g) in accordance with the method of M. PESSON and M. ANTOINE, Bull. Soc. Chim. France 1590 (1970).

Infra-red spectrum (KBr): characteristic bands in cm⁻¹ at 3550, 3480, 3430, 3270, 3100, 2000, 1710, 1690, 1670, 1365 and 1200.

REFERENCE EXAMPLE 15

A solution of the sodium salt of 4-N,N-dimethylcarbamylmethyl-5,6-dioxo-3-thioxo-perhydro-1,2,4-triazine (4 g) in N,N-dimethylformamide (240 cc) is treated with formic acid (0.60 cc) and then heated to 60° C. under nitrogen. 2-Benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (8 g) is then added, followed by a solution of N,N-diisopropylethylamine (2.8 cc) in N,N-dimethylformamide (20 cc) added dropwise in the course of 10 minutes. The mixture is stirred for 2 hours 20 minutes at 60° C. and is then diluted with distilled water (600 cc) and extracted with ethyl acetate (2×250 cc). The organic extracts are washed successively with an 0.1 N hydrochloric acid solution (200 cc), a half-saturated sodium bicarbonate solution (200 cc) and a half-saturated sodium chloride solution (200 cc) and are then dried over magnesium sulphate. The residue obtained by concentrating to dryness under reduced pressure (30 mm Hg; 4 kPa) at 30° C. is chromatographed on a column (height: 30 cm, diameter: 5 cm) of silica gel (0.04–0.06 mm), elution being carried out under 50 kPa with ethyl acetate (2.5 liters) and then with a 95:5 (by volume) mixture of ethyl acetate and methanol (1.5 liters). Fractions 32 to 37 (each of 100 cc) are combined and concentrated to dryness. This gives 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in the form of a salmon-coloured solid.

Infra-red spectrum (CHBr$_3$): characteristic bands (cm$^{-1}$) at 3380, 3200, 1800, 1725, 1685, 1670, 1590, 1520, 1495, 1450, 1040, 945, 755 and 740.

A solution, cooled to $-10°$ C., of 2-benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.4 g) in methylene chloride (48 cc) is treated with N,N-dimethylacetamide (1.47 cc) and then with phosphorus trichloride (0.44 cc), after which the mixture is stirred for 3 hours at about $-10°$ C. The reaction mixture is then diluted with methylene chloride (100 cc) and poured into a half-saturated sodium bicarbonate solution (100 cc). The organic phase is washed with a half-saturated sodium chloride solution (100 cc), dried over magnesium sulphate and then concentrated to dryness under reduced pressure (30 mm Hg; 4 kPa) at 30° C. The residue is chromagtographed over a column (column diameter: 2.2 cm, height: 30 cm) of silica gel (0.04–0.06 mm), elution being carried out with ethyl acetate (600 cc) and 25 cc fractions being collected. Fractions 10 to 21 are combined and concentrated to dryness. 2-Benzhydryloxycarbonyl-3-{2-[4-(N,N-dimethylcarbamylmethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.3 g) is obtained.

Infra-red spectrum (CHBr$_3$): characteristic bands (cm$^{-1}$) at 3400, 1790, 1730, 1690, 1670, 1590, 1520, 1500, 1460, 1050, 760 and 740.

Proton nuclear magnetic resonance spectrum (350 MHz, CDCl$_3$, δ in ppm, J in Hz): 2.97 and 3.40 (2s, 2×3H, —CON(CH$_3$)$_2$); 3.60 and 3.75 (2d, J=18, 2H, —SCH$_2$—); 4.08 (s, 3H, =NOCH$_3$); 4.73 (s broad, 2H, —CH$_2$CON<); 5.08 (d, J=4, 1H, H in the 6-position); 5.93 (dd, J=4 and 9, 1H, H in the 7-position); 6.77 (s, 1H, H in the 5-position of the thiazole); 6.88 (d, J=16, 1H, —CH=CH—S—); 6.92 (s, 1H, —CO$_2$CH(C$_6$H$_5$)$_2$); 7.0 to 7.6 (hump, 27H, aromatics, —CONH— and —CH=CHS—); 7.81 (s broad, 1H, —NH— of the trityl); 11.25 (s, broad, 1H,

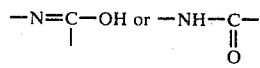

of the triazine).

Distilled water (9 cc) is added to a solution of 2-benzhydryloxycarbonyl-3-2-[4-(N,N-dimethylcarbamylmethyl)-5,6-dioxo-1,4,5,6-tetrahydro-1,2,4-triazin-3-yl]-thiovinyl-7-[2-methoxyimino-2-(2-tritylamino-thiazol-4-yl)-acetamido]-8-oxo-5-thia-1-aza-bicyclo[4.2.0]-oct-2-ene (syn isomer, E-form) (1.3 g) in 98% strength formic acid (15 cc) and the reaction mixture is heated at 50° C. for 45 minutes. After filtration to remove the insoluble matter, the solution is concentrated to dryness under reduced pressure (10 mm Hg; 1.33 kPa) at 40° C. The residue is taken up, and triturated, in ethanol (20 cc), which is then concentrated under reduced pressure (30 mm Hg; 4 kPa) at 30° C. The solid is taken up in ethanol (25 cc) and filtered off, after which it is washed successively with ethanol (3×5 cc) and ethyl ether (3×10 cc) and dried. 7-[2-(2-Amino-thiazol-4-yl)-acetamido]-2-carboxy-3-{2-[4-(N,N-dimethylcarbamylmethyl)-5,6-dioxo-1,4,5,6-tetrahydro-1,2,4-triazin-5-yl]-thiovinyl}-5-thia-1-aza-bicyclo[4.2.0]oct-2-ene (syn isomer, E-form) (0.62 g) is obtained.

Infra-red spectrum (KBr): characteristic bands (cm$^{-1}$) at 3420, 3320, 3210, 1780, 1720, 1690, 1660, 1530, 1040 and 945.

Proton nuclear magnetic resonance spectrum (350 MHz, DMSO d$_6$, δ in ppm, J in Hz): 2.88 and 3.80 (2s, 2×3H, —CON(CH$_3$)$_2$); 3.61 and 3.82 (2d, J=18, 2H, —SCH$_2$—); 3.85 (s, 3H, =NOCH$_3$); 4.80 (s broad, 2H, —CH$_2$CON<); 5.21 (d, J=4, 1H, H in the 6-position); 5.79 (dd, J=4 and 9, 1H, H in the 7-position); 6.75 (s, 1H, H of the thiazole); 6.88 and 7.10 (2d, J=16, 2H, —CH=CH—S—); 7.19 (s broad, 2H, —NH$_2$); 9.60 (d, J=9, 1H, —CONH—C$_7$); 12.73 (s, 1H,

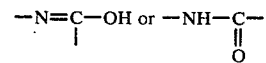

of the triazine).

The sodium salt of 4-(N,N-dimethylcarbamylmethyl)-5,6-dioxo-4-thioxo-perhydro-1,2,4-triazine can be obtained by the method of M. PESSON and M. ANTOINE, Bull. Soc. Chim. Fr. (1970) 1590, by the action of ethyl oxalate on 4-(N,N-dimethylcarbamylmethyl)-thiosemicarbazide in methanol in the presence of sodium methylate.

Infra-red spectrum (KBr): characteristic bands (cm$^{-1}$) at 3200, 1696, 1640, 1580 and 1530.

REFERENCE EXAMPLE 16

A solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (18.2 g), 5,6-dioxo-4-ethoxycarbonylmethyl-3-thioxo-perhydro-1,2,4-triazine (8.4 g) and diisopropylethylamine (3.11 cc) in dimethylformamide (182 cc) is heated at 80° C. for 1 hour 20 minutes. The mixture is then cooled, diluted with ethyl acetate (2,000 cc) and washed with a saturated sodium bicarbonate solution (3×100 cc) and a saturated sodium chloride solution (2×100 cc), dried over magnesium sulphate, filtered and concentrated to dryness under reduced pressure (20 mm Hg; 2.7 kPa). The residue is chromatographed on a column (column diameter: 4.9 cm, height: 31 cm) of Merck silica gel (0.06–0.2 mm) (313 g) and elution is carried out with a 20:80 (by volume) mixture of cyclohexane and ethyl acetate (2,000 cc) and then with ethyl acetate (2,200 cc), 100 cc fractions being collected. Fractions 10 to 40 are concentrated to dryness under reduced pressure (20 mm Hg; 2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2- tritylamino-thiazol-4-yl)-acetamido[-8-oxo-5-oxide-5-thia-1-aza-bicyclo[4.2.9]oct-2-ene (syn isomer, E-form) (6.15 g) is thus obtained in the form of a yellow froth.

Infra-red spectrum (KBr): characteristic bands (cm$^{-1}$) at 3400, 1795, 1720, 1685, 1590, 1515, 1490, 1445, 1210, 1040, 935, 750 and 700.

Proton nuclear magnetic resonance spectrum (350 MHz, CDCl$_3$, δ in ppm, J in Hz): 1.28 (t, J=7, 3H, —CH$_2$CH$_3$); 3.32 and 4.50 (2d, J=18, 2H,

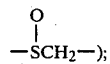

4.02 (s, 3H, —OCH$_3$); 4.23 (q, J=7, 2H, —O—CH$_2$CH$_3$); 4.60 (s, 2H, >NCH$_2$COO—); 4.63 (d, J=4, 1H, H in the 6-position); 6.05 (dd, J=4 and 9, 1H, H in the 7-position); 6.70 (s, 1H, H of the thiazole); 6.76 (d, J=16, 1H, —CH=CHS—); 6.95 (s, 1H, —COOCH<); 11.54 (s, 1H, =N—NHCO— or

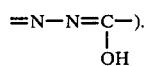

Phosphorus trichloride (1 cc) is added to a solution, cooled to −10° C., of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (6 g) and dimethylacetamide (2.27 cc) in methylene chloride (60 cc), and the mixture is kept at −10° C. for 1 hour 20 minutes. It is then diluted with ethyl acetate (750 cc) and this mixture is washed with a saturated sodium bicarbonate solution (3×100 cc) and a saturated sodium chloride solution (2×100 cc) and evaporated to dryness under reduced pressure (20 mm Hg; 2.7 kPa). The residue is chromatographed over a column (column diameter: 2.1 cm, height: 18 cm) of Merck silica gel (0.06–0.2 mm) (35 g) and elution is carried out with ethyl acetate (0.5 liter), 30 cc fractions being collected. Fractions 2 to 7 are concentrated to dryness under 20 mm Hg (2.7 kPa) and 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5.2 g) is thus obtained in the form of a yellow froth.

Infra-red spectrum (KBr): characteristic bands (cm$^{-1}$) at 3400, 1780, 1720, 1685, 1590, 1525, 1490, 1445, 1210, 1035, 940, 750 and 700.

Proton nuclear magnetic resonance spectrum (350 MHz, CDCl$_3$, δ in ppm, J in Hz): 1.28 (t, J=7, 3H, —CH$_2$CH$_3$); 3.55 and 3.64 (2d, J=18, 2H, —SCH$_2$-); 4.06 (s, 3H, —OCH$_3$); 4.26 (q, J=7, 2H, —OCH$_2$CH$_3$); 4.63 (s, 2H,>N—CH$_2$COO—); 5.09 (d, J=4, 1H, H in the 6-position); 5.94 (dd, J=4 and 9, 1H, H in the 7-position); 6.72 (s, 1H, H of the thiazole); 6.75 (d, J=16, 1H, —CH=CHS—); 6.94 (s, 1H, —COOCH<); 11.05 (s, 1H, =N—NHCO— or

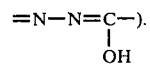

A solution of 2-benzhydryloxycarbonyl-3-[2-(5,6-dioxo-4-ethoxycarbonylmethyl-1,4,5,6-tetrahydro-1,2,4-triazin-3-yl)-thiovinyl]-7-[2-methoxyimino-2-(2-tritylamino-thiazol-4-yl)-acetamido]-8-oxo-5-thia-1-aza-bicyclo[4.2.0]oct-2-ene (syn isomer, E-form) (5 g) in 98% strength formic acid (100 cc) and distilled water (30 cc) is heated at 50° C. for 15 minutes. The mixture is cooled, diluted with water (70 cc) and filtered, and the filtrate is concentrated to dryness under reduced pressure (20 mm Hg; 2.7 kPa). The residue is taken up in ethanol (3×50 cc) and is each time concentrated to dryness under reduced pressure (20 mm Hg; 2.7 kPa); the solid obtained is then suspended in refluxing ethanol (50 cc), cooled, filtered off and dried in vacuo (20 mm Hg; 2.7 kPa). This gives 7-[2-(2-aminothiazol-4-yl)-2-methoxyimino-acetamido]-2-carboxy-3-[2-(5,6-dioxo-4-ethoxycarbonylmethyl-1,4,5,6-tetrahydro-1,2,4-triazin-3-yl)-thiovinyl]-8-oxo-5-thia-1-aza-bicyclo[4.2.0]oct-2-ene (syn isomer, E-form) (1.9 g) in the form of a yellow solid.

Infra-red spectrum (KBr): characteristic bands (cm$^{-1}$) at 3340, 3220, 3130, 1780, 1725, 1690, 1590, 1530, 1040 and 945.

Proton nuclear magnetic resonance spectrum (350 MHz, DMSO d$_6$, δ in ppm, J in Hz): 1.22 (t, J=7, 3H, CH$_3$—CH$_2$—); 3.60 and 3.85 (2d, J=18, 2H, —SCH$_2$—); 3.85 (s, 3H, —OCH$_3$); 4.15 (q, J=7, 2H, —OCH$_2$—CH$_3$); 4.66 (s, 2H,>N—CH$_2$CO—); 5.18 (d, J=4, 1H, H in the 6-position); 5.77 (dd, J=4 and 9, 1H, H in the 7-position); 6.72 (s, 1H, H of the thiazole); 6.87 (d, J=16, 1H, —CH=CHS—); 7.08 (d, J=16, 1H, —CH=CHS—) 7.15 (s broad, 2H, —NH$_2$); 9.58 (d, J=9, 1H, —CONH—); 12.80 (s, 1H, =NNHCO— or

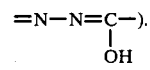

5,6-Dioxo-4-ethoxycarbonylmethyl-3-thioxo-perhydro-1,2,4-triazone can be obtained as follows:

A solution of ethyl isothiocyanoacetate in anhydrous ethanol (185 cc) is added, in the course of 5 minutes, to a suspension of ethyl hydrazino-oxalate (24.4 g) in anhydrous ethanol (185 cc) at 25° C. The mixture dissolves, after which a white precipitate again forms. The mixture is kept stirred for 20 hours under nitrogen, after which a solution prepared from sodium (8.5 g) in ethanol (185 cc) is added in the course of 15 minutes and the mixture is heated under reflux for 4 hours. The red-brown suspension obtained is concentrated to dryness under reduced pressure (20 mm Hg; 2.7 kPa) and the residue is dissolved by adding 4 N hydrochloric acid (100 cc) and ethyl acetate (2,000 cc). The insoluble matter is filtered off and the organic phase is washed with a saturated sodium chloride solution (4×250 cc), dried over magnesium sulphate, filtered and concentrated to dryness under reduced pressure (20 mm Hg; 2.7 kPa). This gives a red-brown gum (43 g) which is dissolved in a saturated sodium bicarbonate solution (300 cc). The brown solution obtained is washed with isopropyl ether (3×100 cc) and brought to pH 1 with the requisite amount of 1 N hydrochloric acid, and is extracted with ethyl acetate (500 cc). The organic phase is washed with a saturated sodium chloride solution (2×50 cc), dried over magnesium sulphate, filtered in the presence of decolorising charcoal and concentrated to dryness under reduced pressure (20 mm Hg; 2.7 kPa). This gives 5,6-dioxo-4-ethoxycarbonylmethyl-3-thioxo-perhydro-1,2,4-triazine (9.5 g) in the form of a brown solid.

Infra-red spectrum (KBr): characteristic bands (cm$^{-1}$) at 3500-2800, 1740, 1700, 1645, 1380, 1235 and 1200.

Proton nuclear magnetic resonance spectrum (80 MHz, DMSO d$_6$, δ in ppm, J in Hz): 1.38 (t, J=7, 3H, —CH$_2$CH$_3$); 4.30 (q, J=7, 2H, —CH$_2$CH$_3$); 5.03 (s, 2H, >N—CH$_2$CO—); 12.50 (s, 1H, —NHCO—).

Ethyl isothiocyanoacetate can be prepared according to D. HOPPE and R. FOLLMANN, Chem. Ber. 109 3047 (1976).

REFERENCE EXAMPLE 17

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]-oct-2-ene (syn isomer, E-form) (10.04 g) (obtained as described in reference example 3), dimethylformamide (200 cc), 4-allyl-5,6-dioxo-3-thioxoperhydro-1,2,4-triazine (2.22 g) and N,N-diisopropylethylamine (2.1 cc) is stirred for 3 hours under nitrogen at 60° C. The mixture is then diluted with ethyl acetate (600 cc), and this mixture is washed with water (2×200 cc) and half-saturated aqueous sodium chloride (2×100 cc), dried over sodium sulphate, filtered and concentrated to dryness at 20° C. under 20 mm Hg. The residue is taken up in methylene chloride (50 cc), Merck silica gel (0.05-0.2 mm) (20 g) is added and the mixture is concentrated to dryness at 20° C. under 20 mm Hg. The powder is deposited on a column (column diameter: 6.1 cm) of Merck silica gel (0.05-0.2 mm) (200 g). Elution is carried out with a 20:80 (by volume) mixture of cyclohexane and ethyl acetate (2 liters), a 10:90 (by volume) mixture of cyclohexane and ethyl acetate (1 liter) and then with ethyl acetate (2 liters), 120 cc fractions being collected. Fractions 8 to 28 are concentrated to dryness at 20° C. under 20 mm Hg. 3-[2-(4-Allyl-5,6-dioxo-1,4,5,6-tetrahydro-1,2,4-triazin-3-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.7 g) is obtained in the form of an orange-coloured froth.

Infra-red spectrum (CHBr$_3$): characteristic bands (cm$^{-1}$) at 3380, 1800, 1720, 1670, 1515, 1045 and 940.

Proton nuclear magnetic resonance spectrum (350 MHz, DMSO d$_6$, δ in ppm, J in Hz): 3.60 and 4.29 (2d, J=18, 2H, —SCH$_2$—); 3.85 (s, 3H, —OCH$_3$); 4.45 (d, J=5, 2H, >NCH$_2$—); 5.05 (d, J=4, 1H, H in the 6-position); 5.17 to 5.27 (Mt, 2H, =CH$_2$); 5.78 to 5.92 (2 Mt, 2H, H in the 7-position and —CH=CH$_2$); 6.78 (s, 1H, H of the thiazole); 6.95 (d, J=16, 1H, —CH=CHS—); 6.97 (s, 1H, —COOCH<); 7.09 (d, J=16, 1H, =CHS—); 8.78 (s, 1H, —NHC(C$_6$H$_5$)$_3$); 9.04 (d, J=9, 1H, —CONH—) 12.62 (s, 1H, =N—NH—CO— or

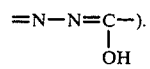

Phosphorus trichloride (0.40 cc) is added to a mixture, cooled to −10° C., of 3-{2-[4-(all-3-yl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-1,3-thiazol-4-yl)-acetamido]-8-oxo-5-oxide-5-thia-1-aza-bicyclo[4.2.0]oct-2-ene (syn isomer, E-form) (2.34 g) and dimethylacetamide (0.85 cc) in methylene chloride (23 cc), and the mixture is stirred for 30 minutes at −10° C. It is then poured into ethyl acetate (250 cc) and this mixture is washed with water (50 cc), a saturated sodium bicarbonate solution (50 cc) and a saturated sodium chloride solution (2×50 cc), dried over sodium sulphate, filtered and concentrated to dryness at 30° C. under 20 mm Hg. The residue, dissolved in methylene chloride (10 cc), is fixed on Merck silica gel (0.05-0.2 mm) (10 g) and deposited on a column (column diameter: 1.4 cm) of silica gel (30 g). Elution is carried out with a 20:80 (by volume) mixture of cyclohexane and ethyl acetate (500 cc), 60 cc fractions being collected. Fractions 2 to 4 care evaporated to dryness at 20° C. under reduced pressure (20 mm Hg). 3-{2-[4-(all-3-yl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.34 g) is obtained in the form of a yellow froth.

Infra-red spectrum (CHBr$_3$): characteristic bands (cm$^{-1}$) at 3380, 1780, 1720, 1680, 1515, 1490, 1445, 1040, 940, 750 and 735.

Proton nuclear magnetic resonance spectrum (350 MHz, CDCl$_3$, δ in ppm, J in Hz): 3.57 and 3.66 (2d, J=18, 2H, —SCH$_2$—); 4.03 (s, 3H, —OCH$_3$); 4.52 (d, J=4, 2H, >NCH$_2$—); 5.09 (d, J=4, 1H, H in the 6-position); 5.26 to 5.38 (2d, 2H, =CH$_2$); 5.78 to 5.88 (mt, 1H, —CH=CH$_2$); 5.92 (dd, J=4 and 9, 1H, H in the 7-position); 6.74 (s, 1H, H of the thiazole); 6.86 (d, J=16, —CH=CHS—); 6.96 (s, 1H, —COOCH—); 7.05 (d, J=9, 1H, —CONH—); 11.68 (s, 1H, =NNHCO— or

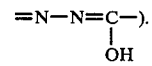

3-2-[4-(all-3-yl)-5,6-dioxo-1,4,5,6-tetrahydro-1,2,4-triazin-3-yl]-thiovinyl-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form (1.34 g) is dissolved in formic acid (13 cc), water (6.5 cc) is added and the mixture is heated at 50° C. for 30 minutes, while stirring. After cooling, the mixture is filtered and the solution is concentrated to dryness at 30° C. under reduced pressure (0.05 mm Hg). The residue is taken up in ethanol (50 cc), the solvent is driven off under reduced pressure (20 mm Hg) at 20° C. and this operation is repeated 3 times. The residue is treated with ethanol (100 cc) under reflux, a slight amount of insoluble matter is removed by filtration, and the filtrate is concentrated to 50 cc at 30° C. under reduced pressure (20 mm Hg) and then cooled for 1 hour at +4° C. After filtering off and drying the precipitate, 3-{2-[4-(all-3-yl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form) is obtained in the form of a yellow powder.

Infra-red spectrum (KBr): characteristic bands (cm$^{-1}$) at 3600, 2300, 1775, 1710, 1680, 1535, 1040 and 945.

Proton nuclear magnetic resonance spectrum (350 MHz, DMSO d$_6$, δ in ppm, J in Hz): 3.63 and 3.80 (2d, J=18, 2H, —SCH$_2$—); 3.88 (s, 3H, —OCH$_3$); 4.48 (d, J=4, 2H, >NCH$_2$—); 5.19 to 5.27 (mt, 3H, =CH$_2$ and H in the 6-position); 5.74 to 5.92 (mt, 2H, —CH=CH$_2$ and H in the 7-position); 6.74 (s, 1H, H of the thiazole); 6.91 (d, J=16, 1H, —CH=CHS—); 7.09 (d, J=16, 1H, =CHS—); 7.18 (s, —NH$_3^+$); 9.60 (d, J=9, 1H, —CONH—); 12.61 (s, 1H, =N—NHCO— or

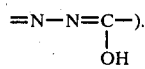

4-Allyl-5,6-dioxo-3-thioxo-perhydro-1,2,4-triazine can be prepared according to the method described in Belgian Patent No. 830,455.

REFERENCE EXAMPLE 18

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (5.02 g), dimethylformamide (93 cc), 4-(2,2-dimethyl-dioxolan-4-yl-methyl)-5,6-dioxo-3-thioxo-perhydro-1,2,4-triazine (1.5 g) and N,N-diisopropylethylamine (1.05 cc) is stirred at 60° C., under nitrogen, for 3 hours. It is then diluted with ethyl acetate (200 cc) and this mixture is washed with water (4×200 cc), dried over sodium sulphate, filtered and concentrated to dryness at 20° C. under 20 mm Hg (2.7 kPa). The residue is fixed on Merck silica gel (0.06-0.2 mm) (10 g) and the powder is deposited on a column (column diameter: 2.5 cm, height: 40 cm) of Merck silica gel (0.06-0.2 mm) (100 g). Elution is carried out with ethyl acetate (1.3 liters), 60 cc fractions being collected. Fractions 6 to 20 are concentrated to dryness at 20° C. under 20 mm Hg (2.7 kPa) and 2-benzhydryloxycarbonyl-3- 2-[4-(2,2-dimethyl-dioxolan-4-yl-methyl)-5,6-dioxo-1,4,5,6-tetrahydro-1,2,4-triazin-3-yl]-thiovinyl -7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.48 g) is obtained in the form of a yellow froth.

Proton nuclear magnetic resonance spectrum (350 MHz, CDCl3, δ in ppm, J in Hz): 1.32 and 1.43 (2s, 6H, —C(CH3)2); 3.34 and 4.05 (2d, J=18, 2H,

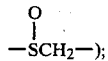

3.74 (t, J=6, 2H, —CH2O—); 3.84 (s, 3H, =NOCH3) 3.95 (t, J=6, 2H, >N—CH2—); 4.38 (quintuplet, J=6, 1H, >CH—O—); 4.65 (d, J=4, 1H, H in the 6-position); 6.06 (dd, J=4 and 9, 1H, H in the 7-position); 6.71 (s, 1H, H of the thiazole); 6.84 (d, J=16, 1H, —CH=CHS—); 6.96 (s, 1H, —COOCH>); 11.60 (s, 1H, =N—NHCO—).

A solution of 2-benzhydryloxycarbonyl-3-{2-[4-(2,2-dimethyl-dioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form (2.48 g) in methylene chloride (22.9 g ) and dimethylacetamide (0.85 cc) is treated with phosphorus trichloride (0.4 cc) at −10° C. for 40 minutes. The mixture is poured into ethyl acetate (250 cc) and this mixture is washed successively with saturated sodium bicarbonate solution (200 cc), water (2×100 cc) and a saturated sodium chloride solution (100 cc), dried over sodium sulphate, filtered and concentrated to dryness at 20° C. under 20 mm Hg (2.7 kPa). The residue is taken up in methylene chloride (20 cc), Merck silica gel (0.06-0.2 mm) (10 g) is added, the mixture is concentrated to dryness at 20° C. under 20 mm Hg and the powder obtained is deposited on a column (column diameter: 1.5 cm, height: 15 cm) of Merck silica gel (0.06-0.2 mm) (40 g). Elution is carried out with methylene chloride (500 cc), 60 cc fractions being collected. Fractions 2 to 7 are combined and concentrated to dryness at 20° C. under 20 mm Hg, and 2-benzhydryloxycarbonyl-3-{2-[4-(2,2-dimethyldioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.4 g) is obtained in the form of a yellow froth.

A mixture of 2-benzhydryloxycarbonyl-3-{2-[4-(2,2-dimethyl-dioxolan-4-yl-methyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.4 g), formic acid (13 cc) and water (6.5 cc) is heated at 50° C. for 30 minutes. It is then cooled to 20° C., filtered and concentrated to dryness at 30° C. under 0.05 mm Hg (0.007 kPa). The residue is taken up in ethanol (100 cc), the solvent is driven off at 20° C. under 20 mm Hg (2.7 kPa) and the operation is repeated twice. The yellow solid is taken up in boiling ethanol (100 cc), the mixture is filtered, the filtrate is concentrated to 50 cc at 20° C. (20 mm Hg; 2.7 kPa) and then filtered, and the solid is washed with diethyl ether (20 cc) and dried. 7-[2-(2-Amino-thiazol-4-yl)-2-methoxyimino-acetamido]-2-carboxy-3-{2-[4-(2,3-dihydroxypropyl)-5,6-dioxo-1,4,5,6-tetrahydro-1,2,4-triazin-3-yl]-thiovinyl}-8-oxo-5-thia-1-aza-bicyclo-[4.2.0]oct-2-ene (syn isomer, E-form) (0.49 g) is obtained.

The nuclear magnetic resonance shows that this product contains about 25% of formic acid ester of one or other of the alcohol groups.

Infra-red spectrum (KBr): characteristic bands (cm−1) at 3650–2200, 1770, 1710, 1680, 1590, 1530, 1045 and 945.

Proton nuclear magnetic resonance spectrum (350 MHz, DMSO d6+D2O, δ in ppm, J in Hz): diol: 3.87 (s, 3H, =NOCH3); 5.20 (d, J=4, 1H, H in the 6-position); 5.75 (d, J=4, H in the 7-position); 6.74 (s, 1H, H of the thiazole); 6.95 and 7.10 (2d , J=16, 2H, —CH=CH—S—); formic acid ester: 3.87 (s, 3H, =NOCH3); 5.18 (d, J=4, 1H, H in the 6-position); 5.75 (d, J=4, 1H, H in the 7-position); 6.74 (s, 1H, H of the thiazole); 6.93 and 7.08 (2d, J=16, 2H, —CH=CHS—); 8.22 (s, 1H, HCOO—).

4-(2,2-Dimethyl-dioxolan-4-yl-methyl)-5,6-dioxo-3-thioxo-perhydro-1,2,4-triazine can be prepared in the following manner:

A solution of sodium (1.12 g) in anhydrous methanol (50 cc) is prepared, 4-(2,2-dimethyl-dioxolan-4-yl-methyl)-thiosemicarbazide (10 g) is added under nitrogen, whilst stirring at 25° C., diethyl oxalate (6.6 cc) is then introduced dropwise in the cource of 10 minutes, and the mixture is heated under reflux for 2 hours. It is then allowed to cool to 20° C., diluted with diethyl ether (1 liter) and filtered, and after drying a white solid (3.7 g) is obtained. The product is taken up in methylene chloride (200 cc) and the mixture is stirred in the presence of 1 N hydrochloric acid (10 cc). The organic phase is decanted, washed with saturated aqueous sodium chloride (2×50 cc), dried over sodium sulphate and concentrated to dryness at 20° C. under 20 mm Hg (2.7 kPa). The oil which remains is taken up in methylene chloride (50 cc), crystallisation is started by scratching, and the mixture is left at 4° C. for 3 hours. After filtration and drying, 4-(2,2-dimethyl-dioxolan- 4-yl-methyl)-5,6-dioxo-3-thioxo-perhydro-1,2,4-triazine (1.5 g) is obtained in the form of white crystals.

Infra-red spectrum (KBr): characteristic bands (cm$^{-1}$) at 3600–3100, 1680, 1575, 1535, 1210 and 1060.

Proton nuclear magnetic resonance spectrum (80 MHz, DMSO d$_6$, δ in ppm, J in Hz): 1.30 and 1.42 (2s, 6H, >C(CH$_3$)$_2$); 3.95 (m, 2H, —CH$_2$O—); 4.50 (m, 3H,

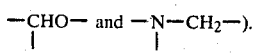

4-(2,2-Dimethyl-dioxolan-4-yl-methyl)-thiosemicarbazide can be prepared in the following manner:

A mixture of methyl N-(2,2-dimethyl-dioxolan-4-yl-methyl)-dithiocarbamate (23,6 g) prepared according to U.S. Pat. No. 4,064,242, absolute ethanol (500 cc) and hydrazine hydrate (5.6 g) is heated under reflux for 2 hours 30 minutes. It is then concentrated to dryness at 20° C. under 20 mm Hg (2.7 kPa) and the residue is taken up in diethyl ether (100 cc). After filtration and drying, 4-(2,2-dimethyl-dioxolan-4-yl-methyl)-thiosemicarbazide (15.2 g) is obtained in the form of a cream-coloured solid melting at 145° C.

Infra-red spectrum (KBr): characteristic bands (cm$^{-1}$) at 3340, 3200, 1630, 1555, 1510, 1380, 1370, 1240, 1210 and 1060.

Proton nuclear magnetic resonance spectrum (80 MHz, CDCl$_3$, δ in ppm, J in Hz): 1.38 and 1.48 (2s, 6H, >C(CH$_3$)$_2$); 3.72 (dd, J=5 and 6, 2H, —CH$_2$N<); 3.90 (s, 2H, —NH$_2$); 4.10 (dd, J=6 and 7, 2H, —CH$_2$O—) 4.38 (m, 1H, >CHO—); 7.78 (t, J=5, 1H, —CH$_2$NH—); 7.98 (s, 1H,

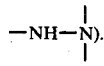

REFERENCE EXAMPLE 19

A solution of 7-[2-(2-amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (0.58 g) (obtained as described in reference example 3) and of the sodium salt of 5,6-dioxo-4-(2-hydroxyethyl)-3-thioxo-perhydro-1,2,4-triazine (0.31 g) in N,N-dimethylformamide (10 cc) is heated for 4 hours 30 minutes at 60° C. The reaction mixture is cooled and diluted with ethyl ether (150 cc) and the precipitate is filtered off, washed with ether (2×25 cc) and dried. Crude 7-[2-(2-amino-thiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.6 g) is obtained in the form of an amorphous beige powder.

Rf=0.42; silica gel chromatographic plate; eluant: a 60:20:20 (by volume) mixture of ethyl acetate, acetic acid and water.

The product can be purified as follows: it is redissolved in a dilute sodium hydroxide solution (50 cc) (pH=8) and the mixture is then brought to pH 5 by means of dilute hydrochloric acid; after filtering off a small amount of insoluble matter, the solution obtained is chromatographed on a column (diameter: 2.4 cm) of XAD-2 resin, with successive elution of the impurities with distilled water (1 liter) and then of the pure product with a 95:5 (by volume) mixture of water and ethanol (1 liter). After concentration under reduced pressure (5 mm Hg) at 30° C., and drying, 7-[2-(2-aminothiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl{-8-oxo-5-thia-1-aza-bicyclo-[4.2.0]oct-2-ene (syn isomer, E-form) (0.2 g) is obtained in the form of light yellow crystals.

Proton nuclear magnetic resonance spectrum (350 MHz, DMSO d$_6$, δ in ppm, J in Hz): 3.60 (t, J=5, 2H, >N—CH$_2$—CH$_2$OH); 3.84 (s, 3H, =NOCH$_3$); 3.92 (t, J=5, 2H, >N—CH$_2$CH$_2$OH); 5.10 (d, J=4, 1H, H in the 6-position); 5.65 (dd, J=4 and 9, 1H, H in the 7-position); 6.39 (d, J=16, 1H, —CH=CH—S—); 6.73 (s, 1H, H in the 5-position of the thiazole); 7.17 (s broad, 2H, —NH$_2$); 7.37 (d, J=16, 1H, —CH=CH—S—); 9.54 (d, J=9, 1H, —CONH—C$_7$).

7-[2-(2-Amino-thiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}8-oxo-5-thia-1-aza-bicyclo[4.2.0]oct-2-ene (syn isomer, E-form) (0.13 g) is dissolved in a N/100 sodium bicarbonate solution (21 cc). The solution is frozen at −80° C. and lyophilised. The sodium salt of 7-[2-(2-amino-thiazol-4-yl)-2-methoxyimino-acetamido]-2-carboxy-3-{2-[5,6-dioxo-4-(2-hydroxyethyl)-1,4,5,6-tetrahydro-1,2,4-triazin-3-yl]-thiovinyl}-8-oxo-5-thia-1-aza-bicyclo[4.2.0]oct-2-ene (syn isomer, E-form) (0.145 g) is obtained in the form of a white lyophilisate.

Rf=0.28; silica gel chromatographic plate; eluant; a 60:20:20 (by volume) mixture of ethyl acetate: acetic acid and water.

Proton nuclear magnetic resonance spectrum (350 MHz, DMSO d$_6$, δ in ppm, J in Hz): 3.50 (AB not resolved, 2H, —SCH$_2$—); 3.60 (t, J=6, 2H, >NCH$_2$CH$_2$OH); 3.91 (t, J=6, 2H, >N—CH$_2$CH$_2$OH); 3.87 (s, 3H, =NOCH$_3$); 5.07 (d, J=4, 1H, H in the 6-position); 5.60 (dd, J=4 and 9, 1H, H in the 7-position); 6.31 (d, J=16, 1H, —CH=CH—S—); 6.71 (s, 1H, H in the 5-position of the thiazole); 7.17 (s broad, 2H, —NH$_2$); 7.36 (d, J=16, 1H, —CH=CHS—); 9.54 (d, J=9, 1H, —CONH—).

5,6-Dioxo-4-(2-hydroxyethyl)-3-thioxo-perhydro-1,2,4-triazine can be prepared by applying the method described by M. PESSON and M. ANTOINE, Bull. Soc. Chim. France 1590 (1970), and working as follows:

4-(Hydroxyethyl)-thiosemicarbazide (5 g) and ethyl oxalate (5.5 cc) are added to a solution of sodium methylate (prepared from sodium (0.85 g) and methanol (37 cc), and the mixture is heated under reflux for 3 hours. After it has cooled, the precipitate is filtered off and washed with methanol (2×5 cc). The crude sodium salt is obtained, and is then taken up in distilled water (25 cc); the solution is filtered, and acidified to pH 2 with 1 N hydrochloric acid. The precipitate is filtered off, washed with water and dried in air. 5,6-Dioxo-4-(2-hydroxyethyl)-3-thioxo-perhydro-1,2,4-triazine (2.4 g) (m.p.=230° C.) is obtained.

The sodium salt can be prepared by treating 5,6-dioxo-4-(2-hydroxyethyl)-3-thioxo-perhydro-1,2,4-triazine (4.73 g), in anhydrous methanol, with sodium 2-ethylhexanoate. This gives 4.7 g of the sodium salt.

Infra-red spectrum (KBr): principal bands (cm$^{-1}$) at 3420, 3200, 3070, 1655, 1575, 1560, 1395, 1205, 1080, 1045 and 835.

4-(2-Hydroxyethyl)-thiosemicarbazide can be obtained according to the method described by Y.

KAZAKOV and I. Y. POTOVSKII, Doklady Acad. Nauk. SSSR, 134, 824 (1960).

7[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) can be prepared in the following manner:

A solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]-oct-2-ene (syn isomer, E-form) (5.93 g) in a mixture of pure formic acid (80 cc) and water (25 cc) is heated at 50° C. for 30 minutes. The mixture is then cooled to 20° C., filtered and concentrated to dryness at 30° C. under 20 mm Hg (2.7 kPa). The residue is taken up in acetone (150 cc), the mixture is concentrated to dryness at 20° C. under 20 mm Hg (2.7 kPa), the operation is repeated twice more and the residue is then triturated in ether (75 cc) and filtered off. 7-[2-(2-Amino-thiazol-4-yl)-2-methoxyimino-acetamido]-2-carboxy-8-oxo-3-(2-tosyloxyvinyl)-5-thia-1-aza-bicyclo[4.2.0]oct-2-ene (syn isomer, E-form) (3.4 g) is obtained in the form of a yellow powder.

REFERENCE EXAMPLE 20

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]-oct-2-ene (syn isomer, E-form) (10.04 g) (obtained as described in reference example 3), dimethylformamide (200 cc), 4-(2-acetamidoethyl)-5,6-dioxo-3-thioxo-perhydro-1,2,4-triazine (2.76 g) and diisopropylethylamine (2.1 cc) is stirred at 60° C. for 3 hours, under nitrogen. The cooled mixture is then diluted with ethyl acetate (800 cc) and the organic phase is washed with water (1.2 liters), dried over sodium sulphate, filtered and concentrated to dryness under reduced pressure (20 mm Hg) at 20° C. The residue is triturated in ether (150 cc), the insoluble matter is filtered off, and after drying 3-{2-[4-(2-acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (9.5 g) is obtained in the form of a light brown solid.

Infra-red spectrum (CHBr₃): characteristic bands (cm⁻¹) at 3370, 1795, 1710, 1680, 1520, 1495, 1445, 750 and 735.

Proton nuclear magnetic resonance spectrum (350 MHz, DMSO d₆, δ in ppm, J in Hz): 1.75 (s, 3H, —COCH₃); 3.65 and 3.90 (2d, J=18, 2H, —SCH₂—); 3.86 (s, 3H, —OCH₃); 3.88 (t, 2H, >NCH₂—); 5.26 (d, J=4, 1H, H in the 6-position); 5.78 (dd, J=4 and 9, 1H, H in the 7-position); 6.73 (s, 1H, H of the thiazole); 6.92 (d, J=16, 1H, —CH=CHS—); 6.95 (s, 1H,

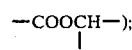

7.0 (d, J=16, 1H, =CHS—);7.78 (t, J=6, —NH-COCH₃); 8.81 (s, 1H, —NHC(C₆H₅)₃); 9.60 (d, J=9, 1H, —CONH—); 12.60 (s, 1H, =N—NHCO— or

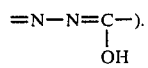

Dimethylacetamide (3.4 cc) followed by phosphorus trichloride (1.49 cc) is added to a solution, cooled to −10° C., of 3-{2-[4-(2-acetamidoethyl)-5,6-dioxo-1,4,5,6-tetrahydro-1,2,4-triazin-3-yl]-thiovinyl}-2-benzhydryl-oxycarbonyl-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form (9.03 g) in methylene chloride (85 cc). The mixture is stirred for 2 hours at −10° C. and is then diluted with methylene chloride (500 cc), and this mixture is washed with a half-saturated sodium bicarbonate solution (250 cc) and a saturated sodium chloride solution (250 cc), dried over sodium sulphate and concentrated to dryness under reduced pressure (20 mm Hg) at 20° C. The chestnut-coloured solid obtained is dissolved in a mixture of ethyl acetate, methylene chloride and methanol (120:120:80 cc) and the solution is chromatographed over a column (column diameter: 4 cm) of Merck silica gel (0.04–0.06 mm). Elution is carried out with a 95:5 (by volume) mixture of ethyl acetate and methanol (1.5 liters) under a pressure of 40 kPa, 125 cc fractions being collected. Fractions 6 to 10 are concentrated to dryness under reduced pressure (20 mm Hg) at 20° C. 3-{2-[4-(2-Acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.33 g) is obtained in the form of a beige solid.

Infra-red spectrum (CHBr₃): characteristic bands (cm⁻¹) at 3380, 1785, 1710, 1680, 1520, 1495, 1445, 755 and 740.

Proton nuclear magnetic resonance spectrum (350 MHz, DMSO d₆, δ in ppm, J in Hz): 1.75 (s, 3H, —COCH₃); 3.32 (mt, 2H, —CH₂NHCO—); 3.62 and 4.30 (2d, J=18, 2H, —SCH₂—); 3.86 (t, 2H, >NCH₂—); 3.86 (s, 3H, —OCH₃); 5.05 (d, J=4, 1H, H in the 6-position); 5.85 (dd, J=4 and 9, 1H, H in the 7-position); 6.80 (s, 1H, H of the thiazole); 6.96 (d, J=16, 1H, —CH=CHS—); 6.97 (s, 1H, —COOCH>); 7.12 (d, J=16, 1H, =CHS—); 7.98 (t, J=6, 1H, —NH COCH₃); 8.75 (s, 1H, —NHC(C₆H₅)₃); 9.04 (d, J=9, 1H, —CONH—); 12.60 (s, 1H, =N—N-CHO—or

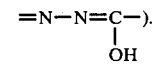

3-{2-[4-(2-Acetamidoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.15 g) is dissolved in formic acid (80 cc), water (30 cc) is added and the mixture is heated at 60° C. for 30 minutes, whilst stirring. It is then cooled, filtered and concentrated to dryness under reduced pressure (0.05 mm Hg) at 50° C. The residue is taken up in ethanol (250 cc), the mixture is concentrated to dryness under reduced pressure (20 mm Hg) at 30° C., the operation is repeated and the solid is then taken up in ethanol (40 cc) whilst stirring at 40° C. After cooling, filtering and drying, 3-{2-[4-(2-acetamidoethyl)-5,6-dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form) (1.56 g) is obtained in the form of a yellow powder.

Infra-red spectrum (KBr): characteristic bands (cm⁻¹) at 3500, 2500, 1775, 1710, 1685 to 1630, 1540, 1045 and 950.

Proton nuclear magnetic resonance spectrum (350 MHz, DMSO d₆, δ in ppm, J in Hz): 1.90 (s, 3H, —CH₃); 3.48 (m, 2H, —CH₂NH—); 3.62 and 3.73 (2d, J=18, 2H, —SCH₂—); 4.0 (s, 3H, —OCH₃); 5.15 (d, J=4, 1H, H in the 6-position); 5.82 (dd, J=4 and 9, 1H, H in the 7-position); 6.78 (s, 1H, H of the thiazole); 6.86 (d, J=16, 1H, —CH=CHS—); 7.31 (d, J=16, 1H, =CHS—); 7.73 (s, 3H, —NH₃⁺); 9.50 (d, J=9, 1H, —CONH—); 12.54 (s broad, 1H, —CONHN=or

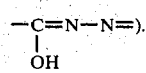

A portion of the preceding product (0.128 g) is dissolved in an 0.1 M sodium bicarbonate solution (2 cc), and the resulting solution is filtered and lyophilised. The sodium salt of 3-{2-[4-(acetamidoethyl)-5,6--dioxo-1,4,5,6-tetrahydro-1,2,4-triazin-3-yl]-thiovinyl}-7-[2-(2-amino-thiazol-4-yl)-2-methoxyimino-acetamido]-2-carboxy-8-oxo-5-thia-1-aza-bicyclo[4.2.0]oct-2-ene (syn isomer, E-form) (0.127 g) is obtained.

4-(2-Acetamidoethyl)-5,6-dioxo-3-thioxo-perhydro-1,2,4-triazine (3.61 g) is obtained from 4-(2-acetamidoethyl)-thiosemicarbazide (4.41 g) and ethyl oxalate (3.4 cc) in the presence of sodium methylate, by application of the method described by M. PESSON and M. ANTOINE, Bull. Soc. Chim. France 1590 (1970). The product has the following properties: instantaneous m.p [Kofler]>260° C.; infra-red spectrum (KBr): characteristic bands (cm⁻¹) at 3365, 3050, 2000, 1710, 1630, 1600-1580, 1545, 1350, 1330 and 1200; proton nuclear magnetic resonance spectrum (80 MHz, DMSO d₆, δ in ppm, J in Hz): 1.7 (s, 3H, —CH₃); 3 to 3.7 (mt, —CH₂NHCO— and H₂O); 4.3 (t, 2H, >N CH₂—); 7.85 (t, 1H, —NHCO—); 12.5 (m, 2H, —NH— of the ring).

The thiosemicarbazide starting material can be obtained in the following manner:

A solution of methyl N-(2-acetamidoethyl)-dithiocarbamate (57.7 g) and hydrazine hydrate (14.6 cc) in absolute ethanol (300 cc) is heated under reflux for 2 hours. The mixture is then cooled to 4° C. and is filtered, and the insoluble matter is dried at 30° C. under 0.05 mm Hg. (4-(2-Acetamidoethyl)-thiosemicarbazide (39.5 g) is obtained in the form of white crystals (instantaneous m.p. [Kofler]=171° C.).

Infra-red spectrum (KBr): characteristic bands (cm⁻¹) at 3280, 3180, 1650, 1560 to 1535, 1360 and 1280.

REFERENCE EXAMPLE 21

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (6.02 g) (obtained as described in reference example 3), dimethylformamide (60 cc), 2-acetamidomethyl-5-mercapto-1,3,4-thiadiazole (2.27 g) and diisopropylethylamine (1.15 cc) is stirred for 2 hours 30 minutes at 60° C. under nitrogen. The cooled mixture is diluted with ethyl acetate (250 cc), and this mixture is washed with water (150 cc), 0.1 N hydrochloric acid (100 cc), a saturated sodium bicarbonate solution (100 cc) and water (2×100 cc), dried over sodium sulphate, filtered and concentrated to dryness at 20° C. under reduced pressure (20 mm Hg). The residue, fixed on Merck silica gel (0.05-0.5 mm) (20 g), is deposited on a column (column diameter: 2.5 cm) of silica gel (0.05-0.2 mm) (70 g). Elution is carried out with ethyl acetate (2.5 liters), 100 cc fractions being collected. Fractions 9 to 23 are evaporated to dryness at 20° C. under reduced pressure (20 mm Hg) and 3-[2-(2-acetamidomethyl-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) is obtained in the form of a brown froth.

Infra-red spectrum (KBr): characteristic bands (cm⁻¹) at 3400, 1795, 1720, 1670, 1525, 1495, 1450, 1370, 1040, 940, 750 and 700.

Proton nuclear magnetic resonance spectrum (350 MHz, CDCl₃, δ in ppm, J in Hz): 1.97 (s, 3H, —COCH₃); 3.30 and 4.15 (2d, J=18, 2H, —SCH₂—); 4.08 (s, 3H, —OCH₃); 4.64 (d, J=4, 1H, H in the 6-position); 4.72 (AB, 2H, —CH₂NHCO—); 6.14 (dd, J=4 and 9, 1H, H in the 7-position); 6.72 (s, 1H, H of the thiazole); 6.97 (s, 1H,

Dimethylacetamide (1.1 cc) and phosphorus trichloride (0.519 cc) are added to a solution, cooled to −10° C., of 3-[2-(2-acetamidomethyl-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form (3 g) in methylene chloride (29 cc), and the mixture is then stirred for 1 hour at −10° C. Thereafter it is poured into ethyl acetate (250 cc) and this mixture is washed with a saturated sodium bicarbonate solution (250 cc) and with water (2×100 cc), dried over sodium sulphate, filtered and concentrated to dryness at 20° C. under reduced pressure (20 mm Hg). The residue is dissolved in methylene chloride (10 cc) and the solution is chromatographed on a column (column diameter: 4 cm) of Merck silica gel (0.04-0.06 mm). Elution is carried out with a 80:20 (by volume) mixture of ethyl acetate and cyclohexane (2.5 liters) under a pressure of 40 kPa, 100 cc fractions being collected. Fractions 11 to 21 are evaporated to dryness at 20° C. under reduced pressure (20 mm Hg) and 3-[2-(2-acetamido-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is obtained in the form of a yellow froth.

Infra-red spectrum (KBr): characteristic bands (cm⁻¹) at 3400, 3280, 1785, 1720, 1670, 1530, 1495, 1450, 1370, 1040, 945, 755 and 700.

Proton nuclear magnetic resonance spectrum (350 MHz, CDCl₃, δ in ppm, J in Hz): 2.0 (s, 3H, —COCH₃); 3.58 and 3.68 (2d, J=18, 2H, —SCH₂—); 4.08 (s, 3H, —OCH₃); 4.75 (d, J=5, 2H, —CH₂NHCO—); 5.10 (d, J=4, 1H, H in the 6-position); 5.97 (dd, J=4 and 9, 1H, H in the 7 -position); 6.55 (t, J=5, 1H, —NHCO—); 6.76 (s, 1H, H of the thiazole); 7.0 (s, 1H, —COOCH>); 7.05 (s, 1H, —NH—C(C₆H₅)₃); 7.18 (d, J=16, 1H, —CH=CHS—).

3-[2-(2-Acetamidomethyl-1,3,4-thiadiazol-5-yl)-thiovinyl]-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.1 g) is dissolved in formic acid (21 cc), water (12 cc) is added and the mixture is heated at 50° C. for 30 minutes. It is then cooled to about 20° C., filtered and concentrated to dryness at 50° C. under reduced pressure (0.05 mm Hg), the residue is taken up in ethanol (50 cc) and the solvent is driven off at 20° C. under reduced pressure (20 mm Hg); this operation is repeated twice, after which the residue is taken up in ethanol (50 cc) under reflux. The mixture is filtered hot to remove a small amount of insoluble matter, and the filtrate is concentrated to 20 cc under reduced pressure (20 mm Hg) at 20° C. and filtered. After drying, 3-[2-(2-acetamidomethyl-1,3,4-thiadiazol-5-yl)-thiovinyl]-7-[2-(2-aminothiazol-4-yl)-2-methoxyimino-acetamido]-2-carboxy-8-oxo-5-thia-1-aza-bicyclo[4.2.0]oct-2-ene (syn isomer, E-form) (0.75 g) is obtained in the form of a cream-coloured powder.

Infra-red spectrum (KBr): characteristic bands (cm$^{-1}$) at 3320, 1770, 1660, 1540, 1380 and 1040.

Proton nuclear magnetic resonance spectrum (350 MHz, DMSO d$_6$, δ in ppm, J in Hz): 1.90 (s, 3H, —COCH$_3$); 3.68 and 3.92 (2d, J=18, 2H, —S—CH$_2$-); 3.87 (s, 3H, —OCH$_3$); 4.22 (d, J=4, 1H, H in the 6-position); 4.60 (AB limit, 2H, —CH$_2$NHCo—); 5.82 (dd, J=4 and 9, 1H, H in the 7-position); 6.75 (s, 1H, —OCH$_3$); 7.15 (d, J=16, 1H, —CH=CHS—); 7.20 (s, 3H, —NH$_3$=); 7.25 (d, J=16, 1H, =CHS—); 9.63 (d, J=9, 1H, —CONH—).

2-Acetamidomethyl-5-mercapto-1,3,4-thiadiazole can be prepared by application of the method described in Japanese Patent 76/80857.

REFERENCE EXAMPLE 22

A mixture of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo-[4.2.0]oct-2-ene (syn isomer, E-form) (10 g), dimethylformamide (200 cc) and the sodium salt of 1-(2,2-dimethoxyethyl)-5-mercapto-tetrazole (5.75 g) is stirred for 24 hours at 50° C. under nitrogen. It is then diluted with ethyl acetate (200 cc) and water (200 cc), and the organic phase is decanted, washed with water (3×200 cc) and saturated aqueous sodium chloride (100 cc), filtered and concentrated to dryness under 20 mm Hg (2.7 kPa) at 20° C. The residue is chromatographed on a column (column diameter: 6 cm, height: 30 cm) of Merck silica gel (0.04-0.06 mm). Elution is carried out with a 50:50 (by volume) mixture (3.8 liters) and a 25:75 (by volume) mixture (4.6 liters) of cyclohexane and ethyl acetate, 120 cc fractions being collected. Fractions 40 to 69 are concentrated to dryness under 20 mm Hg (2.7 kPa) at 20° C., and 2-benzhydryloxycarbonyl-3--{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3.4 g) is obtained in the form of a brown froth, which is used, as obtained, in the subsequent operations.

A solution of 2-benzhydryloxycarbonyl-3--{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) 3.37 g) in methylene chloride (25 cc) and dimethylacetamide (1.31 cc) is treated with phosphorus trichloride (0.58 cc) at −8° C. for 30 minutes, whilst stirring. The mixture is diluted with methylene chloride (75 cc), and this mixture is washed with a half-saturated sodium bicarbonate solution (2×50 cc) and water (2×50 cc), dried over sodium sulphate, filtered and concentrated to dryness under 20 mm Hg (2.7 kPa) at 20° C. The residue is chromatographed on a column (column diameter: 4 cm, height: 20 cm) of Merck silica gel (0.04-0.06 mm). Elution is carried out with a 50:50 (by volume) mixture of cyclohexane and ethyl acetate (1.8 liters), under a pressure of 40 kPa, 60 cc fractions being collected. Fractions 16 to 24 are evaporated to dryness and 2-benzhydryloxycarbonyl-3-{2-[1-(2,2-dimethoxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.1 g) is obtained in the form of a cream-coloured froth.

Infra-red spectrum (KBr): characteristic bands (cm$^{-1}$) at 3400, 1790, 1725, 1690, 1520, 1500, 1450, 1210, 1050, 1040, 945, 755 and 705.

Proton nuclear magnetic resonance spectrum (350 MHz, DMSO d$_6$, δ in ppm, J in Hz): 3.31 (s, 6H, >C(OCH$_3$)$_2$); 3.65 and 3.91 (2d, J=18, 2H, —SCH$_2$—); 3.83 (s, 3H, =NOCH$_3$); 4.48 (d, J=6, 2H, >NCH$_2$CH<); 4.70 (t, J=6, >NCH$_2$CH<); 5.23 (d, J=4, H$_6$); 5.78 (dd, J=4 and 9, H$_7$); 6.74 (s, H of the thiazole); 6.96 (s, —COOCH); 7.02 and 7.08 (2d, J=16, 2H, —CH=CH—S—); 8.79 (s, —NH—); 9.60 (d, J=9, —NHCO—).

A solution of 2-benzhydryloxycarbonyl-3-{2-[1-(-2,2-dimethoxyethyl)-tetrazol-5-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.06 g) in formic acid (42 cc) is heated for 30 minutes at 50° C. It is then concentrated to dryness under 0.05 mm Hg (0.007 kPa) at 30° C., the residue is taken up in acetone (100 cc), the mixture is again concentrated to dryness, under 20 mm Hg (2.7 kPa) at 20° C., and this operation is repeated 4 times. The yellow solid obtained is treated with acetone (30 cc) under reflux, and the mixture is allowed to cool and filtered. After drying the product, 7-[2-(2-amino-thiazol-4-yl)-2-methoxyimino-acetamido]-2-carboxy-3{2-[1-(2,2-dimethoxyethyl)-tetrazol-5-yl]-thiovinyl}-8-oxo-5-thia-1-aza-bicyclo[4.2.0]oct-2-ene (syn isomer, E-form) (0.43 g) is obtained in the form of a yellow powder.

Infra-red spectrum (KBr): characteristic bands (cm$^{-1}$) at 3350, 1780, 1680, 1655, 1620, 1530, 1120, 1040 and 940.

Proton nuclear magnetic resonance spectrum (350 MHz, CF$_3$CO$_2$D, δ in ppm, J in Hz): 3.61 (s, 6H, >C(OCH$_3$)$_2$); 3.92 (s broad, 2H, —SCH$_2$—); 4.31 (s, 3H, =NOCH$_3$); 4.73 (d, J=6, 2H, >NCH$_2$—); 5.0 (t, J=6, 1H, —CH$_2$—CH<); 5.38 (d, J=4, H$_6$); 6.05 (dd, J=4 and 9, H$_7$); 7.16 and 7.88 (2d, J=16, —CH=CH—); 7.50 (s, H of the thiazole).

The sodium salt of 1-(2,2-dimethoxyethyl)-5-mercapto-tetrazole can be prepared in the following manner:

A solution of sodium azide (65 g) in 95% strength ethanol (1,680 cc) is heated under reflux. A solution of 2,2-dimethoxyethyl isothiocyanate (147.2 g) in 95 % strength ethanol (320 cc) is added dropwise, with stirring, in the course of 1 hour 30 minutes, and the mixture is heated under reflux for 12 hours. It is then concentrated to dryness at 40° C. under 20 mm Hg (2.7 kPa), the residue is taken up in acetone (600 cc), the mixture is filtered and diethyl ether (1 liter) is added. The crystallisation is started, and a further amount of diethyl ether (2.5 liters) is added. The batch is left at 20° C. for 24 hours and is then filtered. After drying, the sodium salt of 1-(2,2-dimethoxyethyl)-5-mercapto-tetrazole, in the form of the hydrate (208.2 g), is obtained.

Infra-red spectrum (KBr): characteristic bands (cm$^{-1}$) at 3480, 3220, 2840, 1660, 1400, 1290, 1115, 1070, 1025 and 790.

REFERENCE EXAMPLE 23

A mixture of 2-benzhydryloxycarbonyl-8-oxo-5-oxide-3-(2-tosyloxyvinyl)-7-[2-(2-tritylamino-thiazol-4-yl)-2-vinyloxyimino-acetamido]-5-thia-1-aza-bicyclo[4.2.0]-oct-2-ene (syn isomer, E-form) (0.4 g), dimethylformamide (5 cc), 5-mercapto-1-methyl-tetrazole (0.1 g) and N,N-diisopropylethylamine (0.15 cc) is heated at 60° C. for 4 hours. It is then taken up in ethyl acetate (50 cc) and the organic phase is washed with water (50 cc), 0.1 N hydrochloric acid (50 cc), a half-saturated sodium bicarbonate solution (50 cc) and a saturated sodium chloride solution (50 cc), dried over sodium sulphate, filtered and concentrated to dryness under 20 mm Hg (2.7 kPa) at 30° C. The residue is chromatographed on a column (column diameter: 1.5 cm, height: 15 cm) of Merck silica gel (0.06–0.2 mm) (50 g). Elution is carried out with as 90:10 (by volume) mixture of methylene chloride and ethyl acetate (2.5 liters) under a pressure of 40 kPa, 25 cc fractions being collected. Fractions 18 to 42 are concentrated to dryness under 20 mm Hg (2.7 kPa) at 20° C. This gives 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]-oct-2-ene (syn isomer, E-form) (0.15 g), having the following characteristics;

Infra-red spectrum (KBr): characteristic bands (cm$^{-1}$) at 3340, 2940, 2860, 1800, 1730, 1690, 1640, 1575, 1525, 1500, 1450, 1215, 1045, 1005, 950, 765 and 760.

Proton nuclear magnetic resonance spectrum (350 MHz, CDCl$_3$, δ in ppm, J in Hz): 3.31 and 4.05 1 (2d, J=18, 2H, —SCH$_2$—); 3.92 (s, 3H, —CH$_3$); 4.26 (dd, J=2 and 6, 1H,

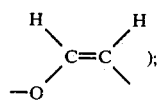

4.76 (dd, J=2 and 14, 1H,

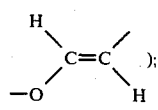

4.67 (d, J=4, 1H, H in the 6-position); 6.18 (dd, J=4 and 9, 1H, H in the 7-position); 6.78 (s, 3H, H of the thiazole); 6.95 (s, 1H, —COOCH<); 7.0 (d, J=15, 1H, —C<u>H</u>=CHS—); 7.05 (dd, J=4 and 6, 1H, —OC<u>H</u>=); 7.10 (s, 1H,

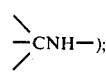

7.58 (d, J=15, 1H, —CH=C<u>H</u>S—).

A solution of 2-benzhydryloxycarbonyl-3-[2-(1-methyl-tetrazol-5-yl)-thiovinyl]-8-oxo-5-oxide-7-[2-(2-tritylamino-thiazol-4-yl)-2-vinyloxyimino-acetamido]-5-thia-1-aza-bicyclo[4.2.0]oct-2-ene (syn isomer, E-form) (3 g) in methylene chloride (31.7 cc) and dimethylacetamide (1.22 cc) is treated with phosphorus trichloride (0.554 cc) at −10° C. for 20 minutes. The mixture is poured into ethyl acetate (250 cc) and this mixture is washed with a saturated sodium bicarbonate solution (250 cc), water (250 cc) and a saturated sodium bicarbonate solution (250 cc), dried over sodium sulphate, filtered and concentrated to dryness under 20 mm Hg (2.7 kPa) at 20° C. The product is fixed on Merck silica gel (0.06–0.2 mm) (10 g) and is chromatographed on a column (column diameter: 1.5 cm) of Merck silica gel (0.06–0.2 mm) (30 g). Elution is carried out with an 80:20 (by volume) mixture (250 cc), a 70:30 (by volume) mixture (250 cc) and a 60:40 (by volume) mixture (250 cc) of cyclohexane and ethyl acetate, 60 cc fractions being collected. Fractions 5 to 10 are concentrated to dryness under 20 mm Hg (2.7 kPa) at 20° C., and 2-benzhydryloxycarbonyl-3-[2-(1-methyl-tetrazol-5-yl)-thiovinyl]-8-oxo-7-[2-(2-tritylamino-thaizol-4-yl)-2-vinyloxyimino-acetamido]-5-thia-1-aza-bicyclo[4.2.0]oct-2-ene (syn isomer, E-form) (1.92 g) is obtained in the form of a cream-coloured froth.

Rf=0.58 [silica gel chromatographic plate, eluant: a 50:50 (by volume) mixture of cyclohexane and ethyl acetate].

A mixture of 2-benzhydryloxycarbonyl-3-[2-(1-methyl-tetrazol-5-yl)-thiovinyl]-8-oxo-7-[2-(2-tritylamino-thiazol-4-yl)-vinyloxyimino-acetamido]-5-thia-1-aza-bicyclo[4.2.0]oct-2-ene (syn isomer, E-form) (1.92 g), formic acid (15 cc) and water (7 cc) is stirred at 50° C. for 15 minutes. It is then filtered and concentrated to dryness under 0.05 mm Hg (0.007 kPa) at 30° C. The oil which remains is taken up in ethanol (100 cc), the solvent is driven off under 20 mm Hg (2.7 kPa) at 20° C., and this operation is repeated a second time. The residue is taken up in ethanol (100 cc), and the mixture is heated under reflux, whilst stirring, and is cooled and filtered. After drying, 7-[2-(2-amino-thiazol-4-yl)-2-vinyloxyimino-acetamido]-2-carboxy-3-[2-(1-methyltetrazol-5-yl)-thiovinyl]-8-oxo-5-thia-1-aza-bicyclo[4.2.0]oct-2-ene (syn isomer, E-form) (0.72 g) is obtained in the form of a yellow powder.

Infra-red spectrum (KBr): characteristic bands (cm$^{-1}$) at 3340, 1770, 1680, 1620, 1530 and 1380.

Proton nuclear magnetic resonance spectrum (350 MHz, DMSO d$_6$, δ in ppm, J in Hz): 3.64 and 3.89 (2d, J=18, 2H, —SCH$_2$—); 4.0 (s, 3H, —CH$_3$); 4.22 (dd, J=2 and 6, 1H,

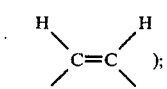

4.65 (dd, J=2 and 14, 1H,

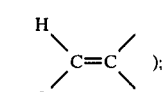

5.22 (d, J=4, 1H, H in the 6-position); 5.82 (dd, J=4 and 9, 1H, H in the 7-position); 6.75 (s, 1H, H of the thiazole); 6.95 (d, J=16, 1H, —C<u>H</u>=CHS—); 6.96 (dd, J=6 and 14, 1H, —OC<u>H</u>=CH$_2$); 7.13 (d, J=16, 1H, =C<u>H</u>S—); 9.83 (d, J=9, 1H, —CONH—).

2-Benzhydryloxycarbonyl-8-oxo-5-oxide-3-(2-tosyloxyvinyl)-7-[2-(2-tritylamino-thiazol-4-yl)-2-vinyloxyimino-acetamido]-5-thia-1-aza-bicyclo[4.2.0]oct-2-ene (syn isomer, E-form) can be prepared in the following manner:

A solution of 85% strength m-chloroperbenzoic acid (0.33 g) in methylene chloride (7 cc) is added dropwise, in the course of 10 minutes, to a solution, cooled to −10° C., of 2-benzhydryloxycarbonyl-8-oxo-3-(2-tosyloxyvinyl)-7-[2-(2-tritylamino-thiazol-4-yl)-2-vinyloxyimino-acetamido]-5-thia-1-aza-bicyclo[4.2.0]oct-2-ene and oct-3-ene (syn isomer, mixture of the E- and Z-forms) in methylene chloride (5 cc). The mixture is stirred for 1 hour at −10° C. and is then diluted with methylene chloride (30 cc), and this mixture is washed with a saturated sodium bicarbonate solution (2×50 cc) and a half-saturated sodium chloride solution (50 cc), dried over sodium sulphate, filtered and concentrated to dryness under 20 mm Hg (2.7 kPa) at 30° C. The residue is chromatographed on a column (column diamter: 1 cm, height: 10 cm) of Merck silica gel (0.06–0.2 mm). Elution is carried out with methylene chloride (500 cc), a 97:3 (by volume) mixture (1 liter) and a 95:5 (by volume) mixture (1.5 liters) of methylene chloride and ethyl acetate, 25 cc fractions being collected. Fractions 14 to 24 are evaporated to dryness under 20 mm Hg (2.7 kPa) at 20° C. 2-Benzhydryloxycarbonyl-8-oxo-5-oxide-3-(2-tosyloxyvinyl)-7-[2-(2-tritylamino-thiazol-4-yl)-vinyloxyimino-acetamido]-5-thia-1-aza-bicyclo[4.2.0]-oct-2-ene (syn isomer E-form) (0.45 g) is obtained.

Infra-red spectrum (KBr): characteristic bands (cm$^{-1}$) at 1800, 1725, 1690, 1635, 1520, 1495, 1450, 1195, 1180, 1070, 1050, 1000, 945, 740 and 700.

Proton nuclear magnetic resonance spectrum (350 MHz, CDCl$_3$, δ in ppm, J in HZ): 2.45 (s, 3H, —CH$_3$); 3.19 and 3.77 (2d, J=18, 2H, —SCH$_2$—); 4.27 (dd, J=2 and 6, 1H,

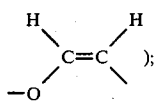

4.62 (d, J=4, 1H, H in the 6-position); 4.76 (dd, J=2 and 13, 1H,

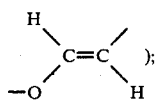

6.20 (dd, J=4 and 9, 1H, H in the 7-position); 6.80 (s, 1H, H of the thiazole); 6.90 (s, 1H, —COOCH<); 6.92 and 7.10 (2d, J=12, 2H, —CH=CH—); 7.05 (dd, J=6 and 13, 1H, =NOCH=); 7.73 (d, J=8, 2H, H in the ortho-position of the —OSO$_2$— group).

2-Benzhydryloxycarbonyl-8-oxo-3-(2-tosyloxyvinyl)-7-[2-(2-tritylamino-thiazol-4-yl)-2-vinyloxyimino-acetamido]-5-thia-1-aza-bicyclo[4.2.0]oct-2-ene and -3-ene (a mixture of the E: and Z-forms) can be prepared in the following manner:

p-Toluenesulphonyl chloride (0.65 g) is added to a solution, cooled to −15° C., of 2-benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]-oct-2-ene (syn isomer) (2.4 g) in methylene chloride (30 cc), after which a solution of triethylamine (0.44 cc) in methylene chloride (5 cc) is added dropwise in the course of 10 minutes. The mixture is stirred for 30 minutes at −15° C., the temperature is allowed to return to +20° C. in the course of 1 hour, and the mixture is then diluted with methylene chloride (50 cc) washed with a saturated sodium bicarbonate solution (3×50 cc) and with water (3×50 cc), dried over sodium sulphate, filtered and concentrated to dryness under 20 mm Hg (2.7 kPa) at 30° C.

The residue is taken up in ethyl acetate (5 cc), and diisopropyl ether (50 cc) is added, the mixture is stirred for 10 minutes and filtered, and after drying, a beige powder (1.6 g) is obtained, which consists principally of 2-benzhydryloxycarbonyl-8-oxo-3-(2-tosyloxyvinyl)-7-[2-(2-tritylamino-thiazol-4-yl)-2-vinyloxyiminoacetamido]-5-thia-1-aza-bicyclo[4.2.0]oct-2-ene and -oct-3-ene (a mixture of the E- and Z-forms).

Infra-red spectrum (KBr): characteristic bands (cm$^{-1}$) at 1790, 1725, 1690, 1640, 1525, 1495, 1450, 1195, 1180, 1075, 1005, 950, 755 and 705.

Proton nuclear magnetic resonance spectrum (350 MHz, CDCl$_3$, δ in ppm, J in Hz): 2.45 (s, 3H, —CH$_3$); 3.40 and 3.55 (2d, J=18, 2H, —SCH$_2$—); 4.27 (dd, J=2 and 6, 1H,

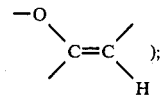

4.77 (dd, J=2 and 16, 1H,

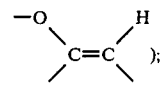

5.09 (d, J=4, 1H, H in the 6-position); 5.94 (dd, J=4 and 9, 1H, H in the 7-position); 6.81 (s, 1H, H of the thiazole); 6.91 (s, 1H, —COOCH<); 7.07 (dd, J=6 and 16, 1H, —CH=CH$_2$); 7.74 (d, J=8, 2H, H of the sulphonyl group).

2-Benzhydryloxycarbonyl-3-(2-oxoethyl)-8-oxo-7-[2-(2-tritylamino-thiazol-4-yl)-2-vinyloxyimino-acetamido]-5-thia-1-aza-bicyclo[4.2.0]oct-2-ene (syn isomer) can be prepared as follows:

A solution of 2-benzhydryloxycarbonyl-3-(2-dimethylaminovinyl)-8-oxo-7-[2-(2-tritylamino-thiazol-4-yl)-2-vinyloxyimino-acetamido]-5-thia-1-aza-bicyclo-[4.2.0]oct-2-ene (syn isomer, E-form) (2.5 g), in ethyl acetate (70 cc) is stirred in the presence of 1 N hydrochloric acid (50 cc) for 1 hour, at 25° C. The organic phase is decanted, washed with a half-saturated sodium bicarbonate solution (2×50 cc) and a half-saturated sodium chloride solution (50 cc), dried over sodium sulphate, filtered and concentrated to dryness under 20 mm Hg (2.7 kPa) at 20° C. A brown froth (2.4 g) is obtained, which consists principally of 2-benzhydryloxycarbonyl-3-(2-oxoethyl)-8-oxo-7-[2-(2-tritylamino-thiazol-4-yl)-2-vinyloxyimino-acetamido]-5-thia-1-azabicyclo[4.2.0]oct-2-ene (syn isomer).

Infra-red spectrum (KBr): characteristic bands (cm$^{-1}$) at 1785, 1725, 1685, 1640, 1530, 1495, 1450, 1000, 950, 755 and 700.

Proton nuclear magnetic resonance spectrum (350 MHz, CDCl$_3$, δ in ppm, J in Hz): 3.26 and 3.58 (2d, J=18, 2H, —SCH$_2$—); 3.53 and 3.69 (2d, J=18, 2H, —CH$_2$—); 4.28 (dd, J=2 and 6, 1H, 4.78 (dd, J=2 and 17, 1H,

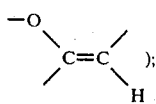

5.12 (d, J=4, 1H, H in the 6-position); 6.0 (dd, J=4 and 9, 1H, H in the 7-position); 6.8 (s, 1H, H of the thiazole); 6.90 (s, 1H, —COOCH<); 7.08 (dd, J=6 and 17, 1H, —CH=CH₂); 9.55 (s, 1H, —CHO).

REFERENCE EXAMPLE 24

7-Amino-2-benzhydryloxycarbonyl-8--oxo-5-oxide-3-(2-tosyloxyvinyl)-5-thia-1-aza-bicyclo[4.2.0]oct-2-ene can be obtained in the following manner, in the E-form:

A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E-form) (54.3 g) (obtained as described in reference example 2) and hydrated p-toluenesulphonic acid (30.4 g) in acetonitrile (1.4 liters) is stirred at 35° C. for 2 hours. It is then concentrated to dryness at 30° C. under 20 mm Hg (2.7 kPa), the residue is taken up in ethyl acetate (1 liter) and this solution is washed with a half-saturated sodium bicarbonate solution (2×500 cc) and a half-saturated sodium chloride solution (2×500 cc), dried over sodium sulphate and concentrated to dryness at 20° C. under 20 mm Hg (2.7 kPa). The residue is triturated in ether (200 cc). 7-Amino-2-benzhydryloxycarbonyl-8-oxo-5-oxide-3-(2-tosyloxyvinyl)-5-thia-1-aza-bicyclo[4.2.0]oct-2-ene (E-form)( (28.13 g) is obtained in the form of a light brown powder.

Rf=0.32; silica gel chromatographic plate [using an 85:15 (by volume) mixture of methylene chloride and methanol].

A mixture of 7-amino-2-benzhydryloxycarbonyl-8-oxo-5-oxide-3-(2-tosyloxyvinyl)-5-thia-1-aza-bicyclo-[4.2.0]oct-2-ene (E-form) (1.16 g), dimethylformamide (35 cc), 5-[2-methoxyimino-2-(2-tritylamino-thiazol-4-yl)-acetylthio]-2-methyl-1,3,4-thiadiazole (syn isomer) (1.67 g) and N,N-diisopropylethylamine (0.35 cc) is stirred for 1 hour at 60° C. under nitrogen. The mixture is diluted with ethyl acetate (140 cc) and the solution is washed with water (3×70 cc), dried over sodium sulphate, filtered and concentrated to dryness at 20° C. under 20 mm Hg (2.7 kPa). The residue is taken up in methylene chloride (25 cc), Merck silica gel (0.06–0.2 mm) (5 g) is added, the mixture is concentrated to dryness at 20° C. under 20 mm Hg (2.7 kPa) and the powder is deposited on a column (column diameter: 2 cm) of Merck silica gel (0.06–0.2 mm) (35 g). Elution is carried out successively with the following mixtures of cyclohexane and ethyl acetate: 80:20 (by volume) (100 cc), 60:40 (by volume) (250 cc), 40:60 (by volume) (500 cc), and 20:80 (by volume) (500 cc) and with pure ethyl acetate (500 cc), 60 cc fractions being collected. Fractions 17 to 26 are concentrated to dryness at 20° C. under 20 mm Hg (2.7 kPa) and 2-benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, E-form) (0.56 g) is obtained in the form of a pinkish froth.

Infra-red spectrum (CHBr₃): characteristic bands (cm⁻¹) at 3380, 1800, 1725, 1680, 1515, 1490, 1445, 1045, 935 and 750.

Proton nuclear magnetic resonance spectrum (350 MHz, CDCl₃, δ in ppm, J in Hz): 2.72 (s, 3H, —CH₃); 3.28 and 4.08 (2d, J=18, 2H, —SCH₂—); 4.07 (s, 3H, —OCH₃); 4.60 (d, J=4, 1H, H in the 6-position); 6.16 (dd, J=4 and 9, 1H, H in the 7-position); 6.71 (s, 1H, H of the thiazole); 6.93 (s, 1H

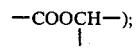

7.07 (s, 1H, —NH C(C₆H₅)₃); 7.23 and 7.33 (2d, J=16, —CH=CH—).

Phosphorus trichloride (0.93 cc) is added at −8° C., with stirring, to a solution of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-oxide-5-thia-1-aza-bicyclo[4.2.0]oct-2-ene (syn isomer, E-form) (5.11 g) and dimethylacetamide (2.1 cc) in methylene chloride (50 cc). The mixture is stirred for 1 hour at −8° C. and is then diluted with ethyl acetate (1 liter), and this mixture is washed with a half-saturated sodium bicarbonate solution (2×250 cc) and a half-saturated sodium chloride solution (2×250 cc), dried over sodium sulphate and concentrated to dryness at 20° C. under 20 mm Hg (2.7 kPa). The product, dissolved in a 40:60 (by volume) mixture of cyclohexane and ethyl acetate (50 cc), is chromatographed on a column (column diameter: 5 cm) of Merck silica gel (0.04–0.06 mm) (150 g). Elution is carried out with the preceding mixture (3 liters) under a pressure of 4 kPa, 125 cc fractions being collected. Fractions 10 to 20 are concentrated to dryness at 20° C. under 20 mm Hg (2.7 kPa). 2-Benzhydryloxycarbonyl-7-[2-methoxyimino-2-(2-tritylamino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (2.69 g) is obtained in the form of a yellow froth.

Infra-red spectrum (CHBr₃): characteristic bands (cm⁻¹) at 3390, 1785, 1720, 1685, 1515, 1495, 1445, 1045, 940 and 755.

Proton nuclear magnetic resonance spectrum (350 MHz, CDCl₃, δ in ppm, J in Hz): 2.75 (s, 3H, —CH₃); 3.60 and 3.69 (2d, J=18, 2H, —SCH₂—); 4.09 (s, 3H, —OCH₃); 5.09 (d, J=4, 1H, H in the 6-position; 5.93 (dd, J=4 and 9, 1H, H in the 7-position; 6.75 (s, 1H, H of the thiazole); 6.98 (s, 1H,

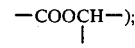

7.0 (s, 1H, —NH—C(C₆H₅)₃); 7.22 (d, J=14, 1H, —CH=CHS—).

A mixture of 2-benzhydryloxycarbonyl-7-[2-methoxyimino-2-(2-tritylamino-thiazol-4-yl)-acetamido]-3-[2(2-methyl-1,3,4-thiadiazol-5-yl)-thiovinyl]-8oxo-5-thia-1-aza-bicyclo[4.2.0]oct-2-ene (syn isomer, E-form) (2.37 g) in formic acid (30 cc) containing water (14 cc) is stirred at 50° C. for 15 minutes. It is allowed to cool, diluted with water (16 cc) and filtered. The filtrate is concentrated to dryness at 30° C. under 0.05 mm Hg (0.007 kPa) and the residue is taken up in ethanol (3×50 cc), the mixture being concentrated to dryness each time. The solid obtained is stirred in ethanol (35 cc) for 25 minutes at 50° C. and is then filtered off, washed with ethyl ether (2×20 cc) and dried. 7-[2-(2-Amino-thiazol-4-yl)-2-methoxyimino-acetamido]-2-carboxy-3-[2-(2-methyl-1,3,4-thiadiazol-5-yl)-thiovinyl]-8-oxo-5-thia-1-aza-bicyclo[4.2.0]oct-2-ene (syn isomer, E-form) (1.18 g) is obtained in the form of a yellow powder.

Infra-red spectrum (KBr): characteristic bands (cm$^{-1}$) at 3400, 3200, 3100, 2200, 1775, 1675, 1530, 1045 and 940.

Proton nuclear magnetic resonance spectrum (350 MHz, DMSO d$_6$, δ in ppm, J in Hz): 2.74 (s, 3H, —CH$_3$); 3.67 and 3.94 (2d, J=18, 2H, —SCH$_2$—); 3.86 (s, 3H, —OCH$_3$); 5.21 (d, J=4, 1H, H in the 6-position); 5.80 (2d, J=4 and 9, 1H, H in the 7-position); 6.75 (s, 1H, H of the thiazole); 7.12 and 7.17 (2d, J=16, 2H, —CH=CHS—); 7.20 (s, 2H, —NH$_2$); 9.63 (d, J=9, 1H, —CONH—).

5-[2-Methoxyimino-2-(2-tritylamino-thiazol-4-yl)acetylthio]-2-methyl-1,3,4-thiadiazole (syn isomer) can be prepared in the following manner:

N,N'-Dicyclohexylcarbodiimide (4.96 g) is added as a single shot, with stirring, to a suspension, cooled to 4° C., of [2-methoxyimino-2-(2-tritylamino-thiazol-4-yl)]-acetic acid (syn isomer) (8.88 g) and 5-mercapto-2-methyl-1,3,4-thiadiazole (2.64 g) in ethyl acetate (200 cc). The suspension is stirred for 4 hours at 4° C. and is then filtered, and the filtrate is washed with water (2×200 cc), a half-saturated sodium bicarbonate solution (2×100 cc) and a saturated sodium chloride solution (100 cc), dried over sodium sulphate, filtered, concentrated to 20 cc at 20° C. under 20 mm Hg (2.7 kPa), and again filtered. The filtrate is diluted with petroleum ether (200 cc) and the mixture is filtered, a yellow powder (6.2 g), corresponding to a crude form of the expected product, being collected.

Purification is carried out in the following manner: the preceding product is treated with cyclohexane (200 cc) under reflux, the mixture is filtered hot, the filtrate is concentrated to 30 cc (at 20° C. under 20 mm Hg; 2.7 kPa), the concentrate is filtered and 5-[2-methoxyimino-2-(2-tritylamino-thiazol-4-yl)-acetylthio]-2-methyl-1,3,4-thiadiazole, syn isomer, (4.5 g) is collected.

Proton nuclear magnetic resonance spectrum (80 MHz, CDCl$_3$, δ in ppm, J in Hz): 2.85 (s, 3H, —CH$_3$); 4.08 (s, 3H, =NOCH$_3$); 6.60 (s, 1H, H of the thiazole).

Infra-red spectrum (CHBr$_3$): characteristic bands (cm$^{-1}$) at 1695, 1605, 1580, 1530, 1490, 1450, 1050 and 900.

REFERENCE EXAMPLE 25

Thiourea (0.18 g) is added to a solution of 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.4 g) in ethanol (25 cc), tetrahydrofurane (25 cc) and water (5 cc) and the solution is stirred for 4 hours at 20° C. It is then concentrated to dryness under reduced pressure (20 mm Hg, 2.7 kPa). The residue is triturated with water (10 cc), the mixture is brought to pH 7 with a sodium bicarbonate solution, and the precipitate is filtered off, washed with water (5 cc) and dried. A light beige solid (1.3 g) is obtained, which is dissolved in chloroform (10 cc). The solution obtained is added dropwise to isopropyl ether (100 cc), whilst stirring. The insoluble matter formed is filtered off and redissolved in tetrahydrofurane (25 cc), the solution formed is filtered in the presence of decolorising charcoal and the filtrate is concentrated to a volume of 5 cc under reduced pressure (20 mm Hg, 2.7 kPa). Ethyl acetate (25 cc) is added to this solution. The solid formed is filtered off, washed with ethyl acetate (10 cc) and dried. 2-Benzhydryloxycarbonyl-7-[2-hydroxyimino-2-(2-aminothiazol-4-yl)-acetamido]-3-[2-(2-methyl-1,3,4-thiadiazol-5-yl)-thiovinyl]-8-oxo-5-thia-1-aza-bicyclo-[4.2.0]oct-2-ene (syn isomer, E-form) (0.9 g) is thus obtained in the form of a beige solid.

Infra-red spectrum (KBr): characteristic bands (cm$^{-1}$) at 3380, 3200, 3100, 1785, 1720, 1685, 1630, 1535, 1500, 1445, 1210, 950, 760, 745 and 705.

Proton nuclear magnetic resonance spectrum (350 MHz, DMSO d$_6$, δ in ppm, J in Hz): 2.71 (s, 3H, —CH$_3$ Het); 3.72 and 3.98 (2 d, J=18, 2H, —SCH$_2$—); 5.28 (d, J=4, 1H, H in the 6-position); 5.90 (dd, J=4 and 9, 1H, H in the 7-position); 6.80 (s, 1H, H of the thiazole); 6.98 (s, 1H, —COOCH<); 7.05 (d, J=16, 1H, —CH=CHS—); 7.26 (d, J=16, 1H, —CH=CHS—); 9.65 (d, J=9, 1H, —CONH—); 11.85 (s broad, 1H, =NOH).

2-Benzhydryloxycarbonyl-7-[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.3 g) is dissolved in 98% strength formic acid (6 cc). Distilled water (6 cc) is added and the mixture is heated at 60° C. for 15 minutes. The cloudy solution is cooled and is filtered in the presence of decolorising charcoal, and the filtrate is evaporated to dryness under reduced pressure (20 mm Hg, 2.7 kPa). Ethanol (10 cc) is added to the residue, the mixture is concentrated to dryness under reduced pressure (20 mm Hg, 2.7 kPa), this operation is repeated twice, the suspension of the residue in ethanol (10 cc) is then heated under reflux and cooled, and the product is filtered off and dried under reduced pressure (0.5 mm Hg, 0.07 kPa). This gives 2-carboxy-7-[2-hydroxyimino-2-(2-amino-thiazol-4-yl)-acetamido]-3-[2-(2-methyl-1,3,4-thiadiazol-5-yl)-thiovinyl]-8-oxo-5-thia-1-aza-bicyclo[4.2.0]oct-2-ene (syn isomer, E-form) (0.07 g) in the form of a yellow solid.

Infra-red spectrum (KBr): characteristic bands (cm$^{-1}$) at 3600, 2200, 1770, 1660, 1630, 1530, 1390 and 950.

Proton nuclear magnetic resonance spectrum (350 MHz, DMSO d$_6$, δ in ppm, J in Hz): 2.74 (s, 3H, —CH$_3$ Het); 3.64 and 3.90 (2 d, J=18, 2H, —SCH$_2$—); 5.20 (d, J=4, 1H, H in the 6-position); 5.80 (dd, J=4 and 9, 1H, H in the 7-position); 6.65 (s, 1H, H of the thiazole). 7.08 (s, broad, 2H, —NH$_2$); 7.10 and 7.20 (2 d, J=14, 2H, —CH=CH—S—); 9.46 (d, J=9, 1H, —CONH—); 11.28 (s broad, 1H, =NOH).

2-Benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) can be prepared in the following manner:

2-Benzhydryloxycarbonyl-7-(4-bromo-3-oxo-butyramido)-3-[2-(2-methyl-1,3,4-thiadiazol-5-yl)-thiovinyl]-8-oxo-5-thia-1-aza-bicyclo[4.2.0]oct-2-ene (E isomer) (1.8 g) is suspended in a mixture of tetrahydrofurane (23 cc) and water (4.7 cc) at 10° C. Acetic acid (7.8 cc) is then added, the mixture is cooled to 0° C. with ice, a solution of sodium nitrite (0.187 g) in water (2.3 cc) is added and the reaction mixture is allowed to return to 20° C. in the course of 4 hours. The resulting solution is diluted with iced water (150 cc). The precipitate is filtered off and dissolved in ethyl acetate (100 cc), and the organic phase is washed with a saturated sodium bicarbonate solution (2×25 cc) and a saturated sodium chloride solution (2×25 cc), dried over magnesium sulphate, filtered and concentrated to dryness under reduced pressure (20 mm Hg, 2.7 kPa). This gives 2-benzhydryloxycarbonyl-7-(4-bromo-2-hydroxyimino-3-oxo-butyramido)-3-[2-(2-methyl-1,3,4-thiadiazol-5-yl)-thiovinyl]-8-oxo-5-thia-1-aza-bicyclo[4.2.0]oct-2-ene (syn isomer, E-form) (1.5 g) in the form of a brown solid.

Infra-red spectrum (KBr): characteristic bands (cm$^{-1}$) at 1785, 1715, 1685, 1540, 1495, 1455, 1205, 950, 760, 745 and 700.

Proton nuclear magnetic resonance spectrum (350 MHz, CDCl$_3$, δ in ppm, J in Hz): 2.76 (s, 3H, —CH$_3$ Het); 4.53 (s, 2H, —COCH$_2$Br); 5.12 (d, J=4, 1H, H in the 6-position); 5.85 (dd, J=4 and 9, 1H, H in the 7-position); 7.01 (s, 1H, —COOCH<); 9.43 (d, J=9, 1H, —CONH—); 16.50 (s broad, 1H, =NOH).

A solution of bromine (5.79 g) in methylene chloride (3.53 cc) is added dropwise to a solution of diketene (3.04 g) in methylene chloride (3.53 cc) in the course of 35 minutes, at −30° C. The solution is then stirred at the same temperature for 30 minutes. One-tenth of this solution is taken and added dropwise to a stirred solution of 7-amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) (1.38 g) and bis-trimethylsilyl-acetamide (1.11 cc) in ethyl acetate (20 cc) in the course of 10 minutes at −15° C., and the solution is then stirred at the same temperature for 30 minutes. Thereafter, water (20 cc) is added and the organic phase is decanted, washed with a saturated sodium chloride solution (3×10 cc), dried over magnesium sulphate, filtered and concentrated to dryness under reduced pressure (20 mm Hg. 2.7 kPa). This gives 2-benzhydryloxycarbonyl-7-(4-bromo-3-oxo-butyramido)-3-[2-(2-methyl-1,3,4-thiadiazol-5-yl)-thiovinyl]-8-oxo-5-thia-1-aza-bicyclo[4.2.0]oct-2-ene (E isomer) (1.9 g) in the form of a brown solid.

Infra-red spectrum (KBr): characteristic bands (cm$^{-1}$) at 1780, 1720, 1680, 1535, 1490, 1450, 1250, 940, 760 and 700.

Proton nuclear magnetic resonance spectrum (350 MHz, CDCl$_3$, δ in ppm, J in Hz): 2.75 (s, 3H, —CH$_3$ of the heterocyclic ring); 3.58 and 3.84 (2 d, J=19, 2H, —SCH$_2$—); 3.75 (s, 2H, —COCH$_2$CO—): 4.03 (s, 2H, —CH$_2$Br); 5.04 (d, J=4, 1H, H in the 6-position); 5.85 (dd, J=4 and 9, 1H, H in the 7-position); 6.98 (s, 1H, —COOCH<).

7-Amino-2-benzhydryloxycarbonyl-3-[2-(2-methyl-1,3,4-thiadiazol-5-yl)-thiovinyl]-8-oxo-5-thia-1-aza-bicyclo[4.2.0]oct-2-ene (E isomer) can be prepared in the following manner:

A solution of p-toluenesulphonic acid monohydrate (8.43 g) in acetonitrile (46 cc) is added, in the course of 3 minutes, to a suspension of 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.2 g) in acetonitrile (138 cc) at 35° C. The mixture becomes homogeneous, and is kept at 38° C. for 40 minutes, after which it is poured into a solution of sodium bicarbonate (7.44 g) in water (600 cc). The mixture is extracted with ethyl acetate (300 cc, followed by 3×100 cc). The organic phases are combined, washed with a saturated sodium bicarbonate solution (100 cc) and then with a saturated sodium chloride solution (2×100 cc), dried over magnesium sulphate, filtered and concentrated to dryness under reduced pressure (20 mm Hg, 2.7 kPa). This gives 7-amino-2-benzhydryloxycarbonyl-3-[2-(2-methyl-1,3,4-thiadiazol-5-yl)thiovinyl]-8-oxo-5-thia-1-aza-bicyclo[4.2.0]oct-2-ene (E isomer) (6.8 g) in the form of a brown gummy material.

Infra-red spectrum (KBr): characteristic bands (cm$^{-1}$) at 3400, 3340, 1780, 1720, 1670, 1560, 1500, 1455, 950, 760, 745 and 700.

Proton nuclear magnetic resonance spectrum (80 MHz, CDCl$_3$, δ in ppm, J in Hz): 2.72 (s, 3H, —CH$_3$ of the heterocyclic ring); 3.46 (s broad, 2H, —SCH$_2$—); 4.77 (d, J=4, 1H, H in the 6-position); 5.00 (d, J=4, 1H, H in the 7-position); 7.00 (s, 1H, —COOCH<); 7.18 (s broad, 2H, —CH=CH—).

2-Benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) can be prepared as follows:

Phosphorus trichloride (4.7 cc) is added, in the course of 5 minutes, to a solution of 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) (17 g) and dimethylacetamide (10.9 cc) in methylene chloride (170 cc) at −10° C., and the mixture is kept at this temperature for one hour. It is then diluted with ethyl acetate (2,000 cc) at 0° C., and this mixture is washed with a saturated sodium bicarbonate solution (three×250 cc) and a saturated sodium chloride solution (250 cc), dried over magnesium sulphate, filtered and evaporated to dryness under reduced pressure. The residue is chromatographed on a column (column diameter: 4.5 cm; height: 37 cm) of Merck silica gel (0.063–0.2 mm) (291 g), elution being carried out with a 92.5:7.5 (by volume) mixture of methylene chloride and ethyl acetate (3 liters) and 100 cc fractions being collected. Fractions 12 to 29, containing the product, are evaporated to dryness under reduced pressure (20 mm Hg, 2.7 kPa). This gives 2-benzhydryloxycarbonyl-7-tert.-butoxycarbonylamino-3-[2-(2-methyl-1,3,4-thiadiazol-5-yl)-thiovinyl]-8-oxo-5-thia-1-aza-bicyclo[4.2.0]oct-2-ene (E isomer) (9.25 g) in the form of a light yellow solid.

Infra-red spectrum (KBr): characteristic bands (cm$^{-1}$) at 3370, 1790, 1715, 1700, 1520, 1160, 945, 740 and 700.

Proton nuclear magnetic resonance spectrum (80 MHz, CDCl$_3$, δ in ppm, J in Hz): 1.50 (s, 9H, (CH$_3$)$_3$C—); 2.75 (s, 3H, —CH$_3$ of the heterocyclic ring); 3.68 (s broad, 2H, —SCH$_2$—); 5.03 (d, J=4, 1H, H in the 6-position); 5.28 (d, J=9, 1H, —CONH—); 5.65 (dd, J=4 and 9, 1H, H in the 7-position); 7.00 (1H, s, —COOCH<).

2-Benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) can be prepared as follows:

A solution of 2-benzhydryloxycarbonyl-7-tert.-butoxycarbonylamino-8-oxo-5-oxide-3-(2-tosyloxyvinyl)-5-thia-1-aza-bicyclo[4.2.0]oct-2-ene (E isomer) (20 g), 2-methyl-1,3,4-thiadiazoline-5-thione (4.87 g) and diisopropyl ethylamine (5.04 cc) in dimethylformamide (200 cc) is heated to 60° C. for 2 hours. The mixture is poured onto iced water (2,000 cc), the mixture is extracted with ethyl acetate (2,000 cc followed by 500 cc), and the organic phases are combined, washed with a saturated sodium bicarbonate solution (250 cc), distilled water (4×250 cc) and a saturated sodium chloride solution (250 cc), dried over magnesium sulphate, filtered in the presence of decolorising charcoal and concentrated to dryness under reduced pressure (30 mm Hg, 4 kPa) at 30° C. This gives 2-benzhydryloxycarbonyl-7-tert.-butoxycarbonylamino-3-[2-(2-methyl-1,3,4-thiadiazol-5-yl)-thiovinyl]-8-oxo-5-oxide-5-thia-1-aza-bicyclo[4.2.0]oct-2-ene (E isomer) (17 g) in the form of a green-brown gummy material. This material is redissolved in ethyl acetate (60 cc), reprecipitated by means of isopropyl ether (600 cc), filtered off and dried. The expected product is thus obtained in the form of a yellow powder.

Infra-red spectrum (KBr): characteristic bands (cm$^{-1}$) at 3410, 1795, 1720, 1500, 1160, 1050, 940, 755, 740 and 700.

Proton nuclear magnetic resonance spectrum (350 MHz, CDCl$_3$, δ in ppm, J in Hz): 1.50 (s, 9H, (CH$_3$)$_3$C—); 2.75 (s, 3H, —CH$_3$ Het); 3.30 and 4.15 (2 d, J=18, 2H,

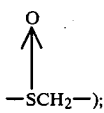

4.55 (d, J=4, 1H, H in the 6-position); 5.7 to 5.9 (m, 2H, —CONH— and H in the 7-position); 6.97 (s, 1H, —COOCH<); 7.53 (d J=16, 1H, —CH=CHS—).

REFERENCE EXAMPLE 26

7-Amino-2-carboxy-3-[2-(1-methyl-tetrazol-5-yl)-thiovinyl]-8-oxo-5-thia-1-aza-bicyclo[4.2.0]oct-2-ene (E-form) (0.51 g) is dissolved in a mixture of water (10 cc), sodium bicarbonate (0.63 g) and acetone (7.5 cc). The solution is cooled to −8° C. and a solution of 4-bromo-2-methoxyimino-3-oxo-butyryl chloride, syn isomer (0.363 g) in acetone (5 cc) is added dropwise in the course of 5 minutes. The mixture is again stirred for 50 minutes whilst the temperature is allowed to rise from −8° C. to +5° C. The mixture is then filtered, the acetone is evaporated at 20° C. under 20 mm hg (2.7 kPa), the residue is diluted with water (50 cc), (2.7 kPa), the residue is diluted with water (50 cc), this solution is washed with ethyl acetate (50 cc), the aqueous phase is diluted with water (100 cc), ethyl acetate (150 cc) is added and the mixture is acidified to pH 2.3 by means of a 4 N hydrochloric acid solution. The organic layer is washed with a half-saturated sodium chloride solution (100 cc), dried over sodium sulphate and concentrated to dryness at 20° C. under 20 mm Hg (2.7 kPa).

The solution of the product thus obtained, in ethanol (5 cc), is added, at 20° C., to a solution of thiourea (0.11 g) in ethanol (5 cc) and water (10 cc). The mixture is stirred for 35 minutes at 20° C., the pH is then adjusted to 6 by adding sodium bicarbonate, the mixture is acidified by adding formic acid (1 cc) and concentrated to dryness at 20° C. under 20 mm Hg (2.7 kPa), and the residue is taken up in ethanol (3×50 cc), the mixture being evaporated to dryness each time at 20° C. under 20 mm Hg. The residue is then extracted with ethanol (250 cc) under reflux, the mixture is filtered, the filtrate is concentrated to 25 cc at 20° C. under 20 mm Hg (2.7 kPa), this residue is left for 15 minutes at 5° C. and is then again filtered, and the solid is washed with ethanol (5 cc) and ether (2×10 cc). 7-[2-(2-Aminothiazol-4-yl)-2-methoxyimino-acetamido]-2-carboxy-3-[2-(1-methyl-tetrazol-5-yl)-thiovinyl]-8-oxo-5-thia-1-azabicyclo[4.2.0]oct-2-ene (syn isomer, E-form) (0.28 g) is obtained in the form of a yellow powder, the characteristics of which are identical to those of the product described above in reference example 4.

7-Amino-2-carboxy-3-[2-(1-methyl-tetrazol-5-yl)-thiovinyl]-8-oxo-5-thia-1-aza-bicyclo[4.2.0]oct-2-ene (E-form) can be obtained in the following manner:

A mixture of 7-amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) (3 g) in formic acid (105 cc) and water (40 cc) is treated at 50° C. for 30 minutes. It is then concentrated to dryness at 20° C. under 0.05 mm Hg (0.007 kPa), the residue is taken up in ethanol (2×100 cc), the mixture being concentrated to dryness each time at 20° C. under 20 mm Hg (2.7 kPa), and the solid obtained is triturated in ethanol (50 cc), filtered off and washed with diethyl ether (2×25 cc).

7-Amino-2-carboxy-3-[2-(1-methyl-tetrazol-5-yl)-thiovinyl]-8-oxo-5-thia-1-aza-bicyclo[4.2.0]oct-2-ene (E-form) is obtained as the formate (1.5 g).

Proton nuclear magnetic resonance spectrum (350 MHz, DMSO d$_6$, δ in ppm, J in Hz): 3.64 and 3.89 (2d, J=18, 2H, —SCH$_2$—); 4.02 (s, 3H, —CH$_3$); 5.15 (d, J=4, 1H, H in the 6-position); 5.77 (dd, J=4 and 9, 1H, H in the 7-position); 6.97 and 7.13 (2d, J=16, 2H, —CH=CH—); 9.07 (d, J=9, 1H, —CONH—).

7-Amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) can be obtained in the following manner:

2-Benzhydryloxycarbonyl-7-tert.-butoxycarbonylamino-3-[2-(1-methyl-tetrazol-5-yl)-thiovinyl]-8-oxo-5-thia-1-aza-bicyclo[4.2.0]oct-2-ene (E-form) (8 g), dissolved in acetonitrile (80 cc) is treated with p-toluenesulphonic acid hydrate (4.9 g) under the conditions described as above. After this treatment, 7-amino-2-benzhydryloxycarbonyl-3-[2-(1-methyl-tetrazol-5-yl)-thiovinyl]-8-oxo-5-thia-1-aza-bicyclo[4.2.0]oct-2-ene (E-form) (5.7 g) is obtained in the form of a light brown solid.

Infra-red spectrum (KBr): characteristic bands (cm$^{-1}$) at 1775, 1710, 1495, 1455, 1210, 755 and 705.

A solution of 2-benzhydryloxycarbonyl-7-tert.-butoxycarbonylamino-3-[2-(1-methyl-tetrazol-5-yl)-thiovinyl]-8-oxo-5-oxide-5-thia-1-aza-bicyclo[4.2.0]oct-2-ene (E-form) (13.8 g) in methylene chloride (250 cc) and dimethylacetamide (7.65 g) is treated with phosphorus tribromide (11.9 g) at −20° C. for 10 minutes. The mixture is poured into a saturated potassium bicarbonate solution (250 cc), with vigorous stirring, and the organic phase is washed with a saturated sodium chloride solution (100 cc), dried over sodium sulphate, filtered and concentrated to dryness at 20° C. under 20 mm Hg (2.7 kPa). The residue is chromatographed on a column (column diameter: 3 cm, height: 32 cm) of Merck silica gel (0.06–0.2 mm) (260 g). Elution is carried out with a 70:30 (by volume) mixture of cyclohexane and ethyl acetate (1.5 liters), 100 cc fractions being collected. Fractions 7 to 14 are concentrated to dryness at 20° C. under 20 mm Hg (2.7 kPa) and 2-benzhydryloxycarbonyl-7-tert.-butoxycarbonylamino-3-[2-(1-methyl-tetrazol-5-yl)-thiovinyl]-8-oxo-5-thia-1-aza-bicyclo[4.2.0]oct-2-ene (E-form) (8.5 g) is obtained in the form of a yellow powder.

Infra-red spectrum (KBr): characteristic bands (cm$^{-1}$) at 3340, 1790, 1705, 1690, 1510, 1160, 940, 730 and 700.

4-Bromo-2-methoxyimino-3-oxo-butyryl chloride, syn isomer, can be prepared in the following manner:

Dimethylformamide (2 drops) is added to a solution, at 20° C., of 2-methoxyimino-3-oxo-butyric acid, syn isomer (4.08 g) in diethyl ether (50 cc), after which oxalyl chloride (2 cc) dissolved in diethyl ether (5 cc) is added dropwise in the course of 15 minutes. The mixture is stirred for 1 hour at 20° C., dimethylformamide (1 drop) is added again and the reaction is continued for 15 minutes. The mixture is concentrated to dryness at 20° C. under 20 mm Hg (2.7 kPa) and the residue is taken up in petroleum ether (2×30 cc), the solvent being evaporated each time at 20° C. under 20 mm Hg (2.7 kPa). The 2-methoxyimino-3-oxo-butanoyl chloride, syn isomer, thus obtained is dissolved in methylene chloride (50 cc) and a 5.4 N solution of hydrogen chloride in ether (0.2 cc), and bromine (1.14 cc), are added to this solution at 20° C. The mixture is stirred for 20 hours at 20° C. and then concentrated to dryness at 20° C. under 20 mm Hg (2.7 kPa), and a brown oil (5.42 g) consisting principally of 4-bromo-2-methoxyimino-3-oxo-butyryl chloride, syn isomer, is obtained.

Proton nuclear magnetic resonance spectrum (60 MHz, CDCl$_3$, δ in ppm, J in Hz): 4.25 (s, 3H, —OCH$_3$); 4.34 (s, 2H, —CH$_2$—).

2-Methoxyimino-3-oxo-butyric acid, syn isomer, can be prepared in the following manner:

A mixture of ethyl 2-methoxyimino-3-oxo-butyrate, syn isomer (52 g), ethanol (300 cc) and 1 N sodium hydroxide solution (330 cc) is heated under reflux for 15 hours. The mixture is concentrated by evaporation of ethanol at 20° C. under a pressure of 20 mm Hg (2.7 kPa) and is then extracted with methylene chloride (150 cc). The aqueous phase is treated with animal charcoal (1 g), filtered, saturated with sodium chloride, cooled to 4° C. and acidified to pH2 with 2 N hydrochloric acid in the presence of methylene chloride (200 cc). It is then re-extracted with the same solvent (2×100 cc), followed by ethyl acetate (6×200 cc). The organic phases are dried over sodium sulphate and concentrated to dryness separately at 20° C. under 20 mm Hg (2.7 kPa). The residues are combined and treated with isopropyl ether (80 cc) for 4 hours, with very vigorous stirring. The crystals obtained are filtered off and dried, and 2-methoxyimino-3-oxo-butyric acid, syn isomer (8.9 g) is thus obtained.

Infrared spectrum (CHCl$_3$): characteristic bands (cm$^{-1}$) at 3400, 2830, 2300, 1730, 1695, 1370 and 1035.

Proton nuclear magnetic resonance spectrum (60 MHz, CDCl$_3$, δ in ppm, J in Hz): 2.48 (s, 3H, CH$_3$CO—); 4.18 (s, 3H, —OCH$_3$); 11.2 (s, 1H, —COOH).

Ethyl 2-methoxyimino-3-oxo-butyrate, syn isomer, is prepared according to R. BUCOURT et al., Tetrahedron 34, 2233 (1978).

REFERENCE EXAMPLE 27

A solution of N,N-diisopropylethylamine in dry N,N-dimethylformamide (50 cc) is added to a solution of 2-benzhydryloxycarbonyl-7-[2-methoxyimino-2-(2-tritylamino-thiazol-4-yl)-acetamido]-8-oxo-3-(2-tosyloxyvinyl)-5-thia-1-aza-bicyclo[4.2.0]oct-2-ene (syn isomer) (E-form) (5.5 g) (obtained as described in reference example 3) and of 5,6-dioxo-4-(2-hydroxyethyl)-3-thioxo-perhydro-1,2,4-triazine (2.08 g) in dry N,N-dimethylformamide (150 cc) in the course of 15 minutes, at 60° C. The reaction mixture is stirred for 3 hours at 60° C. and then diluted with ethyl acetate (600 cc). The organic phase is washed with a saturated sodium chloride solution (150 cc) and then with distilled water (3×150 cc), after which it is dried over magnesium sulphate. After filtration and concentration to dryness under reduced pressure (30 mm Hg; 4 kPa) at 40° C., the residue is chromatographed on Merck silica gel (0.04–0.06 mm) (column diameter: 6 cm, height: 30 cm), elution being carried out with a 15:85 (by volume) mixture of cyclohexane and ethyl acetate (7.5 liters) under a pressure of 40 kPa. The eluate is collected in fractions of about 100 cc. Fractions 24 to 70 are combined and concentrated to dryness under reduced pressure (30 mm Hg; 4 kPa) at 40° C. This gives 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (3.31 g) in the form of a light yellow solid.

Rf×0.33 [silica gel chromatographic plate, eluant: a 10:90 (by volume) mixture of cyclohexane and ethyl acetate].

Infra-red spectrum (CHBr$_3$): characteristic bands in cm$^{-1}$ at 3380, 1785, 1715, 1680, 1585, 1520, 1495, 1450, 1050, 940, 755 and 740.

Proton nuclear magnetic resonance spectrum (350 MHz, CDCl$_3$, δ in ppm, J in Hz): 3.44 and 3.60 (AB, J=18, 2H, —SCH$_2$—); 3.81 (mf, 2H, —CH$_2$OH); 4.00 (s, 3H, =NOCH$_3$); 5.00 (d, J=4, 1H, H in the 6-position); 5.90 (dd, J=4 and 9, 1H, H in the 7-position); 6.70 (s, 1H, H of the thiazole); 6.81 (d, J=15, 1H, —CH=CH—S—); 6.90 (s, 1H, —CH (C$_6$H$_5$)$_2$); 5.72 to 7.6 (mf, aromatics, —CONH—, —CH=CHS—, (C$_6$H$_5$)$_3$CNH—).

A solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazolo-4-yl)-acetamido]-8-oxo-5-thia-1-aza-bicyclo[4.2.0]oct-2-ene (syn isomer, E-form) (2.5 g), in dry tetrahydrofurane (250 cc) is cooled to −50° C. and treated with chlorosulphonyl isocyanate (11 cc). The mixture is stirred for 55 minutes, whilst allowing the temperature to rise slowly to −5° C., and a saturated sodium bicarbonate solution (150 cc) and ethyl acetate (250 cc) are then added. The aqueous phase is extracted with ethyl acetate (100 cc) and the combined organic extracts are washed with a saturated sodium chloride solution (2×100 cc) and then dried over magnesium sulphate and filtered. After evaporation of the solvent under reduced pressure (30 mm Hg; 4 kPa) at 40° C., and drying, 2-benzhydryloxycarbonyl-3-{2-[4-(2-carbamyloxyethyl)-5,6dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.6 g) is obtained in the form of a yellow powder.

Infra-red spectrum (KBr): characteristic bands in cm$^{-1}$ at 3350, 2600, 1785, 1720, 1685, 1530, 1490, 1450, 755 and 700.

Proton nuclear magnetic resonance spectrum (350 MHz, DMSO d$_6$, δ in ppm, J in Hz): 3.30 and 3.64 (2d, J=18, 2H, —SCH$_2$—); 3.84 (s, 3H, =NOCH$_3$); 4.03 and 4.11 (2t, J=5, 2×2H, >NCH$_2$CH$_2$OCO—); 5.24 (d, J=4, 1H, H in the 6-position); 5.77 (dd, J=4 and 9, 1H, H in the 7-position); 6.71 (s, 1H, H of the thiazole); 6.94 (s, 1H, —CH(C$_6$H$_5$)$_2$); 6.93 and 7.02 (AB, J=16, 2H, —CH=CH—S—); 7.15 to 7.60 (Mt, 25H, aromatics); 8.25 to 8.80 (2s, 2H, —OCONH₂); 9.60 (d, J=9, 1H, —CONH—C₇); 12.60 (s, 1H,

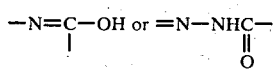

of the triazine).

A solution of 2-benzhydryloxycarbonyl-3-{-2-[4-(2-carbamyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.6 g) in formic acid (47 cc) is diluted with distilled water (20 cc) and the mixture is heated at 50° C. for 20 minutes and then diluted with a further amount of distilled water (27 cc); after filtering off the insoluble matter, the filtrate is concentrated to dryness under reduced pressure (5 mm Hg; 0.67 kPa) at 30° C. The residue is triturated with anhydrous ethanol (50 cc), which is then evaporated under reduced pressure (30 mm Hg; 4 kPa) at 40° C. This operation is repeated twice more, and the residue is then taken up in ethanol 40 cc), filtered off, washed with ether (2×50 cc) and dried. 7-[2-(2-Amino-thiazol-4-yl)-2-methoxyimino-acetamido]-3-{2-[4-carbamyloxyethyl)-5,6-dioxo-1,4,5,6-tetrahydro-1,2,4-triazin-3-yl]-thiovinyl}-2-carboxy-8-oxo-5-thia-1-aza-bicyclo[4.2.0]oct-2-ene (syn isomer, E-form) (1.5 g) is obtained in the form of a cream-coloured powder.

Infra-red spectrum (KBr): characteristic bands in cm⁻¹ at 3550, 2200, 1770, 1710, 1680, 1050 and 940.

Proton nuclear magnetic resonance spectrum (350 MHz, DMSO d₆, δ in ppm, J in Hz): 3.62 and 3.82 (2d, J=18, 2H, —SCH₂—); 3.86 (s, 3H, =NOCH₃); 4.06 and 4.15 (2t, J=5, 2×2H, >NCH₂CH₂O—); 5.21 (d, J=9, 1H, H in the 6-position); 5.78 (dd, J=4 and 9, 1H, H in the 7-position); 6.50 (s broad, 2H, —OCONH₂); 6.75 (s, 1H, H of the thiazole); 6.92 and 7.08 (2d, J=16, 2H, —CH=CH—S—); 7 to 7.50 (s broad, 2H, —NH₂ of the thiazole); 9.66 (d, J=9, 1H, —CONH—C₇); 12.62 (s, 1H,

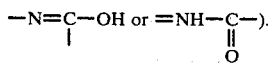

REFERENCE EXAMPLE 28

5,6-Dioxo-4-(2-hydroxyethyl)-perhydro-1,2,4-triazine (7 g) is added to a solution of 2-benzhydryloxycarbonyl-7-[2-methoxyimino-2-(2-tritylamino-thiazol-4-yl)-acetamido]-8-oxo-5-oxide-3-(2-tosyloxyvinyl)-5-thia-1-aza-bicyclo[4.2.0]oct-2-ene (syn isomer, E-form) (18 g) (obtained as described in reference example 3) in dry N,N-dimethylformamide (490 cc) at 65° C., after which a solution of N,N-diisopropylethylamine (2.32 g) in dry N,N-dimethylformamide (160 cc) is introduced dropwise in the course of 10 minutes. The reaction mixture is stirred for 3 hours at 65° C. and then diluted with ethyl acetate (2 liters) and washed with distilled water (4×500 cc). The organic phase is dried over magnesium sulphate and concentrated under reduced pressure (35 mm Hg; 4.7 kPa) at 40° C. The residue is chromatographed on Merck silica gel (0.2–0.04 mm) (column diameter: 4 cm) (200 g), elution being carried out with a 20:80 (by volume) mixture of cyclohexane and ethyl acetate and fractions of about 250 cc being collected. Fractions 6 to 41 are concentrated to dryness under reduced pressure (35 mm Hg; 4.7 kPa) at 40° C. 2-Benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-triazol-4-yl)-acetamido]-8-oxo-5-oxide-5-thia-1-aza-bicyclo[4.2.0]-oct-2-ene (syn isomer, E-form) (17.16 g) is obtained in the form of a light brown powder.

Infra-red spectrum (KBr): characteristic bands in cm⁻¹ at 1800, 1720, 1685, 1525, 1495, 1450, 1045, 945, 755 and 700.

Proton nuclear magnetic resonance spectrum (350 MHz, DMSO d₆, δ in ppm, J in Hz): 3.60 and 4.28 (2d, J=17.5, 2×1H, —S(O)CH₂—); 3.57 and 3.88 (2 Mt, 2×2H, >NCH₂CH₂OH); 3.84 (s, 3H, =NOCH₃); 5.04 (d, J=4, 1H, H in the 6-position); 5.84 (dd, J=4 and 9, 1H, H in the 7-position); 6.77 (s, 1H, H of the thiazole); 6.96 (s, 1H, —CH(C₆H₅)₂); 6.96 and 7.09 (AB, J=16, 2×1H, —CH=CH—S—); 7.15 to 7.60 (Mt, 25H, aromatics); 8.72 (s, 1H,

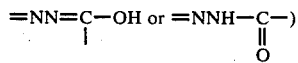

Triethylamine (0.38 cc) and 4-N,N-dimethylaminopyridine (0.05 g), followed by a solution of formic anhydride (4.9 millimols) in methylene chloride (10 cc) (prepared according to G. A. OLAH et al., Angew. Chem. 91 649 (1979)) are added to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.5 g) in dry tetrahydrofurane (100 cc), cooled to −10° C. The reaction mixture is stirred for 3 hours at about 20° C. and is then filtered, diluted with ethyl acetate (450 cc) and washed successively with 0.2 N hydrochloric acid (50 cc), distilled water (100 cc), a saturated sodium bicarbonate solution (100 cc) and a saturated sodium chloride solution (100 cc). The organic phase is dried over magnesium sulphate, filtered and concentrated under reduced pressure (30 mm Hg; 4 kPa) at 40° C. Crude 2-benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (2.7 g) is obtained in the form of a brown powder.

Rf=0.68 [silica gel chromatographic plate; eluant: an 80:20 (by volume) mixture of ethyl acetate and methanol].

Crude product (3.35 g) obtained as above is dissolved in dry methylene chloride (50 cc). N,N-dimethylacetamide (1.42 cc) is added, the mixture is then cooled to −10° C. and phosphorus trichloride (0.67 cc) is introduced. The reaction mixture is stirred for 1 hour at about −10° C. and then treated with N,N-dimethylacetamide (0.2 cc) and phosphorus trichloride (0.1 cc). After 20 minutes at −10° C., the reaction mixture is diluted with ethyl acetate (500 cc) and a saturated sodium bicarbonate solution (150 cc). The organic phase is decanted, washed with distilled water (2×50 cc) and with a saturated sodium chloride solution (100 cc), dried over magnesium sulphate and filtered. Evaporation of the solvent under reduced pressure (35 mm Hg; 4.7 kPa) at 40° C. gives a residue (3.6 g) which is chromatographed on a column (column diameter: 5 cm, height: 30 cm) of Merck silica gel (0.063–0.04 mm), elution being carried out, under a pressure of 40 kPa, with a 40:60 (by volume) mixture of cyclohexane and ethyl acetate (4 liters), and fractions of about 50 cc being collected. Fractions 38 to 76 are evaporated to dryness under reduced pressure (35 mm Hg; 4.7 kPa) at 40° C. 2-Benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.3 g) is obtained in the form of a light yellow powder.

Proton nuclear magnetic resonance spectrum (350 MHz, DMSO d$_6$, δ in ppm, J in Hz): 3.65 and 3.88 (AB, J=18, 2H, —SCH$_2$—); 3.84 (s, 3H, =NOCH$_3$); 4.10 and 4.32 (2t, J=5, 2×2H, >NCH$_2$OCHO); 5.21 (d, J=4, 1H, H in the 6-position); 5.75 (dd, J=4 and 9, 1H, H in the 7-position); 6.72 (s, 1H, H of the triazole); 6.95 (s, 1H, —CH(C$_6$H$_5$)$_2$); 6.93 and 7.02 (AB, J=16, 2H, —CH=CH—S—); 7.1 to 7.5 (Mt, 25H, aromatics); 8.80 (s, broad, 1H, (C$_6$H$_5$)$_3$CNH—); 9.60 (d, J=9, 1H, —CONH—C$_7$); 12.60 (s broad, 1H,

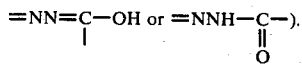

A solution of 2-benzhydryloxycarbonyl-3-{2-[5,6-dioxo-4-(2-formyloxyethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.25 g) in formic acid (15 cc) is diluted with distilled water (4 cc) and heated for 25 minutes at 50° C., after which it is diluted with more distilled water (11 cc). After filtering off the insoluble matter, the filtrate is concentrated under reduced pressure (5 mm Hg; 0.67 kPa) at 30° C.; the residue is triturated in ethannol (50 cc), which is evaporated under reduced pressure (35 mm Hg; 4.7 kPa) at 40° C. This latter operation is repeated 4 times, after which the solid residue is taken up in ethanol (20 cc), filtered off, washed with diisopropyl ether (2×25 cc) and dried. The product is dissolved in pure formic acid (10 cc) and the solution is heated for 1 hour 30 minutes at 45° C. and then concentrated to dryness under reduced pressure (5 mm Hg; 0.67 kPa) at 40° C. The residue is triturated in anhydrous ethanol (30 cc) and the latter is then evaporated under reduced pressure (30 mm Hg; 4 kPa) at 40° C.; this operation is repeated twice more. 7-[2-(2-Amino-thiazol-4-yl)-2-methoxy-imino-acetamido]-2-carboxy-3-{2-[5,6-dioxo-4-(2-formyloxyethyl)-1,4,5,6-tetrahydro-1,2,4-triazin-3-yl]-thiovinyl}-8-oxo-5-thia-1-aza-bicyclo[4.2.0]-oct-2-ene (syn isomer, E-form) (0.54 g) is obtained in the form of a yellow powder.

Infra-red spectrum (KBr): characterisic bands in cm$^{-1}$ at 3400, 3200, 2200, 1775, 1710, 1680, 1530, 1040 and 945.

Proton nuclear magnetic resonance spectrum (350 MHz, DMSO d$_6$, δ in ppm, J in Hz): 3.62 and 3.82 (AB, J=18, 2H, —SCH$_2$—); 3.84 (s, 3H, =NOCH$_3$); 4.15 and 4.32 (2t, J=5, 2×2H, >NCH$_2$CH$_2$—OCHO); 5.21 (d, J=4, 1H, H in the 6-position); 5.78 (dd, J=4 and 9, 1H, H in the 7-position); 6.73 (s, 1H, H of the triazole); 6.89 and 7.10 (2d, J=16, 2H, —CH=CH—S—); 7.16 (s, broad, 2H, —NH$_2$); 8.18 (s, 1H, HCOO—); 9.59 (d, J=9, 1H, —CONH—C$_7$); 12.60 (s broad, 1H,

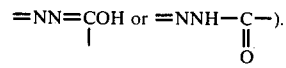

REFERENCE EXAMPLE 29

Sodium bicarbonate (0.64 g) is added to a solution of 2-benzhydryloxycarbonyl-3-{2-[4-(2-hydroxyethyl)-5,6-dioxo-1,4,5,6-tetrahydro-1,2,4-triazin-3-yl)]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (2.05 g) (obtained as described in reference example 27) in dry tetrahydrofurane (25 cc) at 22° C., after which a solution of acetic anhydride (0.4 cc) in dry tetrahydrofurane (5 cc) is introduced dropwise in the course of 15 minutes. 4-Dimethylaminopyridine (0.05 g) dissolved in dry tetrahydrofurane (1 cc) is then added and the reaction mixture is stirred for 10 minutes at 25° C. It is then diluted with distilled water (50 cc) and ethyl acetate (120 cc). The organic phase is decanted and washed successively with 0.5 N hydrochloric acid (80 cc), a saturated sodium bicarbonate solution (80 cc) and a saturated sodium chloride solution (100 cc). After drying over magnesium sulphate and filtering, the solution is concentrated to dryness under reduced pressure (30 mm Hg; 4 kPa) at 40° C. A crude product (2.05 g) is obtained in the form of a yellow powder.

Crude product (2.5 g) obtained as above is chromatographed on a column (column diameter: 4 cm, height: 30 cm) of Merck silica (0.04–0.06 mm), elution being carried out with a 40:60 (by volume) mixture of cyclohexane and ethyl acetate (3 liters) under a pressure of 40 kPa, and 100 cc fractions being collected. Fractions 11 to 26 are concentrated to dryness under reduced pressure (30 mm Hg; 4 kPa) at 40° C. 3-{2-[4-(2-Acetoxyethyl)-5,6-dioxo-1,4,5,6-tetrahydro-1,2,4-triazin-3-yl]-thiovinyl}-2-benzhydrykloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.84 g) is obtained in the form of a light yellow froth.

Infra-red spectrum (CHBr$_3$): characteristic bands in cm$^{-1}$ at 3400, 2820, 1790, 1720, 1685, 1590, 1495, 1450, 1050, 940, 760 and 740.

Proton nuclear magnetic resonance spectrum (350 MHz, DMSO d$_6$, δ in ppm, J in Hz): 1.97 (s, 3H, CH$_3$CO$_2$—); 3.63 and 3.88 (AB, J=18, 2H, —SCH$_2$—); 3.83 (s, 3H, =NOCH$_3$); 4.06 (t, J=5, 2H, >N—CH$_2$CH$_2$OCOCH$_3$); 4.23 (t, J=5, 2H, >NCH$_2$—CH$_2$OCOCH$_3$); 5.21 (d, J=4, 1H, H in the 6-position); 5.76 (dd, J=4 and 9, 1H, H in the 7-position); 6.71 (s, 1H, H of the thiazole); 6.91 (d, J=16, 1H, —CH=CH—S—); 6.93 (s, 1H, —CH(C$_6$H$_5$)$_2$); 7.0 (d, J=16, 1H, —CH=CH—S—); 7.2 to 7.5 (mt, 25H, aromatics); 9.60 (d, J=9, 1H, —CONH—); 12.58 (s broad, 1H,

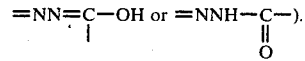

3-{2-[4-(2-Acetoxyethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.8 g) is dissolved in formic acid (40 cc). After addition of distilled water (15 cc), the reaction mixture is heated at 60° C. for 30 minutes and then filtered and concentrated to dryness under reduced pressure (5 mm Hg; 0.67 kPa) at 40° C. The residue is triturated in ethanol (50 cc), which is then evaporated under reduced pressure (30 mm Hg; 4 kPa) at 40° C. This operation is repeated twice more. The residue is dissolved in boiling ethanol (150 cc); after filtering the hot solution, the filtrate is allowed to cool and is kept for 2 days at 5° C. The solid is filtered off, washed with diethyl ether (20 cc) and then dried. 3-{2-[4-(2-Acetoxyethyl)-5,6-dioxo-1,4,5,6-tetrahydro-1,2,4-triazin-3-yl]-thiovinyl}-7-[2-(2-aminothiazol-4-yl)-2-methoxyiminoacetamido]-8-oxo-5-thia-1-aza-bicyclo[4.2.0]oct-2-ene (syn isomer, E-form) (0.65 g) is obtained in the form of a pale yellow powder.

Infra-red spectrum (KBr): characteristic bands in cm$^{-1}$ at 3320, 3220, 3150, 2300, 1780, 1740, 1720, 1680, 1635, 1590, 1535, 1375, 1210, 1040 and 950.

Proton nuclear magnetic resonance spectrum (350 MHz, DMSO d$_6$, δ in ppm, J in Hz): 2.0 (s, 3H, CH$_3$CO$_2$—); 3.63 and 3.82 (AB, J=18, 2H, —SCH$_2$—); 3.85 (s, 3H, =NOCH$_3$); 4.08 (t, J=5, 2H, >NCH$_2$CH$_2$OCOCH$_3$); 4.25 (t, J=5, 2H, >NCH$_2$CH$_2$OCOCH$_3$); 5.20 (d, J=4, 1H, H in the 6-position); 5.78 (dd, J=4 and 9, 1H, H in the 7-position); 6.73 (s, 1H, H of the thiazole); 6.90 (d, J=16, 1H, —CH=CH—S—); 7.12 (d, J=16, 1H, —CH=CHS—); 7.18 (s broad, 2H, —NH$_2$); 9.60 (s, J=9, 1H, —CONH—C$_7$); 12.6 (s broad, 1H,

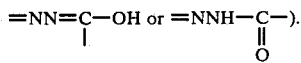

REFERENCE EXAMPLE 30

A solution of N,N'-dicyclohexylcarbodiimide (0.72 g) in methylene chloride (20 cc) is added, in the course of 5 minutes, to N-tert.-butoxycarbonylglycine (1.12 g), dissolved in dry methylene chloride (30 cc), at 0° C. The reaction mixture is stirred for 30 minutes at a temperature of between 0° and 5° C. and is then filtered rapidly. The filtrate is added dropwise, in the course of 10 minutes, to a solution of 2-benzhydryloxycarbonyl-3-{2-[5,6-dioxo-4-(2-hydroxyethyl)-1,4,5,6-tetrahydro-1,2,4-triazin-3-yl]-thiovinyl}-7-]2-methoxyimino-2-(2-tritylamino-thiazol-4-yl)-acetamido]-8-oxo-5-oxide-5-thia-1-aza-bicyclo[4.2.0]oct-2-ene (syn isomer, E-form) (3 g) (as obtained in reference example 28) in dry tetrahydrofurane (70 cc), which is cooled to 0° C. The reaction mixture is stirred for 45 minutes at 20° C. and is then diluted with ethyl acetate (500 cc) and washed successively with distilled water (200 cc), a saturated sodium bicarbonate solution (100 cc), distilled water (100 cc) and a saturated sodium chloride solution (50 cc). The organic phase is dried over sodium sulphate, filtered and concentrated under reduced pressure (30 mm Hg; 4 kPa) at 40° C. Crude 2-benzhydryloxycarbonyl-3-{2-[4-(2-N-tert.-butoxycarbonylglycyloxyethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-oxide- 5-thia-1-aza-bicyclo[4.2.0]oct-2-ene (syn isomer, E-form) (3.45 g) is obtained in the form of a brown powder.

This crude product (3.3 g) is dissolved in dry methylene chloride (45 cc). The solution, cooled to −10° C., is treated with N,N-dimethylacetamide (1.24 cc) and then with phosphorus trichloride (0.6 cc). After 1 hour 30 minutes at −10° C., the reaction mixture is diluted with ethyl acetate (600 cc) and washed successively with a saturated sodium bicarbonate solution (100 cc), distilled water (2×100 cc) and a saturated sodium chloride solution (2×200 cc). After drying over sodium sulphate and filtering, the organic solution is concentrated to dryness under reduced pressure (30 mm Hg; 4 kPa) at 40° C. The residue is chromatographed on a column (column diameter: 4 cm, height: 30 cm) of Merck silica gel (0.04–0.062 mm), elution being carried out under a pressure of 40 kPa with a 10:90 (by volume mixture of cyclohexane and ethyl acetate (1.5 liters) and 50 cc fractions being collected. Fractions 7 to 22 are combined and concentrated to dryness under reduced pressure (30 mm Hg; 4 kPa) at 30° C. 2-Benzhydryloxycarbonyl-3-{2-[4-(N-2-tert.-butoxycarbonylglycyloxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-aza-bicyclo[4.2.0]oct-2-ene (syn isomer, E-form) (1.44 g) is obtained in the form of a yellow powder.

Infra-red spectrum (KBr): characteristic bands in cm$^{-1}$ at 1785, 1715, 1685, 1530, 1495, 1445, 1160, 1030, 945, 755 and 700.

Proton nuclear magnetic resonance spectrum (350 MHz, DMSO d$_6$, δ in ppm, J in Hz): 1.36 (s, 9H, (CH$_3$)$_3$CO—); 3.25 and 3.86 (2d, J=18, 1H, —SCH$_2$—); 3.65 (d, J=9, 2H, —COCH$_2$NH—); 3.84 (s, 3H, =NOCH$_3$); 4.05 and 4.26 (2t, J=5, 2×2H, >NCH$_2$CH$_2$OCO—); 5.23 (d, J=4, 1H, H in the 6-position); 5.50 (d, J=9, 1H, —CH$_2$NHCO—); 5.76 (dd, J=4 and 9, 1H, H in the 7-position); 6.71 (s, 1H, H of the thiazole); 6.91 (s, 1H, —CH(C$_6$H$_5$)$_2$); 6.90 and 7 (2d, J=16, 2H, —CH=CH—S—); 7.15 to 7.5 (mt, 25H, aromatics); 8.78 (s broad, 1H, (C$_6$H$_5$)$_3$CNH—); 9.60 (d, J=9, 1H, —CONH—); 12.60 (s, 1H,

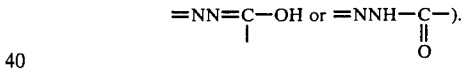

A solution of 2-benzhydryloxycarbonyl-3-{2-[4-(N--2-tert.-butoxycarbonylglycyloxy-ethyl)-5,6-dio xo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-aza-bicyclo[4.2.0]oct-2-ene (syn isomer, E-form) (1.5 g) in formic acid (15 cc) is diluted with distilled water (4 cc) and heated at 50° C. for 30 minutes, after which it is diluted with distilled water (11 cc). After filtering off the insoluble matter, the filtrate is evaporated to dryness under reduced pressure (5 mm Hg; 0.67 kPa) at 30° C. The residue is triturated with dry ethanol (60 cc), which is then evaporated under reduced pressure (30 mm Hg; 4 kPa) at 40° C. This latter operation is repeated 3 times in total, after which the solid residue is taken up in isopropyl ether (50 cc), filtered off, washed with ethyl ether (3×20 cc) and dried. The formate of 7-[2-(2-amino-thiazol-4-yl)-2-methoxyimino-acetamido]-2-carboxy-3-{2-[5,6-dioxo-4-(2-glycyloxyethyl)-1,4,5,6-tetrahydro-1,2,4-triazin-3-yl]-thiovinyl}8-oxo-5-thia-1-aza-bicyclo[4.2.0]oct-2-ene (syn isomer, E-form) (0.8 g) is obtained in the form of a light yellow powder.

Infra-red spectrum (KBr): characteristic bands in cm$^{-1}$ at 3550, 2200, 1755, 1705, 1675, 1580, 1530 and 1035.

Proton nuclear magnetic resonance spectrum (350 MHz, DMSO d$_6$, δ in ppm, J in Hz): 3.51 and 3.62

(AB,J=18, 2H, —SCH$_2$—); 3.72 (mt, 2H, —COCH$_2$NH$_2$); 3.82 (s, 3H, =NOCH$_3$); 4.12 and 4.40 (2Mt, 2×2H, >NCH$_2$CH$_2$OCO—); 5.10 (d, J=4,1H H in the 6-position); 5.67 (dd, J=4 and 9, 1H, H in the 7-position); 6.44 (d, J=16, 1H, —C$\underline{H}$=CH—S—); 6.72 (s, 1H, H of the thiazole); 7.18 (s broad, 3H, —NH$_3^{30}$ of the thiazole); 8.12 (s, 1H, HCO$_2$—); 9.56 (d, J=9, 1H, —CONH—C$_7$).

REFERENCE EXAMPLE 31

A solution of N,N'-dicyclohexylurea (0.5g) in methylene chloride (10 cc) is added dropwise, in the course of 10 minutes, to a solution, cooled to +5° C., of N-tert.-butoxycarbonylglycine (0.84 g) in methylene chloride (20 cc). The mixture is stirred for 30 minutes at 5° C. and is filtered, and the filtrate is poured dropwise, in the course of 20 minutes, into a solution, cooled to 5° C, of 3-{2-[4-(2-aminoethyl)-5,6-dioxo-1,4,5,6-tetrahydro-1,2,4-triazin-3-yl]-thiovinyl}-2 -benzhydryloxycarbonyl-7-[2-methoxyimino-2-(2-tritylamino-thiazol-4-yl)-acetamido]-8-oxo-5-oxide-5-thia-1-aza-bicyclo[4.2.-0]oct-2-ene (syn isomer, E-form) (2.04 g), triethylamine (0.34 cc) and dimethylaminopyridine (50 mg) in methylene chloride (100 cc). The temperature is allowed to rise to 20° C. whilst stirring, and after 1 hour the mixture is concentrated to about 30 cc under 20 mm Hg (2.7 kPa) at 20° C. The residue is diluted with ethyl acetate (70 cc) and this mixture is washed with a saturated sodium bicarbonate solution (2×50 cc) and water (3×50 cc), dried over sodium sulphate, filtered and concentrated to dryness under 20 mm Hg (2.7 kPa) at 20° C. The residue is taken up in tetrahydrofurane (10 cc) and the mixture is left at 4° C. for 48 hours. It is then filtered and the filtrate is concentrated to dryness under 20 mm Hg (2.7 kPa) at 20° C.; the residue is triturated in diethyl ether (50 cc), filtered off and dried. 2-Benzhydryloxycarbonyl-3-{2-[4 (2-tert.-butoxycarbonyl-glycylamino-ethyl)-5,6-dioxo-1,4,5,6-tetrahydro-1,2,4-triazin-3-yl]-thiovinyl}- 7-[2-methoxyimino-2-(2-tritylamino-thiazol-4-yl)-acetamido]-8-oxo-5-oxide-5-thia-1-aza-bicyolo[; 4.2.0]oct-2-ene (syn isomer, E-form) (1.72 g) is obtained in the form of a brown powder.

Infra-red spectrum (KBr): characteristic bands in cm$^{-1}$ at 3380, 1800, 1710, 1690, 1590, 1515, 1495, 1450, 1210, 1165, 1050, 1040, 945, 755 and 700.

Proton nuclear magnetic resonance spectrum (350 MHz, DMSO d$_6$, δ in ppm, J in Hz): 1.35 (s, 9H, —C(CH$_3$)$_3$); 3.33 (m, 2H, >N—CH$_2$CH$_2$NH—); 3.54 (t, J=5, 2H, >NCH$_2$C$\underline{H_2}$NH—); 3.63 (d, J=5, 2H, —COCH$_2$NH—); 3.6 and 4.3 (2d, J=18, 2H, —SCH$_2$—); 3.86 (s, 3H, =NOCH$_3$); 5.06 (d, J=4, 1H, H$_6$); 5.86 (dd, J=4 and 9, 1H, H$_7$); 6.78 (s, 1H, H of the thiazole); 6.85 and 7.12 (2d, J=16, 2H, —CH=CH—); 6.97 (s, 1H, —COOC$\underline{H}$<); 7.18 (s, 1H, N$\underline{H}$ of the thiazole); 8.0 (t, J=5, 1H, —COCH$_2$N$\underline{H}$—); 8.75 (s broad, 1H, >NCH$_2$CH$_2$N$\underline{H}$—); 9.03 (d, J=9, 1H, —CONH—); 12.6 (s, 1H, —NH of the triazine).

A solution of 2-benzhydryloxycarbonyl-3-{2-[4-(2-ter t.-butoxycarbonylglycylamino-ethyl)-5,6-dioxo-1,4,5,6-tetrahydro-1,2,4-triazin-3-yl]-thiovinyl}-2-[2-methoxyimino-2-(2-tritylamino-thiazol-4-yl-acetamido]-8-oxo-5-oxide-5-thia-1-aza-bicyclo[4.2.0]oct-2-ene (syn isomer, E-form) (1.65 g) in methylene chloride (30 cc) and dimethylacetamide (0.56 cc) is treated with phosphorus trichloride (0.5 cc) at −10° C. for 1 hour 30 minutes. The mixture is diluted with methylene chloride (150 cc), washed with a half-saturated sodium bicarbonate solution (2×100 cc) and a half-saturated sodium chloride solution (2×200 cc), dried over sodium sulphate, filtered and concentrated to dryness under 20 mm Hg (2.7 kPa) at 20° C.

The product is chromatographed on a column (column diameter: 2 cm, height: 34 cm) of Merck silica gel (0.06–0.2 mm) (50 g). Elution is carried out with a 50:50 (by volume) mixture of cyclohexane and ethyl acetate (250 cc) and with a 25:75 (by volume) mixture (500 cc), and with ethyl acetate (1.5 liters), 60 cc fractions being collected. Fractions 9 to 24 are concentrated to dryness and 2 -benzhydryloxycarbonyl-3-{2-[4-(2-tert.butoxyca rbonylglycylamino-ethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo]4.2.0[oct-2-ene (syn isomer, E-form) (0.78 g) is obtained in the form of a cream-coloured froth.

Infra-red spectrum (KBr): characteristic bands in cm$^{-1}$ at 3400, 3300, 1785, 1710, 1680, 1590, 1530, 1495, 1450, 1200, 1165, 1050, 950, 755 and 700.

Proton nuclear magnetic resonance spectrum (350 MHz, DMSO d$_6$, δ in ppm, J in Hz): 1.38 (s, 9H, —C(CH$_3$)$_3$); 3.30 (m, 2H, >NCH$_2$C$\underline{H_2}$NH—); 3.45 (d, J=5, —COCH$_2$NH—); 3.65 and 3.88 (2d, J=16, 2H, —SCH$_2$—); 3.85 (t, J=6, 2H, >$\underline{N}$CH$_2$CH$_2$NH—); 3.85 (s, 3H, =NOCH$_3$); 5.24 (d, J=4, H$_6$); 5.76 (dd, J=4 and 9, H$_7$); 6.92 and 7.00 (2d, J=16, —C$\underline{H}$=C$\underline{H}$—); 6.93 (s, —COOCH<); 7.79 (t, J=5, 1H, —CH$_2$NH CO—); 8.80 (s, N$\underline{H}$— of the thiazole); 9.59 (d, J=9, —CONH—); 12.53 (s, —NH— of the triazine).

A solution of 2-benzhydryloxycarbonyl-3-{2-[4-(2-t-ert.butoxycarbonylglycylamino-ethyl)-5,6-dioxo-1,4,5,6-tetrahydro-1,2,4-triazin-3-yl]-thiovinyl}-7-]2-methoxyimino-2-(2-tritylamino-thiazol-4-yl)-acetamido]-8-oxo-5-thia-1;1 -aza-bicyclo[4.2.0]oct-2-ene (syn isomer, E-form) (0.73 g) in a mixture of formic acid (15 cc) and water (15 cc) is treated at 50° C. for 30 minutes. It is then concentrated to dryness under 0.05 mm Hg (0.007 kPa) at 50° C., and the residue is taken up in ethanol (3×150 cc), the mixture being evaporated each time under 20 mm Hg (2.7 kPa) at 20° C. Thereafter, the solid is taken up in ethanol (25 cc) at 45° C., and the mixture is stirred for 30 minutes, allowed to cool and filtered. After drying, 7-[2-(2-amino-thiazol-4-yl)-2-methoxyimino-acetamido]-2-carboxy-3-{2-[5,6-dioxo-4-(2-glycylaminoethyl)-1,4,5,6-tetra-1,2,4-triazin-3-yl]-thiovinyl}-8-oxo-5-thia-1-aza-bicyclo[4.2.0]oct-2-ene (syn isomer, E-form) formate (0.39 g) is obtained in the form of a yellow powder.

Infra-red spectrum (KBr): characteristic bands in cm$^{-1}$ at 3700 to 2200, 1765, 1705, 1675, 1610, 1585, 1530, 1035 and 930.

Proton nuclear magnetic resonance spectrum (350 MHz, DMSO d$_6$, δ in ppm, J in Hz): 3.2 to 3.6 (m, 8H, —SCH$_2$—, >NCH$_2$CH$_2$N< and —COCH$_2$N<); 3.85 (s, =NOCH$_3$); 5.12 (d, J=4, H$_6$); 5.67 (dd, J=4 and 9, H$_7$); 6.35 (d, J=16, =C$\underline{H}$=CHS—); 6.73 (s, H of the thiazole); 7.15 (s broad, —NH$_2$); 8.2 (s, H of the formate); 8.6 (m, —CH$_2$N$\underline{H}$CO—); 9.54 (d, J=9, —NH-CO—).

3-{2-[4-(2-Aminoethyl)-5,6-dioxo-1,4,5,6-tetrahydro-1,2,4-triazin-3-yl]-thiovinyl}-2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) can be obtained in the following manner:

A solution of hydrated p-toluenesulphonic acid (1.14 g) in acetonitrile (15 cc) is added dropwise, in the course of 10 minutes, to a solution, at 40° C., of 2-benzhydryloxycarbonyl-3-{2-[4(2-tert.-butoxycarbonylamino-ethyl)-5,6-dioxo-1,4,5,6-tetrahydro-1,2,4-triazin-3-yl]-thiovinyl}-7-]2-methoxyimino-2-(2-tritylaminothiazol-4-yl)-acetamido]-8-oxo-5-oxide-5-thia-1-aza-bicyclo[4.2.0]oct-2-ene (syn isomer, E-form) (3.36 g) (prepared as described in Example 28 ) in acetonitrile (45 cc). The mixture is stirred for 2 hours at 40° C. and is then allowed to cool. A half-saturated sodium bicarbonate solution (100 cc) is introduced, and the batch is stirred vigorously for 1 hour and then filtered. After drying, 3-{2-[4-(2-aminoethyl)-5,6-dioxo-1,4,5,6-tetrahydro-1,2,4-triazin-3-yl]-thiovinyl}2-benzhydryloxycarbonyl-7-[2-methoxyimino-2-(2-tritylamino-thiazol-4-yl)-acetamido]-8-oxo-5-oxide-5-thia-1-aza-bicyclo[4.2.0]-oct-2-ene (syn isomer, E-form) (2.73 g) is obtained in the form of a brown powder.

Infra-red spectrum (KBr); characteristic bands in cm$^{-1}$ at 3250 to 2300, 1800, 1715, 1685, 1595, 1520, 1500, 1450, 1215, 1180, 1040, 945, 755 and 700.

Proton nuclear magnetic resonance spectrum (350 MHz, DMSO d$_6$, δ in ppm, J in Hz); 3.08 (m, 2H, >N—CH$_2$<u>CH$_2$</u>—NH$_2$); 3.63 and 4.30 (2d, J=18, 2H, —SCH$_2$—); 3.85 (s, 3H, =NOCH$_3$); 4.09 (t, J=6, 2H, ><u>NCH</u>$_2$CH$_2$NH$_2$); 5.07 (d, J=4, H$_6$); 5.87 (dd, J=4 and 9, H$_7$); 6.80 (s, H of the thiazole); 6.95 (s, —COO—CH<); 7.07 and 7.13 (2d, J=16, —CH=CH—); 9.0 (d, J=9, —NHCO—); 12.62 (s broad, —NH—of the triazine).

REFERENCE EXAMPLE 32

A mixture of 2 -benzhydryloxycarbonyl-3-{2-[4-(2,2-dimethoxyethyl-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8oxo-5-thia-1-aza-bicyclo[4.2.0]oct-2-ene (syn isomer, E-form) (2.9 g), tetrahydrofurane (50 cc) and methoxyamine hydrochloride (0.49 g) is heated under reflux for 24 hours. It is then concentrated to dryness under 20 mm Hg (2.7 kPa) at 30° C., the residue is triturated in water (20 cc) and the product is filtered off, washed with ethanol (2×10 cc) and dried. 2-Benzhydryloxycarbonyl-3-{2-[5,6-dioxo-4-(2-methoxyiminoethyl)-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-aza-bicyclo-[4.2.0]oct-2-ene (mixture of the syn, E, syn and anti, E, syn isomers) (0.92 g) is obtained.

Infra-red spectrum (KBr): characteristic bands in cm$^{-1}$ at 3700 at 2500, 1785, 1715, 1685, 1585, 1550, 1495, 1450, 1050, 950, 745 and 700.

Proton nuclear magnetic resonance spectrum (350 MHz, DMSO d$_6$, δ in ppm, J in Hz): 3.35 (s, 3H, —CH=N—O—CH$_3$); 3.70 and 3.90 (2d, J=18, 2H, —SCH$_2$—); 3.95 (s, 3H, =NOCH$_3$); 5.30 (d, J=4, 1H, H in the 6-position); 5.88 (dd, J=4 and 9, 1H, H in the 7-position); 6.95 and 7.05 (2d, J=16, 2H, —CH=CH—); 9.84 (d, J=9, 1H, —CONH—); 12.70 (s, 1H, =N NH CO— or=N

A solution of 2-benzhydryloxycarbonyl-3-{2-[5,6-dioxo-4-(2-methoxyiminoethyl)-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.0]oct-2-ene (mixture of the syn, E, syn and anti, E, syn isomers) (0.85 g) in formic acid (20 cc) and water (15 cc) is stirred for 30 minutes at 50° C. It is then concentrated to dryness under 0.05 mm Hg (0.007 kPa) at 45° C., the residue is taken up in ethanol (40 cc), the mixture is evaporated to dryness under 20 mm Hg (2.7 kPa) at 20° C., and this operation is repeated twice. The yellow solid obtained is triturated in ethanol (20 cc) at 50° C., the mixture is allowed to cool and the product is filtered off. 7-[2-(2-Aminothiazol-4-yl)-2-methoxyimino-acetamido]-2-carboxy-3-{2-[5,6-dioxo-4-(2-methoxyiminoethyl)-1,4,5,6-tetrahydro-1,2,4-triazin-3-yl]-thiovinyl}-8-oxo-5-thia-1-aza-bicyclo[4.2.0]oct-2-ene (mixture of the syn, syn, E and syn, anti, E isomers) (0.44 g) is obtained in the form of a yellow powder.

Infra-red spectrum (KBr): characteristic bands in cm$^{-1}$ at 3700 to 2000, 1775, 1710, 1690, 1630, 1585, 1550, 1050 and 945.

Proton nuclear magnetic resonance spectrum (350 MHz, DMSO d$_6$, δ in ppm, J in Hz): 5.24 (d, J=4, 1H, H in the 6-position); 5.80 (dd, J=4 and 9, 1H, H in the 7-position); 6.95 and 7.10 (2d, J=16, 2H, —CH=CH—); 9.77 (d, J=9, 1H, —CONH—).

REFERENCE EXAMPLES 33 to 63

Proceeding analogously, the products according to the invention are used to prepare the products of the general formula

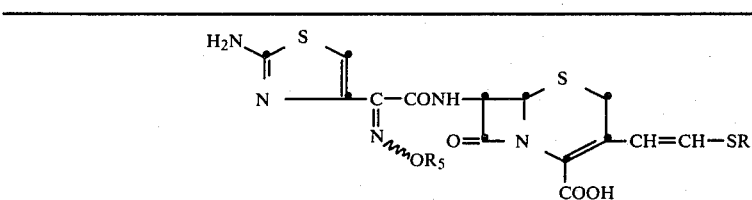

| Example | R | R$_5$ | Stereochemistry | (1) Infra-red spectrum (KBr): characteristic bands (cm$^{-1}$) (2) Proton nuclear magnetic spectrum, 350 MHz, DMSO D$_6$, δ in ppm, J in Hz |
|---|---|---|---|---|
| 33 | —CH$_2$—CH(NH$_2$)—COOH | —CH$_3$ | syn isomer E-form | Product obtained as the formate (1) 3500, 2000, 1750, 1660, 1530, 1035 and 940. |

-continued

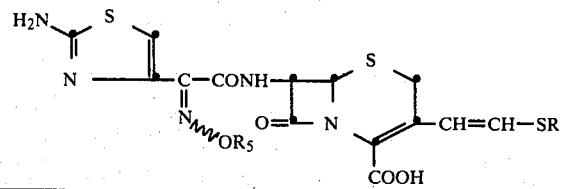

| Example | R | R₅ | Stereo-chemistry | (1) Infra-red spectrum (KBr): characteristic bands (cm⁻¹)<br>(2) Proton nuclear magnetic resonance spectrum, 350 MHz, DMSO d₆, δ in ppm, J in Hz |
|---|---|---|---|---|
| | | | | (2) 3 to 3.70 (hump, 4H, —SCH₂— of the cephalosporin and side chain); 3.87 (s, 3H, —OCH₃); 5.15 (d, J = 4, 1H, H in the 6-position); 5.65 to 5.72 (hump, 2H, H in the 7-position and >CH COOH); 6.77 (s, 1H, H of the thiazole); 6.92 (AB, 2H, —CH=CH—); 7.20 (s, 3H, —NH₃⁺); 9.58 (d, J = 9, 1H, —CONH—). |
| 34 | (CH₂)₂NHCOCH₃ on tetrazole N | —CH₃ | syn isomer E-form | (1) 3500, 2500, 1775, 1660, 1540, 1040 and 945<br>(2) 1.90 (s, 3H, —CH₃); 3.44 (t, 2H, >N CH₂—); 3.60 (q, 2H, —CH₂NHCO—); 3.64 and 3.76 (2d, J = 18, 2H, —S CH₂—); 4.0 (s, 3H, —OCH₃); 5.16 (d, J = 4, 1H, H in the 6-position); 5.82 (dd, J = 4 and 9, 1H, H in the 7-position); 6.60 (s, 3H, —NH₃⁺); 6.78 (s, 1H, H of the thiazole); 6.96 (d, J = 16, 1H, —CH=CH S—); 7.37 (d, J = 16, 1H, =CHS—); 7.86 (t, J = 5, 1H, —NHCOCH₃); 9.50 (d, J = 9, 1H, —CONH—). |
| 35 | thiadiazole with CH₃ | —CH₃ | syn isomer E-form | (2) 2.57 (s, 3H, —CH₃); 3.65 and 3.95 (2d, J = 18, 2H, —SCH₂—); 3.86 (s, 3H, —OCH₃); 5.23 (d, J = 4, 1H, H in the 6-position); 5.82 (dd, J = 4 and 9, 1H, H in the 7-position); 6.75 (s, 1H, H of the thiazole); 7.04 (d, J = 16, 1H, —CH=CHS—); 7.36 (d, J = 16, 1H, =CHS—); 9.63, (d, J = 9, 1H, —CONH—) |

-continued

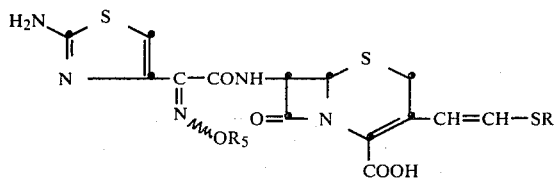

| | | | | |
|---|---|---|---|---|
| 36 | (pyridine ring) | —CH₃ | syn isomer E-form | (1) 3500, 2820, 2600, 1775, 1670, 1650, 1630, 1575, 1450, 1415, 1380, 1040, 940 and 765<br>(2) 3.72 and 3.95 (2d, J = 18, 2H, H in the 4-position); 3,85 (s, 3H, —OCH₃); 5.20 (d, J = 4, 1H, H in the 6-position); 5.77 (dd, J = 4 and 9; 1H, H in the 7-position); 6.76 (s, 1H, H of the thiazole); 7.15 (d, J = 17, 1H, —CH=CHS—); 7.18 (s, 2H, amino); 7.44 (d, J = 16, 17, —CH=CHS—); 7.75 and 8.2 (d, t, 1H, J = 8, H in the 4-position of the pyridine); 8.50 (t, 1H, J = 4, H₂ of the pyridine); 9.50 (d, J = 9, 1H, —CONH—). |
| 37 | N—N<br>\\ //<br>—NHCOCH₃ | —CH₃ | syn isomer E-form | (1) 3300, 1760, 1660, 1550, 1510, 1035 and 940<br>(2) 2.10 (s, 3H, CH₃CONH—); 3.72 and 3.98 (AB, J = 17, 2H, —SCH₂—); 3.86 (s, 3H, =NOCH₃); 5.2 (d, J = 4, 1H, H in the 6-position); 5.78 (dd, J = 4 and 9, 1H, H in the 7-position); 6.76 (s, 1H, H of the thiazole); 7.20 (s, 2H, —NH₂); 7.19 (d, J = 10, 1H, —CH=CH—S—); 7.33 (d, J = 10, 1H, —CH=CH—S—); 7.78 (d, J = 9, 1H, H in the 5-position of the pyridazine); 8.12 (s, 1H, CH₃CONH—); 9.65 (d, J = 9, 1H, —CONH—); 8.27 (d, J = 9, 1H, H in the 4-position of the pyridazine); 11.1 (s broad, 1H, —CO₂H). |
| 38 | H<br>N—N<br>\\ /<br>N=O<br>\|<br>CH₂CH₃ | —CH₃ | syn isomer E-form | (1) 3500, 2200, 1770, 1700, 1680, 1530, 1040 and 940<br>(2) 1.22 (t, J = 7, 3H, —CH₃); 3.65 and 3.80 (2d, J = 18, 2H, 7, 2H, ⟩NCH₂—); 3.86 (s, 3H, —OCH₃); 5.20 (d, J = 4, 1H, H in the 6-position); 5.78 (dd, J = 4 and 9, 1H, H in the 7-position); 6.75 (s, 1H, H of the thiazole); 6.95 (d, J = |

-continued

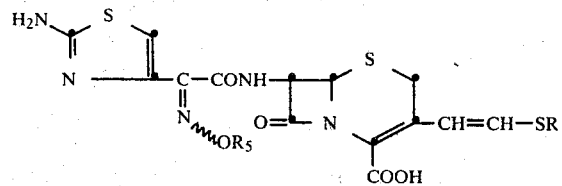

| | | | | |
|---|---|---|---|---|
| | | | | 16, 1H, —CH=CHS—); 7.13 (d, J = 16, 1H, =CHS—); 7.18 (s, 3H, —NH$_3^+$); 9.63 (d, J = 9, 1H, —CONH—). |
| 39 | 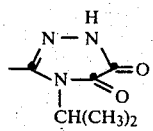 | —CH$_3$ | syn isomer E-form | (1) 3500, 2200, 1775, 1705, 1680, 1530, 1050 and 950 (2) 1.48 (d, J = 7, 6H, —CH(CH$_3$)$_2$); 3.64 and 3.82 (2d, J = 18, 2H, —SCH$_2$—); 3.85 (s, 3H, —OCH$_3$); 4.42 (mt, 1H, —CH(CH$_3$)$_2$); 5.22 (d, J = 4, 1H, H in the 6-position); 5.78 (dd, J = 4 and 9, 1H, H in the 7-position); 6.74 (s, 1H, H of the thiazole); 6.93 (d, J = 16, 1H, —CH=CHS—); 7.07 (d, J = 16, 1H, =CHS—); 7.18 (s, 3H, —NH$_3^+$); 9.62 (d, J = 9, 1H, —CONH—); 12.55 (s, 1H, =NNHCO— or =N—N=C—OH). |
| 40 | 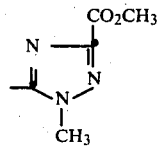 | —CH$_3$ | syn isomer E-form | (1) 3450, 3320, 2200, 1770, 1735, 1660, 1630, 1535, 1385, 1220, 1040 and 945 (2) 3.66 and 3.90 (2d, J = 18, 2H, —SCH$_2$—); 3.85 (s, 3H, =NOCH$_3$); 3.87 (s, 3H, —CO$_2$CH$_3$); 3.90 (s, 3H, >NHC$_3$ of the triazole); 5.20 (d, J = 9, 1H, H in the 6-position); 5.79 (dd, J = 4 and 9, 1H, H in the 7-position); 6.74 (s, 1H, H of the thiazole); 6.98 and 7.03 (AB, J = 14, 2H, —CH=CH—S—); 7.20 (s broad, 2H, —NH$_2$); 9.63 (d, J = 9, 1H, —CONH—C$_7$). |
| 41 | 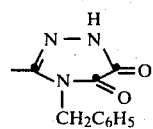 | —CH$_3$ | syn isomer E-form | (1) 3500, 2300, 1770, 1710, 1680, 1585, 1530, 1045 and 945 (2) 3.58 and 3.78 (2d, J = 18, 2H, —SCH$_2$—); 3.88 (s, 3H, —OCH$_3$); 5.10 (s, 2H, >NCH$_2$—); 5.18 (d, J = 4, 1H, H in the 6-position); 5.78 (dd, J = 4 and 9, 1H, H in the 7-position); 6.75 (s, 1H, H of the thiazole); 6.86 (d, J = 16, 1H, —CH=CHS—); 7.05 (d, J = 16, 1H, =CHS—); 7.20 (s, 3H, —NH$_3^+$); 9.60 (d, J = 9, 1H, —CONH—); 12.69 (s, 1H, =NNHCO—). |

-continued

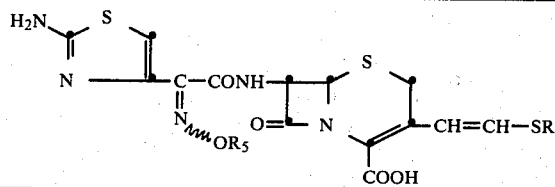

| | | | | |
|---|---|---|---|---|
| 42 | ![structure with N-N-H, (CH2)2SCH3] | —CH₃ | syn isomer E-form | (1) 3600, 2200, 1770, 1710, 1680, 1585, 1535, 1040 and 945<br>(2) 2.12 (s, 3H, —SCH₃); 2.73 (t, J = 7, 2H, —CH₂S—CH₃); 3.64 and 3.82 (2d, J = 18, 2H, —SCH₂—); 3.85 (s, 3H, —OCH₃); 4.0 (t, J = 7, 2H, >NHC₂—); 5.20 (d, J = 4, 1H, H in the 6-position); 5.78 (dd, J = 4 and 9, 1H, H in the 7-position); 6.73 (s, 1H, H of the thiazole); 6.92 (d, J = 16, 1H, —CH=CHS—); 7.12 (d, J = 16, 1H, =CHS—); 7.15 (s, 3H, —NH₃⁺); 9.66 (d, J = 9, 1H, —CONH—); 12.61 (s, 1H, NNHCO—). |
| 43 | ![structure with N-N-H, CH₂CH(OCH₃)₂] | —CH₃ | syn isomer E-form | (1) 3500, 3300, 1780, 1715, 1680, 1590, 1535, 1050 and 950<br>(2) 3.62 and 3.81 (2d, J = 18, —SCH₂—); 3.84 (s, 3H, —OCH₃); 3.97 (d, J = 3, 2H, >NCH₂—); 4.58 (t, J = 3, 1H, —CH(OCH₃)₂); 5.20 (d, J = 4, 1H, H in the 6-position); 5.77 (dd, J = 4 and 9, 1H, H in the 7-position); 6.74 (s, 1H, H of the thiazole); 6.91 (d, J = 16, 1H, —CH=CHS—); 7.09 (d, J = 16, 1H, =CHS—); 7.17 (s, 3H, —NH₃⁺); 9.60 (d, J = 9, 1H, —CONH—); 12.64 (s, 1H, =NNHCO—). |
| 44 | ![pyrimidine structure] | —CH₃ | syn isomer E-form | (1) 3320, 3200, 3100 to 2100, 1770, 1665, 1560, 1550, 1040, 945, 770 and 750<br>(2) 3.72 and 3.90 (2d, J = 18, 2H, —SCH₂— in the 4-position); 3.86 (s, 3H, =NOCH₃); 5.20 (d, J = 4, 1H, —H in the 6-position); 5.77 (dd, J = 4 and 9, 1H, —H in the 7-position); 6.74 (s, 1H, —H of the thiazole ring); 7.12 and 7.46 (2d, J = 16, 2H, trans vinyl protons); 7.14 (s, 2H, —NH₂ of thiazole ring); 7.27 (broad, 1H, —H in the 5-position of the pyrimidine ring); 8.66 (d, J = 5, 2H, —H in the 4- and 6-position of the pyrimidine ring); |

-continued

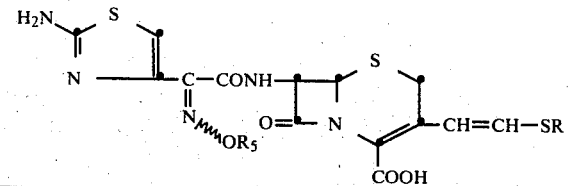

| Example | R | R$_5$ | Stereochemistry | (1) Infrared spectrum (KBr): Characteristic bands (cm$^{-1}$)<br>(2) Proton nuclear magnetic resonance spectrum, 250 MHz, CF$_3$COOD, δ in ppm, J in Hz |
|---|---|---|---|---|
| | | | | 9.60 (d, J = 9, 1H, —CONH—). Product obtained as the formate |
| 45 | 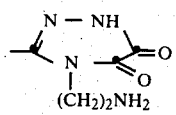<br>(CH$_2$)$_2$NH$_2$ | —CH$_3$ | syn isomer E-form | (1) 3500, 2200, 1770, 1710, 1680, 1630, 1530, 1380, 1040 and 930<br>(2) 3.12 (m, 2H, —CH$_2$—CH$_2$—NH$_2$); 3.51 and 3.60 (2d, J = 18, 2H, —SCH$_2$—); 3.85 (s, 3H, CH$_3$ON=); 4.12 (t, J = 6, 2H, NCH$_2$—CH$_2$—NH$_2$); 5.12 (d, J = 4, 1H, H$_6$); 5.67 (dd, J = 4 and 9, 1H, H$_7$); 6.44 (d, J = 8, 1H, —CH=CHS—); 6.73 (s, 1H, H of the thiazole); 7.2 (s broad, 2H, —NH$_2$); 8.18 (s, 1H, H of the formate); 9.55 (d, J = 9, 1H, —NHCO—) |
| 46 | 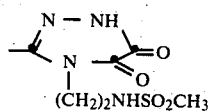<br>(CH$_2$)$_2$NHSO$_2$CH$_3$ | —CH$_3$ | syn isomer E-form | (1) 3400, 3300, 3200, 1775, 1710, 1680, 1590, 1530, 1320, 1150, 1140 and 945<br>(2) 2,90 (s, 3H, —SO$_2$CH$_3$); 3.20 (mt, 2H, —CH$_2$NH—); 3.61 and 3.78 (2d, J = 18, 2H, —SCH$_2$—); 3.96 (s, 3H, =NOCH$_3$); 3.96 (t, J = 5, 2H, N—CH$_2$—); 5.17 (d, J = 4, 1H, H in the 6-position); 5.73 (dd, J = 4 and 9, 1H, H in the 7-position); 6.74 (s, 1H, H of the thiazole); 6.79 (d, J = 16, 1H, —CH=CHS—); 7.17 (s, 2H, —NH$_2$); 9.60 (d, J = 9, 1H, —CONH—) |

| Example | R | R$_5$ | Stereochemistry | (1) Infrared spectrum (KBr): Characteristic bands (cm$^{-1}$)<br>(2) Proton nuclear magnetic resonance spectrum, 350 MHz, CF$_3$COOD, δ in ppm, J in Hz |
|---|---|---|---|---|
| 47 | 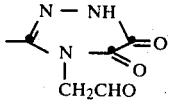<br>CH$_2$CHO | —CH$_3$ | syn isomer E-form | (1) 3700, 2300, 1770, 1715, 1685, 1630, 1590, 1525, 1060, 1030 and 940<br>(2) 3.86 (s broad, 2H, —SCH$_2$—); 4.43 (s, 3H, =NOCH$_3$—); 5.18 (s broad, 2H, >N—CH$_2$—); 5.35 (d, J = 4, 1H, H in the 6-position); 5.88 (d, J = 4, 1H, H in the 7-position); 7.24 and 7.74 (2d, J = 16, 2H, —CH=CHS—); 8.14 (s, 1H, H of the thiazole); 9.77 (s, 1H, —CHO—) |

-continued

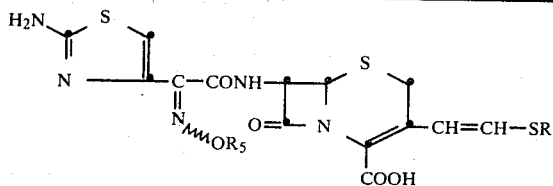

| Example | R | $R_5$ | Stereo-chemistry | (1) Infrared spectrum (KBr): Characteristic bands $(cm^{-1})$ (2) Proton nuclear magnetic resonance spectrum, 350 MHz, DMSO $d_6$, δ in ppm, J in Hz |
|---|---|---|---|---|
| 48 | 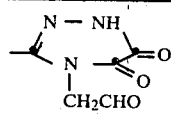 | $-CH_3$ | anti isomer Z-form | (1) 3700, 2200, 1770, 1715, 1680, 1590, 1530, 1045 (2) 3.77 and 3.84 (2d, J = 18, 2H, $-SCH_2-$); 5.18 (s, 2H, $>N-CH_2-$); 5.38 (d, J = 4, 1H, H in the 6-position); 6.02 (d, J = 4, 1H, H in the 7-position); 6.84 and 7.05 (2d, J = 10, 2H, $-CH=CHS-$); 7.48 (s, 1H, H of the thiazole); 9.72 (s, 1H, $-CHO$) |
| 49 | 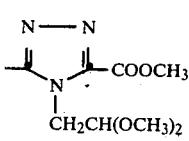 | $-CH_3$ | syn isomer E-form | (1) 3430, 3200, 1775, 1735, 1680, 1620, 1535, 1385, 1050, 945 (2) 3.65 (s, 6H, $-CH(OCH_3)_2$); 4.21 (s, 3H, $-COOCH_3$); 4.29 (s, 3H, $=NOCH_3$); 5.38 (d, J = 4, 1H, H in the 6-position); 6.08 (d, J = 4, 1H, H in the 7-position); 7.07 and 7.95 (zd, J = 16, 2H, $-CH=CHS-$); 7.48 (s, 1H, H of the thiazole) |

| Ex-ample | R | $R_5$ | Stereo-chemistry | (1) Infrared spectrum (KBr): Characteristic bands $(cm^{-1})$ (2) Proton nuclear magnetic resonance spectrum, 350 MHz, DMSO $d_6$, δ in ppm, J in Hz |
|---|---|---|---|---|
| 50 | 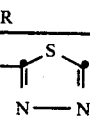 | $-CH_3$ | syn isomer E-form | (1) 2820, 1775, 1675, 1630, 1530, 1490, 1450, 1370, 1040, 750, 700 (2) 3.68 and 3.96 (2d, J = 18, 2H, $-SCH_2-$); 3.84 (s, 3H, $=NOCH_3$); 5.21 (d, J = 4, 1H, H in the 6-position); 5.80 (dd, J = 4 and 9, 1H, H in the 7-position); 6.73 (s, 1H, H of the thiazole); 7.18 to 7.22 (hump, 4H, $-NH_2-$ and $-CH=CH-$); 9.03 (d, J = 9, 1H, $-CONH-$); 9.60 (s, 1H, H of the thiadiazole) |
| 51 | 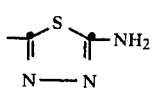 | $-CH_3$ | syn isomer E-form | (1) 3320, 3200, 3100, 2820, 2000; 1770, 1670, 1610, 1380, 1040, 940 (2) 3.83 (s, 3H, $=NOCH_3$); 5.12 (d, J = 4, 1H, H in the 6-position); 5.76 (dd, J = 4 and 9, 1H, H in the 7-position); 6.74 (s, 1H, H of the thiazole); 6.95 (d, J = 16, 1H, $-CH=CHS-$); 7.02 (d, J = 16, 1H, $=CHS-$); 7.18 (s broad, 2H, $-NH_2$ of the thiazole); 7.48 (s broad, 2H, $-NH_2$ of the thiadiazole); 9.60 (d, J = 9, 1H, $-CONH-$) Product obtained as the formate |

-continued

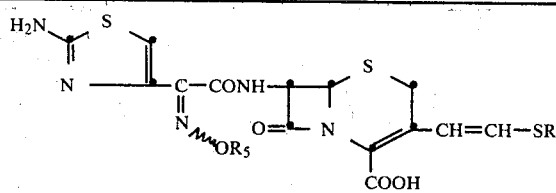

| No. | Structure | R | Isomer | Data |
|---|---|---|---|---|
| 52 | ![structure with thiazole-CH2N(CH3)2] | —CH3 | syn isomer E-form | (1) 3400, 3330, 3250, 2000, 1765, 1665, 1600, 1530, 1035, 960<br>(2) 2.36 (s, 6H, —N(CH3)2); 3.67 and 3.92 (2d, J = 18, 2H, —SCH2—); 3.88 (s, 3H, =NOCH3); 5.28 (d, J = 4, 1H, H in the 6-position); 5.80 (dd, J = 4 and 9, 1H, H in the 7-position); 6.76 (s, 1H, H of the thiazole); 7.10 (d, J = 16, 1H, —CH=CHS—); 7.20 (s, 2H, —NH2); 7.25 (d, J = 16, 1H, =CHS—); 9.60 (d, J = 9, 1H, —CONH—) |
| 53 | ![structure with (CH2)2NHCOOCH3] | —CH3 | syn isomer E-form | (1) 3340, 3210, 3100, 2200, 1770, 1710, 1685, 1625, 1590, 1530, 1035, 945<br>(2) 3.55 (s, 3H, —COOCH3); 3.62 and 3.79 (2d, J = 18, 2H, —SCH2—); 3.85 to 3.93 (mt, 5H, =NOCH3 and >NCH2—); 5.19 (d, J = 4, 1H, H in the 6-position); 5.75 (dd, J = 4 and 9, 1H, H in the 7-position); 6.74 (s, 1H, H of the thiazole); 9.58 (d, J = 9, 1H, —CONH—); 12.53 (s broad, 1H, =NNHCO— or =NN=C—)<br>$\quad\quad\quad\quad\quad\quad\quad\quad\quad$ OH |
| 54 | ![structure with (CH2)2NHCONHCH3] | —CH3 | syn isomer E-form | (1) 3320, 3200, 1775, 1710, 1680, 1635, 1585, 1535, 1040, 945<br>(2) 3.30 (m, 5H, —CH2NH— and >NCH3—); 3.60 and 3.78 (2d, J = 18, 2H, —SCH2—); 3.85 (s broad, 5H, =NOCH3 and >NCH2—); 5.18 (d, J = 4, 1H, H6); 5.74 (dd, J = 4 and 9, 1H, H7); 6.09 (t, J = 6, 1H, —NH—CH2—); 6.74 (s, 1H, H of the thiazole); 6.82 and 7.12 (2d, J = 16, 2H, —CH=CH—); 9.58 (d, J = 9, 1H, —CONH—); 12.52 (s, 1H, =N—NHCO— or =N—N=C—)<br>$\quad\quad\quad\quad\quad\quad\quad\quad\quad$ OH |
| 55 | ![triazine-dione with N-CH3 and N-CH3] | —CH3 | syn and anti isomers (50:50 mixture); E-form | (1) 3500, 2300, 1770, 1710, 1670, 1575, 1530, 1030, 940<br>(2) syn isomer, E-form 3.35 and 3.48 (2s, 2 × 3H, 2-CH3 of the triazine); 3.66 and 3.90 (2d, J = 18, 2H, —SCH2—); 3.87 (s, 3H, =NOCH3); 5.18 (d, J = 4, 1H, H in the 6-position); 5.82 (dd, J = 4 |

-continued

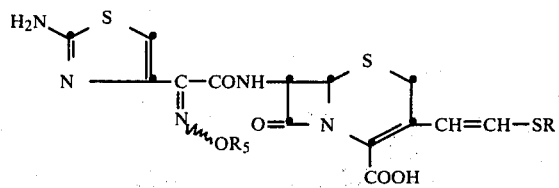

| | | | | |
|---|---|---|---|---|
| | | | | and 9, 1H, H in the 7-position); 6.74 (s, 1H, H of the thiazole); 6.95 and 7.14 (2d, J = 16, 2H, —CH=CH—S—); 7.18 (s broad, 2H, —NH$_2$); 9.64 (d, J = 9, 1H, —CONH—). anti isomer, E-form 3.35 and 3.48 (2s, 2 × 3H, 2 CH$_3$ of the triazine); 3.66 and 3.90 (2d, J = 18, 2H, —SCH$_2$—); 3.98 (s, 3H, =NOCH$_3$); 5.19 (d, J = 4, 1H, H in the 6-position); 5.81 (dd, J = 4 and 9, 1H, H in the 7-position); 6.95 and 7.15 (2d, J = 16, 2H, —CH=CH—S—); 7.09 (s broad, 2H, —NH$_2$); 9.48 (d, J = 9, 1H, —CONH—) |
| 56 | 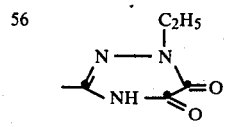 | —CH$_3$ | syn isomer E-form | (1) 3700, 2200, 1770, 1720, 1665, 1630, 1590, 1040, 945<br>(2) 1.25 (t, J = 7, 3H, —CH$_2$CH$_3$); 3.71 and 3.88 (2d, J = 18, 2H, —SCH$_2$—); 3.80 to 3.90 (hump, 5H, —CH$_2$CH$_3$ and —OCH$_3$); 5.19 (d, J = 4, 1H, H in the 6-position); 5.75 (dd, J = 4 and 9, 1H, H in the 7-position); 6.77 (s, 1H, H of the thiazole); 7.10 (s broad, 2H, —CH=CH—); 7.20 (s, 2H, —NH$_2$); 9.62 (d, J = 9, 1H, —CONH—) |
| 57 | 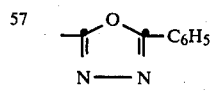 | —CH$_3$ | syn isomer E-form | (1) 3400 to 2000, 3330, 1760, 1630, 1540, 1380, 1055, 750, 710, 695<br>(2) 3.68 and 3.94 (2d, J = 18, 2H, —SCH$_2$—); 3.86 (s, 3H, =NOCH$_3$); 5.22 (d, 1H, H in the 6-position); 5.82 (dd, 1H, H in the 7-position); 6.74 (s, 1H, H of the thiazole ring); 7.10 (d, J = 16, 1H, —CH=CHS—); 7.18 (s, 2H, NH$_2$); 7.26 (d, J = 16, 1H, —CH=CHS—); 7.83 (mt, 3H, p and m protons of —C$_6$H$_5$), 8.0 (d, J = 7, 2H, o-protons of the —C$_6$H$_5$); 9.61 (d, J = 9, 1H, —CONH—) |
| 58 | 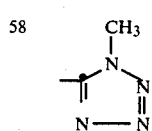 | —CH$_2$CN | syn isomer E-form | (1) 1770, 1680, 1620, 1530, 1380<br>(2) 3.66 and 3.88 (2d, J = 18, 2H, —SCH$_2$—); 4.02 (s, 3H, —CH$_3$); 5.0 (s, 2H, —OCH$_2$—); 5.22 (d, J = 4, 1H, H in the 6-position); 5.80 (dd, J = 4 and 9, 1H, H in the 7-position); 6.89 (s, 1H, H of the thiazole); 6.99 (d, J = 16, 1H, —CH=CHS—); 7.12 (d, J = 16, 1H, =CHS—); 9.82 (d, J = 9, 1H, —CONH—)<br>Product obtained as the formate |

-continued

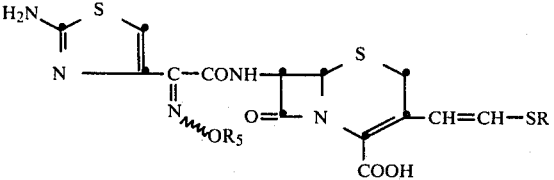

| Example | R | R₅ | Stereo-chemistry | (1) Infrared spectrum (KBr): Characteristic bands (cm⁻¹)<br>(2) Proton nuclear magnetic resonance spectrum, 350 MHz, CF₃COOD, δ in ppm, J in Hz |
|---------|---|-----|-----------------|------|
| 59 | (CH₂)₂N(CH₃)₂ 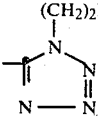 | —CH₃ | syn isomer E-form | (1) 3400, 3200, 2000, 1770, 1670, 1615, 1530, 1035<br>(2) 2.70 (s, 6H, —N(CH₃)₂); 2.75 (t, J = 7, 2H, —CH₂N⟨); 3.85 (s, 3H, =NOCH₃); 3.95 (t, J = 7, 2H, —CH₂CH₂N(CH₃)₂); 5.16 (d, J = 4, 1H, H in the 6-position); 5.85 (dd, J = 4 and 9, 1H, H in the 7-position); 6.74 (s, 1H, H of the thiazole); 6.80 (d, J = 16, 1H, —CH=CHS—); 6.90 (d, J = 16, 1H, =CHS—); 7.20 (s, 2H, —NH₂); 9.63 (d, J = 9, 1H, —CONH—) |
| 60 | 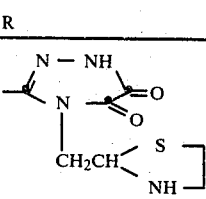 | —CH₃ | syn isomer E-form | (1) 3400, 3280, 3200, 2000, 1775, 1710, 1680, 1610, 1380, 1035, 750, 685<br>(2) 4.32 (s, 3H, =NOCH₃); 5.40 (d, J = 4, 1H, H in the 6-position); 6.04 (d, J = 4, H in the 7-position); 7.25 and 7.78 (2d, J = 16, 2H, —CH=CH—); 7.50 (s, 1H, H of the thiazole) |
| 61 | 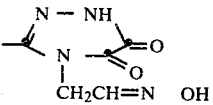 | —CH₃ | mixture of the syn, syn E and syn anti E isomers | (1) 3700 to 3200, 1770, 1710, 1680, 1585, 1530, 1040, 940<br>(2) 3.89 (s, 2H. —SCH₂—); 4.30 (s, 3H, =NOCH₃); 5.39 (d, J = 4, 1H, H in the 6-position); 6.04 (d, J = 4, 1H, H in the 7-position); 7.28 and 7.77 (2d, J = 16, 2H, —CH=CHS—); 7.50 (s, 1H, H of the thiazole) |
| 62 | 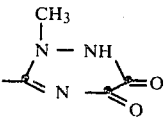 | —CH₃ | syn isomer E-form | (1) 3600, 2300, 1765, 1720, 1670, 1600, 1525, 1280, 1075, 1040, 930<br>(2) 3.77 and 3.88 (2d, J = 18, 2H, —SCH₂—); 4.30 (s, 3H, =NOCH₃); 5.41 (d, J = 4, 1H, H in the 6-position); 6.0 (d, J = 4, 1H, H in the 7-position); 7.50 (s, 1H, H of the thiazole) |

| Example | R | R₅ | Stereo-chemistry | (1) Infrared spectrum (KBr): Characteristics bands (cm⁻¹)<br>(2) Proton nuclear magnetic resonance spectrum, 350 MHz, CDCl₃, δ in ppm, J in Hz |
|---------|---|-----|-----------------|------|

-continued

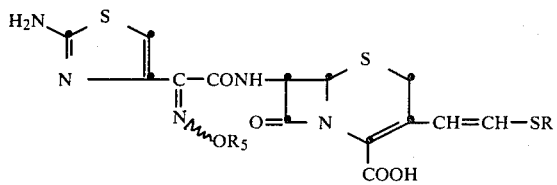

| 63 | 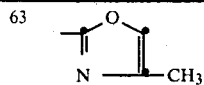 | —CH₃ | syn isomer E-form | (1) 3300, 2940, 1770, 1675, 1530, 1380, 1040, 940, 730, 700<br>(2) 2.10 (s, 3H, —CH₃); 3.66 and 3.90 (2d, J = 18, 2H, —SCH₂—); 3.86 (s, 3H, =NOCH₃); 5.19 (d, 1H, H in the 6-position); 5.78 (dd, 1H, H in the 7-position); 6.74 (s, 1H, H of the thiazole ring); 7.0 (d, J = 16, 1H, —CH=CHS—); 7.14 (d, J = 16, 1H, —CH=CHS—); 7.20 (s, 2H, —NH₂); 7.94 (s, 1H, H of the oxazole ring); 9.72 (d, J = 9, 1H, —CONH—) |
|---|---|---|---|---|

We claim:

1. A 3-vinyl-cephalosporin derivative of the formula:

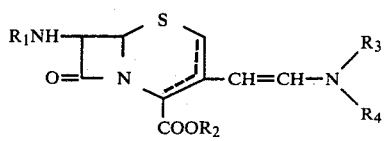

in the bicyclooct-2-ene or bicyclooct-3-ene form, and in which the substituent in the 3-position of the bicyclooctene exhibits the E- or Z-stereoisomeric configuration and (a) the symbol $R_1$ represents a radical of the formula:

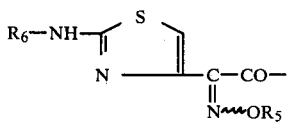

which is in the syn- or anti-form (and in which $R_5$ is a hydrogen atom or an alkyl, vinyl or cyanomethyl radical, or a protective group chosen from trityl, tetrahydropyranyl or 2-methoxy-prop-2-yl and $R_6$ is a protective radical chosen from tert.-butoxycarbonyl, 2,2,2-trichloro-ethoxycarbonyl, chloroacetyl, trichloroacetyl, trityl, benzyl, dibenzyl, benzyloxy-carbonyl, p-nitrobenzyloxycarbonyl, p-methoxybenzyloxycarbonyl, formyl or trifluoroacetyl) or $R_1$ is a benzhydryl or trityl radical or an acyl radical of the formula:

R₇-CO—

[in which $R_7$ is hydrogen, alkyl, alkyl substituted by one or more halogen atoms or by a phenyl or phenoxy radical, or phenyl]
or $R_1$ is a radical of the formula:

R₈OCO (in which $R_8$ is a branched unsubstituted alkyl radical or a branched or straight alkyl radical carrying 1 or more substituents [chosen from halogen atoms and cyano, trialkylsilyl, phenyl, and phenyl substituted by 1 or more alkoxy, nitro or phenyl radicals], vinyl, allyl or quinolyl), or a nitrophenylthio radical, or $R_1$NH is replaced by a methyleneamino radical in which the methylene radical is substituted by dialkylamino, phenyl or phenyl substituted by one or more methoxy or nitro radicals and the symbol $R_2$ represents an enzymatically easily removable radical of the formula:

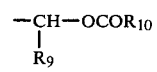

(in which $R_9$ represents a hydrogen atom or an alkyl radical and $R_{10}$ represents an alkyl or the cyclohexyl radical) or a methoxymethyl, tert.-butyl, benzhydryl, p-nitrobenzyl or p-methoxybenzyl radical, or (b) the symbol $R_1$ represents an alkanoyl radical containing 1 to 8 carbon atoms, an alkanoyl radical containing 2 to 8 carbon atoms substituted by chlorine or bromine atoms, an acyl radical of the formula:

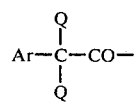

(in which each Q is H or methyl and Ar represents a thien-2-yl, thien-3-yl, fur-2-yl, fur-3-yl, pyrrol-2-yl or pyrrol-3-yl radical or phenyl or phenyl substituted by halogen atoms or by hydroxyl radicals, by alkyl radicals (containing 1 to 3 carbon atoms) or by alkoxy radicals (containing 1 to 3 carbon atoms) of which at least one is situated in the meta- or para- position of the phenyl radical),
an acyl radical of the formula:

Ar-X-CH₂-CO—

(in which X is oxygen or sulphur and Ar is as defined above or Ar-X represents pyridyl-4-ylthio, an acyl radical corresponding to the formula:

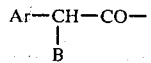

(in which Ar is as defined above and B represents an amino radical which is protected [by a benzyloxycarbonyl, alkoxycarbonyl, cyclopentyloxycarbonyl, cyclohexyloxycarbonyl, benzhydryloxycarbonyl, trityl or 2,2,2-trichloro-ethoxycarbonyl group], a sulpho radical, a hydroxyl or carboxyl radical or hydroxyl or carboxyl protected by esterification, respectively with an alkanoic acid or an alcohol each containing 1 to 6 carbon atoms) or a 5-amino-adipyl radical or a 5-amino-adipyl radical [in which the amino group is protected by an alkanoyl radical (containing 1 to 3 carbon atoms and unsubstituted or substituted by a chlorine atom) and in which the carboxyl group is protected by a benzhydryl, 2,2,2-trichloroethyl, tert.-alkyl containing 4 to 6 carbon atoms, or nitrobenzyl group] or $R_1NH-$ is replaced by a cyclic imide group of a dicarboxylic acid and $R_2$ represents a tert.-alkyl radical containing 4 to 6 carbon atoms, a tert.-alkenyl radical containing 6 or 7 carbon atoms, tert.-alkynyl radical containing 6 or 7 carbon atoms, benzyl, methoxybenzyl, nitrobenzyl, 2,2,2-trichloroethyl, benzhydryl, succinimidomethyl or phthalimidomethyl and the symbols $R_3$ and $R_4$, which are identical or different, represent alkyl radicals, alkyl radicals substituted by a hydroxyl, alkoxy, amino, alkylamino or dialkylamino radical, or phenyl radicals or form, together with the nitrogen atom to which they are attached, a saturated heterocyclic ring of 5 or 6 members, or a said ring containing another heteroatom chosen from nitrogen, oxygen or sulphur, and unsubstituted or substituted by an alkyl radical, the alkyl or acyl portions of radicals mentioned above being (unless stated to the contrary) straight or branched and containing 1 to 4 carbon atoms, as well as mixtures of its isomers.

2. A 3-vinyl cephalosporin derivative according to claim 1, in which the symbol $R_1$ is as defined in claim 1 in (a) or represents a radical of the formula:

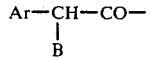

as defined in claim 1, or $R_1NH$ is replaced by a dicarboxylic acid cyclic imide group, the symbol $R_2$ is as defined in claim 1 and the symbols $R_3$ and $R_4$ are alkyl radicals or form, together with the nitrogen atom to which they are attached, a saturated heterocyclic 5-membered or 6-membered ring optionally containing another hetero-atom chosen from amongst nitrogen, oxygen or sulphur, and unsubstituted or substituted by an alkyl radical, as well as mixtures of its isomers.

3. A 3-vinyl-cephalosporin derivative according to claim 1, in which
(a) the symbol $R_1$ is a radical of the formula:

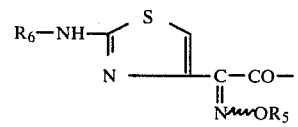

(in which $R_5$ is an alkyl or vinyl radical and $R_6$ is a trityl radical), a trityl radical, an acyl radical of the formula:

[in which $R_7$ is an alkyl radical or an alkyl radical substituted by a phenyl or phenoxy radical or a phenyl radical], a radical of the formula:

[in which $R_8$ is a branched unsubstituted alkyl radical, or a branched or straight alkyl radical substituted by a phenyl or nitrophenyl radical] and the symbol $R_2$ represents a pivalyloxymethyl, benzhydryl or p-nitrobenzyl radical, or (b) the symbol $R_1$ represents a radical of the formula:

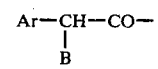

in which Ar is a phenyl radical and B is an amino radical protected by an alkoxycarbonyl group, or $R_1NH-$ represents a phthalimido radical, and the symbol $R_2$ represents a benzhydryl or nitrobenzyl radical, and the symbols $R_3$ and $R_4$ represent alkyl radicals containing 1 or 2 carbon atoms, or form, together with the nitrogen atom to which they are attached, a morpholino radical, as well as mixtures of its isomers.

4. 2-Benzhydryloxycarbonyl-7-tert.-butoxy-carbonylamino-3-(2-dimethylamino-vinyl)-8-oxo-5-thia-1-aza-bicyclo[4.2.0]oct-2-ene, E-form.

5. 2-Benzhydryloxycarbonyl-3-(2-dimethylamino-vinyl)-8-oxo-7-tritylamino-5-thia-1-aza-bicyclo[4.2.0]-oct-2-ene, E-form.

6. 2-Benzhydryloxycarbonyl-3-(2-dimethylamino-vinyl)-8-oxo-7-phenylacetamido-5-thia-1-aza-bicyclo-[4.2.0]oct-2-ene, E-form.

7. 2-Benzhydryloxycarbonyl-7-[2-methoxyimino-2-(2-tritylamino-thiazol-4-yl)-acetamido]-3-(2-dimethylamino-vinyl)-8-oxo-5-thia-1-aza-bicyclo[4.2.0]oct-2-ene, syn isomer, E-form.

* * * * *